US011896651B2

(12) United States Patent
Ruan et al.

(10) Patent No.: US 11,896,651 B2
(45) Date of Patent: Feb. 13, 2024

(54) GENE EDITING OF DEEP INTRONIC MUTATIONS

(71) Applicant: Genzyme Corporation, Cambridge, MA (US)

(72) Inventors: Guoxiang Ruan, Northborough, MA (US); Abraham Scaria, Framingham, MA (US)

(73) Assignee: GENZYME CORPORATION, Cambridge, MA (US)

( * ) Notice: Subject to any disclaimer, the term of this patent is extended or adjusted under 35 U.S.C. 154(b) by 289 days.

(21) Appl. No.: 15/574,420

(22) PCT Filed: Apr. 15, 2016

(86) PCT No.: PCT/US2016/027987
§ 371 (c)(1),
(2) Date: Nov. 15, 2017

(87) PCT Pub. No.: WO2016/186772
PCT Pub. Date: Nov. 24, 2016

(65) Prior Publication Data
US 2019/0022192 A1 Jan. 24, 2019

Related U.S. Application Data
(60) Provisional application No. 62/162,720, filed on May 16, 2015.

(51) Int. Cl.
| | |
|---|---|
| *A61K 38/46* | (2006.01) |
| *A61K 31/7105* | (2006.01) |
| *A61K 31/7088* | (2006.01) |
| *A61P 27/02* | (2006.01) |
| *C12N 9/22* | (2006.01) |
| *C12N 15/11* | (2006.01) |
| *C12N 15/90* | (2006.01) |

(52) U.S. Cl.
CPC ........ *A61K 38/465* (2013.01); *A61K 31/7088* (2013.01); *A61K 31/7105* (2013.01); *A61P 27/02* (2018.01); *C12N 9/22* (2013.01); *C12N 15/11* (2013.01); *C12N 15/907* (2013.01); *C12N 2310/20* (2017.05); *C12N 2750/14143* (2013.01); *C12N 2800/80* (2013.01)

(58) Field of Classification Search
CPC ............ C12N 2310/20; C12N 2800/80; C12N 2750/14143; C12N 15/11; C12N 15/111; C12N 9/22; A61K 31/7105; A61K 38/465
See application file for complete search history.

(56) References Cited

U.S. PATENT DOCUMENTS
| | | | |
|---|---|---|---|
| 7,407,801 B2* | 8/2008 | Ostedgaard | C12N 15/86 435/456 |
| 8,697,359 B1 | 4/2014 | Zhang | |
| 9,938,521 B2* | 4/2018 | Maeder | C12N 15/11 |
| 2018/0171357 A1* | 6/2018 | Jantz | C12N 15/86 |

FOREIGN PATENT DOCUMENTS
| | | | | |
|---|---|---|---|---|
| WO | WO2009121536 A1 | 10/2009 | | |
| WO | WO-2012099540 A1 * | 7/2012 | | C12N 15/85 |
| WO | WO-2014/204724 A1 | 12/2014 | | |
| WO | WO-2015/070083 A1 | 5/2015 | | |
| WO | WO-2015089354 A1 * | 6/2015 | | A61K 38/465 |
| WO | WO-2017136335 A1 * | 8/2017 | | C12N 7/00 |

OTHER PUBLICATIONS

Nunez et al. Cas1-Cas2 complex formation mediates spacer acquisition during CRISPR-Cas adaptive immunity. vol. 21, No. 6, pp. 528-534, May 4, 2014. (Year: 2014).*
Hsu et al. Development and Applications of CRISPR-Cas9 for genome engineering. Cell, vol. 157, pp. 1262-1278, Jun. 5, 2014. (Year: 2014).*
Cox et al. Therapeutic genome editing: prospects and challenges. Nature Medicine, vol. 21, No. 2, pp. 121-131, Feb. 2015. (Year: 2015).*
Willett et al. Immunology of AAV-mediated gene transfer in the eye. Frontiers in Immunology, vol. 4, article 261, Aug. 30, 2013, printed as pp. 1-8. (Year: 2013).*
Maguire et al. Safety and efficacy of gene transfer for Leber's Congenital Amaurosis. The New England Journal of Medicine, vol. 358, No. 21, pp. 2240-2248, Apr. 27, 2008. (Year: 2008).*
Shibata et al. Development of a hypoxia-responsive vector for tumor-specific gene therapy. Gene Therapy, vol. 7, pp. 493-498, 2000. (Year: 2000).*
Young, T.L. Ophthalmic genetics/inherited eye disease. Current Opinion in Ophthalmology, vol. 14, pp. 296-303, 2003. (Year: 2003).*
Senís et al. CRISPR/Cas9-mediated genome engineering: An adeno-associated viral (AAV) vector toolbox. Biotechnology Journal, vol. 9, pp. 1402-1412, and p. Jan. 26, 26/26 of Supporting Information, Sep. 4, 2014. (Year: 2014).*
Isomura et al. Role of the proximal enhancer of the major immediate-early promoter in human cytomegalovirus replication. Journal of Virology, vol. 78, No. 23, pp. 12788-12799, 2004. (Year: 2004).*
Abeliovich, D. et al. (Nov. 1992). "Screening for Five Mutations Detects 97% of Cystic Fibrosis (Cf) Chromosomes and Predicts a Carrier Frequency of 1:29 in The Jewish Ashkenazi Population," *Am J Hum Genet.* 51(5):951-956.

(Continued)

*Primary Examiner* — Jennifer Dunston
(74) *Attorney, Agent, or Firm* — MORRISON & FOERSTER LLP

(57) ABSTRACT

Provided herein are compositions, methods, kits, and viral particles for treating a disease or disorder associated with a deep intronic mutation using an engineered, non-naturally occurring Clustered Regularly Interspaced Short Palindromic Repeats (CRISPR)-CRISPR associated (Cas) (CRISPR-Cas) system. In some aspects, provided herein is a self-limiting CRISPER-Cas system.

6 Claims, 9 Drawing Sheets

Specification includes a Sequence Listing.

(56) References Cited

OTHER PUBLICATIONS

Aminoff, M. et al. (Mar. 1999). "Mutations In Cubn, Encoding The Intrinsic Factor-Vitamin $B_{12}$ Receptor, Cubilin, Cause Hereditary Megaloblastic Anaemia 1," *Nat Genet* 21(3):309-313.

Anonymous (May 14, 2015). "Addgene: CRISPR in the Lab: A Practical Guide", located at <http://www.Addgene.Org/Crispr/Guide/>, retrieved Dec. 23, 2016, 13 pages.

Barbelanne, M. et al. (Oct. 15, 2013, E-Pub. Jun. 15, 2013). "Pathogenic NPHP5 Mutations Impair Protein Interaction with Cep290, A Prerequisite For Ciliogenesis," *Hum. Mol. Genet.* 22(12):2482-2494.

Beroud, C. et al. (Jan. 2004). "Dystrophinopathy Caused by Mid-Intronic Substitutions Activating Cryptic Exons in the DMD Gene," *Neuromuscul Disord.* 14(1):10-18.

Bonifert, T. (Aug. 2014, e-pub. Jun. 25, 2014). "Pure and Syndromic Optic Atrophy Explained by Deep Intronic OPA1 Mutations and an Intralocus Modifier," *Brain* 137(Pt8):2164-2177.

Brandl, C. et al. (2015, E-Pub. Dec. 3, 2014). "Creation of Targeted Genomic Deletions Using Talen or Crispr/Cas Nuclease Pairs in One-Cell Mouse Embryos," *Febs Open Bio.* 5:26-35.

Braun, T.A. (Dec. 20, 2013, e-pub. Aug. 4, 2013). "Non-Exomic and Synonymous Variants in ABCA4 are an Important Cause of Stargardt Disease," *Hum. Mol. Genet.* 22(25):5136-5145.

Burnight, E.R. et al. (Jul. 2014). "CEP290 Gene Transfer Rescues Leber Congenital Amaurosis Cellular Phenotype," *Gene Ther.* 21(7):662-672.

Chang, B. et al. (Jun. 1, 2006, E-Pub. Apr. 21, 2006). "In-Frame Deletion in a Novel Centrosomal/Ciliary Protein CEP290/NPHP6 Perturbs its Interaction with RPGR and Results in Early-Onset Retinal Degeneration in the Rd16 Mouse," *Hum. Mol. Genet.* 15(11):1847-1857.

Cheng, T.C. et al. (May 1984). "β-Thalassemia in Chinese: Use of In Vivo RNA Analysis and Oligonucleotide Hybridization in Systematic Characterization of Molecular Defects," *Proc Nat Acad Sci USA* 81(9):2821-2825.

Chillon, M. et al. (Mar. 1995). "A Novel Donor Splice Site in Intron 11 ofthe CFTR Gene, Created by Mutation 1811+1.6kba-->G, Produces A New Exon: High Frequency in Spanish Cystic Fibrosis Chromosomes and Association With Severe Phenotype," *Am J Hum Genet* 56(3):623-629.

Christie, P.T. et al. (Aug. 2001). "X-Linked Hypophosphatemia Attributable To Pseudoexons Of The PHEX Gene," *J Clin Endocrinol Metab.* 86(8):3840-3844.

Collin, R.W. et al. (Mar. 2012, E-Pub Mar. 27, 2012). "Antisense Oligonucleotide (AON)-Based Therapy for Leber Congenital Amaurosis Caused by a Frequent Mutation in CEP290," *Mol. Ther. Nucleic Acids* 1(3):E14, pp. 1-7.

Cooper, D.N. et al. (Jun. 2010, E-Pub Apr. 13, 2010). "Genes, Mutations, and Human Inherited Disease at the Dawn of the Age of Personalized Genomics," *Hum. Mutat.* 31(6):631-655.

Coutinho, G. et al. (Feb. 2005). "Functional Significance of a Deep Intronic Mutation in the ATM Gene and Evidence for an Alternative Exon 28a," *Hum Mutat* 25(2):118-124.

Craige, B. et al. (Sep. 6, 2010). "CEP290 Tethers Flagellar Transition Zone Miorotubules To The Membrane and Regulates Flagellar Protein Content," *J. Cell Biol.* 190(5):927-940.

Cremers, F.P. et al. (May 15, 2002). "Molecular Genetics of Leber Congenital Amaurosis," *Human Molecular Genetics* 11(10):1169-1176.

Davis, R.L. et al. (Feb. 2009). "A Deep Intronic Mutation in FGB Creates a Consensus Exonic Splicing Enhancer Motif that Results in a Fibrino Genemia Caused by Aberrant mRNA Splicing, Which can be Corrected In Vitro with Antisense Oligonucleotide Treatment," *Hum Mutat* 30(2):221-227.

Deburgrave, N. et al. (Feb. 2007). "Protein-and mRNA-Based Phenotype-Genotype Correlations in DMD /BMD With Point Mutationsand Molecular Basis for BMD with Nonsense and Frame Shift Mutations in the DMD Gene," *Hum Mutat.* 28(2):183-195.

Dehainault, C. et al. (Apr. 2007, e-pub. Feb. 14, 2007). "A Deep Intronic Mutation in the RB1 Gene Leads to Intronic Sequence Exonisation," *Eur J. Hum Genet.* 15(4):473-477.

Den Hollander, A.I. et al. (Sep. 2006). "Mutations in the CEP290 (NPHP6) Gene are a Frequent Cause of Leber Congenital Amaurosis," *Am. J. Hum. Genet.* 79(3):556-561.

Dobkin, C. et al. (Mar. 1983). "Abnormal Splice in a Mutant Human β-Globin Gene Not at the Site of a Mutation," *Proc Nat Acad Sci Usa* 80(5):1184-1188.

Frio, T.R. (Sep. 2009). "A Single-Base Substitution within an Intronic Repetitive Element Causes Dominant Retinitis Pigmentosa with Reduced Penetrance," *Hum. Mutat.* 30(9):1340-1347.

Gerard, X. et al. (Jun. 2012, E-Pub. Jun. 26, 2012). "Aon-Mediated Exon Skipping Restores Ciliation in Fibroblasts Harboring the Common Leber Congenital Amaurosis CEP290 Mutation," *Mol. Ther. Nucleic Acids* 1(6):E29, 9 Pages.

Graham, R.R. et al. (May 2006, E-Pub. Apr. 16, 2006). "A Common Haplotype of Interferon Regulatory Factor 5 (IRF5) Regulates Splicing and Expression and is Associated with Increased Risk of Systemic Lupus Erythematosus," *Nat Genet* 38(5):550-555.

Guo, D.C. et al. (2008, E-Pub. Sep. 17, 2008). "An FBN1 Pseudoexon Mutation in a Patient with Marfan Syndrome: Confirmation of Cryptic Mutations Leading to Disease," 53(11-12):1007-1011.

Harland, M. et al. (Nov. 1, 2001). "A Deep Intronic Mutation in CDKN2A is Associated With Disease in a Subset of Melanoma Pedigrees," *Hum Mol Genet.* 10(23):2679-2686.

Hilgert, N. (May 2008, E-Pub. Jan. 23, 2008). "A Splice-Site Mutation and Overexpression of MYO6 Cause a Simlar Phenotype in Two Families With Autosomal Dominant Hearing Loss," *Eur J Hum Genet* 16(5):593-602.

Holbrook, J.A. et al. (Aug. 2004, E-Pub. Jul. 29, 2004). "Nonsense-Mediated Decay Approaches the Clinic," *Nat Genet.* 36(8):801-808.

Homolova, K. et al. (Apr. 2010, E-Pub. Jan. 29, 2010). "The Deep Intronic C.903+469T>C Mutation in the MTRR Gene Creates an SF2/Asf Binding Exonic Splicing Enhancer, which Leads to Pseudoexon Activation and Causes the Cble Type of Homocystinuria," *Hum Mutat.* 31(4):437-444.

Ikeda, H. et al. (Oct. 1997). "Molecular Analysis of Dihydropteridine Reductase Deficiency: Identification of Two Novel Mutations in Japanese Patients," *Hum Genet* 100(5-6):637-642.

Ikezawa, M. et al. (1999). "Newly Recognized Exons Induced by a Splicing Abnormality from an Intronic Mutation of the Dystrophin Gene Resulting In Duchenne Muscular Dystrophy. Mutations," (In Brief No. 213. Online) *Hum Mutat* 13(2):170, 4 pages.

Ishii, S. et al. (Apr. 2002, E-Pub Feb. 4, 2002). "Alternative Splicing in the α-Galactosidase a Gene: Increased Exon Inclusion Results in the Fabry Cardiac Phenotype," *Am J Genet* 70(4):994-1002.

Jansen, R. et al. (2002). "Identification of Genes that are Associated With DNA Repeats in Prokaryotes," *Mol. Microbiol.* 43(6):1565-1575.

Jinek, M. et al. (2013, E-Pub. Jan. 29, 2013). "RNA-Programmed Genome Editing in Human Cells," *Elife* 2:E00471, 9 Pages.

Jinek, M. et al. (Aug. 17, 2012). "A Programmable Dual-RNA-Guided DNA Endonuclease in Adaptive Bacterial Immunity," *Science* 337(6096):816-821.

King, K. et al. (Dec. 2002; E-Pub. Sep. 14, 2002). "Unusual Deep Intronic Mutations in the COL4A5 Gene Cause X Linked Alport Syndrome," *Hum Genet* 111(6):548-554.

Kleinstiver, B.P. et al. (Jan. 28, 2016, E-Pub. Jan 6, 2016). "High-Fidelity CRISPR-Cas9 Variants with Undetectable Genome-Wide Off-Targets," *Nature* 529(7587):490-495.

Koenekoop, R.K. (Jul.-Aug. 2004). "An Overview of Leber Congenital Amaurosis: A Model to Understand Human Retinal Development," *Survey of Ophthalmology* 49(4):379-398.

Leber, T.K.G.V. (1869) "About retinitis pigmentosa and congenital Amaurosis " *Graefe's Archive For Clinical and Experimental Ophthalmology* 15(3):1-25 (with Google translation).

Lee, P.L. et al. (2007, E-Pub. Dec. 21, 2007). "SLC40A1 C.1402G> A Results in Aberrant Splicing, Ferroportin Truncation After Glycine 330, and an Autosomal Dominant Hemochromatosis Phenotype," *Acta Haematol.* 118(4):237-241.

Lee, W. et al. (Mar. 1, 2005, E-Pub. Sep. 9, 2004). "Molecular Analysis of a Large Cohort of Patients with the Hyper Immunoglobulin M (Igm) Syndrome," *Blood* 105(5):1881-1890.

(56) References Cited

OTHER PUBLICATIONS

Levitus, M. et al. (Sep. 2005, E-Pub. Aug. 21, 2005). "The DNA Helicase Brip1 is Defective in Fanconi Anemia Complementation Group J," *Nat Genet.* 37(9):934-935.
Levy, C. et al. (May 2015). "Measles Virus Glycoprotein Pseudotyped Lentiviral Vectors Transduce Cytokine Stimulatedand Resting Hematopoietic Stem Cells at an Efficiency Without Precedent," *Molecular Therapy* 23(Supplement 1):S1.
Makarova, K.S. et al. (Jun. 2011, E-Pub. May 9, 2011). "Evolution and Classification of the CRISPR-CAS Systems," *Nat. Rev. Microbiol.* 9(6):467-477.
Mali, P. et al. (Feb. 15, 2013, E-Pub. Jan. 3, 2013). "RNA-Guided Human Genome Engineering Via Cas9," *Science* 339(6121):823-866.
Martinez-Duncker, I. et al. (Apr. 1, 2005, E-Pub. Dec. 2, 2004). "Genetic Complementation Reveals a Novel Human Congenital Disorder of Glycosylation of Type II, Due to Inactivation of the Golgi Cmp-Sialic Acid Transporter," *Blood* 105(7):2671-2676.
Masala, M.V. et al. (May-Jun. 2007, E-Pub. May 4, 2007). "Epidemiologyand Clinical Aspects of Werner's Syndrome in North Sardinia: Description of a Cluster," *Eur J Dermatol* 17(3):213-216.
Mayer, K. et al. (Nov. 15, 2000). "Three Novel Types of Splicing Aberrations in the Tuberous Sclerosis Tsc2 Gene Caused by Mutations Apart from Splice Consensus Sequences," *Biochim Biophys Acta.* 1502(3):495-507.
McConville, C.M. et al. (Aug. 1996). "Mutations Associated with Variant Phenotypes in Ataxia-Telangiectasia," *Am J Hum Genet* 59(2):320-330.
Metherell, L.A. et al. (Sep. 2001, E-Pub Jul. 20, 2001). "Pseudoexon Activation as a Novel Mechanism for Disease Resulting in Atypical Growth-Hormone Insensitivity," *Am J Hum Genet.* 69(3):641-646.
Michel-Calemard, L. et al. (Feb. 2009, E-Pub. Nov. 17, 2008). "Pseudoexon Activation in the PKHD1 Gene: A French Founder Intronic Mutation Ivs46+653a>G Causing Severe Autosomal Recessive Polycystic Kidney Disease," *Clin Genet* 75(2):203-206.
Mitchell, G. et al. (Feb. 1991). "Splice-mediated insertion of an Alu sequence inactivates ornithine delta-aminotransferase: a role for Alu elements in human mutation," *Proc Natl Acad Sci USA* 88(3):815-819.
Mojica, F.J. et al. (Feb. 2005). "Intervening Sequences of Regularly Spaced Prokaryotic Repeats Derive from Foreign Genetic Elements," *J. Mol. Evol.* 60(2):174-182.
Monnier, N. et al. (Jan. 2001). "A Novel 3600+11.5 Kb C>G Homozygous Splicing Mutation in a Black African, Consanguineous CF Family," *J Med Genet* 38(1)E4, 2 Pages.
Monnier, N. et al. (May 15, 2003). "A Homozygous Splicing Mutation Causing a Depletion of Skeletal Muscle RYR1 is Associated with Multi-Minicore Disease Congenital Myopathy with Ophthalmoplegia," *Hum Mol Genet* 12(10):1171-1178.
Montermini, L. et al. (Aug. 1997). "The Friedreich Ataxia Gaa Triplet Repeat: Premutation and Normal Alleles," *Hum Mol Genet.* 6(8):1261-1266.
Moore, R. et al. (Jan. 30, 2015, E-Pub. Dec. 18, 2014). "CRISPR-Based Self-Cleaving Mechanism for Controllable Gene Delivery in Human Cells", *Nucleic Acids Research* 43(2):1297-1303.
Neidhardt, J. et al. (Aug. 2007). "Identification and Characterization of a Novel RPGR Isoform in Human Retina," *Hum. Mutat.* 28(8):797-807.
Noack, D. et al. (Sep. 28, 2001). "An Unusual Intronic Mutation in the CYBB Gene Giving Rise to Chronic Granulomatous Disease," *Biochim Biophys Acta.* 1537(2):125-131.
Nozu, K. et al. (Nov. 2009). "A Deep Intronic Mutation in the SLC12A3 Gene Leads to Gitelman Syndrome," *Pediatr Res.* 66(5)590-593.
Ouellet, D. L. et al. (May 1, 2015). "Deletion of GAA Repeats Expansion from the Lntron 1 of the Frataxin Gene Using Crispr/Cas9 System," *Molecular Therapy* 23:S52-S53, No. 128, Located At <Http://Www.Cell.Com/Molecular-Therapy-Family/Molecular-Therapy/Abstract/S1525-0016(16)33733-9>, Last Visited On Jan. 31, 2018, 2 Pages.

Perrault, I. et al. (Apr. 2007). "Spectrum of NPHP6/CEP290 Mutations in Leber Congenital Amaurosis and Delineation of the Associated Phenotype," *Hum. Mutat.* 28(4):416, 11 Pages.
Perrin, G. et al. (1996). "Two Novel Mutations Affecting mRNA Splicing of the Neurofibromatosis Type 1 (NF1) Gene," *Hum Mutat* 7(2):172-175.
Pezeshkpoor, B. et al. (Sep. 2013). "Deep Intronic 'Mutations' Cause Hemophilia A: Application of Next Generation Sequencing in Patients without Detectable Mutation in F8 cDNA," *J Thromb Haemost* 11(9):1679-1687.
Pros, E. et al. (Mar. 2009, Feb. 20, 2009). "Antisense Therapeutics For Neurofibromatosis Type 1 Caused by Deep Intronic Mutations," *Hum Mutat.* 30(3):454-462.
Purevsuren, J. et al. (Sep.-Oct. 2008, E-Pub. Aug. 9, 2008). "Study of Deep Intronic Sequence Exonization in a Japanese Neonate with a Mitochondrial Trifunctional Protein Deficiency," *Mol Genet Metab.* 95(1-2):46-51.
Ran, F.A. et al. (Sep. 12, 2013). "Double Nicking by RNA-Guided CRISPR Cas9 for Enhanced Genome Editing Specificity," *Cell* 154(6):1380-1389.
Ran, F.A. et al. (Apr. 9, 2015, E-Pub. Apr. 1, 2015). "In Vivo Genome Editing Using *Staphylococcus Aureus* Cas9," *Nature* 520(7546):186-191.
Ran, F.A. et al. (Nov. 2013, E-Pub. Oct. 24, 2013). "Genome Engineering Using the CRISPR-Cas9 System," *Nat. Protoc.* 8(11):2281-2308.
Raponi, M. et al. (Mar. 2006). "Functional Splicing Assay Shows a Pathogenic Intronic Mutation in Neurofibromatosis Type 1 (NF1) Due to Intronic Sequence Exonization," *Hum Mutat.* 27(3):294-295.
Rathmann, M. et al. (Dec. 1996). "Mucopolysaccharidos is Type II (Hunter Syndrome): Mutation "Hot Spots" in the Iduronate-2-Sulfatase Gene," *Am J Hum Genet* 59(6):1202-1209.
Richards, A.J. et al. (Jul. 2006). "High Efficiency of Mutation Detection in Type 1 Stickler Syndrome Using a Two-Stage Approach: Vitreoretinal Assessment Coupled with Exon Sequencing for Screening COL2A1," *Hum Mutat.* 27(7):696-704.
Rincon, A. et al. (Dec. 2007). "Propionicand Methylmalonic Acidemia: Antisense Therapeutics for Intronic Variations Causing Aberrantly Spliced Messenger RNA," *Am J Hum Genet.* 81(6):1262-1270.
Rodriguez-Pascau, L. et al. (Nov. 2009). "Antisense Oligonucleotide Treatment for a Pseudoexon-Generating Mutation in the NPC1 Gene Causing Niemann-Pick Type C Disease," *Hum Mutat* 30(11):E993-E1001.
Rump, A. et al. (Apr. 26, 2006; E-Pub. Mar. 3, 2006). "A Splice-Supporting Intronic Mutation in the Last Bp Position of a Cryptic Exon Within Intron 6 of the CYBB Gene Induces Its IncorporationintoThe mRNA Causing Chronic Granulomatous Disease (Cgd)," *Gene* 371(2):174-181.
Sakamoto, O. et al. (Nov. 2001, E-Pub. Oct. 13, 2001). "A Novel Intronic Mutation of the TAZ (G4.5) Gene in a Patient with Barth Syndrome: Creation of a 5' Splice Donor Site with Variant GC Consensusand Elongation of the Upstream Exon," *Hum Genet.* 109(5):559-563.
Sakuma, T. et al. (2014, Jun. 23, 2014). "Multiplex Genome Engineering In Human Cells Using All-In-One Crispr/Cas9 Vector System," *Sci. Rep.* 4:5400, 6 Pages.
Schollen, E. et al. (Apr. 2007, E-Pub. Feb. 16, 2007). "Characterization of Two Unusual Truncating PMM2 Mutations in Two CDG-la Patients," *Mol Genet Metab.* 90(4):408-413.
Sevenet, N. et al. (Dec. 1999). "Spectrum of hSNF5/IN/1 Somatic Mutations In Human Cancer and Genotype-Phenotype Correlations," *Hum Mol Genet* 8(13):2359-2368.
Slaymaker, I.M. et al. (Jan. 1, 2016, E-Pub. Dec. 1, 2015). "Rationally Engineered Cas9 Nucleases with Improved Specificity," *Science* 351(6268):84-88.
Spena, S. et al. (Oct. 2007). "Pseudo-Exon Activation Caused by a Deep-Intronic Mutation in the Fibrinogen y-Chain Gene as a Novel Mechanism for Congenital Afibrinogenaemia," *Br J Haematol.* 139(1):128-132.
Steele-Stallard, H.B. (Aug. 8, 2013). "Screening for Duplications, Deletions and a Common Intronic Mutation Detects 35% of Second Mutations in Patients with USH2A Monoallelic Mutations on Sanger Sequencing," *Orphanet J. Rare Dis.* 8:122, 11 pages.

(56) References Cited

OTHER PUBLICATIONS

Stone, E.M. (Dec. 2007). "Leber Congenital Amaurosis—A Model for Efficient Genetic Testing of Heterogeneous Disorders: LXIV Edward Jackson Memorial Lecture," *Am. J. Ophthalmol.* 144(6):791-811.
Stum, M. et al. (Nov. 2006). "Spectrum of HSPG2 (Perlecan) Mutations in Patients with Schwartz-Jampel Syndrome," *Hum Mutat.* 27(11):1082-1091.
Takeshima, Y. et al. (Jun. 2010, E-Pub May 20, 2010). "Mutation Spectrum Of The Dystrophin Gene In 442 Duchenne/Becker Muscular Dystrophy Cases From One Japanese Referral Center," *J Hum Genet.* 55(6):379-388.
Tan, E. et al. (Mar. 2001). "The Relationship Between Opsin Overexpression and Photoreceptor Degeneration," *Invest. Ophthalmol. Vis. Sci.* 42(3):589-600.
Treisman, R. et al. (Apr. 14, 1983). "Specific Transcription and RNA Splicing Defects in Five Cloned β-Thalassaemia Genes," *Nature* 302(5909):591-596.
Tsuruta, M. et al. (1998). "Molecular Basis Of Intermittent Maple Syrup Urine Disease: Novel Mutations in the E2 Gene of the Branched-Chain α-Keto Acid Dehydrogenase Complex," *J Hum Genet* 43(2):91-100.
Tuffery-Giraud, S. et al. (Jun. 2003). "Pseudoexon Activation in the DMD Gene as Novel Mechanism for Becker Muscular Dystrophy," *Hum Mutat.* 21(6):608-614.
Valdmanis, P.N. et al. (Nov. 2009). "A Mutation that Creates a Pseudoexon In SOD1 Causes Familial ALS," *Ann Hum Genet* 73(Pt 6):652-657.
Varon, R. et al. (Oct. 2003, E-Pub. Sep. 21, 2003). "Partial Deficiency of the C-Terminal-Domain Phosphatase of RNA Polymerase II is Associated with Congenital Cataracts Facial Dysmorphism Neuropathy Syndrome," *Nat Genet* 35(2)185-189.
Verpy, E. (Sep. 2000). "A Defect in Harmonin, a PDZ Domain-Containing Protein Expressed in the Inner Ear Sensory Hair Cells, Underlies Usher Syndrome Type 1C," *Nat. Genet.* 26(1):51-55.
Vetrini, F. et al. (May 2006). "Aberrant Splicing in the Ocular Albinism Type 1 Gene (OA1/GPR143) is Corrected In Vitro by Morpholino Antisense Oligonucleotides," *Hum Mutat.* 27(5):420-426.
Wang, D. et al. (Jul. 1, 2015). "Adenovirus-Mediated Somatic Genome Editing of Pten by CRISPR/Cas9 in Mouse Liver in Spite of Cas9-Specific Immune Responses," *Hum. Gene Ther.* 26(7):432-442.
Webb, T.R. (Aug. 15, 2012, e-pub. May 22, 2012). "Deep Intronic Mutation in OFD1, Identified by Targeted Genomic Next-Generation Sequencing, Causes a Severe form of X-linked Retinitis Pigmentosa (RP23)," *Hum. Mol. Genet.* 21(16):3647-3654.
Wilson, A. et al. (Aug. 1998, E-Pub. Jun. 29, 1998). "Functionally Null Mutations in Patients with the cblG-Variant Form of Methionine Synthase Deficiency," *Am J. Hum Genet.* 63(2):409-414.
Wiszniewski, W. et al. (Mar. 2011, E-Pub. Dec. 14, 2010). "Potential Involvement of More than One Locus in Trait Manifestation for Individuals with Leber Congenital Amaurosis," *Hum. Genet.* 129(3):319-327.
Yagi, M. et al. (Feb. 2003). "Two Alternative Exons can Result from Activation of the Cryptic Splice Acceptor Site Deep within Intron 2 of the Dystrophin Gene in a Patient with as yet Asymptomatic Dystrophinopathy," *Hum Genet.* 112(2):164-170.
Yamaguchi, H. et al. (Jun. 2010). "Aberrant Splicing of the Milk Fat Globule-EGF Factor 8 (MFG-E8) Gene in Human Systemic Lupus Erythematosus," *Eur J Immunol.* 40(6):1778-1785.
Zheng, Q. et al. (Sep. 2014). "Precise Gene Deletion and Replacement Using the CRISPR/Cas9 System in Human Cells," *Biotechniques* 57(3):115-124.
Zuris, J.A. et al. (Jan. 2015, E-Pub. Oct. 30, 2014). "Efficient Delivery of Genome-Editing Proteins In Vitro and In Vivo," *Nat Biotechnol.* 33(1):73-80.
International Preliminary Report on Patentability dated Nov. 21, 2017, for PCT Patent Application No. PCT/US2016/027987, filed Apr. 15, 2016, 15 pages.
International Search Report dated Nov. 25, 2016, for PCT Patent Application No. PCT/US2016/027987, filed Apr. 15, 2016, 8 pages.
Maeder, M.L. et al. (May 13, 2015). "687. Therapeutic Correction Of An LCA-Causing Splice Defect In The CEP290 Gene By CRISPR/Cas-Mediated Genome Editing," Molecular Therapy Supplement 1(23): S273-S274.
Ousterout, D.G. et al. (Feb. 2015). "Multiplex CRISPR/Cas9-Based Genome Editing For Correction Of Dystrophin Mutations That Cause Duchenne Muscular Dystrophy," Nature Communications 6(1):1-13.
Written Opinion of the International Searching Authority dated Nov. 25, 2016, for PCT Patent Application No. PCT/US2016/027987, filed Apr. 15, 2016, 14 pages.

\* cited by examiner

US 11,896,651 B2

GENE EDITING OF DEEP INTRONIC MUTATIONS

CROSS-REFERENCE TO RELATED APPLICATIONS

This application is a National Phase application under 35 U.S.C. § 371 of International Application No. PCT/US2016/027987, filed Apr. 15, 2016, which claims priority to U.S. Provisional Application No. 62/162,720, filed May 16, 2015, each of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 159792013400SEQLIST.txt, date recorded: Aug. 31, 2018, size: 50 KB).

FIELD OF THE INVENTION

The present invention relates to methods for treating a disease or disorder associated with a deep intronic mutation using an engineered, non-naturally occurring Clustered Regularly Interspaced Short Palindromic Repeats (CRISPR)-CRISPR associated (Cas) (CRISPR-Cas) system, as well as compositions, kits, and viral particles related thereto.

BACKGROUND OF INVENTION

Mutations in non-coding sequences such as introns have been implicated in a wide range of diseases. The human genome contains a higher proportion of longer introns than other organisms such as worms and flies; greater than 90% of human introns are more than 100 nucleotides in length, with more than one-third of all introns being 2,000 nucleotides or longer (*Molecular Biology of the Cell*, 6$^{th}$ ed. (Alberts, B. et al, eds., 2014). In addition, deep intronic mutations have been identified as an important and potentially ignored cause of human disease, with much of the effort in identifying disease-linked mutations focused on coding sequence (Homolova, K. et al. (2010) *Hum. Mutat.* 31:437-444). Due to the complexity of mRNA splicing in humans, these deep intronic mutations can potentially cause a variety of pathological conditions due to mechanisms including, inter alia, mRNA destabilization, degradation, and mis-splicing (e.g., creating a cryptic splice site). Indeed, some have estimated that up to 5% of Mendelian diseases in humans may be associated with a deep intronic mutation (Cooper. D. N. et al. (2010) *Hum. Mutat.* 31:631-655).

As an illustrative example of a disorder that, in some cases, has been linked to a deep intronic mutation, Leber congenital amaurosis (LCA) is the most severe form of inherited retinal dystrophy with onset of symptoms in the first year of life (Leber, T. K. G. v. (1869) *Graefe's Archive for Clinical and Experimental Ophthalmology* 15: 1-25). Visual acuity in LCA patients is rarely better than 20/400 (Cremers. F. P. et al. (2002) *Human molecular genetics* 11:1169-1176). LCA affects approximately 1 per 30,000 individuals in the general population and accounts for 5% of all inherited retinal dystrophies (Koenekoop, R. K. (2004) *Survey of ophthalmology* 49:379-398). The most frequent genetic cause of LCA, accounting for approximately 15% of all LCA cases in European countries and in the United States, is a deep-intronic mutation c.2991+1655A>G in the intron 26 of CEP290 gene, which generates a cryptic splice donor site resulting in the inclusion of an aberrant exon containing a premature stop codon (p.C998X) to CEP290 mRNA (den Hollander, A. I. et al. (2006) *Am. J. Hum. Genet.* 79:556-561; Perrault, I. et al. (2007) *Hum. Mutat.* 28:416; Stone. E. M. (2007) *Am. J. Ophthalmol.* 144:791-811; Wiszniewski. W. et al. (2011) *Hum. Genet.* 129:319-327). The LCA disease caused by CEP290 mutation is known as LCA10. Alternative splicing of the cryptic exon into CEP290 mRNA occurs in some, but not all, mRNA transcripts in the homozygous affected individuals (den Hollander. A. I. et al. (2006) *Am. J. Hum. Genet.* 79:556-561), stressing the hypomorphic nature of this intronic mutation.

The human CEP290 gene encompasses 54 exons that encode a 2479 amino acid protein. CEP290 is a centrosomal protein that plays an important role in both cilium assembly and ciliary protein trafficking (Barbelanne, M. et al. (2013) *Hum. Mol. Genet.* 22:2482-2494; Craige, B. et al. (2010) *J. Cell Biol.* 190:927-940). In photoreceptors, the retinal cells most affected by CEP290 mutations. CEP290 localizes to the connecting cilium (Chang. B. et al. (2006) *Hum. Mol. Genet.* 15:1847-1857), which connects the inner and the outer segment of photoreceptors.

Currently there is no cure for CEP290 mutation-caused LCA. The two preclinical approaches for addressing this disease are gene augmentation and antisense oligonucleotides (AONs). The size of human CEP290 complementary DNA (cDNA) exceeds the cargo size (~4.8 kb) of recombinant adeno-associated viruses (rAAVs). The lentiviral vector system can accommodate the full-length CEP290 cDNA; however, it may not be able to precisely control the expression level of CEP290. Previous reports have demonstrated that photoreceptors are sensitive to the level of transgene expression, and overexpression of CEP290 is cytotoxic (Burnight, E. R. et al. (2014) *Gene Ther.* 21:662-672; Tan, E. et al. (2001) *Invest. Ophthalmol. Vis. Sci.* 42:589-600). An alternative strategy is to use AONs to interfere with the aberrant splicing of CEP290 (Collin, R. W. et al. (2012) *Mol. Ther. Nucleic Acids* 1:e14; Gerard, X. et al. (2012) *Mol. Ther. Nucleic Acids* 1:e29). However, this approach requires weekly or monthly subretinal injections for years by a retinal specialist.

Accordingly, there is an urgent need for improved therapeutic approaches for treating disorders linked to deep intronic mutations, such as CEP290 mutation-caused LCA10.

BRIEF SUMMARY OF THE INVENTION

The invention provides compositions for treating a disease or disorder associated with a deep intronic mutation in a gene of an individual comprising an engineered, non-naturally occurring Clustered Regularly Interspaced Short Palindromic Repeats (CRISPR)-CRISPR associated (Cas) (CRISPR-Cas) system comprising a) a first guide RNA and a second guide RNA wherein the first guide RNA and the second guide RNA hybridize to the opposite strands of the target DNA sequences flanking the deep intronic mutation, and b) a Cas protein, wherein the Cas protein cleaves the target DNA molecule at sites flanking the deep intronic mutation thereby excising a portion of the target DNA comprising the deep intronic mutation. In some embodiments, the invention provides compositions for treating a disease or disorder associated with a deep intronic mutation in a gene of an individual comprising nucleic acid encoding an engineered, non-naturally occurring Clustered Regularly Interspaced Short Palindromic Repeats (CRISPR)-CRISPR associated (Cas) (CRISPR-Cas) system comprising a) a first guide RNA and a second guide RNA wherein the first guide RNA and the second guide RNA hybridize to the opposite strands of the target DNA sequences flanking the deep intronic mutation, and b) a nucleotide sequence encoding a Cas protein, wherein the Cas protein cleaves the target DNA molecule at sites flanking the deep intronic mutation thereby excising a portion of the target DNA comprising the deep intronic mutation. In some embodiments, the disease or disorder associated with a deep intronic mutation is afibrinogenemia, Alport syndrome, Amyotrophic lateral sclerosis, ataxia telangiectasia, autosomal recessive polycystic kidney disease. Barth syndrome, beta-thalassemia, congenital afibrinogenemia, congenital cataracts facial dysmorphism neuropathy syndrome, congenital disorder of glycosylation type Ia, congenital disorder of glycosylation type II, cystic fibrosis, dihydropteridine reductase deficiency, Fabry disease, familial platelet disorder with predisposition to acute myelogenous leukemia. Fanconi anemia. Gitelman syndrome, growth hormone insensitivity, Friedrich's ataxia, hemophilia A, hereditary megaloblastic anaemia 1. Hermansky-Pudlak syndrome, homocytinuria, maple syrup urine disease. Marfan syndrome, methionine synthase deficiency, methylmalonic academia, mitochondrial trifunctional protein deficiency, mucupolysaccaridosis type II, multi-minicore disease, muscular dystrophy, neurofibromatosis type I, Niemann-Pick disease type C, ocular albinism type I, ornithine delta-aminotransferaase deficiency, predisposition to systemic lupus erythematosus, propionic academia, rhabdoid tumors, Schwartz-Jampel syndrome, Stickler syndrome, systemic lupus erythematosus, tuberous sclerosis, Werner syndrome, X-linked hyperimmunoglobulinemia M, or X-linked hypophosphatemia. In some embodiments, the deep intronic mutation is a deep intronic mutation presented in Table 1.

In some aspects, the invention provides compositions for treating an ocular disease or disorder associated with a deep intronic mutation in a gene of an individual comprising nucleic acid encoding an engineered, non-naturally occurring Clustered Regularly Interspaced Short Palindromic Repeats (CRISPR)-CRISPR associated (Cas) (CRISPR-Cas) system comprising a) a first guide RNA and a second guide RNA wherein the first guide RNA and the second guide RNA hybridize to the opposite strands of the target DNA sequences flanking the deep intronic mutation, and b) a nucleotide sequence encoding a Cas protein, wherein the Cas protein cleaves the target DNA molecule at sites flanking the deep intronic mutation thereby excising a portion of target DNA comprising the deep intronic mutation. In some embodiments, the invention provides compositions for treating an ocular disease or disorder associated with a deep intronic mutation in a gene of an individual comprising an engineered, non-naturally occurring Clustered Regularly Interspaced Short Palindromic Repeats (CRISPR)-CRISPR associated (Cas) (CRISPR-Cas) system comprising a) a first guide RNA and a second guide RNA wherein the first guide RNA and the second guide RNA hybridize to the opposite strands of the target DNA sequences flanking the deep intronic mutation, and b) a Cas protein, wherein the Cas protein cleaves the target DNA molecule at sites flanking the deep intronic mutation thereby excising a portion of target DNA comprising the deep intronic mutation. In some embodiments, the ocular disease is Leber congenital amaurosis, optic atrophy, retinitis pigmentosa, retinoblastoma, Stargardt disease, Usher syndrome, or X-linked retinitis pigmentosa. In some embodiments, the deep intronic mutation is a deep intronic mutation presented in Table 2.

In some embodiments of the above embodiments, the ocular disease is Leber congenital amaurosis. In some embodiments, the first guide RNA and second guide RNA guide sequences hybridize to the opposite strands of the target DNA sequences flanking a deep intronic mutation of the centrosomal protein 290 kDa (CEP290) gene. In some embodiments, the deep intronic mutation is a c.2991+1655A>G mutation. In some embodiments, the first guide RNA is encoded by DNA comprising the sequences of SEQ ID NO:41 (for SpCas9), SEQ ID NO:45 (for SaCas9), SEQ ID NO:46 (for SaCas9), or SEQ ID NO:47 (for SaCas9). In some embodiments, the first guide RNA is encoded by DNA comprising the sequence of SEQ ID NO:19 (for SpCas9), SEQ ID NO:50 (for SaCas9). SEQ ID NO:51 (for SaCas9), or SEQ ID NO:52 (for SaCas9). In some embodiments, the second guide RNA is encoded by DNA comprising the sequences of SEQ ID NO:42 (for SpCas9), SEQ ID NO:43 (for SpCas9), SEQ ID NO:44 (for SpCas9), SEQ ID NO:48 (for SaCas9), or SEQ ID NO:49 (for SaCas9). In some embodiments, the second guide RNA is encoded by DNA comprising the sequence of SEQ ID NO:20 (for SpCas9), SEQ ID NO:21 (for SpCas9), SEQ ID NO:22 (for SpCas9), SEQ ID NO:53 (for SaCas9), or SEQ ID NO:54 (for SaCas9). In some embodiments, the CEP290 is a human CEP290. In some embodiments, the CEP290 comprises a deep intronic mutation of the sequence set forth in SEQ ID NO:23.

In some embodiments of the above embodiments, the deep intronic mutation is located about 1-10,000 nucleotides, about 1-1000 nucleotides or about 100-1000 nucleotides downstream of a 5' splice donor site of the gene. In some embodiments, the deep intronic mutation is located about 1-10,000 nucleotides, about 1-1000 nucleotides or about 100-1000 nucleotides upstream of a 3' splice acceptor site of the gene. In some embodiments, the deep intronic mutation introduces a splice donor site or a splice acceptor site in the gene.

In some embodiments of the above embodiments, the Cas protein is a Cas9 protein. In some embodiments, the Cas 9 protein is a *Streptococcus pyogenes* Cas9 protein (SEQ ID NO:40), a *Staphylococcus aureus* Cas9 protein (SEQ ID NO: 55), a *Streptococcus thermophilus* Cas9 protein, a *Neisseria meningitidis* Cas9 protein, or a *Treponera denticola* Cas9 protein. In some embodiments, the Cas9 is codon optimized for expression in a eukaryotic cell. In some embodiments, the eukaryotic cell is a mammalian cell. In some embodiments, the eukaryotic cell is a human cell.

In some embodiments of the above embodiments, the CRISPR-Cas system further comprises one or more nuclear localization signal(s) (NLS(s)). In some embodiments, the Cas protein comprises one or more NLS. In some embodiments, the NLS is a C-terminal sequence in the SV40 Large T-antigen. In some embodiments, the NLS comprises the sequence PKKKRKV (SEQ ID NO:26) or PKKKRKVEDPKKKRKVD (SEQ ID NO:27).

In some embodiments of the above embodiments, the first guide RNA and/or the second guide RNA comprise are fused to a trans-activating cr (tracr) sequence. In some embodiments, the tracr sequence comprises the nucleotide sequence encoded by SEQ ID NO:25.

In some embodiments of the above embodiments, the CRISPR-Cas system (e.g., the first guide RNA, the second guide RNA and the Cas protein) is complexed to a lipid, a cationic lipid, a liposome, a polycation or an agent that enhances the cellular uptake of nucleic acid and/or the protein.

In some embodiments of the above embodiments, nucleic acid encoding the first guide RNA, the second guide RNA and the Cas protein are expressed in eukaryotic cells. In some embodiments, the nucleic acid encoding the first guide RNA, the second guide RNA and/or the Cas protein are operably linked to one or more regulatory control elements. In some embodiments, the first guide RNA and/or the second guide RNA is operably linked to a RNA polymerase III promoter. In some embodiments, the RNA polymerase III promoter is a U6, a 7SK or an H1 promoter. In some embodiments, the nucleic acid encoding the Cas protein is operably linked to a RNA polymerase 1 promoter. In some embodiments, the RNA polymerase II promoter is a cytomegalovirus (CMV) immediate early promoter, a minimal promoter fragment derived from the CMV promoter (minCMV promoter), a RSV LTR, a MoMLV LTR, a phosphoglycerate kinase-1 (PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), a E2F promoter, a EF1α promoter, a telomerase (hTERT) promoter, a cytomegalovirus enhancer/chicken beta-actin/Rabbit 3-globin promoter (CAG) promoter, a rod opsin promoter, a cone opsin promoter, a beta phosphodiesterase (PDE) promoter, a retinitis pigmentosa (RP1) promoter, or an interphotoreceptor retinoid-binding protein gene (IRBP) promoter.

In some embodiments of the above embodiments, the nucleic acid encoding one or more of the first guide RNA, the second guide RNA or the Cas protein are located on the same or different vectors of the system. In some embodiments, the vector is a plasmid. In some embodiments, the vector is complexed to a delivery system. In some embodiments, the vector is complexed to a lipid, a cationic lipid, a liposome, a polycation or an agent that enhances the cellular uptake of nucleic acid.

In some embodiments of the above embodiments, the vector is a recombinant adeno-associated virus (rAAV) vector, a recombinant adenoviral vector, a recombinant lentiviral vector or a recombinant herpes simplex virus (HSV) vector. In some embodiments, the vector is a recombinant adenoviral vector. In some embodiments, the recombinant adenoviral vector is derived from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the recombinant adenoviral vector is derived from adenovirus serotype 2 or a variant of adenoviral serotype 5.

In some embodiments, the vector is a recombinant lentiviral vector. In some embodiments, the recombinant lentiviral vector is derived from a lentivirus pseudotyped with vesicular stomatitis virus (VSV), lymphocytic choriomeningitis virus (LCMV), Ross river virus (RRV), Ebola virus, Marburg virus, Mokala virus, Rabies virus, RD114, or variants therein.

In some embodiments, the vector is an rHSV vector. In some embodiments, the rHSV vector is derived from rHSV-1 or rHSV-2.

In some embodiments, the vector is a recombinant AAV (rAAV) vector. In some embodiments, the nucleic acid encoding one of more of the first guide RNA, the second guide RNA, or the Cas protein is flanked by one or more AAV inverted terminal repeat (ITR) sequences. In some embodiments, the nucleic acid encoding one of more of the first guide RNA, the second guide RNA, or the Cas protein is flanked by two AAV ITRs. In some embodiments, the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype ITRs. In some embodiments, the AAV ITRs are AAV2 ITRs. In some embodiments, the vector is a self-complementary vector.

In some embodiments, the vector is encapsidated in a viral particle. In some embodiments, the viral particle is a recombinant adenovirus particle encapsidating a recombinant adenoviral vector. In some embodiments, the recombinant adenovirus particle comprises a capsid from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the recombinant adenovirus particle comprises an adenovirus serotype 2 capsid or a variant of an adenoviral serotype 5 capsid.

In some embodiments, the viral particle is a recombinant lentiviral particle encapsidating a recombinant lentiviral vector. In some embodiments, the recombinant lentiviral particle comprises a capsid pseudotyped with vesicular stomatitis virus (VSV), lymphocytic choriomeningitis virus (LCMV), Ross river virus (RRV), Ebola virus, Marburg virus, Mokala virus. Rabies virus. RD114 or variants therein.

In some embodiments, the viral particle is a recombinant HSV particle encapsidating a recombinant HSV vector. In some embodiments, the recombinant HSV particle is an rHSV-1 particle or an rHSV-2 viral particle.

In some embodiments, the viral particle is a recombinant AAV viral particle comprising a recombinant AAV vector. In some embodiments, the recombinant AAV viral particle comprises an AAV serotype capsid from Clades A-F. In some embodiments, the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the ITR and the capsid of the rAAV viral particle are derived from the same AAV serotype. In some embodiments, the ITR and the capsid of the rAAV viral particles are derived from different AAV serotypes. In some embodiments, the recombinant AAV viral particle comprises an AAV1, AAV2, AAV8, AAVrh8R. AAV9, and/or AAVrh10 capsid. In some embodiments, the AAV1, AAV2, AAV8, AAVrh8R, AAV9, and/or AAVrh10 capsid comprises a tyrosine mutation or a heparan binding mutation. In some embodiments, the rAAV vector comprises AAV2 ITRs.

In some aspects the invention provides methods for treating a disease or disorder associated with a deep intronic mutation in a gene of an individual comprising administering to the individual a therapeutically effective amount of a composition comprising an engineered, non-naturally occurring Clustered Regularly Interspaced Short Palindromic Repeats (CRISPR)-CRISPR associated (Cas) (CRISPR-Cas) system comprising a) a first guide RNA and a second guide RNA wherein the first guide RNA and the second guide RNA hybridize to the opposite strands of the target DNA sequences flanking the deep intronic mutation, and b) a Cas protein, wherein the Cas protein cleaves the target DNA molecule at sites flanking the deep intronic mutation thereby excising a portion of target DNA comprising the deep intronic mutation. In some embodiments the invention provides methods for treating a disease or disorder associated with a deep intronic mutation in a gene of an individual comprising administering to the individual a therapeutically effective amount of a composition comprising nucleic acid encoding an engineered, non-naturally occurring Clustered Regularly Interspaced Short Palindromic Repeats (CRISPR)-CRISPR associated (Cas) (CRISPR-Cas) system comprising a) a first guide RNA and a second guide RNA wherein the first guide RNA and the second guide RNA hybridize to the opposite strands of the target DNA sequences flanking the deep intronic mutation, and b) a nucleotide sequence encoding a Cas protein, wherein the Cas protein cleaves the target DNA molecule at sites flanking the deep intronic mutation thereby excising a portion of target DNA comprising the deep intronic mutation. In some embodiments, the disease or disorder associated with a deep intronic mutation is afibrinogenemia, Alport syndrome, Amyotrophic lateral sclerosis, ataxia telangiectasia, autosomal recessive polycystic kidney disease, Barth syndrome, beta-thalassemia, congenital afibrinogenemia, congenital cataracts facial dysmorphism neuropathy syndrome, congenital disorder of glycosylation type Ia, congenital disorder of glycosylation type II, cystic fibrosis, dihydropteridine reductase deficiency, Fabry disease, familial platelet disorder with predisposition to acute myelogenous leukemia, Fanconi anemia, Gitelman syndrome, growth hormone insensitivity, Friedrich's ataxia, hemophilia A, hereditary megaloblastic anaemia 1. Hermansky-Pudlak syndrome, homocytinuria, maple syrup urine disease. Marfan syndrome, methionine synthase deficiency, methylmalonic academia, mitochondrial trifunctional protein deficiency, mucupolysaccaridosis type II, multi-minicore disease, muscular dystrophy, neurofibromatosis type 1. Niemann-Pick disease type C, ocular albinism type I, omithine delta-aminotransferaase deficiency, predisposition to systemic lupus erythematosus, propionic academia, rhabdoid tumors, Schwartz-Jampel syndrome, Stickler syndrome, systemic lupus erythematosus, tuberous sclerosis. Werner syndrome, X-linked hyperimmunoglobulinemia M, or X-linked hypophosphatemia. In some embodiments, the deep intronic mutation is a deep intronic mutation presented in Table 1.

In aspects, the invention provides methods for treating an ocular disease or disorder associated with a deep intronic mutation in a gene of an individual comprising administering to the individual a therapeutically effective amount of a composition comprising an engineered, non-naturally occurring Clustered Regularly Interspaced Short Palindromic Repeats (CRISPR)-CRISPR associated (Cas) (CRISPR-Cas) system comprising a) a first guide RNA and a second guide RNA wherein the first guide RNA and the second guide RNA hybridize to the opposite strands of the target DNA sequences flanking the deep intronic mutation, and b) a nucleotide sequence encoding a Cas protein, wherein the Cas protein cleaves the target DNA molecule at sites flanking the deep intronic mutation thereby excising a portion of the target DNA comprising the deep intronic mutation. In some embodiments the invention provides methods for treating an ocular disease or disorder associated with a deep intronic mutation in a gene of an individual comprising administering to the individual a therapeutically effective amount of a composition comprising a nucleic acid encoding an engineered, non-naturally occurring Clustered Regularly Interspaced Short Palindromic Repeats (CRISPR)-CRISPR associated (Cas) (CRISPR-Cas) system comprising a) a first guide RNA and a second guide RNA wherein the first guide RNA and the second guide RNA hybridize to the opposite strands of the target DNA sequences flanking the deep intronic mutation, and b) a nucleotide sequence encoding a Cas protein, wherein the Cas protein cleaves the target DNA molecule at sites flanking the deep intronic mutation thereby excising a portion of the target DNA comprising the deep intronic mutation. In some embodiments, the ocular disease is Leber congenital amaurosis, optic atrophy, retinitis pigmentosa, retinoblastoma, Stargardt disease. Usher syndrome, or X-linked retinitis pigmentosa. In some embodiments, the deep intronic mutation is a deep intronic mutation presented in Table 2.

In some embodiments of the above methods, the individual is a mammal. In some embodiments, the mammal is a human. In some embodiments, the composition is administered to the eye of the individual. In some embodiments, the administration is subretinal or intravitreal.

In some embodiments of the above methods, the ocular disease is Leber congenital amaurosis. In some embodiments, the first guide RNA and second guide RNA guide sequences hybridize to the opposite strands of the target DNA sequences flanking a deep intronic mutation of the centrosomal protein 290 kDa (CEP290) gene. In some embodiments, the deep intronic mutation is a c.2991+1655A>G mutation. In some embodiments, the first guide RNA is encoded by DNA comprising the sequences of SEQ ID NO:41 (for SpCas9), SEQ ID NO:45 (for SaCas9), SEQ ID NO:46 (for SaCas9), or SEQ ID NO:47 (for SaCas9). In some embodiments, the first guide RNA is encoded by DNA comprising the sequence of SEQ ID NO:19 (for SpCas9), SEQ ID NO:50 (for SaCas9). SEQ ID NO:51 (for SaCas9), or SEQ ID NO:52 (for SaCas9). In some embodiments, the second guide RNA is encoded by DNA comprising the sequences of SEQ ID NO:42 (for SpCas9), SEQ ID NO:43 (for SpCas9), SEQ ID NO:44 (for SpCas9), SEQ ID NO:48 (for SaCas9), or SEQ ID NO:49 (for SaCas9). In some embodiments, the second guide RNA is encoded by DNA comprising the sequence of SEQ ID NO:20 (for SpCas9), SEQ ID NO:21 (for SpCas9), SEQ ID NO:22 (for SpCas9), SEQ ID NO:53 (for SaCas9), or SEQ ID NO:54 (for SaCas9). In some embodiments, the CEP290 is a human CEP290. In some embodiments, the CEP290 comprises a deep intronic mutation of the sequence set forth in SEQ ID NO:23.

In some embodiments of the above methods, the deep intronic mutation is located about 1-10,000 nucleotides, about 1-1000 nucleotides or about 100-1000 nucleotides downstream of a 5' splice donor site of the gene. In some embodiments, the deep intronic mutation is located about 1-10,000 nucleotides, about 1-1000 nucleotides or about 100-1000 nucleotides upstream of a 3' splice acceptor site of the gene. In some embodiments, the deep intronic mutation introduces a splice donor site or a splice acceptor site in the gene.

In some embodiments of the above methods, the Cas protein is a Cas9 protein. In some embodiments, the Cas 9 protein is a *Streptococcus pyogenes* Cas9 protein, a *Staphylococcus aureus* Cas9 protein, a *Streptocccus thermophilus* Cas9 protein, a *Neisseria meningitidis* Cas9 protein, or a *Treponenma denticola* Cas9 protein. In some embodiments, the Cas9 is codon optimized for expression in a eukaryotic cell. In some embodiments, the eukaryotic cell is a mammalian cell. In some embodiments, the eukaryotic cell is a human cell.

In some embodiments of the above methods, the CRISPR-Cas system further comprises one or more nuclear localization signal(s) (NLS(s)). In some embodiments, the Cas protein comprises one or more NLS. In some embodiments, the NLS is a C-terminal sequence in the SV40 Large T-antigen. In some embodiments, the NLS comprises the sequence PKKKRKV (SEQ ID NO:26) or PKKKRKVEDPKKKRKVD (SEQ ID NO:27).

In some embodiments of the above methods, the first guide RNA and/or the second guide RNA comprise are fused to a trans-activating cr (tracr) sequence. In some embodiments, the tracr sequence comprises the nucleotide sequence encoded by SEQ ID NO:25.

In some embodiments of the above methods, the CRISPR-Cas system (e.g., the first guide RNA, the second guide RNA and the Cas protein) is complexed to a lipid, a cationic lipid, a liposome, a polycation or an agent that enhances the cellular uptake of nucleic acid and/or the protein.

In some embodiments of the above methods, nucleic acid encoding the first guide RNA, the second guide RNA and the Cas protein are expressed in eukaryotic cells. In some embodiments, the nucleic acid encoding the first guide RNA, the second guide RNA and/or the Cas protein are operably linked to one or more regulatory control elements. In some embodiments, the first guide RNA and/or the second guide RNA is operably linked to a RNA polymerase II promoter. In some embodiments, the RNA polymerase III promoter is a U6, a 7SK or an H1 promoter. In some embodiments, the nucleic acid encoding the Cas protein is operably linked to a RNA polymerase II promoter. In some embodiments, the RNA polymerase II promoter is a cytomegalovirus (CMV) immediate early promoter, a minimal promoter fragment derived from the CMV promoter (minCMV promoter), a RSV LTR, a MoMLV LTR, a phosphoglycerate kinase-1 (PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), a E2F promoter, a EF1α promoter, a telomerase (hTERT) promoter, a cytomegalovirus enhancer/chicken beta-actin/Rabbit β-globin promoter (CAG) promoter, a rod opsin promoter, a cone opsin promoter, a beta phosphodiesterase (PDE) promoter, a retinitis pigmentosa (RP1) promoter, or an interphotoreceptor retinoid-binding protein gene (IRBP) promoter.

In some embodiments of the above methods, the nucleic acid encoding one or more of the first guide RNA, the second guide RNA or the Cas protein are located on the same or different vectors of the system. In some embodiments, the vector is a plasmid. In some embodiments, the vector is complexed to a delivery system. In some embodiments, the vector is complexed to a lipid, a cationic lipid, a liposome, a polycation or an agent that enhances the cellular uptake of nucleic acid.

In some embodiments of the above embodiments, the vector is a recombinant adeno-associated virus (rAAV) vector, a recombinant adenoviral vector, a recombinant lentiviral vector or a recombinant herpes simplex virus (HSV) vector. In some embodiments, the vector is a recombinant adenoviral vector. In some embodiments, the recombinant adenoviral vector is derived from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the recombinant adenoviral vector is derived from adenovirus serotype 2 or a variant of adenoviral serotype 5.

In some embodiments, the vector is a recombinant lentiviral vector. In some embodiments, the recombinant lentiviral vector is derived from a lentivirus pseudotyped with vesicular stomatitis virus (VSV), lymphocytic choriomeningitis virus (LCMV). Ross river virus (RRV). Ebola virus. Marburg virus, Mokala virus. Rabies virus. RD114, or variants therein.

In some embodiments, the vector is an rHSV vector. In some embodiments, the rHSV vector is derived from rHSV-1 or rHSV-2.

In some embodiments, the vector is a recombinant AAV (rAAV) vector. In some embodiments, the nucleic acid encoding one of more of the first guide RNA, the second guide RNA, or the Cas protein is flanked by one or more AAV inverted terminal repeat (ITR) sequences. In some embodiments, the nucleic acid encoding one of more of the first guide RNA, the second guide RNA, or the Cas protein is flanked by two AAV ITRs. In some embodiments, the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype ITRs. In some embodiments, the AAV ITRs are AAV2 ITRs. In some embodiments, the vector is a self-complementary vector.

In some embodiments, the vector is encapsidated in a viral particle. In some embodiments, the viral particle is a recombinant adenovirus particle encapsidating a recombinant adenoviral vector. In some embodiments, the recombinant adenovirus particle comprises a capsid from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the recombinant adenovirus particle comprises an adenovirus serotype 2 capsid or a variant of an adenoviral serotype 5 capsid.

In some embodiments, the viral particle is a recombinant lentiviral particle encapsidating a recombinant lentiviral vector. In some embodiments, the recombinant lentiviral particle comprises a capsid pseudotyped with vesicular stomatitis virus (VSV), lymphocytic choriomeningitis virus (LCMV). Ross river virus (RRV), Ebola virus, Marburg virus, Mokala virus, Rabies virus, RD114 or variants therein.

In some embodiments, the viral particle is a recombinant HSV particle encapsidating a recombinant HSV vector. In some embodiments, the recombinant HSV particle is an rHSV-1 particle or an rHSV-2 viral particle.

In some embodiments, the viral particle is a recombinant AAV viral particle comprising a recombinant AAV vector. In some embodiments, the recombinant AAV viral particle comprises an AAV serotype capsid from Clades A-F. In some embodiments, the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A. AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the ITR and the capsid of the rAAV viral particle are derived from the same AAV serotype. In some embodiments, the ITR and the capsid of the rAAV viral particles are derived from different AAV serotypes. In some embodiments, the recombinant AAV viral particle comprises an AAV1, AAV2, AAV8, AAVrh8R, AAV9, and/or AAVrh10 capsid. In some embodiments, the AAV1, AAV2, AAV8, AAVrh8R, AAV9, and/or AAVrh10 capsid comprises a tyrosine mutation or a heparan binding mutation. In some embodiments, the rAAV vector comprises AAV2 ITRs.

In some embodiments of the above methods, the composition is a pharmaceutical composition.

In some aspects, the invention provides the use of a composition of any one of the above embodiments for treating a disorder associated with a deep intronic mutation in a gene of an individual. In some aspects, the invention provides the use of a composition of any one of the above embodiments in the manufacture of a medicament for treating a disorder associated with a deep intronic mutation in a gene of an individual. In some embodiments, the disease or disorder associated with a deep intronic mutation is afibrinogenemia, Alport syndrome, Amyotrophic lateral sclerosis, ataxia telangiectasia, autosomal recessive polycystic kidney disease, Barth syndrome, beta-thalassemia, congenital afibrinogenemia, congenital cataracts facial dysmorphism neuropathy syndrome, congenital disorder of glycosylation type Ia, congenital disorder of glycosylation type II, cystic fibrosis, dihydropteridine reductase deficiency. Fabry disease, familial platelet disorder with predisposition to acute myelogenous leukemia, Fanconi anemia. Gitelman syndrome, growth hormone insensitivity, Friedrich's ataxia, hemophilia A, hereditary megaloblastic anaemia 1, Hermansky-Pudlak syndrome, homocytinuria, maple syrup urine disease, Marfan syndrome, methionine synthase deficiency, methylmalonic academia, mitochondrial trifunctional protein deficiency, mucopolysaccaridosis type II, multi-minicore disease, muscular dystrophy, neurofibromatosis type I, Niemann-Pick disease type C, ocular albinism type I, omithine delta-aminotransferaase deficiency, predisposition to systemic lupus erythematosus, propionic academia, rhabdoid tumors, Schwartz-Jampel syndrome, Stickler syndrome, systemic lupus erythematosus, tuberous sclerosis. Werner syndrome. X-linked hyperimmunoglobulinemia M, or X-linked hypophosphatemia. In some embodiments, the deep intronic mutation is a deep intronic mutation presented in Table 1. In some embodiments, the disease or disorder associated with a deep intronic mutation is an ocular disease. In some embodiments, the ocular disease is Leber congenital amaurosis, optic atrophy, retinitis pigmentosa, retinoblastoma, Stargardt disease, Usher syndrome, or X-linked retinitis pigmentosa. In some embodiments, the deep intronic mutation is a deep intronic mutation presented in Table 2. In some embodiments, the individual is a mammal. In some embodiments, the mammal is a human. In some embodiments, the ocular disease is Leber congenital amaurosis.

In some embodiments of the above uses, the composition is formulated for administration to the eye of the individual. In some embodiments, the administration is formulated for subretinal or intravitreal administration.

In some embodiments of the above uses, the first guide RNA and second guide RNA guide sequences hybridize to the opposite strands of the target DNA sequences flanking a deep intronic mutation of the centrosomal protein 290 kDa (CEP290) gene. In some embodiments, the deep intronic mutation is a c.2991+1655A>G mutation. In some embodiments, the first guide RNA is encoded by DNA comprising the sequences of SEQ ID NO:41 (for SpCas9), SEQ ID NO:45 (for SaCas9), SEQ ID NO:46 (for SaCas9), or SEQ ID NO:47 (for SaCas9). In some embodiments, the first guide RNA is encoded by DNA comprising the sequence of SEQ ID NO:19 (for SpCas9), SEQ ID NO:50 (for SaCas9). SEQ ID NO:51 (for SaCas9), or SEQ ID NO:52 (for SaCas9). In some embodiments, the second guide RNA is encoded by DNA comprising the sequences of SEQ ID NO:42 (for SpCas9), SEQ ID NO:43 (for SpCas9), SEQ ID NO:44 (for SpCas9), SEQ ID NO:48 (for SaCas9), or SEQ ID NO:49 (for SaCas9). In some embodiments, the second guide RNA is encoded by DNA comprising the sequence of SEQ ID NO:20 (for SpCas9), SEQ ID NO:21 (for SpCas9), SEQ ID NO:22 (for SpCas9), SEQ ID NO:53 (for SaCas9), or SEQ ID NO:54 (for SaCas9). In some embodiments, the CEP290 is a human CEP290. In some embodiments, the CEP290 comprises a deep intronic mutation of the sequence set forth in SEQ ID NO:23.

In some embodiments of the above uses, the deep intronic mutation is located about 1-10,000 nucleotides, about 1-1000 nucleotides or about 100-1000 nucleotides downstream of a 5' splice donor site of the gene. In some embodiments, the deep intronic mutation is located about 1-10,000 nucleotides, about 1-1000 nucleotides or about 100-1000 nucleotides upstream of a 3' splice acceptor site of the gene. In some embodiments, the deep intronic mutation introduces a splice donor site or a splice acceptor site.

In some aspects, the invention provides kits comprising the composition of any one of the above embodiments. In some embodiments, the kit comprises the composition of any one of the above embodiments for use in any of the methods described herein. In some embodiments, the kit further comprises instructions for use.

In some aspects, the invention provides viral particles comprising a viral vector wherein the viral vector comprises nucleic acid encoding an engineered, non-naturally occurring Clustered Regularly Interspaced Short Palindromic Repeats (CRISPR)-CRISPR associated (Cas) (CRISPR-Cas) system comprising a) a first guide RNA and a second guide RNA wherein the first guide RNA and the second guide RNA hybridize to the opposite strands of the target DNA sequences flanking a deep intronic mutation in a gene of an individual, and b) a nucleotide sequence encoding a Cas protein, wherein the Cas protein cleaves the target DNA molecule at sites flanking the deep intronic mutation thereby excising a portion of the target DNA comprising the deep intronic mutation. In some embodiments, the deep intronic mutation in a gene of an individual is associated with afibrinogenemia, Alport syndrome, Amyotrophic lateral sclerosis, ataxia telangiectasia, autosomal recessive polycystic kidney disease, Barth syndrome, beta-thalassemia, congenital afibrinogenemia, congenital cataracts facial dysmorphism neuropathy syndrome, congenital disorder of glycosylation type Ia, congenital disorder of glycosylation type II, cystic fibrosis, dihydropteridine reductase deficiency. Fabry disease, familial platelet disorder with predisposition to acute myelogenous leukemia, Fanconi anemia. Gitelman syndrome, growth hormone insensitivity, Friedrich's ataxia, hemophilia A, hereditary megaloblastic anaemia 1, Hermansky-Pudlak syndrome, homocytinuria, maple syrup urine disease, Marfan syndrome, methionine synthase deficiency, methylmalonic academia, mitochondrial trifunctional protein deficiency, mucopolysaccaridosis type II, multi-minicore disease, muscular dystrophy, neurofibromatosis type I, Niemann-Pick disease type C, ocular albinism type I, omithine delta-aminotransferaase deficiency, predisposition to systemic lupus erythematosus, propionic academia, rhabdoid tumors, Schwartz-Jampel syndrome, Stickler syndrome, systemic lupus erythematosus, tuberous sclerosis. Werner syndrome. X-linked hyperimmunoglobulinemia M, or X-linked hypophosphatemia. In some embodiments, the deep intronic mutation in a gene of an individual is a deep intronic mutation presented in Table 1.

In some embodiments, the viral particle is used to treat an individual with afibrinogenemia. Alport syndrome. Amyotrophic lateral sclerosis, ataxia telangiectasia, autosomal recessive polycystic kidney disease, Barth syndrome, beta-thalassemia, congenital afibrinogenemia, congenital cataracts facial dysmorphism neuropathy syndrome, congenital disorder of glycosylation type Ia, congenital disorder of glycosylation type II, cystic fibrosis, dihydropteridine reductase deficiency, Fabry disease, familial platelet disorder with predisposition to acute myelogenous leukemia, Fanconi anemia, Gitelman syndrome, growth hormone insensitivity, Friedrich's ataxia, hemophilia A, hereditary megaloblastic anaemia 1. Hermansky-Pudlak syndrome, homocytinuria, maple syrup urine disease, Marfan syndrome, methionine synthase deficiency, methylmalonic academia, mitochondrial trifunctional protein deficiency, mucupolysaccaridosis type II, multi-minicore disease, muscular dystrophy, neurofibromatosis type I, Niemann-Pick disease type C, ocular albinism type I, ornithine delta-aminotransferaase deficiency, predisposition to systemic lupus erythematosus, propionic academia, rhabdoid tumors, Schwartz-Jampel syndrome, Stickler syndrome, systemic lupus erythematosus, tuberous sclerosis, Werner syndrome, X-linked hyperimmunoglobulinemia M, or X-linked hypophosphatemia.

In some aspects, the invention provides viral particles comprising a viral vector wherein the viral vector comprises nucleic acid encoding an engineered, non-naturally occurring Clustered Regularly Interspaced Short Palindromic Repeats (CRISPR)-CRISPR associated (Cas) (CRISPR-Cas) system comprising a) a first guide RNA and a second guide RNA wherein the first guide RNA and the second guide RNA hybridize to the opposite strands of the target DNA sequences flanking the deep intronic mutation in a gene of an individual associated with an ocular disease or disorder, and b) a nucleotide sequence encoding a Cas protein, wherein the Cas protein cleaves the target DNA molecule at sites flanking the deep intronic mutation thereby excising a portion of target DNA comprising the deep intronic mutation. In some embodiments, the ocular disease or disorder is Leber congenital amaurosis, optic atrophy, retinitis pigmentosa, retinoblastoma, Stargardt disease. Usher syndrome, or X-linked retinitis pigmentosa. In some embodiments, the deep intronic mutation is a deep intronic mutation presented in Table 2. In some embodiments, the viral particle is used to treat Leber congenital amaurosis, optic atrophy, retinitis pigmentosa, retinoblastoma, Stargardt disease. Usher syndrome, or X-linked retinitis pigmentosa.

In some embodiments, the ocular disease is Leber congenital amaurosis. In some embodiments, the first guide RNA and second guide RNA guide sequences hybridize to the opposite strands of the target DNA sequences flanking a deep intronic mutation of the centrosomal protein 290 kDa (CEP290) gene. In some embodiments, the deep intronic mutation is a c.2991+1655A>G mutation. In some embodiments, the first guide RNA is encoded by DNA comprising the sequences of SEQ ID NO:41 (for SpCas9), SEQ ID NO:45 (for SaCas9), SEQ ID NO:46 (for SaCas9), or SEQ ID NO:47 (for SaCas9). In some embodiments, the first guide RNA is encoded by DNA comprising the sequence of SEQ ID NO:19 (for SpCas9), SEQ ID NO:50 (for SaCas9), SEQ ID NO:51 (for SaCas9), or SEQ ID NO:52 (for SaCas9). In some embodiments, the second guide RNA is encoded by DNA comprising the sequences of SEQ ID NO:42 (for SpCas9), SEQ ID NO:43 (for SpCas9), SEQ ID NO:44 (for SpCas9), SEQ ID NO:48 (for SaCas9), or SEQ ID NO:49 (for SaCas9). In some embodiments, the second guide RNA is encoded by DNA comprising the sequence of SEQ ID NO:20 (for SpCas9), SEQ ID NO:21 (for SpCas9). SEQ ID NO:22 (for SpCas9), SEQ ID NO:53 (for SaCas9), or SEQ ID NO:54 (for SaCas9). In some embodiments, the CEP290 is a human CEP290. In some embodiments, the CEP290 comprises a deep intronic mutation of the sequence set forth in SEQ ID NO:23.\

In some embodiments of the above viral particles, the deep intronic mutation is located about 1-10,000 nucleotides, about 1-1000 nucleotides or about 100-1000 nucleotides downstream of a 5' splice donor site of the gene. In some embodiments, the deep intronic mutation is located about 1-10,000 nucleotides, about 1-1000 nucleotides or about 100-1000 nucleotides upstream of a 3' splice acceptor site of the gene. In some embodiments, the deep intronic mutation introduces a splice donor site or a splice acceptor site in the gene.

In some embodiments of the above viral particles, the Cas protein is a Cas9 protein. In some embodiments, the Cas 9 protein is a *Streptococcus pyogenes* Cas9 protein, a *Staphylococcus aureus* Cas9 protein, a *Streptococcus thermophilus* Cas9 protein, a *Neisseria meningitidis* Cas9 protein, or a *Treponema denticola* Cas9 protein. In some embodiments, the Cas9 is codon optimized for expression in a eukaryotic cell. In some embodiments, the eukaryotic cell is a mammalian cell. In some embodiments, the eukaryotic cell is a human cell.

In some embodiments of the above viral particles, the CRISPR-Cas system further comprises one or more nuclear localization signal(s) (NLS(s)). In some embodiments, the Cas protein comprises one or more NLS. In some embodiments, the NLS is a C-terminal sequence in the SV40 Large T-antigen. In some embodiments, the NLS comprises the sequence PKKKRKV (SEQ ID NO:26) or PKKKRKVEDPKKKRKVD (SEQ ID NO:27).

In some embodiments of the above viral particles, the first guide RNA and/or the second guide RNA comprise are fused to a trans-activating cr (tracr) sequence. In some embodiments, the tracr sequence comprises the nucleotide sequence encoded by SEQ ID NO:25.

In some embodiments of the above viral particles, nucleic acid encoding the first guide RNA, the second guide RNA and the Cas protein are expressed in eukaryotic cells. In some embodiments, the nucleic acid encoding the first guide RNA, the second guide RNA and/or the Cas protein are operably linked to one or more regulatory control elements. In some embodiments, the first guide RNA and/or the second guide RNA is operably linked to a RNA polymerase III promoter. In some embodiments, the RNA polymerase III promoter is a U6, a 7SK or an H1 promoter. In some embodiments, the nucleic acid encoding the Cas protein is operably linked to a RNA polymerase II promoter. In some embodiments, the RNA polymerase II promoter is a cytomegalovirus (CMV) immediate early promoter, a minimal promoter fragment derived from the CMV promoter (minCMV promoter), a RSV LTR, a MoMLV LTR, a phosphoglycerate kinase-1 (PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), a E2F promoter, a EF1α promoter, a telomerase (hTERT)

promoter, a cytomegalovirus enhancer/chicken beta-actin/ Rabbit β-globin promoter (CAG) promoter, a rod opsin promoter, a cone opsin promoter, a beta phosphodiesterase (PDE) promoter, a retinitis pigmentosa (RP1) promoter, or an interphotoreceptor retinoid-binding protein gene (IRBP) promoter.

In some embodiments of the above viral particles, the nucleic acid encoding one or more of the first guide RNA, the second guide RNA or the Cas protein are located on the same or different vectors of the system. In some embodiments, the vector is a plasmid. In some embodiments, the vector is complexed to a delivery system. In some embodiments, the vector is complexed to a lipid, a cationic lipid, a liposome, a polycation or an agent that enhances the cellular uptake of nucleic acid.

In some embodiments of the above viral particles, the vector is a recombinant adeno-associated virus (rAAV) vector, a recombinant adenoviral vector, a recombinant lentiviral vector or a recombinant herpes simplex virus (HSV) vector. In some embodiments, the vector is a recombinant adenoviral vector. In some embodiments, the recombinant adenoviral vector is derived from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the recombinant adenoviral vector is derived from adenovirus serotype 2 or a variant of adenoviral serotype 5. In some embodiments, the viral particle is a recombinant adenovirus particle encapsidating a recombinant adenoviral vector. In some embodiments, the recombinant adenovirus particle comprises a capsid from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the recombinant adenovirus particle comprises an adenovirus serotype 2 capsid or a variant of an adenoviral serotype 5 capsid.

In some embodiments, the vector is a recombinant lentiviral vector. In some embodiments, the recombinant lentiviral vector is derived from a lentivirus pseudotyped with vesicular stomatitis virus (VSV), lymphocytic choriomeningitis virus (LCMV). Ross river virus (RRV), Ebola virus. Marburg virus, Mokala virus. Rabies virus. RD114, or variants therein. In some embodiments, the viral particle is a recombinant lentiviral particle encapsidating a recombinant lentiviral vector. In some embodiments, the recombinant lentiviral particle comprises a capsid pseudotyped with vesicular stomatitis virus (VSV), lymphocytic choriomeningitis virus (LCMV), Ross river virus (RRV), Ebola virus, Marburg virus, Mokala virus, Rabies virus, RD114 or variants therein.

In some embodiments, the vector is an rHSV vector. In some embodiments, the rHSV vector is derived from rHSV-1 or rHSV-2. In some embodiments, the viral particle is a recombinant HSV particle encapsidating a recombinant HSV vector. In some embodiments, the recombinant HSV particle is an rHSV-1 particle or an rHSV-2 viral particle.

In some embodiments, the vector is a recombinant AAV (rAAV) vector. In some embodiments, the nucleic acid encoding one of more of the first guide RNA, the second guide RNA, or the Cas protein is flanked by one or more AAV inverted terminal repeat (ITR) sequences. In some embodiments, the nucleic acid encoding one of more of the first guide RNA, the second guide RNA, or the Cas protein is flanked by two AAV ITRs. In some embodiments, the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype ITRs. In some embodiments, the AAV ITRs are AAV2 ITRs. In some embodiments, the vector is a self-complementary vector. In some embodiments, the viral particle is a recombinant AAV viral particle comprising a recombinant AAV vector. In some embodiments, the recombinant AAV viral particle comprises an AAV serotype capsid from Clades A-F. In some embodiments, the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/ AAV2 chimeric, bovine AAV, or mouse AAV capsid rAAV2/ HBoV1 serotype capsid. In some embodiments, the ITR and the capsid of the rAAV viral particle are derived from the same AAV serotype. In some embodiments, the ITR and the capsid of the rAAV viral particles are derived from different AAV serotypes. In some embodiments, the recombinant AAV viral particle comprises an AAV1, AAV2, AAV8, AAVrh8R, AAV9, and/or AAVrh10 capsid. In some embodiments, the AAV1, AAV2, AAV8, AAVrh8R, AAV9, and/or AAVrh10 capsid comprises a tyrosine mutation or a heparan binding mutation. In some embodiments, the rAAV vector comprises AAV2 ITRs.

In some embodiments of the above viral particles, the viral particle is in a pharmaceutical composition.

In some aspects, the invention provides methods for generating an in vitro model of an ocular disease associated with deep intronic mutation in a gene comprising a) introducing to eukaryotic cells nucleic acid encoding a CRISPR-Cas system, wherein the CRISPR-Cas system comprises i) a single guide RNA that hybridizes to the opposite strand of the target DNA sequence of an intron in the gene, ii) a nucleotide sequence encoding a Cas protein, iii) a single-stranded oligonucleotide comprising a homology directed repair (HDR) template comprising homology arms flanking a desired intronic mutation and a protospacer adjacent motif (PAM); and b) isolating cells that comprise the mutation incorporated into gene.

In some embodiments, the deep intronic mutation is located about 1-10,000 nucleotides, about 1-1000 nucleotides or about 100-1000 nucleotides downstream of a 5' splice donor site of the gene. In some embodiments, the deep intronic mutation is located about 1-10,000 nucleotides, about 1-1000 nucleotides or about 100-1000 nucleotides upstream of a 3' splice acceptor site of the gene. In some embodiments, the deep intronic mutation introduces a splice donor site or a splice acceptor site in the gene.

In some embodiments, the PAM comprises a mutation to avoid cleavage of the single-stranded oligonucleotide by an expressed Cas protein in the cells.

In some embodiments, the Cas protein is a Cas9 protein. In some embodiments, the Cas 9 protein is a *Streptococcus pyogenes* Cas9 protein, a *Staphylococcus aureus* Cas9 protein, a *Streptococcus thermophilus* Cas9 protein, a *Neisseria meningitidis* Cas9 protein, or a *Treponema denticola* Cas9 protein. In some embodiments, the Cas9 is codon optimized for expression in the eukaryotic cells. In some embodiments, the eukaryotic cells are mammalian cells. In some embodiments, the eukaryotic cells are human cells. In some embodiments, the eukaryotic cells are ocular cells. In some embodiments, the ocular cells are retinal cells.

In some embodiments, the CRISPR-Cas system further comprises one or more nuclear localization signal(s) (NLS (s)). In some embodiments, the Cas protein comprises one or more NLS. In some embodiments, the NLS is a C-terminal sequence in the SV40 Large T-antigen. In some embodiments, the NLS comprises the sequence PKKKRKV (SEQ ID NO:26) or PKKKRKVEDPKKKRKVD (SEQ ID NO:27).

In some embodiments, the first guide RNA and/or the second guide RNA comprise are fused to a trans-activating cr (tracr) sequence. In some embodiments, the tracr sequence comprises the nucleotide sequence encoded by SEQ ID NO:25.

In some embodiments, nucleic acid encoding the first guide RNA, the second guide RNA and the Cas protein are expressed in eukaryotic cells. In some embodiments, the nucleic acid encoding the first guide RNA, the second guide RNA and/or the Cas protein are operably linked to one or more regulatory control elements. In some embodiments, the first guide RNA and/or the second guide RNA is operably linked to a RNA polymerase III promoter. In some embodiments, the RNA polymerase III promoter is a U6, a 7SK or an H1 promoter. In some embodiments, the nucleic acid encoding the Cas protein is operably linked to a RNA polymerase II promoter. In some embodiments, the RNA polymerase II promoter is a cytomegalovirus (CMV) immediate early promoter, a minimal promoter fragment derived from the CMV promoter (minCMV promoter), a RSV LTR, a MoMLV LTR, a phosphoglycerate kinase-1 (PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a ISP promoter, chimeric liver-specific promoters (LSPs), a E2F promoter, a EF1α promoter, a telomerase (hTERT) promoter, a cytomegalovirus enhancer/chicken beta-actin/Rabbit β-globin promoter (CAG) promoter, a rod opsin promoter, a cone opsin promoter, a beta phosphodiesterase (PDE) promoter, a retinitis pigmentosa (RP1) promoter, or an interphotoreceptor retinoid-binding protein gene (IRBP) promoter.

In some embodiments, the nucleic acid encoding one or more of the single guide RNA, the Cas protein, or the single-stranded oligonucleotide are located on the same or different vectors of the system.

In some embodiments, the ocular disease is Leber congenital amaurosis, optic atrophy, retinitis pigmentosa, retinoblastoma, Stargardt disease, Usher syndrome, or X-linked retinitis pigmentosa. In some embodiments, the deep intronic mutation is a deep intronic mutation presented in Table 2. In some embodiments, the viral particle is used to treat Leber congenital amaurosis, optic atrophy, retinitis pigmentosa, retinoblastoma, Stargardt disease. Usher syndrome, or X-linked retinitis pigmentosa.

In some embodiments, the ocular disease is Leber congenital amaurosis. In some embodiments, the first guide RNA and second guide RNA guide sequences hybridize to the opposite strands of the target DNA sequences flanking a deep intronic mutation of the centrosomal protein 290 kDa (CEP290) gene. In some embodiments, the deep intronic mutation is a c.2991+1655A>G mutation. In some embodiments, the first guide RNA is encoded by DNA comprising the sequences of SEQ ID NO:41 (for SpCas9), SEQ ID NO:45 (for SaCas9), SEQ ID NO:46 (for SaCas9), or SEQ ID NO:47 (for SaCas9). In some embodiments, the first guide RNA is encoded by DNA comprising the sequence of SEQ ID NO: 19 (for SpCas9), SEQ ID NO:50 (for SaCas9), SEQ ID NO:51 (for SaCas9), or SEQ ID NO:52 (for SaCas9). In some embodiments, the second guide RNA is encoded by DNA comprising the sequences of SEQ ID NO:42 (for SpCas9), SEQ ID NO:43 (for SpCas9), SEQ ID NO:44 (for SpCas9), SEQ ID NO:48 (for SaCas9), or SEQ ID NO:49 (for SaCas9). In some embodiments, the second guide RNA is encoded by DNA comprising the sequence of SEQ ID NO:20 (for SpCas9), SEQ ID NO:21 (for SpCas9), SEQ ID NO:22 (for SpCas9), SEQ ID NO:53 (for SaCas9), or SEQ ID NO:54 (for SaCas9). In some embodiments, the CEP290 is a human CEP290. In some embodiments, the CEP290 comprises a deep intronic mutation of the sequence set forth in SEQ ID NO:23.

In some aspects, the invention provides a method for cleaving a target nucleic acid in a cell comprising delivering to the cell effective amount of a composition comprising: a) a nucleic acid encoding an engineered, non-naturally occurring Clustered Regularly Interspaced Short Palindromic Repeats (CRISPR)-CRISPR associated (Cas) (CRISPR-Cas) system comprising a first guide RNA and a second guide RNA wherein the first guide RNA and the second guide RNA hybridize to opposite strands of target DNA sequences flanking the mutation; and b) a Cas expression cassette comprising: i) a nucleotide sequence encoding a Cas protein, and ii) a first guide RNA target site, wherein the first guide RNA or the second guide RNA hybridizes to the first guide RNA target site; wherein the Cas protein is expressed from the Cas expression cassette; wherein the Cas protein cleaves the target DNA sequences flanking the mutation, thereby excising a portion of target DNA comprising the mutation; and wherein the Cas protein cleaves the Cas expression cassette at the first guide RNA target site, thereby reducing expression of the Cas protein, as compared to expression of the Cas protein prior to cleavage of the Cas expression cassette. In some aspects, the invention provides a method for treating a disease or disorder associated with a mutation in a nucleic acid of an individual comprising administering to the individual a therapeutically effective amount of a composition comprising: a) a nucleic acid encoding an engineered, non-naturally occurring Clustered Regularly Interspaced Short Palindromic Repeats (CRISPR)-CRISPR associated (Cas) (CRISPR-Cas) system comprising a first guide RNA and a second guide RNA wherein the first guide RNA and the second guide RNA hybridize to opposite strands of target DNA sequences flanking the mutation; and b) a Cas expression cassette comprising: i) a nucleotide sequence encoding a Cas protein, and ii) a first guide RNA target site, wherein the first guide RNA or the second guide RNA hybridizes to the first guide RNA target site; wherein the Cas protein is expressed from the Cas expression cassette; wherein the Cas protein cleaves the target DNA sequences flanking the mutation, thereby excising a portion of target DNA comprising the mutation; and wherein the Cas protein cleaves the Cas expression cassette at the first guide RNA target site, thereby reducing expression of the Cas protein, as compared to expression of the Cas protein prior to cleavage of the Cas expression cassette. In some aspects, the invention provides a method for treating an ocular disease or disorder associated with a mutation in a nucleic acid of an individual comprising administering to the individual a therapeutically effective amount of a composition comprising: a) a nucleic acid encoding an engineered, non-naturally occurring Clustered Regularly Interspaced Short Palindromic Repeats (CRISPR)-CRISPR associated (Cas) (CRISPR-Cas) system comprising a first guide RNA and a second guide RNA wherein the first guide RNA and the second guide RNA hybridize to opposite strands of target DNA sequences flanking the mutation; and b) a Cas expression cassette comprising: i) a nucleotide sequence encoding a Cas protein, and ii) a first guide RNA target site, wherein the first guide RNA or the second guide RNA hybridizes to the first guide RNA target site wherein the Cas protein is expressed from the Cas expression cassette; wherein the Cas protein cleaves the target DNA sequences flanking the mutation, thereby excising a portion of target DNA comprising the mutation; and wherein the Cas protein cleaves the Cas expression cassette at the first guide RNA target site, thereby reducing expression of the Cas protein, as compared to expression of the Cas protein prior to cleavage of the Cas expression cassette. In some embodiments, the Cas expression cassette further comprises: iii) a second guide RNA target site, wherein the first guide RNA or the second guide RNA hybridizes to the second guide RNA target site; wherein the Cas protein cleaves the Cas expression cassette at the first and the second guide RNA target sites, thereby reducing expression of the Cas protein, as compared to expression of the Cas protein prior to cleavage of the Cas expression cassette.

In some embodiments of the above methods, the first guide RNA hybridizes to the first guide RNA target site and the second guide RNA target site. In some embodiments, the second guide RNA hybridizes to the first guide RNA target site and the second guide RNA target site. In some embodiments, the first guide RNA hybridizes to the first guide RNA target site, and the second guide RNA hybridizes to the second guide RNA target site. In some embodiments, the Cas expression cassette further comprises further comprises a polyadenylation (polyA) sequence operably linked to the nucleotide sequence encoding the Cas protein. In some embodiments, the polyA sequence is an SV40 polyA sequence. In some embodiments, cleavage of the first or the second guide RNA target site by Cas protein interrupts the operable linkage between the nucleotide sequence encoding the Cas protein and the polyA sequence. In some embodiments, the first or the second guide RNA target site is between the nucleotide sequence encoding the Cas protein and the polyA sequence. In some embodiments, the nucleotide sequence encoding the Cas protein is operably linked to a nucleotide sequence encoding one or more nuclear localization signal(s) (NLS(s)), such that the Cas protein expressed from the Cas expression cassette is fused in-frame with the one or more NLS(s). In some embodiments, the nucleotide sequence encoding the one or more NLS(s) is between the nucleotide sequence encoding the Cas protein and a polyadenylation (polyA) sequence. In some embodiments, the first or the second guide RNA target site is between the nucleotide sequence encoding the one or more NLS(s) and the polyA sequence. In some embodiments, the one or more NLS(s) comprises a C-terminal sequence in the SV40 Large T-antigen. In some embodiments, the one or more NLS(s) comprises the sequence PKKKRKV (SEQ ID NO:26) or PKKKRKVEDPKKKRKVD (SEQ ID NO:27). In some embodiments, the nucleic acid encoding the CRISPR-Cas system and/or the Cas expression cassette are operably linked to one or more regulatory control elements. In some embodiments, the nucleotide sequence encoding the Cas protein is operably linked to a promoter. In some embodiments, cleavage of the first or the second guide RNA target site by the Cas protein interrupts the operable linkage between the regulatory control element and the nucleotide sequence encoding the Cas protein. In some embodiments, the first or the second guide RNA target site is between the promoter and the nucleotide sequence encoding the Cas protein.

In some embodiments of the above methods, the Cas expression cassette further comprises: iii) a second guide RNA target site, wherein the first guide RNA or the second guide RNA hybridizes to the second guide RNA target site, and wherein the second guide RNA target site is adjacent to a protospacer adjacent motif (PAM) specific for the Cas protein; wherein cleavage of the first guide RNA target site by Cas protein interrupts the operable linkage between the regulatory control element and the nucleotide sequence encoding the Cas protein; wherein cleavage of the second guide RNA target site by Cas protein interrupts the operable linkage between the nucleotide sequence encoding the Cas protein and the polyA sequence; and wherein upon expression of the Cas protein and cleavage of the target DNA sequences, the Cas protein cleaves the Cas expression cassette at the first and the second guide RNA target sites, thereby reducing expression of the Cas protein, as compared to expression of the Cas protein prior to cleavage of the Cas expression cassette. In some embodiments, the Cas expression cassette further comprises: iii) a second guide RNA target site, wherein the first guide RNA or the second guide RNA hybridizes to the second guide RNA target site; wherein the first guide RNA target site is between the nucleotide sequence encoding the Cas protein and a promoter operably linked to the nucleotide sequence encoding the Cas protein; wherein the second guide RNA target site is between the nucleotide sequence encoding the Cas protein and a polyA sequence operably linked to the nucleotide sequence encoding the Cas protein; and wherein the Cas protein cleaves the Cas expression cassette at the first and the second guide RNA target sites, thereby reducing expression of the Cas protein, as compared to expression of the Cas protein prior to cleavage of the Cas expression cassette.

In some embodiments of the above methods, the disease or disorder associated with a deep intronic mutation is afibrinogenemia, Alport syndrome, Amyotrophic lateral sclerosis, ataxia telangiectasia, autosomal recessive polycystic kidney disease, Barth syndrome, beta-thalassemia, congenital afibrinogenemia, congenital cataracts facial dysmorphism neuropathy syndrome, congenital disorder of glycosylation type Ia, congenital disorder of glycosylation type II, cystic fibrosis, dihydropteridine reductase deficiency, Fabry disease, familial platelet disorder with predisposition to acute myelogenous leukemia. Fanconi anemia, Gitelman syndrome, growth hormone insensitivity, Friedrich's ataxia, hemophilia A, hereditary megaloblastic anaemia 1, Hermansky-Pudlak syndrome, homocytinuria, maple syrup urine disease. Marfan syndrome, methionine synthase deficiency, methylmalonic academia, mitochondrial trifunctional protein deficiency, mucupolysaccharidosis type II, multi-minicore disease, muscular dystrophy, neurofibromatosis type I. Niemann-Pick disease type C, ocular albinism type I, ornithine delta-aminotransferaase deficiency, predisposition to systemic lupus erythematosus, propionic academia, rhabdoid tumors, Schwartz-Jampel syndrome, Stickler syndrome, systemic lupus erythematosus, tuberous sclerosis. Werner syndrome, X-linked hyperimmunoglobulinemia M, or X-linked hypophosphatemia. In some embodiments, the deep intronic mutation is a deep intronic mutation presented in Table 1.

In some aspects, the invention provides compositions for treating an ocular disease or disorder associated with a deep intronic mutation in a gene of an individual comprising nucleic acid encoding an engineered, non-naturally occurring Clustered Regularly Interspaced Short Palindromic Repeats (CRISPR)-CRISPR associated (Cas) (CRISPR-Cas) system comprising a) a first guide RNA and a second guide RNA wherein the first guide RNA and the second guide RNA hybridize to the opposite strands of the target DNA sequences flanking the deep intronic mutation, and b) a nucleotide sequence encoding a Cas protein, wherein the Cas protein cleaves the target DNA molecule at sites flanking the deep intronic mutation thereby excising a portion of target DNA comprising the deep intronic mutation. In some embodiments, the invention provides compositions for treating an ocular disease or disorder associated with a deep intronic mutation in a gene of an individual comprising an engineered, non-naturally occurring Clustered Regularly Interspaced Short Palindromic Repeats (CRISPR)-CRISPR associated (Cas) (CRISPR-Cas) system comprising a) a first guide RNA and a second guide RNA wherein the first guide RNA and the second guide RNA hybridize to the opposite strands of the target DNA sequences flanking the deep intronic mutation, and b) a Cas protein, wherein the Cas protein cleaves the target DNA molecule at sites flanking the deep intronic mutation thereby excising a portion of target DNA comprising the deep intronic mutation. In some embodiments, the ocular disease is Leber congenital amaurosis, optic atrophy, retinitis pigmentosa, retinoblastoma, Stargardt disease, Usher syndrome, or X-linked retinitis pigmentosa. In some embodiments, the deep intronic mutation is a deep intronic mutation presented in Table 2.

In some embodiments of the above embodiments, the ocular disease is Leber congenital amaurosis. In some embodiments, the first guide RNA and second guide RNA guide sequences hybridize to the opposite strands of the target DNA sequences flanking a deep intronic mutation of the centrosomal protein 290 kDa (CEP290) gene. In some embodiments, the deep intronic mutation is a c.2991+1655A>G mutation. In some embodiments, the first guide RNA is encoded by DNA comprising the sequences of SEQ ID NO:41 (for SpCas9), SEQ ID NO:45 (for SaCas9), SEQ ID NO:46 (for SaCas9), or SEQ ID NO:47 (for SaCas9). In some embodiments, the first guide RNA is encoded by DNA comprising the sequence of SEQ ID NO: 19 (for SpCas9), SEQ ID NO:50 (for SaCas9), SEQ ID NO:51 (for SaCas9), or SEQ ID NO:52 (for SaCas9). In some embodiments, the second guide RNA is encoded by DNA comprising the sequences of SEQ ID NO:42 (for SpCas9), SEQ ID NO:43 (for SpCas9), SEQ ID NO:44 (for SpCas9), SEQ ID NO:48 (for SaCas9), or SEQ ID NO:49 (for SaCas9). In some embodiments, the second guide RNA is encoded by DNA comprising the sequence of SEQ ID NO:20 (for SpCas9), SEQ ID NO:21 (for SpCas9), SEQ ID NO:22 (for SpCas9), SEQ ID NO:53 (for SaCas9), or SEQ ID NO:54 (for SaCas9). In some embodiments, the CEP290 is a human CEP290. In some embodiments, the CEP290 comprises a deep intronic mutation of the sequence set forth in SEQ ID NO:23.

In some embodiments of the above embodiments, the deep intronic mutation is located about 1-10,000 nucleotides, about 1-1000 nucleotides or about 100-1000 nucleotides downstream of a 5' splice donor site of the gene. In some embodiments, the deep intronic mutation is located about 1-10,000 nucleotides, about 1-1000 nucleotides or about 100-1000 nucleotides upstream of a 3' splice acceptor site of the gene. In some embodiments, the deep intronic mutation introduces a splice donor site or a splice acceptor site in the gene.

In some embodiments of the above embodiments, the Cas protein is a Cas9 protein. In some embodiments, the Cas 9 protein is a *Streptococcus pyogenes* Cas9 protein (SEQ ID NO:40), a *Staphylococcus aureus* Cas9 protein (SEQ ID NO: 55), a *Streptococcus thermophilus* Cas9 protein, a *Neisseria meningitidis* Cas9 protein, or a *Treponema denticola* Cas9 protein. In some embodiments, the Cas9 is codon optimized for expression in a eukaryotic cell. In some embodiments, the eukaryotic cell is a mammalian cell. In some embodiments, the eukaryotic cell is a human cell.

In some embodiments of the above embodiments, the first guide RNA and/or the second guide RNA comprise are fused to a trans-activating cr (tracr) sequence. In some embodiments, the tracr sequence comprises the nucleotide sequence encoded by SEQ ID NO:25.

In some embodiments of the above embodiments, the CRISPR-Cas system (e.g., the first guide RNA, the second guide RNA and the Cas protein) is complexed to a lipid, a cationic lipid, a liposome, a polycation or an agent that enhances the cellular uptake of nucleic acid and/or the protein.

In some embodiments of the above embodiments, nucleic acid encoding the first guide RNA, the second guide RNA and the Cas protein are expressed in eukaryotic cells. In some embodiments, the nucleic acid encoding the first guide RNA, the second guide RNA and/or the Cas protein are operably linked to one or more regulatory control elements. In some embodiments, the first guide RNA and/or the second guide RNA is operably linked to a RNA polymerase Ill promoter. In some embodiments, the RNA polymerase III promoter is a U6, a 7SK or an H1 promoter. In some embodiments, the nucleic acid encoding the Cas protein is operably linked to a RNA polymerase II promoter. In some embodiments, the RNA polymerase II promoter is a cytomegalovirus (CMV) immediate early promoter, a minimal promoter fragment derived from the CMV promoter (minCMV promoter), a RSV LTR, a MoMLV LTR, a phosphoglycerate kinase-1 (PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), a E2F promoter, a EF1α promoter, a telomerase (hTERT) promoter, a cytomegalovirus enhancer/chicken beta-actin/Rabbit β-globin promoter (CAG) promoter, a rod opsin promoter, a cone opsin promoter, a beta phosphodiesterase (PDE) promoter, a retinitis pigmentosa (RP1) promoter, or an interphotoreceptor retinoid-binding protein gene (IRBP) promoter.

In some embodiments of the above embodiments, the nucleic acid encoding one or more of the first guide RNA, the second guide RNA or the Cas protein are located on the same or different vectors of the system. In some embodiments, the vector is a plasmid. In some embodiments, the vector is complexed to a delivery system. In some embodiments, the vector is complexed to a lipid, a cationic lipid, a liposome, a polycation or an agent that enhances the cellular uptake of nucleic acid.

In some embodiments of the above embodiments, the vector is a recombinant adeno-associated virus (rAAV) vector, a recombinant adenoviral vector, a recombinant lentiviral vector or a recombinant herpes simplex virus (HSV) vector. In some embodiments, the vector is a recombinant adenoviral vector. In some embodiments, the recombinant adenoviral vector is derived from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the recombinant adenoviral vector is derived from adenovirus serotype 2 or a variant of adenoviral serotype 5.

In some embodiments, the vector is a recombinant lentiviral vector. In some embodiments, the recombinant lentiviral vector is derived from a lentivirus pseudotyped with vesicular stomatitis virus (VSV), lymphocytic choriomeningitis virus (LCMV), Ross river virus (RRV), Ebola virus, Marburg virus, Mokala virus. Rabies virus, RD114, or variants therein.

In some embodiments, the vector is an rHSV vector. In some embodiments, the rHSV vector is derived from rHSV-1 or rHSV-2.

In some embodiments, the vector is a recombinant AAV (rAAV) vector. In some embodiments, the nucleic acid encoding one of more of the first guide RNA, the second guide RNA, or the Cas protein is flanked by one or more AAV inverted terminal repeat (ITR) sequences. In some embodiments, the nucleic acid encoding one of more of the first guide RNA, the second guide RNA, or the Cas protein is flanked by two AAV ITRs. In some embodiments, the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype ITRs. In some embodiments, the AAV ITRs are AAV2 ITRs. In some embodiments, the vector is a self-complementary vector.

In some embodiments, the vector is encapsidated in a viral particle. In some embodiments, the viral particle is a recombinant adenovirus particle encapsidating a recombinant adenoviral vector. In some embodiments, the recombinant adenovirus particle comprises a capsid from Adenovirus serotype 2, 1, 5, 6, 19, 3, 11, 7, 14, 16, 21, 12, 18, 31. 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the recombinant adenovirus particle comprises an adenovirus serotype 2 capsid or a variant of an adenoviral serotype 5 capsid.

In some embodiments, the viral particle is a recombinant lentiviral particle encapsiding a recombinant lentiviral vector. In some embodiments, the recombinant lentiviral particle comprises a capsid pseudotyped with vesicular stomatitis virus (VSV), lymphocytic choriomeningitis virus (LCMV). Ross river virus (RRV), Ebola virus, Marburg virus, Mokala virus, Rabies virus, RD114 or variants therein.

In some embodiments, the viral particle is a recombinant HSV particle encapsidating a recombinant HSV vector. In some embodiments, the recombinant HSV particle is an rHSV-1 particle or an rHSV-2 viral particle.

In some embodiments, the viral particle is a recombinant AAV viral particle comprising a recombinant AAV vector. In some embodiments, the recombinant AAV viral particle comprises an AAV serotype capsid from Clades A-F. In some embodiments, the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A. AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the ITR and the capsid of the rAAV viral particle are derived from the same AAV serotype. In some embodiments, the ITR and the capsid of the rAAV viral particles are derived from different AAV serotypes. In some embodiments, the recombinant AAV viral particle comprises an AAV1, AAV2, AAV8, AAVrh8R, AAV9, and/or AAVrh10 capsid. In some embodiments, the AAV1, AAV2, AAV8, AAVrh8R, AAV9, and/or AAVrh10 capsid comprises a tyrosine mutation or a heparan binding mutation. In some embodiments, the rAAV vector comprises AAV2 ITRs.

In some aspects, the invention provides compositions for cleaving a target nucleic acid in a cell comprising: a) a nucleic acid encoding an engineered, non-naturally occurring Clustered Regularly Interspaced Short Palindromic Repeats (CRISPR)-CRISPR associated (Cas) (CRISPR-Cas) system comprising a first guide RNA and a second guide RNA wherein the first guide RNA and the second guide RNA hybridize to opposite strands of target DNA sequences flanking the mutation; and b) a Cas expression cassette comprising: i) a nucleotide sequence encoding a Cas protein, and ii) a first guide RNA target site, wherein the first guide RNA or the second guide RNA hybridizes to the first guide RNA target site; wherein the Cas protein is expressed from the Cas expression cassette; wherein the Cas protein cleaves the target DNA sequences flanking the mutation, thereby excising a portion of target DNA comprising the mutation; and wherein the Cas protein cleaves the Cas expression cassette at the first guide RNA target site, thereby reducing expression of the Cas protein, as compared to expression of the Cas protein prior to cleavage of the Cas expression cassette. In some aspects, the invention provides a compositions for treating a disease or disorder associated with a mutation in a nucleic acid of an individual comprising: a) a nucleic acid encoding an engineered, non-naturally occurring Clustered Regularly Interspaced Short Palindromic Repeats (CRISPR)-CRISPR associated (Cas) (CRISPR-Cas) system comprising a first guide RNA and a second guide RNA wherein the first guide RNA and the second guide RNA hybridize to opposite strands of target DNA sequences flanking the mutation; and b) a Cas expression cassette comprising: i) a nucleotide sequence encoding a Cas protein, and ii) a first guide RNA target site, wherein the first guide RNA or the second guide RNA hybridizes to the first guide RNA target site; wherein the Cas protein is expressed from the Cas expression cassette; wherein the Cas protein cleaves the target DNA sequences flanking the mutation, thereby excising a portion of target DNA comprising the mutation; and wherein the Cas protein cleaves the Cas expression cassette at the first guide RNA target site, thereby reducing expression of the Cas protein, as compared to expression of the Cas protein prior to cleavage of the Cas expression cassette. In some aspects, the invention provides a compositions for treating an ocular disease or disorder associated with a mutation in a nucleic acid of an individual comprising: a) a nucleic acid encoding an engineered, non-naturally occurring Clustered Regularly Interspaced Short Palindromic Repeats (CRISPR)-CRISPR associated (Cas) (CRISPR-Cas) system comprising a first guide RNA and a second guide RNA wherein the first guide RNA and the second guide RNA hybridize to opposite strands of target DNA sequences flanking the mutation; and b) a Cas expression cassette comprising: i) a nucleotide sequence encoding a Cas protein, and ii) a first guide RNA target site, wherein the first guide RNA or the second guide RNA hybridizes to the first guide RNA target site wherein the Cas protein is expressed from the Cas expression cassette; wherein the Cas protein cleaves the target DNA sequences flanking the mutation, thereby excising a portion of target DNA comprising the mutation; and wherein the Cas protein cleaves the Cas expression cassette at the first guide RNA target site, thereby reducing expression of the Cas protein, as compared to expression of the Cas protein prior to cleavage of the Cas expression cassette. In some embodiments, the Cas expression cassette further comprises: iii) a second guide RNA target site, wherein the first guide RNA or the second guide RNA hybridizes to the second guide RNA target site; wherein the Cas protein cleaves the Cas expression cassette at the first and the second guide RNA target sites, thereby reducing expression of the Cas protein, as compared to expression of the Cas protein prior to cleavage of the Cas expression cassette.

In some embodiments of the above compositions, the first guide RNA hybridizes to the first guide RNA target site and the second guide RNA target site. In some embodiments, the second guide RNA hybridizes to the first guide RNA target site and the second guide RNA target site. In some embodiments, the first guide RNA hybridizes to the first guide RNA target site, and the second guide RNA hybridizes to the second guide RNA target site. In some embodiments, the Cas expression cassette further comprises further comprises a polyadenylation (polyA) sequence operably linked to the nucleotide sequence encoding the Cas protein. In some embodiments, the polyA sequence is an SV40 polyA sequence. In some embodiments, cleavage of the first or the second guide RNA target site by Cas protein interrupts the operable linkage between the nucleotide sequence encoding the Cas protein and the polyA sequence. In some embodiments, the first or the second guide RNA target site is between the nucleotide sequence encoding the Cas protein and the polyA sequence. In some embodiments, the nucleotide sequence encoding the Cas protein is operably linked to a nucleotide sequence encoding one or more nuclear localization signal(s) (NLS(s)), such that the Cas protein expressed from the Cas expression cassette is fused in-frame with the one or more NLS(s). In some embodiments, the nucleotide sequence encoding the one or more NLS(s) is between the nucleotide sequence encoding the Cas protein and a polyadenylation (polyA) sequence. In some embodiments, the first or the second guide RNA target site is between the nucleotide sequence encoding the one or more NLS(s) and the polyA sequence. In some embodiments, the one or more NLS(s) comprises a C-terminal sequence in the SV40 Large T-antigen. In some embodiments, the one or more NLS(s) comprises the sequence PKKKRKV (SEQ ID NO:26) or PKKKRKVEDPKKKRKVD (SEQ ID NO:27). In some embodiments, the nucleic acid encoding the CRISPR-Cas system and/or the Cas expression cassette are operably linked to one or more regulatory control elements. In some embodiments, the nucleotide sequence encoding the Cas protein is operably linked to a promoter. In some embodiments, cleavage of the first or the second guide RNA target site by the Cas protein interrupts the operable linkage between the regulatory control element and the nucleotide sequence encoding the Cas protein. In some embodiments, the first or the second guide RNA target site is between the promoter and the nucleotide sequence encoding the Cas protein.

In some embodiments of the above compositions, the Cas expression cassette further comprises: iii) a second guide RNA target site, wherein the first guide RNA or the second guide RNA hybridizes to the second guide RNA target site, and wherein the second guide RNA target site is adjacent to a protospacer adjacent motif (PAM) specific for the Cas protein; wherein cleavage of the first guide RNA target site by Cas protein interrupts the operable linkage between the regulatory control element and the nucleotide sequence encoding the Cas protein; wherein cleavage of the second guide RNA target site by Cas protein interrupts the operable linkage between the nucleotide sequence encoding the Cas protein and the polyA sequence; and wherein upon expression of the Cas protein and cleavage of the target DNA sequences, the Cas protein cleaves the Cas expression cassette at the first and the second guide RNA target sites, thereby reducing expression of the Cas protein, as compared to expression of the Cas protein prior to cleavage of the Cas expression cassette. In some embodiments, the Cas expression cassette further comprises: iii) a second guide RNA target site, wherein the first guide RNA or the second guide RNA hybridizes to the second guide RNA target site; wherein the first guide RNA target site is between the nucleotide sequence encoding the Cas protein and a promoter operably linked to the nucleotide sequence encoding the Cas protein; wherein the second guide RNA target site is between the nucleotide sequence encoding the Cas protein and a polyA sequence operably linked to the nucleotide sequence encoding the Cas protein; and wherein the Cas protein cleaves the Cas expression cassette at the first and the second guide RNA target sites, thereby reducing expression of the Cas protein, as compared to expression of the Cas protein prior to cleavage of the Cas expression cassette.

In some embodiments of the above compositions, the disease or disorder associated with a deep intronic mutation is afibrinogenemia, Alport syndrome, Amyotrophic lateral sclerosis, ataxia telangiectasia, autosomal recessive polycystic kidney disease. Barth syndrome, beta-thalassemia, congenital afibrinogenemia, congenital cataracts facial dysmorphism neuropathy syndrome, congenital disorder of glycosylation type Ia, congenital disorder of glycosylation type II, cystic fibrosis, dihydropteridine reductase deficiency. Fabry disease, familial platelet disorder with predisposition to acute myelogenous leukemia, Fanconi anemia, Gitelman syndrome, growth hormone insensitivity. Friedrich's ataxia, hemophilia A, hereditary megaloblastic anaemia 1. Hermansky-Pudlak syndrome, homocytinuria, maple syrup urine disease, Marfan syndrome, methionine synthase deficiency, methylmalonic academia, mitochondrial trifunctional protein deficiency, mucupolysaccaridosis type II, multi-minicore disease, muscular dystrophy, neurofibromatosis type I, Niemann-Pick disease type C, ocular albinism type I, ornithine delta-aminotransferaase deficiency, predisposition to systemic lupus erythematosus, propionic academia, rhabdoid tumors, Schwartz-Jampel syndrome, Stickler syndrome, systemic lupus erythematosus, tuberous sclerosis. Werner syndrome, X-linked hyperimmunoglobulinemia M, or X-linked hypophosphatemia. In some embodiments, the deep intronic mutation is a deep intronic mutation presented in Table 1.

In some aspects, the invention provides compositions for treating an ocular disease or disorder associated with a deep intronic mutation in a gene of an individual comprising nucleic acid encoding an engineered, non-naturally occurring Clustered Regularly Interspaced Short Palindromic Repeats (CRISPR)-CRISPR associated (Cas) (CRISPR-Cas) system comprising a) a first guide RNA and a second guide RNA wherein the first guide RNA and the second guide RNA hybridize to the opposite strands of the target DNA sequences flanking the deep intronic mutation, and b) a nucleotide sequence encoding a Cas protein, wherein the Cas protein cleaves the target DNA molecule at sites flanking the deep intronic mutation thereby excising a portion of target DNA comprising the deep intronic mutation. In some embodiments, the invention provides compositions for treating an ocular disease or disorder associated with a deep intronic mutation in a gene of an individual comprising an engineered, non-naturally occurring Clustered Regularly Interspaced Short Palindromic Repeats (CRISPR)-CRISPR associated (Cas) (CRISPR-Cas) system comprising a) a first guide RNA and a second guide RNA wherein the first guide RNA and the second guide RNA hybridize to the opposite strands of the target DNA sequences flanking the deep intronic mutation, and b) a Cas protein, wherein the Cas protein cleaves the target DNA molecule at sites flanking the deep intronic mutation thereby excising a portion of target DNA comprising the deep intronic mutation. In some embodiments, the ocular disease is Leber congenital amaurosis, optic atrophy, retinitis pigmentosa, retinoblastoma, Stargardt disease, Usher syndrome, or X-linked retinitis pigmentosa. In some embodiments, the deep intronic mutation is a deep intronic mutation presented in Table 2.

In some embodiments of the above compositions, the ocular disease is Leber congenital amaurosis. In some embodiments, the first guide RNA and second guide RNA guide sequences hybridize to the opposite strands of the target DNA sequences flanking a deep intronic mutation of the centrosomal protein 290 kDa (CEP290) gene. In some embodiments, the deep intronic mutation is a c.2991+1655A>G mutation. In some embodiments, the first guide RNA is encoded by DNA comprising the sequences of SEQ ID NO:41 (for SpCas9), SEQ ID NO:45 (for SaCas9), SEQ ID NO:46 (for SaCas9), or SEQ ID NO:47 (for SaCas9). In some embodiments, the first guide RNA is encoded by DNA comprising the sequence of SEQ ID NO:19 (for SpCas9), SEQ ID NO:50 (for SaCas9), SEQ ID NO:51 (for SaCas9), or SEQ ID NO:52 (for SaCas9). In some embodiments, the second guide RNA is encoded by DNA comprising the sequences of SEQ ID NO:42 (for SpCas9). SEQ ID NO:43 (for SpCas9), SEQ ID NO:44 (for SpCas9), SEQ ID NO:48 (for SaCas9), or SEQ ID NO:49 (for SaCas9). In some embodiments, the second guide RNA is encoded by DNA comprising the sequence of SEQ ID NO:20 (for SpCas9), SEQ ID NO:21 (for SpCas9), SEQ ID NO:22 (for SpCas9), SEQ ID NO:53 (for SaCas9), or SEQ ID NO:54 (for SaCas9). In some embodiments, the CEP290 is a human CEP290. In some embodiments, the CEP290 comprises a deep intronic mutation of the sequence set forth in SEQ ID NO:23.

In some embodiments of the above compositions, the deep intronic mutation is located about 1-10,000 nucleotides, about 1-1000 nucleotides or about 100-1000 nucleotides downstream of a 5' splice donor site of the gene. In some embodiments, the deep intronic mutation is located about 1-10,000 nucleotides, about 1-1000 nucleotides or about 100-1000 nucleotides upstream of a 3' splice acceptor site of the gene. In some embodiments, the deep intronic mutation introduces a splice donor site or a splice acceptor site in the gene.

In some embodiments of the above compositions, the Cas protein is a Cas9 protein. In some embodiments, the Cas 9 protein is a *Streptococcus pyogenes* Cas9 protein (SEQ ID NO:40), a *Staphylococcus aureus* Cas9 protein (SEQ ID NO: 55), a *Streptococcus thermophilus* Cas9 protein, a *Neisseria meningitidis* Cas9 protein, or a *Treponema denticola* Cas9 protein. In some embodiments, the Cas9 is codon optimized for expression in a eukaryotic cell. In some embodiments, the eukaryotic cell is a mammalian cell. In some embodiments, the eukaryotic cell is a human cell.

In some embodiments of the above compositions, the first guide RNA and/or the second guide RNA comprise are fused to a trans-activating cr (tracr) sequence. In some embodiments, the tracr sequence comprises the nucleotide sequence encoded by SEQ ID NO:25.

In some embodiments of the above compositions, the CRISPR-Cas system (e.g., the first guide RNA, the second guide RNA and the Cas protein) is complexed to a lipid, a cationic lipid, a liposome, a polycation or an agent that enhances the cellular uptake of nucleic acid and/or the protein.

In some embodiments of the above compositions, nucleic acid encoding the first guide RNA, the second guide RNA and the Cas protein are expressed in eukaryotic cells. In some embodiments, the nucleic acid encoding the first guide RNA, the second guide RNA and/or the Cas protein are operably linked to one or more regulatory control elements. In some embodiments, the first guide RNA and/or the second guide RNA is operably linked to a RNA polymerase III promoter. In some embodiments, the RNA polymerase II promoter is a U6, a 7SK or an H1 promoter. In some embodiments, the nucleic acid encoding the Cas protein is operably linked to a RNA polymerase II promoter. In some embodiments, the RNA polymerase 11 promoter is a cytomegalovirus (CMV) immediate early promoter, a minimal promoter fragment derived from the CMV promoter (minCMV promoter), a RSV LTR, a MoMLV LTR, a phosphoglycerate kinase-1 (PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), a E2F promoter, a EF1α promoter, a telomerase (hTERT) promoter, a cytomegalovirus enhancer/chicken beta-actin/Rabbit β-globin promoter (CAG) promoter, a rod opsin promoter, a cone opsin promoter, a beta phosphodiesterase (PDE) promoter, a retinitis pigmentosa (RP1) promoter, or an interphotoreceptor retinoid-binding protein gene (IRBP) promoter.

In some embodiments of the above compositions, the nucleic acid encoding one or more of the first guide RNA, the second guide RNA or the Cas protein are located on the same or different vectors of the system. In some embodiments, the vector is a plasmid. In some embodiments, the vector is complexed to a delivery system. In some embodiments, the vector is complexed to a lipid, a cationic lipid, a liposome, a polycation or an agent that enhances the cellular uptake of nucleic acid.

In some embodiments of the above compositions, the vector is a recombinant adeno-associated virus (rAAV) vector, a recombinant adenoviral vector, a recombinant lentiviral vector or a recombinant herpes simplex virus (HSV) vector. In some embodiments, the vector is a recombinant adenoviral vector. In some embodiments, the recombinant adenoviral vector is derived from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the recombinant adenoviral vector is derived from adenovirus serotype 2 or a variant of adenoviral serotype 5.

In some embodiments, the vector is a recombinant lentiviral vector. In some embodiments, the recombinant lentiviral vector is derived from a lentivirus pseudotyped with vesicular stomatitis virus (VSV), lymphocytic choriomeningitis virus (LCMV), Ross river virus (RRV), Ebola virus, Marburg virus, Mokala virus, Rabies virus, RD114, or variants therein.

In some embodiments, the vector is an rHSV vector. In some embodiments, the rHSV vector is derived from rHSV-1 or rHSV-2.

In some embodiments, the vector is a recombinant AAV (rAAV) vector. In some embodiments, the nucleic acid encoding one of more of the first guide RNA, the second guide RNA, or the Cas protein is flanked by one or more AAV inverted terminal repeat (ITR) sequences. In some embodiments, the nucleic acid encoding one of more of the first guide RNA, the second guide RNA, or the Cas protein is flanked by two AAV ITRs. In some embodiments, the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype ITRs. In some embodiments, the AAV ITRs are AAV2 ITRs. In some embodiments, the vector is a self-complementary vector.

In some embodiments, the vector is encapsidated in a viral particle. In some embodiments, the viral particle is a recombinant adenovirus particle encapsidating a recombinant adenoviral vector. In some embodiments, the recombinant adenovirus particle comprises a capsid from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the recombinant adenovirus particle comprises an adenovirus serotype 2 capsid or a variant of an adenoviral serotype 5 capsid.

In some embodiments, the viral particle is a recombinant lentiviral particle encapsidating a recombinant lentiviral vector. In some embodiments, the recombinant lentiviral particle comprises a capsid pseudotyped with vesicular stomatitis virus (VSV), lymphocytic choriomeningitis virus (LCMV). Ross river virus (RRV), Ebola virus. Marburg virus, Mokala virus, Rabies virus, RD114 or variants therein.

In some embodiments, the viral particle is a recombinant HSV particle encapsidating a recombinant HSV vector. In some embodiments, the recombinant HSV particle is an rHSV-1 particle or an rHSV-2 viral particle.

In some embodiments, the viral particle is a recombinant AAV viral particle comprising a recombinant AAV vector. In some embodiments, the recombinant AAV viral particle comprises an AAV serotype capsid from Clades A-F. In some embodiments, the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A. AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the ITR and the capsid of the rAAV viral particle are derived from the same AAV serotype. In some embodiments, the ITR and the capsid of the rAAV viral particles are derived from different AAV serotypes. In some embodiments, the recombinant AAV viral particle comprises an AAV1, AAV2, AAV8, AAVrh8R, AAV9, and/or AAVrh10 capsid. In some embodiments, the AAV1, AAV2, AAV8, AAVrh8R, AAV9, and/or AAVrh10 capsid comprises a tyrosine mutation or a heparan binding mutation. In some embodiments, the rAAV vector comprises AAV2 ITRs.

All references cited herein, including patent applications and publications, are incorporated by reference in their entirely.

BRIEF DESCRIPTION OF THE DRAWINGS

FIGS. 3A&3B show graphs of basal expression levels of wild-type (FIG. 3A) and mutant (FIG. 3B) mRNAs in wild-type cells (white bars), cells heterozygous for a chromosome bearing the c.2991+1655A>G and c.2991+1666C>G mutations (grey bars), and homozygous c.2991+1655A>G and c.2991+1666C>G cells (mutant cells; black bars), as determined by RT-qPCR. The data are presented as mean±standard deviation of samples from three independent transfections (n=3). Comparisons were performed using one-way ANOVA followed by Tukey's HSD post hoc test. *=p<0.05, =p<0.01, *=p<0.001. FIG. 3C is an immunoblot of lysates prepared from wild-type cells (WT), heterozygous cells (Het), and mutant cells (MT). The membrane was probed for CEP290 (top) and β-Actin as a loading control (bottom).

In FIG. 4A, primers outside expected deletion regions were used. The upper bands are PCR products amplified from the Intron 26 of wild-type CEP290, whereas the lower bands are PCR products amplified from CEP290 allele after expected genomic deletions (labeled as "Wt" and "Trunc." respectively). M, 1 kb DNA ladder. FIG. 4B shows percentage of wild-type and truncated of DNA in mutant cells transfected with paired sgRNAs and SpCas9, as determined by next-generation sequencing (NGS).

FIGS. 5A&5B show expression levels of wild-type (FIG. 5A) and mutant (FIG. 5B) mRNA in wild-type (white bars), heterozygous (grey bars), and mutant (black bars) cells transfected with paired sgRNAs and SpCas9, as measured by RT-qPCR. The data are presented as mean±standard deviation of samples from two independent transfections (n=2). Comparisons were performed using one-way ANOVA followed by Tukey's HSD post hoc test. *=p<0.05. **=p<0.01. FIG. 5C is an immunoblot of lysates prepared from mutant cells transfected with paired sgRNAs and SpCas9. The membrane was probed for CEP290 (top) and β-Actin as a loading control (bottom).

FIG. 6A is a schematic diagram of the pAAV-SpCas9 vector used in self-limiting CRISPR-SpCas9 system. The recognition sequence for the SpCas9 nuclease (sgRNA target sequence plus the PAM motif) is incorporated into the insertion site 1 (between minCMV promoter and SpCas9) and/or the insertion site 2 (between SpCas9-NLS and SV40 pA). NLS, nuclear localization signal. SV40 pA, Simian virus 40 polyadenylation signal. FIG. 6B is immunoblot of lysates prepared from mutant cells transfected with a first AAV packaging plasmid expressing U1D3 sgRNA pair and a second AAV packaging plasmid expressing SpCas9. The SpCas9 plasmid contains U1 sgRNA recognition sequence (U1T) and/or D3 sgRNA recognition sequence (D3T) in the two insertion sites. The mutant cells transfected with the U1D3 plasmid alone was served as control here. The membrane was probed for SpCas9 (top) and β-Actin as a loading control (bottom). FIG. 6C shows targeted deletion after mutant cells were transfected with U1D3 sgRNA pair and self-limiting SpCas9, as determined by PCR. The upper bands are PCR products amplified from wild-type CEP290 intron 26, whereas the lower bands are PCR products amplified from CEP290 allele after U1 and D3 sgRNAs-guided genomic deletion. M, 1 kb DNA ladder. FIGS. 6D&6E show expression levels of wild-type (FIG. 6D) and mutant (FIG. 6E) mRNA in mutant cells transfected with U1D3 sgRNA pair and self-limiting SpCas9, as measured by RT-qPCR. The data are presented as mean±standard deviation of samples from three independent transfections (n=3). Comparisons were performed using one-way ANOVA followed by Tukey's HSD post hoc test. *=p<0.05, =p<0.01. *=p<0.001 as compared to the cells transfected with the U1D3 sgRNA pair alone.

FIG. 7A is a schematic diagram of the dual AAVs used in subretinal injection. FIG. 7B shows targeted deletion with (1) AAV5-RK-EGFP (control) or AAV5-U11D11 sgRNA pair-RK-EGFP and (2) AAV5-SpCas9, as determined by PCR. The upper bands are PCR products amplified from wild-type mouse Cep290 Intron 25, whereas the lower bands are PCR products amplified from Cep290 allele after U11 and D11 sgRNAs-guided genomic deletion. M, 1 kb DNA ladder.

In FIG. 8A, the upper bands are PCR products amplified from the intron 26 of wild-type CEP290, whereas the lower bands are PCR products amplified from CEP290 allele after expected genomic deletions (labeled as "Wt" and "Trunc," respectively). M, 1 kb DNA ladder. FIGS. 8A&8B show expression levels of wild-type (FIG. 8A) and mutant (FIG. 8B) mRNA in mutant cells transfected with paired sgRNAs together with either SaCas9 (white bars) or SpCas9 (grey bars), as measured by RT-qPCR. The data are presented as mean±standard deviation of samples from three independent transfections (n=3). Comparisons were performed using one-way ANOVA followed by Tukey's HSD post hoc test. *=p<0.05, =p<0.01, *=p<0.001. #=p<0.05 as compared to the mutant cells transfected with SaCas9 alone.

DETAILED DESCRIPTION

The invention provides compositions, methods and viral particles for editing of deep intronic mutations. In some embodiments, the composition for treating a disease or disorder associated with a deep intronic mutation in a gene of an individual comprises an engineered, non-naturally occurring Clustered Regularly Interspaced Short Palindromic Repeats (CRISPR)-CRISPR associated (Cas) (CRISPR-Cas) system comprising a) a first guide RNA and a second guide RNA wherein the first guide RNA and the second guide RNA hybridize to the opposite strands of the target DNA sequences flanking the deep intronic mutation, and b) a Cas protein, wherein the Cas protein cleaves the target DNA molecule at sites flanking the deep intronic mutation thereby excising a portion of the target DNA comprising the deep intronic mutation. In other embodiments, the composition for treating a disease or disorder associated with a deep intronic mutation in a gene of an individual comprises nucleic acid encoding an engineered, non-naturally occurring Clustered Regularly Interspaced Short Palindromic Repeats (CRISPR)-CRISPR associated (Cas) (CRISPR-Cas) system comprising a) a first guide RNA and a second guide RNA wherein the first guide RNA and the second guide RNA hybridize to the opposite strands of the target DNA sequences flanking the deep intronic mutation, and b) a nucleotide sequence encoding a Cas protein, wherein the Cas protein cleaves the target DNA molecule at sites flanking the deep intronic mutation thereby excising a portion of the target DNA comprising the deep intronic mutation.

Figure 1:
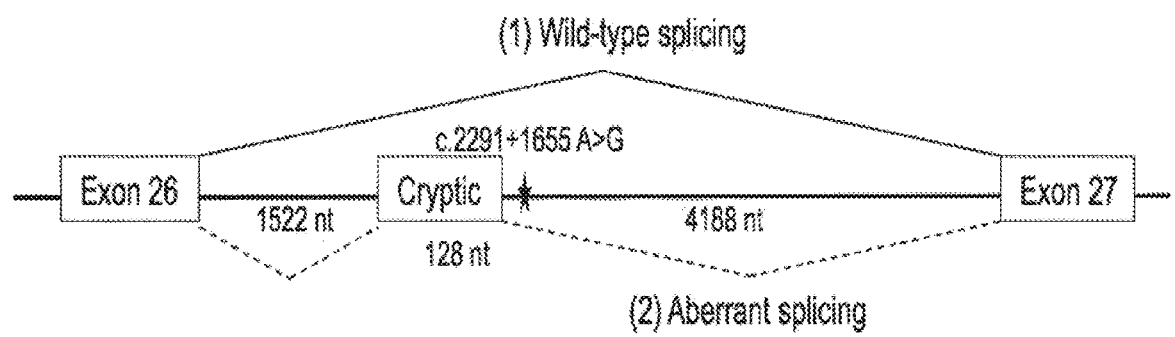
FIG. 1 is a schematic diagram of the intronic c.2291+1655 A>G mutation in the CEP290 gene (set forth in SEQ ID NO: 23). The A>G mutation occurs at position +5 of the 5' splice site of a cryptic exon located within intron 26. The exon-intron structure of CEP290 exon 26 to exon 27 region is represented by boxes and lines, respectively, together with the splicing pattern for wild-type (solid line) and mutant (dashed line) transcripts. The mutated nucleotide is indicated in bold and underlined, and symbolized by a filled star. The 5' splice site sequences (wild-type (SEQ ID NO: 67) and mutant (SEQ ID NO: 68)) of the cryptic exon are presented along with their splice site strength scores, as calculated by BDGP: Splice Site Prediction by Neural Network (see, e.g., www.fruitfly.org/seq_tools/splice.html and Reese, M. G. et al. (1997) J. Comput. Biol. 4:311-323). Exonic nucleotides are shown in capital letters. Exon and intron sizes are annotated below the figure.
Figure 2:
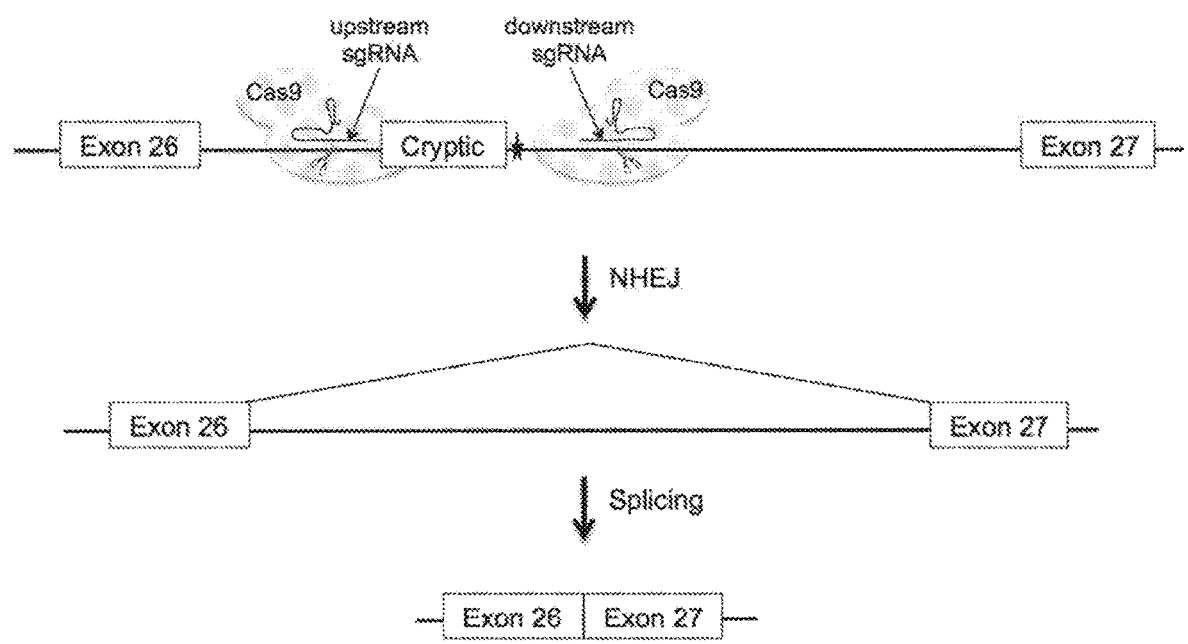
FIG. 2 is a schematic showing the strategy to delete the intron region flanking the c.2991+1655 A>G mutation of CEP290. An upstream sgRNA directs the first Cas9 cleavage located upstream of the intronic mutation, and a downstream sgRNA directs the second Cas9 cleavage located downstream of the mutation. Note the upstream target locus can be located either upstream of the cryptic exon or within the cryptic exon. The two cleavage ends are directly ligated through the non-homologous end-joining (NHEJ) process, with an intron fragment flanking the c.2991+1655 A>G mutation deleted. Intron 26 is further removed by RNA splicing during mRNA processing.

In some aspects the invention provides compositions, methods and viral particles for treating ocular diseases. As described above, the most frequent genetic cause of LCA is a deep-intronic mutation c.2991+1655A>G in the intron 26 of CEP290 gene, which generates a cryptic splice donor site resulting in the inclusion of an aberrant exon containing a premature stop codon (p.C998X) to CEP290 mRNA (FIG. 1). The inventors have designed a simple and efficient method for treating LCA patients that harbor the intronic c.2991+1655 A>G mutation in the CEP290 gene through a targeted genomic DNA deletion in human cells via a pair of single guide RNAs (sgRNAs) and the Clustered regularly interspaced short palindromic repeats (CRISPRs) and CRISPR-associated protein (Cas) system (FIG. 2). This approach effectively and permanently deletes the intronic c.2991+1655 A>G mutation, preventing the splicing of the cryptic exon inserted into the CEP290 mRNA, and in the meantime leaving the endogenous genetic regulatory elements intact.

I. General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4th ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); PCR 2: A Practical Approach (M. J. MacPherson. B.

D. Hames and G. R. Taylor eds., 1995); *Antibodies. A Laboratory Manual* (Harlow and Lane, eds., 1988); *Culture of Animal Cells: A Manual of Basic Technique and Specialized Applications* (R. I. Freshney, 6th ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts. Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 2011).

II. Definitions

As used herein, "CRISPR-Cas" refers to a two component ribonucleoprotein complex with guide RNA and a Cas endonuclease. CRISPR refers to the Clustered Regularly Interspaced Short Palindromic Repeats type II system. While CRISPR was discovered as an adaptive defense system that enables bacteria and archaea to detect and silence foreign nucleic acids (e.g., from viruses or plasmids), it has been adapted for use in a variety of cell types to allow for polynucleotide editing in a sequence-specific manner (see, e.g., Jinek. M. et al. (2012) *Science* 337:816-821 and Ran, F. A. et al. (2013) *Nat. Protoc.* 8:2281-2308). In type II systems, guide RNA interacts with Cas and directs the nuclease activity of the Cas enzyme to target DNA sequences identical to the guide RNA guide sequences. Guide RNA base pairs with the opposite strand of the target sequence. Cas nuclease activity then generates a double-stranded break in the target DNA. In some embodiments, the Cas protein is a Cas9 protein.

As used herein. "CRISPR-Cas single guide RNA" (the terms "single guide RNA" and "sgRNA" may be used interchangeably herein) refers to a single RNA species capable of directing Cas-mediated cleavage of target DNA. In some embodiments, a single guide RNA may contain the sequences necessary for Cas (e.g., Cas9) nuclease activity and a guide sequence identical to a target DNA of interest.

The terms "chimeric RNA", "chimeric guide RNA", "guide RNA", "single guide RNA" and "synthetic guide RNA" may be used interchangeably herein and refer to the polynucleotide sequence comprising the guide sequence, the tracr sequence and the tracr mate sequence. The term "guide sequence" as used herein refers to the about 20 bp sequence within the guide RNA that specifies the target site and may be used interchangeably with the terms "guide" or "spacer" or "protospacer". The term "tracr mate sequence" may also be used interchangeably with the term "direct repeat(s)."

As used herein, an "sgRNA guide sequence" may refer to the nucleotide sequence of an sgRNA that binds to the opposite strand of a target DNA sequence and directs Cas (e.g., Cas9) nuclease activity to that locus. In some embodiments, the sgRNA guide sequence is identical to the target sequence. Full identity is not necessarily required, provided there is sufficient similarity to cause hybridization and promote formation of a CRISPR complex. A guide sequence may comprise any polynucleotide, such as DNA or RNA polynucleotides.

As used herein, a "Cas" polypeptide is a polypeptide that functions as a nuclease when complexed to a guide RNA. e.g., a sgRNA. In some embodiments, the Cas polypeptide is a Cas9 polypeptide (CRISPR-associated 9, also known as Csn1). When bound to a crRNA:tracrRNA guide or single guide RNA. Cas polypeptides (e.g., Cas9) are able to cleave target DNA at a sequence identical to the sgRNA guide sequence and adjacent to a PAM motif. Unlike other Cas polypeptides, Cas9 polypeptides are characteristic of type II CRISPR-Cas systems (for a description of Cas proteins of different CRISPR-Cas systems, see Makarova, K. S., et al. (2011) *Nat. Rev. Microbiol.* 9(6):467-77). As used herein, "Cas" may refer to the ribonucleoprotein complex with an sgRNA or the polypeptide component of the complex, unless specified.

The term "CRISPR RNA (crRNA)" as used herein refers to an RNA comprising the guide sequence used by a CRISPR-Cas system to direct cleavage against a target DNA sequence. The term "trans-activating crRNA (tracrRNA)" as used herein refers to an RNA comprising sequence that forms the structure required for the CRISPR-Cas effector complex that mediates DNA cleavage. In endogenous bacterial and archaeal type II CRISPR-Cas systems, the effector CRISPR-Cas complex includes a Cas protein (e.g., a Cas9 protein) complexed with two polyribonucleotide molecules; a crRNA and a tracrRNA. The crRNA contains an ~20 nucleotide guide sequence that mediates target recognition and a sequence that forms a duplex with a tracrRNA. The crRNA:tracrRNA duplex binds the Cas protein and is required for the CRISPR-Cas effector complex function. In some embodiments, the crRNA and tracrRNA functions may be carried out by a single RNA (a single guide RNA or sgRNA) that contains both the sequence that mediates target recognition and the sequence that generates the structure required for the CRISPR-Cas effector complex.

The term "deep intronic mutation" as used herein refers to a mutation within intronic sequence at a region outside of the wild-type splice acceptor and splice donor sequences. In some cases, a deep intronic mutation may lead to altered splicing of the associated gene, e.g., the inclusion of intronic sequence in the mature mRNA. In non-limiting examples, the deep intronic mutation is greater than about 100 bp downstream (i.e. 3') to an exon, greater than about 100 bp upstream (i.e., 5') to an exon, or greater than about 100 bp downstream of a first exon and greater than about 100 bp upstream of a second exon.

The term "Leber Congenital Amaurosis (LCA)" as used herein refers to a group of early-onset disorders characterized by vision loss, retinal dysfunction, and nystagmus. A variety of mutations have been implicated in LCA, but LCA is typically inherited as an autosomal recessive disorder. For more description and exemplary LCA disease genes and loci, see. e.g., OMIM Entry 204000.

The term "CEP290" as used herein refers to the gene encoding a centrosomal protein involved in ciliogenesis, also known as MKS4, CT87, POC3, rd16, BBS14, LCA10, JBTS5, NPHP6, SLSN6, and 3H11Ag. Mutations in CEP290 have been implicated in LCA. One example of such a mutation is the c.2991+1655A>G mutation that introduces a cryptic splice donor site, resulting in the inclusion of an aberrant exon with a premature stop codon. See. e.g., NCBI Gene ID No. 80184 and UniProt ID No. 015078 for exemplary human gene and protein sequences, respectively. Other examples of CEP290 genes include without limitation mouse CEP290 (e.g., NCBI Gene ID No. 216274), rat CEP290 (e.g., NCBI Gene ID No. 314787), Rhesus monkey CEP290 (e.g., NCBI Gene ID No. 708286), zebrafish CEP290 (e.g., NCBI Gene ID No. 560588), dog CEP290 (e.g., NCBI Gene ID No. 482591), chimpanzee CEP290 (e.g., NCBI Gene ID No. 452113), cat CEP290 (e.g., NCBI Gene ID No. 100113471), chicken CEP290 (e.g., NCBI Gene ID No. 417887), and cow CEP290 (e.g., NCBI Gene ID No. 282707). In some embodiments, a CEP290 gene comprises a deep intronic mutation of the sequence set forth in SEQ ID NO:23.

A "vector," as used herein, refers to a recombinant plasmid or virus that comprises a nucleic acid to be delivered into a host cell, either in vitro or in vivo.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P—NH$_2$) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

A "recombinant viral vector" refers to a recombinant polynucleotide vector comprising one or more heterologous sequences (i.e., nucleic acid sequence not of viral origin). In the case of recombinant AAV vectors, the recombinant nucleic acid is flanked by at least one inverted terminal repeat sequence (ITR). In some embodiments, the recombinant nucleic acid is flanked by two ITRs.

A "recombinant AAV vector (rAAV vector)" refers to a polynucleotide vector comprising one or more heterologous sequences (i.e., nucleic acid sequence not of AAV origin) that are flanked by at least one AAV inverted terminal repeat sequence (ITR). Such rAAV vectors can be replicated and packaged into infectious viral particles when present in a host cell that has been infected with a suitable helper virus (or that is expressing suitable helper functions) and that is expressing AAV rep and cap gene products (i.e, AAV Rep and Cap proteins). When a rAAV vector is incorporated into a larger polynucleotide (e.g., in a chromosome or in another vector such as a plasmid used for cloning or transfection), then the rAAV vector may be referred to as a "pro-vector" which can be "rescued" by replication and encapsidation in the presence of AAV packaging functions and suitable helper functions. A rAAV vector can be in any of a number of forms, including, but not limited to, plasmids, linear artificial chromosomes, complexed with lipids, encapsulated within liposomes, and encapsidated in a viral particle, e.g., an AAV particle. A rAAV vector can be packaged into an AAV virus capsid to generate a "recombinant adeno-associated viral particle (rAAV particle)".

An "rAAV virus" or "rAAV viral particle" refers to a viral particle composed of at least one AAV capsid protein and an encapsidated rAAV vector genome.

A "recombinant adenoviral vector" refers to a polynucleotide vector comprising one or more heterologous sequences (i.e., nucleic acid sequence not of adenovirus origin) that are flanked by at least one adenovirus inverted terminal repeat sequence (ITR). In some embodiments, the recombinant nucleic acid is flanked by two inverted terminal repeat sequences (ITRs). Such recombinant viral vectors can be replicated and packaged into infectious viral particles when present in a host cell that is expressing essential adenovirus genes deleted from the recombinant viral genome (e.g., E1 genes, E2 genes. E4 genes, etc.). When a recombinant viral vector is incorporated into a larger polynucleotide (e.g., in a chromosome or in another vector such as a plasmid used for cloning or transfection), then the recombinant viral vector may be referred to as a "pro-vector" which can be "rescued" by replication and encapsidation in the presence of adenovirus packaging functions. A recombinant viral vector can be in any of a number of forms, including, but not limited to, plasmids, linear artificial chromosomes, complexed with lipids, encapsulated within liposomes, and encapsidated in a viral particle, for example, an adenovirus particle. A recombinant viral vector can be packaged into an adenovirus virus capsid to generate a "recombinant adenoviral particle."

A "recombinant lentivirus vector" refers to a polynucleotide vector comprising one or more heterologous sequences (i.e., nucleic acid sequence not of lentivirus origin) that are flanked by at least one lentivirus terminal repeat sequences (LTRs). In some embodiments, the recombinant nucleic acid is flanked by two lentiviral terminal repeat sequences (LTRs). Such recombinant viral vectors can be replicated and packaged into infectious viral particles when present in a host cell that has been infected with a suitable helper functions. A recombinant lentiviral vector can be packaged into a lentivirus capsid to generate a "recombinant lentiviral particle."

A "recombinant herpes simplex vector (recombinant HSV vector)" refers to a polynucleotide vector comprising one or more heterologous sequences (i.e., nucleic acid sequence not of HSV origin) that are flanked by HSV terminal repeat sequences. Such recombinant viral vectors can be replicated and packaged into infectious viral particles when present in a host cell that has been infected with a suitable helper functions. When a recombinant viral vector is incorporated into a larger polynucleotide (e.g., in a chromosome or in another vector such as a plasmid used for cloning or transfection), then the recombinant viral vector may be referred to as a "pro-vector" which can be "rescued" by replication and encapsidation in the presence of HSV packaging functions. A recombinant viral vector can be in any of a number of forms, including, but not limited to, plasmids, linear artificial chromosomes, complexed with lipids, encapsulated within liposomes, and encapsidated in a viral particle, for example, an HSV particle. A recombinant viral vector can be packaged into an HSV capsid to generate a "recombinant herpes simplex viral particle."

"Heterologous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector is a heterologous nucleotide sequence with respect to the vector.

The term "transgene" refers to a polynucleotide that is introduced into a cell and is capable of being transcribed into RNA and optionally, translated and/or expressed under appropriate conditions. In aspects, it confers a desired property to a cell into which it was introduced, or otherwise leads to a desired therapeutic or diagnostic outcome. In another aspect, it may be transcribed into a molecule that mediates RNA interference, such as miRNA, siRNA, or shRNA.

The terms "genome particles (gp)," "genome equivalents," or "genome copies" as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) Hum. Gene Ther., 10:1031-1039; Veldwijk et al. (2002) Mol. Ther., 6:272-278.

The term "vector genome (vg)" as used herein may refer to one or more polynucleotides comprising a set of the polynucleotide sequences of a vector, e.g., a viral vector. A vector genome may be encapsidated in a viral particle. Depending on the particular viral vector, a vector genome may comprise single-stranded DNA, double-stranded DNA, or single-stranded RNA, or double-stranded RNA. A vector genome may include endogenous sequences associated with a particular viral vector and/or any heterologous sequences inserted into a particular viral vector through recombinant techniques. For example, a recombinant AAV vector genome may include at least one ITR sequence flanking a promoter, a stuffer, a sequence of interest (e.g., an RNAi), and a polyadenylation sequence. A complete vector genome may include a complete set of the polynucleotide sequences of a vector. In some embodiments, the nucleic acid titer of a viral vector may be measured in terms of vg/mL. Methods suitable for measuring this titer are known in the art (e.g., quantitative PCR).

The terms "infection unit (iu)." "infectious particle," or "replication unit." as used in reference to a viral titer, refer to the number of infectious and replication-competent recombinant AAV vector particles as measured by the infectious center assay, also known as replication center assay, as described, for example, in McLaughlin et al. (1988) J. Virol., 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) Exp. Neurobiol., 144:113-124; or in Fisher et al. (1996) J. Virol., 70:520-532 (LFU assay).

An "inverted terminal repeat" or "ITR" sequence is a term well understood in the art and refers to relatively short sequences found at the termini of viral genomes which are in opposite orientation.

An "AAV inverted terminal repeat (ITR)" sequence, a term well-understood in the art, is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity (designated A, A', B, B', C, C' and D regions), allowing intrastrand base-pairing to occur within this portion of the ITR.

A "terminal resolution sequence" or "trs" is a sequence in the D region of the AAV ITR that is cleaved by AAV rep proteins during viral DNA replication. A mutant terminal resolution sequence is refractory to cleavage by AAV rep proteins.

A "helper virus" for AAV refers to a virus that allows AAV (which is a defective parvovirus) to be replicated and packaged by a host cell. A number of such helper viruses have been identified, including adenoviruses, herpesviruses and poxviruses such as vaccinia. The adenoviruses encompass a number of different subgroups, although Adenovirus type 5 of subgroup C (Ad5) is most commonly used. Numerous adenoviruses of human, non-human mammalian and avian origin are known and are available from depositories such as the ATCC. Viruses of the herpes family, which are also available from depositories such as ATCC, include, for example, herpes simplex viruses (HSV), Epstein-Barr viruses (EBV), cytomegaloviruses (CMV) and pseudorabies viruses (PRV).

"Percent (%) sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various ways that are within the skill in the art, for instance, using publicly available computer software programs, for example, those described in Current Protocols in Molecular Biology (Ausubel et al., eds., 1987), Supp. 30, section 7.7.18, Table 7.7.1, and including BLAST, BLAST-2, ALIGN or Megalign (DNASTAR) software. An example of an alignment program is ALIGN Plus (Scientific and Educational Software, Pennsylvania). Those skilled in the art can determine appropriate parameters for measuring alignment, including any algorithms needed to achieve maximal alignment over the full length of the sequences being compared. For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z, where W is the number of nucleotides scored as identical matches by the sequence alignment program in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

An "isolated" molecule (e.g., nucleic acid or protein) or cell means it has been identified and separated and/or recovered from a component of its natural environment.

An "effective amount" is an amount sufficient to effect beneficial or desired results, including clinical results (e.g., amelioration of symptoms, achievement of clinical endpoints, and the like). An effective amount can be administered in one or more administrations. In terms of a disease state, an effective amount is an amount sufficient to ameliorate, stabilize, or delay development of a disease.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein. "treatment" is an approach for obtaining beneficial or desired clinical results. For purposes of this invention, beneficial or desired clinical results include, but are not limited to, alleviation of symptoms, diminishment of extent of disease, stabilized (e.g., not worsening) state of disease, preventing spread (e.g., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, the term "prophylactic treatment" refers to treatment, wherein an individual is known or suspected to have or be at risk for having a disorder but has displayed no symptoms or minimal symptoms of the disorder. An individual undergoing prophylactic treatment may be treated prior to onset of symptoms.

As used herein, a "therapeutic" agent (e.g., a therapeutic polypeptide, nucleic acid, or transgene) is one that provides a beneficial or desired clinical result, such as the exemplary clinical results described above. As such, a therapeutic agent may be used in a treatment as described above.

The term "central retina" as used herein refers to the outer macula and/or inner macula and/or the fovea. The term "central retina cell types" as used herein refers to cell types of the central retina, such as, for example, RPE and photoreceptor cells.

The term "macula" refers to a region of the central retina in primates that contains a higher relative concentration of photoreceptor cells, specifically rods and cones, compared to the peripheral retina. The term "outer macula" as used herein may also be referred to as the "peripheral macula". The term "inner macula" as used herein may also be referred to as the "central macula".

The term "fovea" refers to a small region in the central retina of primates of approximately equal to or less than 0.5 mm in diameter that contains a higher relative concentration of photoreceptor cells, specifically cones, when compared to the peripheral retina and the macula.

The term "subretinal space" as used herein refers to the location in the retina between the photoreceptor cells and the retinal pigment epithelium cells. The subretinal space may be a potential space, such as prior to any subretinal injection of fluid. The subretinal space may also contain a fluid that is injected into the potential space. In this case, the fluid is "in contact with the subretinal space." Cells that are "in contact with the subretinal space" include the cells that border the subretinal space, such as RPE and photoreceptor cells.

The term "bleb" as used herein refers to a fluid space within the subretinal space of an eye. A bleb of the invention may be created by a single injection of fluid into a single space, by multiple injections of one or more fluids into the same space, or by multiple injections into multiple spaces, which when repositioned create a total fluid space useful for achieving a therapeutic effect over the desired portion of the subretinal space.

Reference to "about" a value or parameter herein includes (and describes) embodiments that are directed to that value or parameter per se. For example, description referring to "about X" includes description of "X."

As used herein, the singular form of the articles "a," "an," and "the" includes plural references unless indicated otherwise.

It is understood that aspects and embodiments of the invention described herein include "comprising," "consisting," and/or "consisting essentially of" aspects and embodiments.

III. CRISPR-Cas

Certain aspects of the present disclosure relate to engineered, non-naturally occurring Clustered Regularly Interspaced Short Palindromic Repeats (CRISPR)-CRISPR associated (Cas) (CRISPR-Cas) systems. These systems may be used, inter alia, for treating a disease or disorder associated with a deep intronic mutation in a gene of an individual, e.g., an ocular disease or disorder associated with a deep intronic mutation. In some embodiments, the CRISPR-Cas systems include a first guide RNA and a second guide RNA wherein the first guide RNA and the second guide RNA hybridize to the opposite strands of the target DNA sequences flanking the deep intronic mutation; and a nucleotide sequence encoding a Cas protein, wherein the Cas protein cleaves the target DNA molecule at sites flanking the deep intronic mutation thereby excising a portion of the target DNA comprising the deep intronic mutation.

As described above, the CRISPR-Cas systems were originally discovered as an adaptive defense against foreign nucleic acids in bacteria and archaea. Indeed, CRISPR loci have been identified in more than 40 prokaryotes (see. e.g., Jansen, R. et al. (2002) *Mol. Microbiol.* 43:1565-1575 and Mojica, F. J. et al. (2005) *J. Mol. Evol.* 60:174-182) including without limitation *Aeropyrum, Pyrobaculum, Sulfolobus, Archaeoglobus, Halocarcula, Methanobacteriumn, Methanococcus, Methanosarcina, Methanopyrus, Pyrococcus, Picrophilus, Thernioplasnia, Corynebacterimn, Myobacterirum, Streptonmyces, Aquifrx. Porphvromonas, Chlorobium, Thermus, Bacillus, Listeria, Staphylococcus, Clostridium, Thermoanaerobacter, Mycoplasma, Fusobacteriumn, Azarcus, Chromobacteriun, Neisseria, Nitrosomonas, Desulfovibrio, Geobacter, Myrococcus. Campylobacter. Wolinella. Acinetobacter, Erwinia, Escherichia, Legionella, Methylococcus, Pasteurella, Photobacterium, Salmonella, Xanthomonas, Yersinia, Treponema,* and *Thermotoga.*

In bacteria. Cas (e.g., Cas9) proteins bind to two different guide RNAs: a CRISPR RNA (crRNA) and a trans-activating crRNA (tracrRNA). The crRNA and tracrRNA ribonucleotides base pair and form a structure required for the Cas-mediated cleavage of target DNA. However, it has recently been demonstrated that a single guide RNA (sgRNA) may be engineered to form the crRNA:tracrRNA structure and direct Cas-mediated cleavage of target DNA (Jinek, M., et al. (2012) *Science* 337(6096):816-21). Since the specificity of Cas nuclease activity is determined by the guide RNA, the CRISPR-Cas system has been explored as a tool to direct double-stranded DNA breaks in heterologous cells, enabling customizable genome editing (Mali. P., et al. (2013) *Science* 339(6121):823-6). Further descriptions of exemplary CRISPR-Cas systems and methods of use related thereto may be found, inter alia, in U.S. Pat. No. 8,697,359. In some embodiments, a guide RNA as described herein (e.g., a first or second guide RNA) comprises a single guide RNA (sgRNA) comprising a CRISPR RNA (crRNA) and a trans-activating crRNA (tracrRNA). In some embodiments, a guide RNA as described herein (e.g., a first or second guide RNA) is fused to a trans-activating cr (tracr) sequence. In some embodiments, the trans-activating cr (tracr) sequence comprises the sequence of SEQ ID NO: 25.

As such, the CRISPR-Cas systems described herein may contrast with a naturally occurring CRISPR-Cas system for many reasons. For example, inter alia, the CRISPR-Cas systems of the present disclosure may include one or more guide RNAs that hybridize to a non-natural sequence (e.g., a eukaryotic intron). Naturally occurring CRISPR-Cas systems recognize sequence that bacteria and archaea are typically exposed to, such as plasmid or phage sequence. Also, many of the CRISPR-Cas systems of the present disclosure include a single guide RNA, whereas naturally occurring CRISPR-Cas systems typically involve separate CRISPR RNAs (crRNAs) and trans-activating crRNAs (tracrRNAs).

In some embodiments, a CRISPR-Cas system described herein may be self-limiting. For example, as described below, a CRISPR-Cas system may include one or more guide RNAs that hybridize to target sequence(s) within the system itself, e.g., sequence(s) whose cleavage affects the expression level of system components, such as a Cas protein. Without wishing to be bound to theory, it is thought that since the CRISPR-Cas system need not be persistently expressed in a host cell, engineering the system to be "self-limiting" (e.g., characterized by reduced persistence and/or expression) may be advantageous, e.g., for reducing off-target effects, reducing the potential for unwanted immune responses and/or safety problems, and so forth.

In a self-limiting CRISPR-Cas system, the CRISPR-Cas complex targets one or more sites in the vector used to express one or more components of the complex itself. Thus, upon expression of the guide RNA(s) and the Cas protein, the CRISPR-Cas system targets a locus of interest (e.g., the site of a mutation as described herein) as well as one or more target(s) in the Cas vector, eventually leading to cleavage of the Cas vector and reduction or elimination of Cas protein expression (after cleavage at the locus of interest). Example 3 infra demonstrates that such a self-limiting CRISPR-Cas system is characterized by decreased Cas persistence time while still allowing for effective cleavage at target sequence (s) of interest (e.g., excision of a deep intronic mutation).

Certain aspects of the present disclosure relate to methods for treating a disease or disorder associated with a mutation in a gene of an individual using a self-limiting CRISPR-Cas system. For example, the mutation may be an unwanted sequence (e.g., a deep intronic mutation) that is excised from the gene of the individual by the CRISPR-Cas system. In other embodiments, the mutation may be a missense, point, or other mutation that is corrected by the CRISPR-Cas system (e.g., homologous DNA repair at the cleaved DNA sequence, particularly if a homology template is included). In some embodiments, the CRISPR-Cas system is in a composition. In some embodiments, the composition is administered to the individual in a therapeutically effective amount.

In some embodiments, the composition includes a) a nucleic acid encoding a CRISPR-Cas system comprising a first guide RNA and a second guide RNA, wherein the first guide RNA and the second guide RNA hybridize to opposite strands of target DNA sequences flanking a mutation of interest (including but not limited to a deep intronic mutation described herein); and b) a Cas expression cassette. In some embodiments, the Cas expression cassette includes a nucleotide sequence encoding a Cas protein, and a guide RNA target site. The first or second guide RNA hybridizes to the guide RNA target site, thus allowing the CRISPR-Cas system to catalyze cleavage at the guide RNA target site. The guide RNA target site may also include a protospacer adjacent motif (PAM), specific for the Cas protein, adjacent to the sequence that hybridizes to the guide RNA. Upon expression of the Cas protein, the Cas protein cleaves the target DNA sequences flanking the mutation, thereby excising a portion of target DNA comprising the mutation. Upon expression of the Cas protein, the Cas protein also cleaves the Cas expression cassette at the guide RNA target site, thereby reducing expression of the Cas protein. As such, Cas expression initially increases following introduction of the Cas expression cassette to the cell, but as Cas protein accumulates in the cell, the Cas protein cleaves the Cas expression cassette. As more of the Cas expression cassette is interrupted by the Cas protein, expression of additional Cas protein is reduced (i.e., the Cas limits expression of its own expression cassette and may be considered a self-limiting Cas expression cassette). In some embodiments, expression of the Cas protein is characterized by an initial increase, followed by a decline in expression following cleavage at the guide RNA target site. As described herein, reducing expression of the Cas protein may refer to reducing the amount and/or persistence of the Cas protein. In some embodiments, expression of the Cas protein may be reduced compared with prior to cleavage of the Cas expression cassette (e.g., compared to initial expression of Cas). In some embodiments, expression of the Cas protein may be reduced compared with the use of a Cas expression cassette lacking the guide RNA target site. In some embodiments, the composition comprising a self-limiting Cas expression cassette may be used to cleave a target nucleic acid. In some embodiments, the composition may be used to cleave a target nucleic acid in vitro or in vivo. In some embodiments, the composition may be used to cleave a target nucleic acid comprising a mutation (e.g. a deep intronic mutation). For example, the self-limiting Cas expression cassette is used to treat a disease or disorder associated with a mutation in a nucleic acid.

In some embodiments, the Cas expression cassette further includes a second guide RNA target site, wherein the first guide RNA or the second guide RNA hybridizes to the second guide RNA target site, and wherein the second guide RNA target site is adjacent to a protospacer adjacent motif (PAM) specific for the Cas protein. Upon expression of the Cas protein, the Cas protein cleaves the target DNA sequences flanking the mutation, thereby excising a portion of target DNA comprising the mutation. Further upon expression of the Cas protein, the Cas protein cleaves the Cas expression cassette at both guide RNA target sites, thereby reducing expression of the Cas protein. As exemplified below, one guide RNA may hybridize to two guide RNA target sites; a first guide RNA may hybridize to a first guide RNA target site, and a second guide RNA may hybridize to a second guide RNA target site; or a second guide RNA may hybridize to a first guide RNA target site, and a first guide RNA may hybridize to a second guide RNA site.

In some embodiments, the Cas expression cassette may include one or more promoters, enhancers, introns, polyadenylation (polyA) sequences, terminators, regulatory elements present in 5' or 3' untranslated regions, and so forth useful for directing/promoting the expression of the Cas protein. In some embodiments, the nucleotide sequence encoding the Cas protein may be operably linked to a promoter. In some embodiments, a guide RNA target site may be between the promoter and the nucleotide sequence encoding the Cas protein, resulting in decreased expression of the Cas protein upon cleavage. In some embodiments, expression of Cas protein is decreased by cleavage of the operable link between the promoter and the nucleotide sequence encoding the Cas protein. In some embodiments, the nucleotide sequence encoding the Cas protein may be operably linked to a polyA sequence. In some embodiments, a guide RNA target site may be between the polyA sequence and the nucleotide sequence encoding the Cas protein, resulting in decreased expression of the Cas protein upon cleavage. In some embodiments, expression of Cas protein is decreased by cleavage of the operable link between the nucleotide sequence encoding the Cas protein and the polyadenylation sequence. In some embodiments, a first guide RNA target site may be between the promoter and the nucleotide sequence encoding the Cas protein, and a second guide RNA target site may be between the polyA sequence and the nucleotide sequence encoding the Cas protein, resulting in decreased expression of the Cas protein upon cleavage. In some embodiments, the Cas protein may be fused in-frame to one or more NLS(s), and a guide RNA target site may be between the sequence encoding the one or more NLS(s) and a polyA sequence (particularly if the NLS(s) are fused to the C-terminus of the Cas protein), resulting in decreased expression of the NLS-fused Cas protein upon cleavage.

As described herein, a CRISPR-Cas system such as a self-limiting CRISPR-Cas system may be encoded on one or more vectors, such as any of the vectors or viral vectors/particles described herein. In some embodiments, the nucleic acid encoding the first and second guide RNAs may be on the same vector as the Cas expression cassette. In other embodiments, the nucleic acid encoding the first and second guide RNAs may be a different vector than the Cas expression cassette. For example, the first and second guide RNAs may be encoded by a first rAAV vector, and the Cas expression cassette may be encoded by a second rAAV vector. In some embodiments, the target cell may be transfected with both vectors, thus leading to expression of the self-limiting CRISPR-Cas system.

In some embodiments, the Cas protein cleaves the target DNA molecule at sites flanking a mutation (e.g., a deep intronic mutation) thereby excising a portion of the target DNA comprising the mutation. For example, a DNA repair process such as non-homologous end joining (NHEJ) may repair the cleaved DNA sequence by joining the cleaved ends, thereby excising the portion of the target DNA comprising the deep intronic mutation. In other examples, homologous DNA repair may repair the cleaved DNA sequence, particularly if a homology template is included. As described and exemplified herein, the use of two guide RNAs that flank a target DNA sequence (e.g., a sequence bearing a deep intronic mutation) allows the excision of a portion of the target DNA sequence, such as the sequence bearing the deep intronic mutation (see also Brandl, C. et al. (2014) *FEBS Open Bio.* 5:26-35; Zheng, Q. et al. (2014) *Biotechniques* 57:115-124 for descriptions of exemplary gene deletion strategies using CRISPR-Cas systems). In some embodiments, the excised portion of the target DNA sequence comprises intronic DNA. In some embodiments, the excised portion of the target DNA sequence consists of only intronic DNA.

In some embodiments, the first and/or the second guide RNAs hybridize to the opposite strands of the target DNA sequences flanking the mutation (e.g., a deep intronic mutation). Without wishing to be bound to theory, it is thought that the first and/or the second guide RNAs may hybridize to the opposite strands of the target DNA sequences located within the intron at any distance away from the deep intronic mutation. In some embodiments, the first and/or the second guide RNAs hybridize to the opposite strands of the target DNA sequences between 1 base pair and about 10,000 base pairs from the deep intronic mutation. In some embodiments, the first and/or the second guide RNAs hybridize to the opposite strands of the target DNA sequences located less than about any of the following distances from the deep intronic mutation (in nucleotides): 10,000; 9,500; 9,000; 8,500; 8,000; 7,500; 7,000; 6,500; 6,000; 5,500; 5,000; 4,500; 4,000; 3,500; 3,000; 2,500; 2,000; 1,500; 1,000; 950; 900; 850; 800; 750; 700; 650; 600; 550; 500; 450; 400; 350; 300; 250; 200; 150; 100; 95; 90; 85; 80; 75, 70, 65, 60, 55, 50, 45, 40, 35, 30, 25, 20, 15, 10, 9, 8, 7, 6, 5, 4; 3; 2; or any value therebetween. In some embodiments, the first and/or the second guide RNAs hybridize to the opposite strands of the target DNA sequences located greater than about any of the following distances from the deep intronic mutation (in nucleotides): 1; 2; 3; 4; 5; 6; 7; 8; 9; 10; 15; 20; 25; 30; 35; 40; 45; 50; 55; 60; 65; 70; 75; 80; 85; 90; 95; 100; 150; 200; 250; 300; 350; 400; 450; 500; 550; 600; 650; 700; 750; 800; 850; 900; 950; 1,000; 1,500; 2,000; 2,500; 3,000; 3,500; 4,000; 4,500; 5,000; 5,500; 6,000; 6,500; 7,000; 7,500; 8,000; 8,500; 9,000; 9,500; or any value therebetween. That is, the first and/or the second guide RNAs may hybridize to the opposite strands of the target DNA sequences located at a distance from the deep intronic mutation that may be any of a range of distances (in nucleotides) having an upper limit of 10,000; 9,500; 9,000; 8,500; 8,000; 7,500; 7,000; 6,500; 6,000; 5,500; 5,000; 4,500; 4,000; 3,500; 3,000; 2,500; 2,000; 1,500; 1,000; 950; 900; 850; 800; 750; 700; 650; 600;

550; 500; 450; 400; 350; 300; 250; 200; 150; 100; 95; 90; 85; 80; 75, 70, 65, 60, 55, 50, 45, 40, 35, 30, 25, 20, 15, 10, 9, 8, 7, 6, 5, 4; 3; 2; or any value therebetween and an independently selected lower limit of 1; 2; 3; 4; 5; 6; 7; 8; 9; 10; 15; 20; 25; 30; 35; 40; 45; 50; 55; 60; 65; 70; 75; 80; 85; 90; 95; 100; 150; 200; 250; 300; 350; 400; 450; 500; 550; 600; 650; 700; 750; 800; 850; 900; 950; 1,000; 1,500; 2,000; 2,500; 3,000; 3,500; 4,000; 4,500; 5,000; 5,500; 6,000; 6,500; 7,000; 7,500; 8,000; 8,500; 9,000; 9,500; or any value therebetween, wherein the lower limit is less than the upper limit.

Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are commonly known in the art.

In some embodiments the Cas protein (e.g., the CRISPR enzyme) is a Cas9 protein. In some embodiments, the unmodified CRISPR enzyme has DNA cleavage activity, such as Cas9. Exemplary Cas9 proteins include without limitation *S. pyogenes* Cas9 (see, e.g., SwissProt database Accession No. Q99ZW2), *S. aureus* Cas9 (see. e.g., GenBank Accession No. CCK74173), *S. thermophilus* Cas9 (see, e.g., SwissProt database Accession No. G3ECR1), *N. meningitidis* Cas9 (see, e.g., UniProt accession number C9X1G5), and *T. denticola* Cas9 (see. e.g., GenBank accession number EMB41078). In some embodiments, the Cas9 is from *S. pyogenes* or *S. pneumoniae*. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence.

In some embodiments, an enzyme coding sequence encoding a Cas protein of the present disclosure is codon optimized for expression in a particular cell, such as a eukaryotic cell. Eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon of the native sequence with codons that are more frequently or most frequently used in the genes of that host cell while maintaining the native amino acid sequence. Various species exhibit particular bias for certain codons of a particular amino acid. Codon usage tables are readily available, for example, at the "Codon Usage Database", and these tables can be adapted in a number of ways (see. e.g., Nakamura. Y. et al. (2000) *Nucleic Acids Res.* 28:292). Computer algorithms for codon optimizing a particular sequence for expression in a particular host cell are also available, such as Gene Forge (Aptagen; Jacobus. Pa.), are also available.

In some embodiments, the Cas protein is a fusion protein comprising one or more heterologous protein domains (e.g., about or more than about 1, 2, 3, 4, 5, 6, 7, 8, 9, 10, or more domains in addition to the CRISPR enzyme). A Cas fusion protein may comprise any additional protein sequence, and optionally a linker sequence between any two domains. Examples of protein domains that may be fused to a Cas protein include, without limitation, epitope tags, reporter gene sequences, and protein domains having one or more of the following activities: methylase activity, demethylase activity, transcription activation activity, transcription repression activity, transcription release factor activity, histone modification activity. RNA cleavage activity and nucleic acid binding activity. Examples of epitope tags include without limitation histidine (His) tags. V5 tags. FLAG tags, influenza hemagglutinin (HA) tags, Myc tags. VSV-G tags, and thioredoxin (Trx) tags. Examples of reporter genes include without limitation glutathione-5-transferase (GST), horseradish peroxidase (HRP), chloramphenicol acetyltransferase (CAT) beta-galactosidase, beta-glucuronidase, luciferase, and fluorescent proteins (e.g., GFP, CFP, YFP, BFP, etc.). A Cas protein may be fused to a gene sequence encoding a protein or a fragment of a protein that bind DNA molecules or bind other cellular molecules, including but not limited to maltose binding protein (MBP), S-tag. Lex A DNA binding domain (DBD) fusions, GAL4A DNA binding domain fusions, and herpes simplex virus (HSV) BP16 protein fusions. In some embodiments, the Cas protein is modified for enhanced function.

In some embodiments, the Cas protein is a mutant Cas protein. In some embodiments, the Cas protein (e.g., a Cas9 protein) is a nickase mutant (Ran et al., 2013 *Cell* 156(6): 1380-9). In some embodiments, a Cas9 nickase mutant is used with pairs of guide RNAs to introduce targeted double-strand breaks with reduced off-target DNA cleavage.

In some embodiments, the Cas protein is a high-fidelity Cas protein variant harboring amino acid alterations and displaying robust on-target activity but negligible off-target cleavage (Slaymaker, I. M. et al. (2016) *Science* 351(6268): 84-88; Kleinstiver. B. P. et al. (2016) *Nature* 529:490-495).

In some embodiments, the CRISPR-Cas system further comprises one or more nuclear localization signal(s) (NLS (s)). For example, the Cas protein (e.g., a Cas9 protein) may comprise one or more NLS(s). Exemplary plasmids including a Cas9 with an NLS may be found in Ran. F. A. et al. (2013) *Nat. Protoc.* 8:2281-2308. A variety of NLSs suitable for a range of host cells are known in the art. For example and without limitation, the NLS may be an SV40 NLS (e.g., as described in Mali. P., et al. (2013) *Science* 339(6121): 823-6), an SV40 Large T-antigen monopartite NLS, a nucleoplasmin NLS, and an hnRNP A1 NLS. Exemplary NLS sequences that may be used include without limitation PKKKRKV (SEQ ID NO:26) or PKKKRKVEDPKKKRKVD (SEQ ID NO:27) (see. e.g., Jinek. M. et al. (2013) *eLife* 2:e00471).

Formation of a CRISPR complex (comprising a guide sequence hybridized to the opposite strand of a target sequence and complexed with one or more Cas proteins) typically results in cleavage of one or both strands in or near (e.g. within 1, 2, 3, 4, 5, 6, 7, 8, 9, 10, 20, 50, or more base pairs from) the target sequence in an endogenous CRISPR system. The tracr sequence, which may comprise all or a portion of a wild-type tracr sequence, is also thought to be able to form part of a CRISPR complex, such as by hybridization along at least a portion of the tracr sequence to all or a portion of a tracr mate sequence. e.g., a tracr mate sequence operably linked to a guide sequence.

In general, a tracr mate sequence may include any sequence that has sufficient complementarity with a tracr sequence to promote excision of a guide sequence flanked by tracr mate sequences in a cell containing the corresponding tracr sequence; formation of a CRISPR complex comprising the tracr mate sequence hybridized to the tracr sequence at a target sequence; or both. In some embodiments, the tracr sequence has sufficient complementarity to a tracr mate sequence to hybridize and participate in formation of a CRISPR complex. As described below with respect to target sequences, it is believed that complementarity sufficient at least to be functional is needed (i.e., complete complementarity between the tracr and tracr mate sequences is not required).

Generally, degree of complementarity refers to the optimal alignment of the tracr mate sequence and tracr sequence, along the length of the shorter of the two sequences. Optimal alignment may be determined by any suitable alignment algorithm (e.g., as described herein), and may further account for secondary structures, such as self-complementarity within either the tracr sequence or tracr mate sequence. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence has at least 50%, 60%, 70%, 80%, 90%, 95% or 99% of sequence complementarity along the length of the tracr mate sequence when optimally aligned (e.g., as determined by any of the exemplary alignment methods described herein).

Without wishing to be bound to theory, it is thought that any desired target DNA sequence of interest may be targeted by an sgRNA guide sequence, and that the only requirement for a target DNA sequence is the presence of a protospacer-adjacent motif (PAM) adjacent to the sgRNA target sequence (Mali. P., et al. (2013) *Science* 339(6121):823-6). Different Cas complexes are known to have different PAM motifs. For example, Cas9 from *Streptococcus pyogenes* has a GG dinucleotide PAM motif. For further examples, the PAM motif of *S, aureus* Cas9 is GRRT in which R is a purine (A or G), the PAM motif of *N, meningitidis* Cas9 is GATT, the PAM motif of *S, thermophilus* Cas9 is AGAA, and the PAM motif of *T. denticola* Cas9 is AAAAC.

In general, a guide sequence may be any polynucleotide sequence having sufficient similarity with a target polynucleotide sequence to hybridize with the opposite strand of the target sequence and direct sequence-specific binding of a CRISPR complex to the target sequence. In some embodiments, the degree of identity between a guide sequence and its corresponding target sequence is about or more than about 50%, 60%, 75%, 80%, 85%, 90%, 95%, 97.5%, 99%, or more when optimally aligned using a suitable alignment algorithm. Optimal alignment may be determined with the use of any suitable algorithm for aligning sequences; non-limiting examples include the Smith-Waterman algorithm, the Needleman-Wunsch algorithm, algorithms based on the Burrows-Wheeler Transform (e.g, the Burrows Wheeler Aligner), ClustalW, Clustal X. BLAT. Novoalign (Novocraft Technologies, ELAND (Illumina, San Diego, Calif.), SOAP (available at soap.genomics.org.cn), Maq (available at maq.sourceforge.net), and the like.

In some embodiments, a guide sequence is about or more than about any one of 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about any one of 75, 50, 45, 40, 35, 30, 25, 20, 15, 12, or fewer nucleotides in length. Assays for determining the ability of a guide sequence to direct sequence-specific binding of a CRISPR complex to a target sequence are known in the art. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, e.g., as described in U.S. Pat. No. 8,697,359.

In some embodiments, a guide RNA of the present disclosure (e.g., a first guide RNA) comprises the sequences of SEQ ID NO:41 (for SpCas9), SEQ ID NO:45 (for SaCas9), SEQ ID NO:46 (for SaCas9), or SEQ ID NO:47 (for SaCas9). In some embodiments, a guide RNA of the present disclosure (e.g., a first guide RNA) comprises the sequence of SEQ ID NO:19 (for SpCas9), SEQ ID NO:50 (for SaCas9), SEQ ID NO:51 (for SaCas9), or SEQ ID NO:52 (for SaCas9). In some embodiments, the guide RNA comprises 1, 2, 3, 4, or 5 substitutions, deletions or insertions of the sequences of SEQ ID NO:41 (for SpCas9), SEQ ID NO:45 (for SaCas9), SEQ ID NO:46 (for SaCas9), SEQ ID NO:47 (for SaCas9), SEQ ID NO: 19 (for SpCas9), SEQ ID NO:50 (for SaCas9), SEQ ID NO:51 (for SaCas9), or SEQ ID NO:52 (for SaCas9) while maintaining its function as a guide RNA for Cas cleavage of the CEP290 gene. In some embodiments, the guide RNA is a variant of the guide RNA of SEQ ID NO:41 (for SpCas9), SEQ ID NO:45 (for SaCas9), SEQ ID NO:46 (for SaCas9), SEQ ID NO:47 (for SaCas9), SEQ ID NO:19 (for SpCas9), SEQ ID NO:50 (for SaCas9), SEQ ID NO:51 (for SaCas9), or SEQ ID NO:52 (for SaCas9) with enhanced function as a guide RNA for Cas cleavage of the CEP290 gene.

In some embodiments, a guide RNA of the present disclosure (e.g., a second guide RNA) comprises the sequences of SEQ ID NO:42 (for SpCas9), SEQ ID NO:43 (for SpCas9), SEQ ID NO:44 (for SpCas9), SEQ ID NO:48 (for SaCas9), or SEQ ID NO:49 (for SaCas9). In some embodiments, a guide RNA of the present disclosure (e.g., a second guide RNA) comprises the sequences of SEQ ID NO:20 (for SpCas9), SEQ ID NO:21 (for SpCas9), SEQ ID NO:22 (for SpCas9), SEQ ID NO:53 (for SaCas9), or SEQ ID NO:54 (for SaCas9). In some embodiments, the guide RNA comprises 1, 2, 3, 4, or 5 substitutions, deletions or insertions of the sequences of SEQ ID NO:13, SEQ ID NO:14, SEQ ID NO: 15, SEQ ID NO: 16, SEQ ID NO:17 or SEQ ID NO: 18 while maintaining its function as a guide RNA for Cas cleavage of the CEP290 gene. In some embodiments, the guide RNA is a variant of the guide RNA of SEQ ID NO:42 (for SpCas9), SEQ ID NO:43 (for SpCas9), SEQ ID NO:44 (for SpCas9), SEQ ID NO:48 (for SaCas9), SEQ ID NO:49 (for SaCas9), SEQ ID NO:20 (for SpCas9), SEQ ID NO:21 (for SpCas9), SEQ ID NO:22 (for SpCas9), SEQ ID NO:53 (for SaCas9), or SEQ ID NO:54 (for SaCas9) with enhanced function as a guide RNA for Cas cleavage of the CEP290 gene.

In some embodiments, the tracr sequence and tracr mate sequence are contained within a single transcript, such that hybridization between the two produces a transcript having a secondary structure (e.g., a hairpin). In some embodiments, loop forming sequences for use in hairpin structures are four nucleotides in length. In some embodiments, the loop forming sequences have the sequence GAAA. However, longer or shorter loop sequences may be used, as may alternative sequences. Examples of other loop forming sequences include without limitation CAAA and AAAG. In some embodiments, the transcript or transcribed polynucleotide sequence has at least two or more hairpins, e.g, two, three, four or five hairpins. In some embodiments, the single transcript further includes a transcription termination sequence. e.g., a polyT sequence such as six T nucleotides.

IV. Deep Intronic Mutations

Certain aspects of the present disclosure relate to deep intronic mutations. As described above, a deep intronic mutation may lead to the aberrant inclusion of intronic sequence in a mature (e.g., spliced) mRNA. For example, a deep intronic mutation may introduce a splice donor site, splice acceptor site, or a splicing enhancer site in a gene. As a result, intronic sequence may be included as a cryptic exon. This typically results in a mutated polypeptide, particularly if the cryptic exon includes a frameshift mutation or premature stop codon.

As described above, a deep intronic mutation refers to a mutation outside of the wild-type splice acceptor and splice donor sequences, i.e., as opposed to a mutation at an endogenous splice acceptor or splice donor. Typically, a deep intronic mutation occurs at some distance from the endogenous splice acceptor/splice donor sites.

In some embodiments, a deep intronic mutation is located at least about 100 nucleotides from a 5' splice donor site of the gene. In some embodiments, a deep intronic mutation is located at least about 100 nucleotides from a 3' splice acceptor site of the gene. In some embodiments, a deep intronic mutation is located at least about 100 nucleotides from a 5' splice donor and at least about 100 nucleotides from a 3' splice acceptor site of the gene. In some embodiments, a deep intronic mutation occurs at more than about 100 nucleotides, more than about 150 nucleotides, more than about 200 nucleotides, more than about 250 nucleotides, more than about 300 nucleotides, more than about 350 nucleotides, more than about 400 nucleotides, more than about 450 nucleotides, more than about 500 nucleotides, more than about 550 nucleotides, more than about 600 nucleotides, more than about 650 nucleotides, more than about 700 nucleotides, more than about 750 nucleotides, more than about 800 nucleotides, more than about 850 nucleotides, more than about 900 nucleotides, more than about 950 nucleotides, more than about 1,000 nucleotides, more than about 1,500 nucleotides, more than about 2,000 nucleotides, more than about 2,500 nucleotides, more than about 3,000 nucleotides, more than about 3,500 nucleotides, more than about 4,000 nucleotides, more than about 4,500 nucleotides, more than about 5,000 nucleotides, more than about 5,500 nucleotides, more than about 6,000 nucleotides, more than about 6,500 nucleotides, more than about 7,000 nucleotides, more than about 7,500 nucleotides, more than about 8,000 nucleotides, more than about 8,500 nucleotides, more than about 9,000 nucleotides, more than about 9,500 nucleotides, more than about 10,000 nucleotides, more than about 15,000 nucleotides, more than about 20,000 nucleotides, more than about 25,000 nucleotides, more than about 30,000 nucleotides, more than about 35,000 nucleotides, more than about 40,000 nucleotides, more than about 45,000 nucleotides, more than about 50,000 nucleotides, more than about 55,000 nucleotides, more than about 60,000 nucleotides, more than about 65,000 nucleotides, more than about 70,000 nucleotides, more than about 75,000 nucleotides, more than about 80,000 nucleotides, or more than about 85,000 nucleotides from an endogenous splice acceptor and/or splice donor site (e.g., a 5' splice donor and/or 3' splice acceptor site).

In some embodiments, a deep intronic mutation occurs at a distance from an endogenous splice acceptor and/or splice donor site (e.g., a 5' splice donor site or 3' splice acceptor) that is less than about any of the following distances (in nucleotides): 85,000; 80,000; 75,000; 70,000; 65,000; 60,000; 55,000; 50,000; 45,000; 40,000; 35,000; 30,000; 25,000; 20,000; 15,000; 10,000; 9,500; 9,000; 8,500; 8,000; 7,500; 7,000; 6,500; 6,000; 5,500; 5,000; 4,500; 4,000; 3,500; 3,000; 2,500; 2,000; 1,500; 1,000; 950; 900; 850; 800; 750; 700; 650; 600; 550; 500; 450; 400; 350; 300; 250; 200; or 150. In some embodiments, a deep intronic mutation occurs at a distance from an endogenous splice acceptor and/or splice donor site that is greater than about any of the following distances (in nucleotides): 100, 150, 200, 250, 300, 350, 400, 450, 500, 550, 600, 650, 700, 750, 800, 850, 900; 950; 1,000; 1,500; 2,000; 2,500; 3,000; 3,500; 4,000; 4,500; 5,000; 5,500; 6,000; 6,500; 7,000; 7,500; 8,000; 8,500; 9,000; 9,500; 10,000; 15,000; 20,000; 25,000; 30,000; 35,000; 40,000; 45,000; 50,000; 55,000; 60,000; 65,000; 70,000; 75,000; or 80,000. That is, distance from the deep intronic mutation to the endogenous splice acceptor and/or splice donor site (e.g., a 5' splice donor site) may be any of a range of distances (in nucleotides) having an upper limit of 85,000; 80,000; 75,000; 70,000; 65,000; 60,000; 55,000; 50,000; 45,000; 40,000; 35,000; 30,000; 25,000; 20,000; 15,000; 10,000; 9,500; 9,000; 8,500; 8,000; 7,500; 7,000; 6,500; 6,000; 5,500; 5,000; 4,500; 4,000; 3,500; 3,000; 2,500; 2,000; 1,500; 1,000; 950; 900; 850; 800; 750; 700; 650; 600; 550; 500; 450; 400; 350; 300; 250; 200; or 150 and an independently selected lower limit of 100, 150, 200, 250, 300, 350, 400, 450, 500, 550, 600, 650, 700, 750, 800, 850, 900; 950; 1,000; 1,500; 2,000; 2,500; 3,000; 3,500; 4,000; 4,500; 5,000; 5,500; 6,000; 6,500; 7,000; 7,500; 8,000; 8,500; 9,000; 9,500; 10,000; 15,000; 20,000; 25,000; 30,000; 35,000; 40,000; 45,000; 50,000; 55,000; 60,000; 65,000; 70,000; 75,000; or 80,000; wherein the lower limit is less than the upper limit.

Certain aspects of the present disclosure relate to methods, kits, compositions, and viral particles that may be used, inter alia, for treating a disease or disorder associated with a deep intronic mutation, e.g., in a gene of an individual. A variety of deep intronic mutations are known in the art. Exemplary deep intronic mutations associated with disease are provided in Table 1 below (note that the specific mutations, genes, and intron sizes provided in Table 1 refer to human DNA sequence as the reference).

TABLE 1

Exemplary diseases associated with deep intronic mutations.

| Phenotype | Gene | Mutation | Intron size | Pub Med Article # |
|---|---|---|---|---|
| Afibrinogenemia | FGB | IVS1 + 2076A > G | 2675 | 18853456 |
| Alport syndrome | COL4A5 | IVS6 + 1873G > A | 2591 | 12436246 |
| Alport syndrome | COL4A5 | IVS29 + 2750A > G | 8019 | 12436246 |
| Amyotrophic lateral sclerosis | SOD1 | IVS4 + 792C > G | 1095 | 19847927 |
| Ataxia-telangicctasia | ATM | IVS26 + 2968A > G | 3126 | 15643608 |
| Ataxia-telangicctasia | ATM | IVS37 + 1126A > G | 2175 | 8755918 |
| Autosomal recessive polycystic kidney disease | PKHD1 | IVS46 + 653A > G | 12453 | 19021639 |
| Barth syndrome | TAZ | IVS3 + 110G > A | 229 | 11735032 |
| Beta-thalassernia | HBB | IVS2 + 645C > T | 850 | 6585831 |
| Beta-thalassemia | HBB | IVS2 + 705T > G | 850 | 6298782 |
| Beta-thalassemia | HBB | IVS2 + 745C > G | 850 | 6188062 |
| Congenital afibrinogenemia | FGG | IVS6 + 660A > T | 979 | 17854317 |
| Congenital cataracts facial, dysmorphism neuropathy syndrome | CTDP1 | IVS6 + 389C > T | 2505 | 14517542 |
| Congenital disorder of glycosylation, type Ia | PMM2 | IVS7 + 19139C > T | 34617 | 17307006 |
| Congenital disorder of glycosylation, type II | SLC35A1 | IVS6 + 286insCACT | 444 | 15576474 |
| Cystic fibrosis | CFTR | IVS12 + 1634A > G | 2519 | 7534040 |
| Cystic fibrosis | CFTR | IVS19 + 11505C > G | 12808 | 11134243 |
| Cystic fibrosis | CFTR | IVS22 + 12191C > T | 14967 | 1384328 |

TABLE 1-continued

Exemplary diseases associated with deep intronic mutations.

| Phenotype | Gene | Mutation | Intron size | Pub Med Article # |
|---|---|---|---|---|
| Dihydropteridine reductase deficiency | QDPR | IVS3 + 2552A > G | 9078 | 9341885 |
| Fabry disease | GLA | IVS4 + 919G > A | 1719 | 11828341 |
| Familial melanoma | CDKN2A | IVS2 + 105A > G | 2659 | 11726555 |
| Familial platelet disorder with predisposition to acute myelogenous leukemia | CYBB | IVS5 + 979G > 17 | 2140 | 11566256 |
| Familial platelet disorder with predisposition to acute myelogenous leukemia | CYBB | IVS6 + 1657A > G | 2803 | 16516412 |
| Fanconi anemia | BRIP1 | IVS11 + 2767A > T | 3264 | 16116423 |
| Gitelman syndrome | SLC12A3 | IVS13 + 1361C > T | 1551 | 19668106 |
| Growth hormone insensitivity | GHR | IVS6 + 792A > CT | 11204 | 11468686 |
| Friedrich's ataxia | FXN | GAA triplet repeat | 10437 | 9259271 |
| Hearing Loss | MYO6 | IVS23 + 2321T > G | 4185 | 18212818 |
| Hemophilia A | F8 | IVS1 + 1567A > G | 22809 | 18160816 |
| Hemophilia A | F8 | IVS10 + 325A > G | 3903 | 15284851 |
| Hemophilia A | F8 | IVS18 + 530C > T | 1738 | 23809411 |
| Hemophilia A | F8 | IVS18 + 941C > T | 1738 | 23809411 |
| Hereditary megaloblastic anaemia 1 | CUBN | IVS23 + 881C > G | 1320 | 10080186 |
| Hermansky-Pudlak syndrome | HPS3 | IVS16 + 2499G > A | 4111 | 7901342 |
| Homocystinuria | MTRR | IVS6 + 469T > C | 2420 | 20120036 |
| Maple syrup urine disease | DBT | IVS8 – 550A > G | 4057 | 9621512 |
| Marfan syndrome | FBN1 | IVS63 + 375G > T | 2793 | 18795226 |
| Methionine synthase deficiency | MIR | IVS3 + 2305A > G | 2470 | 9683607 |
| Methionine synthase deficiency | MTR | IVS6 + 1088G > A | 2759 | 9683607 |
| Methylmalonic acidemia | MUT | IVS11 + 3691C > A | 7582 | 17966092 |
| Mitochondrial trifunctional protein deficiency | HADHB | IVS7 + 615A > G | 1453 | 18693053 |
| Mucopolysaccharidosis, type II | IDS | IVS7 + 3083A > G | 3215 | 8940265 |
| Multi-minicore disease | RYR1 | IVS100 + 2990A > G | 4438 | 12719381 |
| Muscular dystrophy | DMD | IVS1 + 36846G > A | 191081 | 14659407 |
| Muscular dystrophy | DMD | IVS1 + 36947G > A | 191081 | 17041906 |
| Muscular dystrophy | DMD | IVS2 + 5591T > A | 170318 | 12522557 |
| Muscular dystrophy | DMD | IVS9 + 46806C > T | 52717 | 14659407 |
| Muscular dystrophy | DMD | IVS25 + 2036A > G | 8606 | 12754707 |
| Muscular dystrophy | DMD | IVS25 + 2240A > G | 8606 | 10094556 |
| Muscular dystrophy | DMD | IVS27 + 6298C > A | 7141 | 20485447 |
| Muscular dystrophy | DMD | IVS60 + 80228G > T | 95846 | 14659407 |
| Muscular dystrophy | DMD | IVS62 + 62296A > G | 62581 | 12754707 |
| Muscular dystrophy | DMD | IVS65 + 1215A > G | 2830 | 17041906 |
| Muscular dystrophy | DMD | IVS67 + 2714C > T | 21056 | 20485447 |
| Neurofibromatosis, type I | NF1 | IVS3 + 2025T > G | 4092 | 19241459 |
| Neurofibromatosis, type I | NF1 | IVS39 + 332A > G | 4339 | 8829638 |
| Neurofibromatosis, type I | NF1 | IVS39 + 4060A > G | 4339 | 16470740 |
| Neurofibromatosis, type I | NF1 | IVS54 + 790C > G | 1110 | 19241459 |
| Niemann-Pick disease, type C | NPC1 | IVS9 + 2021G > A | 3030 | 19718781 |
| Ocular albinism, type I | GPR143 | IVS7 + 748G > A | 1618 | 16550551 |
| Ornithine delta-aminotransferase deficiency | OAT | IVS3 + 303C > G | 3007 | 1992472 |
| Predisposition to systemic lupus erythematosus | IRF5 | IVS1 + 198G > T | 4021 | 16642019 |
| Propionic acidemia | PCCA | IVS14 + 2778A > G | 4193 | 17966092 |
| Propionic acidemia | PCCB | IVS6 + 462A > G | 9808 | 17966092 |
| Rhabdoid tumors | SNF5/INI1 | IVS1 + 559A > G | 4493 | 10556283 |
| Schwartz-Jampel syndrome | HSPG2 | IVS6 + 481C > T | 1914 | 16927315 |
| Stickler syndrome | COL2A1 | IVS23 + 135G > A | 371 | 16752401 |
| Systemic lupus erythematosus | MFGES | IVS6 + 936A > G | 1739 | 20213738 |
| Tuberous sclerosis | TSC2 | IVS8 + 281C > T | 1568 | 11068191 |
| Werner syndrome | WRN | IVS18 + 7636A > G | 10659 | 17478382 |
| X-linked hyperimmunoglobulinemia M | CD40L | IVS3 + 1011A > T | 1925 | 15358621 |
| X-linked hypophosphatemia | PHEX | IVS7 + 1268G > T | 2855 | 11502821 |

In some embodiments, the disease or disorder associated with a deep intronic mutation is afibrinogenemia, Alport syndrome, Amyotrophic lateral sclerosis, ataxia telangiectasia, autosomal recessive polycystic kidney disease. Barth syndrome, beta-thalassemia, congenital afibrinogenemia, congenital cataracts facial dysmorphism neuropathy syndrome, congenital disorder of glycosylation type Ia, congenital disorder of glycosylation type II, cystic fibrosis, dihydropteridine reductase deficiency. Fabry disease, familial platelet disorder with predisposition to acute myelogenous leukemia, Fanconi anemia. Gitelman syndrome, growth hormone insensitivity, Friedrich's ataxia, hemophilia A, hereditary megaloblastic anaemia 1. Hermansky-Pudlak syndrome, homocytinuria, maple syrup urine disease, Marfan syndrome, methionine synthase deficiency, methylmalonic academia, mitochondrial trifunctional protein deficiency, mucupolysaccaridosis type II, multi-minicore disease, muscular dystrophy, neurofibromatosis type I. Niemann-Pick disease type C, ocular albinism type I, ornithine delta-aminotransferaase deficiency, predisposition to systemic lupus erythematosus, propionic academia, rhabdoid tumors, Schwartz-Jampel syndrome. Stickler syndrome, systemic lupus erythematosus, tuberous sclerosis, Werner syndrome, X-linked hyperimmunoglobulinemnia M, or X-linked hypophosphatemia. In some embodiments, the deep intronic mutation is a deep intronic mutation presented in Table 1.

In some embodiments, the disease or disorder associated with a deep intronic mutation is an ocular disease. As used herein, the term "ocular disease" is used in the broadest sense and may refer to a disease originating in, or resulting in a pathological condition of, any structure of the eye, including without limitation the cornea, iris, lens, retina, optic nerve, aqueous humor, conjunctiva, one or more ocular muscles, selera, vitreous body, macula, fovea, ciliary body, one or more ligaments or suspensory ligament zonules, pupil, anterior chamber, and/or posterior chamber. Exemplary deep intronic mutations associated with ocular disease are provided in Table 2 below (note that the specific mutations, genes, and intron sizes provided in Table 2 refer to human DNA sequence as the reference).

TABLE 2

Ocular diseases associated with deep intronic mutations.

| Phenotype | Gene | Mutation | Intron size | Pub Med Article # |
|---|---|---|---|---|
| Leber congenital amaurosis | CEP290 | IVS26 + 1655A > G | 5838 | 16909394 |
| Optic atrophy | OPA1 | IVS4b + 364G > A | 1031 | 24970096 |
| Retinitis pigmentosa | PRPF31 | IVS13 + 654C > G | 1992 | 19618371 |
| Retinoblastoma | RB1 | IVS23 + 6594A > G | 7991 | 17299438 |
| Stargardt disease | ABCA4 | IVS30 + 2001G > A | 4396 | 23918662 |
| Usher syndrome | USH1C | VNTR in intron 5 | 182 | 10973247 |
| Usher syndrome | USH2A | IVS40 + 8877A > G | 11020 | 23924366 |
| X-linked retinitis pigmentosa | OFD1 | IVS9 + 706A > G | 1715 | 22619378 |
| X-linked retinitis pigmentosa | RPGR | IVS9 + 363G > A | 2105 | 17405150 |

In some embodiments, the ocular disease is Leber congenital amaurosis, optic atrophy, retinitis pigmentosa, retinoblastoma, Stargardt disease, Usher syndrome, or X-linked retinitis pigmentosa. In some embodiments, the deep intronic mutation is a deep intronic mutation presented in Table 2.

In some embodiments, the ocular disease is Leber congenital amaurosis. Leber Congenital Amaurosis (LCA) refers to a group of ocular disorders characterized by symptoms such as severe vision loss, nystagmus, retinal dysfunction, photophobia, oculodigital sign (e.g., rubbing, poking, and pressing of the eye), and keratoconus. LCA typically presents at birth with profound vision loss and nystagmus. While instances of LCA are typically inherited as an autosomal recessive disorder, mutations in a variety of genetic loci have been implicated. For example, Table 3 lists some of the loci implicated in forms of LCA.

TABLE 3

LCA disease loci.

| Type of LCA | Mutated Gene | Genetic Locus in Humans |
|---|---|---|
| LCA1 | GUCY2D | 17p13.1 |
| LCA2 | RPE65 | 1p31 |
| LCA3 | SPATA7 | 14q31.3 |
| LCA4 | AIPL1 | 17p13.1 |
| LCA5 | LCA5 | 6q14.1 |
| LCA6 | RPGRIP1 | 14q11 |
| LCA7 | CRX | 19q13.3 |
| LCA8 | CRB1 | 1q31-32 |
| LCA9 | NMNAT1 | 1p36 |
| LCA10 | CEP290 | 12q21 |
| LCA11 | IMPDH1 | 7q31.3-q32 |
| LCA12 | RD3 | 1q32.3 |
| LCA13 | RDH12 | 14q24.1 |
| LCA14 | LRAT | 4q31 |
| LCA15 | TULP1 | 6p21.3 |
| LCA16 | KCNJ13 | 4q31 |
| LCA17 | GDF6 | 8q22 |
| LCA18 | PRPH2 | 6p21 |

The most frequent type of LCA is caused by a mutation in CEP290, which encodes a centrosomal protein that plays an important role in centrosome and cilia development (see, e.g., NCBI Gene ID No. 80184 and UniProt ID No. 015078 for exemplary human gene and protein sequences, respectively). CEP290 is essential in the formation of the primary cilium on the cell membrane that plays an important role in the photoreceptors at the back of the retina and in the kidney, brain, and many other organs of the body. CEP290 is also known as MKS4, CT87, POC3, rd16, BBS14, LCA10, JBTS5, NPHP6, SLSN6, and 3H11Ag. In some embodiments, the causative mutation is a c.2991+1655A>G mutation that introduces a cryptic splice donor site, resulting in the inclusion of an aberrant exon with a premature stop codon. In some embodiments, the first guide RNA and second guide RNA guide sequences hybridize to the opposite strands of the target DNA sequences flanking a deep intronic mutation of the centrosomal protein 290 kDa (CEP290) gene. In certain embodiments, the deep intronic mutation is a c.2991+1655A>G mutation. In some embodiments, the CEP290 is a human CEP290 (see, e.g., the human CEP290 sequence according to NCBI Reference Sequence NG_008417). In some embodiments, the CEP290 comprises a deep intronic mutation of the sequence set forth in SEQ ID NO:23.

Certain aspects of the present disclosure further relate to methods for generating an in vitro model of an ocular disease associated with deep intronic mutation in a gene. In some embodiments, the methods include introducing to eukaryotic cells nucleic acid encoding a CRISPR-Cas system, wherein the CRISPR-Cas system comprises i) a single guide RNA to target DNA sequences of an intron in the gene, ii) a nucleotide sequence encoding a Cas protein, iii) a single-stranded oligonucleotide comprising a homology directed repair (HDR) template comprising homology arms flanking a desired intronic mutation and a protospacer adjacent motif (PAM); and isolating cells that comprise the mutation incorporated into gene. Exemplary methods related to this approach are illustrated in the Examples below. As described above. CRISPR-Cas-mediated DNA cleavage may be repaired by NHEJ, resulting in, e.g., excision of a target DNA sequence. However. CRISPR-Cas-mediated DNA cleavage may also be repaired by homology directed repair (HDR), resulting in, e.g., introduction of a sequence present in the HDR template (e.g., an introduced deep intronic mutation). See. e.g., Ran. F. A. et al. (2013) Nat. Protoc. 8:2281-2308. These methods may include any features, aspects, or elements described herein with respect to methods of treatment, viral particles, compositions, and kits.

A homology directed repair (HDR) template may take a variety of forms, such as a double-stranded DNA polynucleotide or a single-stranded DNA oligonucleotide (ssODN). The HDR template may include one or more homology arms flanking a desired intronic mutation. These homology arms may be in the sense or antisense direction, relative to the target locus. In some embodiments, the one or more homology arms may be at least about 40 base pairs, at least about 50 base pairs, at least about 60 base pairs, at least about 70 base pairs, at least about 80 base pairs, at least about 90 base pairs, or at least about 100 base pairs away from the target locus.

The HDR template may also include a protospacer adjacent motif (PAM). In some embodiments, the PAM comprises a mutation to avoid cleavage of the single-stranded oligonucleotide by an expressed Cas protein in the cells. For example, the PAM may be mutated such that the particular expressed Cas protein does not cleave the HDR template, or mutated such that an identifying sequence (e.g., a unique restriction site, as illustrated in the Examples below) is introduced upon CRISPR-Cas-mediated editing of a genomic locus.

Any suitable eukaryotic cell may be used for the in vitro model. In some embodiments, the eukaryotic cell is a mammalian or human cell. In some embodiments, the eukaryotic cell is a cell line, such as a human cell line (e.g., HeLa. A549, 293, and so forth), a mammalian cell line, a vertebrate cell line, or an insect cell line (e.g., Sf9 or S2). In some embodiments, the eukaryotic cell is a retinal cell (e.g., a WERI cell), such as a photoreceptor cell.

V. Methods of Delivery

Certain aspects of the present disclosure relate to treating a disease or disorder associated with a deep intronic mutation in a gene of an individual. In some aspects, the invention provides methods for treating a disease or disorder associated with a deep intronic mutation in a gene of an individual comprising administering to the individual a therapeutically effective amount of a composition of the present disclosure, e.g., a composition comprising nucleic acid encoding an engineered, non-naturally occurring CRISPR-Cas system of the present disclosure. In some embodiments, the nucleic acid encoding the engineered, non-naturally occurring CRISPR-Cas system may be DNA or RNA. In some embodiments, the Cas protein is delivered as a protein.

Vectors

In some embodiments, the nucleic acid encoding one or more of the first guide RNA, the second guide RNA or the Cas protein are located on the same or different vectors of the system. In some embodiments, one or more vectors driving expression of one or more elements of a CRISPR system are introduced into a cell such that expression of the elements of the CRISPR system direct formation of a CRISPR complex at one or more target sites. For example, a Cas enzyme, a guide sequence linked to a tracr-mate sequence, and a tracr sequence may each be operably linked to separate regulatory elements on separate vectors. Alternatively, two or more of the elements described above may be expressed from the same or different regulatory elements, and/or may be combined in a single vector, optionally with one or more additional vectors providing any components of the CRISPR system not included in the first vector. CRISPR system elements that are combined in a vector may be arranged in any suitable orientation. For example, the coding sequence of one element may be located on the same or opposite strand of the coding sequence of a second element, and/or oriented in the same or opposite direction.

In some embodiments, a single promoter drives expression of a transcript encoding a Cas protein and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the Cas protein, guide sequence, tracr mate sequence, and tracr sequence are operably linked to and expressed from the same promoter. In some embodiments, the first guide RNA, the second guide RNA and/or the nucleic acid encoding the Cas protein are operably linked to one or more regulatory control elements and/or promoters.

In some embodiments, the vector is a plasmid.

In some embodiments, the first guide RNA, the second guide RNA and the Cas protein are expressed in eukaryotic cells. In some embodiments, the first guide RNA, the second guide RNA and the Cas protein are operably linked to one or more promoters that allow for expression in a eukaryotic cell. A variety of promoters that are expressed in eukaryotic cells are known in the art. Exemplary promoters are provided without limitation below.

In some embodiments, the first guide RNA and/or the second guide RNA is operably linked to a RNA polymerase III promoter. RNA polymerase III promoters may include a full-length promoter or a fragment thereof sufficient to drive transcription by RNA polymerase III. For a more detailed description of RNA polymerase III promoter types, structural features, and interactions with RNA polymerase III, as well as suitable RNA polymerase III promoters, see Schramm. L, and Hernandez. N. (2002) *Genes Dev.* 16:2593-620. Any suitable RNA polymerase III promoter known in the art may be used, including without limitation promoters for a tRNA, 5S RNA, U6 snRNA, H1, 7SK, RNase P, the RNA component of the Signal Recognition Particle, and snoRNAs (see, e.g., Ma, H. et al. (2014) *Mol. Ther. Nucleic Acids* 3:e161). In some embodiments, the RNA polymerase III promoter is a U6, H1, or 7SK promoter. In some embodiments, the first guide RNA and/or the second guide RNA is operably linked to a RNA polymerase III terminator. Examples of RNA polymerase III terminators may include, without limitation, a string of uridine nucleotides of at least 5-6 bases in length (for more information on RNA polymerase III terminators, see Marck, C., et al. (2006) *Nucleic Acids Res* 34(6):1816-35).

In some embodiments, the nucleic acid encoding the Cas protein is operably linked to a RNA polymerase II promoter. RNA polymerase II promoters may include a full-length promoter or a fragment thereof sufficient to drive transcription by RNA polymerase II. Any suitable RNA polymerase II promoter known in the art may be used, including without limitation the cytomegalovirus (CMV) immediate early promoter, the minimal promoter fragment derived from the CMV promoter (minCMV promoter), the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit β-globin promoter (CAG promoter; Niwa et al., *Gene.* 1991, 108(2):193-9) and the elongation factor 1-alpha promoter (EF1-alpha) promoter (Kim et al., *Gene,* 1990, 91(2):217-23 and Guo et al., *Gene Ther.,* 1996, 3(9):802-10). In some embodiments, the promoter comprises a human β-glucuronidase promoter or a cytomegalovirus enhancer linked to a chicken β-actin (CBA) promoter. The promoter can be a constitutive, inducible or repressible promoter. In some embodiments, the promoter is capable of expressing the heterologous nucleic acid in a cell of the eye. In some embodiments, the promoter is capable of expressing the heterologous nucleic acid in photoreceptor cells or RPE. In embodiments, the promoter is a rhodopsin kinase (RK) promoter; e.g., a human RK promoter. In some embodiments, the promoter is an opsin promoter; e.g., a human opsin promoter or a mouse opsin promoter. In some embodiments, the promoter is a rod opsin promoter, a cone opsin promoter, a beta phosphodiesterase (PDE) promoter, a retinitis pigmentosa (RP1) promoter, or an interphotoreceptor retinoid-binding protein gene (IRBP) promoter.

Inducible promoters allow regulation of gene expression and can be regulated by exogenously supplied compounds, environmental factors such as temperature, or the presence of a specific physiological state. e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., *Proc. Natl. Acad. Sci. USA,* 93:3346-3351 (1996)), the tetracycline-repressible system (Gossen et al., *Proc. Natl. Acad. Sci. USA,* 89:5547-5551 (1992)), the tetracycline-inducible system (Gossen et al., *Science,* 268:1766-1769 (1995), see also Harvey et al., *Curr. Opin. Chem. Biol.,* 2:512-518 (1998)), the RU486-inducible system (Wang et al., *Nat. Biolech.,* 15:239-243 (1997) and Wang et al., *Gene Ther.,* 4:432-441 (1997)) and the rapamycin-inducible system (Magari et al., *J. Clin. Invest.,* 100:2865-2872 (1997)). Still other types of inducible promoters which may be useful in this context are those which are regulated by a specific physiological state. e.g., temperature, acute phase, a particular differentiation state of the cell, or in replicating cells only.

In another embodiment, the native promoter, or fragment thereof, for the transgene will be used. The native promoter can be used when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: neuronal such as neuron-specific enolase (NSE) promoter (Andersen et al., *Cell. Mol. Neurobiol.,* 13:503-15 (1993)), neurofilament light-chain gene promoter (Piccioli et al., *Proc. Natl. Acad. Sci. USA,* 88:5611-5 (1991)), and the neuron-specific vgf gene promoter (Piccioli et al., *Neuron,* 15:373-84 (1995)). In some embodiments, the tissue-specific promoter is a promoter of a gene selected from: neuronal nuclei (NeuN), glial fibrillary acidic protein (GFAP), adenomatous polyposis coli (APC), and ionized calcium-binding adapter molecule 1 (Iba-1). Other appropriate tissue specific promoters will be apparent to the skilled artisan. In some embodiments, the promoter is a chicken Beta-actin promoter.

The present invention contemplates the use of a recombinant viral genome for introduction of one or more nucleic acid sequences (e.g., a guide RNA and/or a nucleotide sequence encoding a Cas protein) for packaging into a viral particle, e.g., a viral particle described below. The recombinant viral genome may include any element to establish the expression of the guide RNA and/or nucleotide sequence encoding a Cas protein, for example, a promoter, an ITR, a ribosome binding element, terminator, enhancer, selection marker, intron, polyA signal, and/or origin of replication. Exemplary viral genome elements and delivery methods for a range of viral particles are described in greater detail below.

Non-Viral Delivery Systems

Conventional non-viral gene transfer methods may also be used to introduce nucleic acids into cells or target tissues. Non-viral vector delivery systems include DNA plasmids. RNA (e.g., a guide RNA or a nucleotide sequence encoding a Cas protein), naked nucleic acid (e.g., DNA or RNA), and nucleic acid (e.g., DNA or RNA) complexed to a delivery system. For example, the vector may be complexed to a lipid (e.g., a cationic or neutral lipid), a liposome, a polycation, a nanoparticle, or an agent that enhances the cellular uptake of nucleic acid. The vector may be complexed to an agent suitable for any of the delivery methods described herein.

Methods of non-viral delivery of nucleic acids include lipofection, electroporation-based transfection methods sold under the trademark NUCLEOFECTION®, microinjection, biolistics, nanoparticles (see, e.g., Jin, S. et al. (2009) *Methods Mol. Biol.* 544:547-557), virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Lipofectamine®, Transfectam™, and Lipofectin™). Cationic and neutral lipids that are suitable for efficient receptor-recognition lipofection of polynucleotides include those of Felgner, WO 91/17424; WO 91/16024.

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Other compounds that may be complexed with a vector of the present disclosure include without limitation a cationic peptide (e.g., poly-L-lysine), a salt (e.g., calcium phosphate), DEAE dextran, a dendrimer (e.g., polyamidoamine or PAMAM), polyethylene glycol, polyethylenimine (PEI) and conjugates thereof, and the like. For a more detailed discussion of such agents, see. e.g., Luo. D, and Saltzman. W. M. (2000) *Nature Biotechnology* 18:33-37.'

In some embodiments, the nucleic acid is in a pharmaceutical formulation. In some embodiments, the pharmaceutical formulation includes a pharmaceutically acceptable carrier. Such carriers are well known in the art (sec. e.g., Remington's Pharmaceutical Sciences, 15th Edition, pp. 1035-1038 and 1570-1580). In some embodiments, the pharmaceutical compositions comprising a nucleic acid described herein and a pharmaceutically acceptable carrier is suitable for ocular injection. Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. The pharmaceutical composition may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidosage forms. The compositions are generally formulated as sterile and substantially isotonic solution.

Viral Particles

In some embodiments, the vector is a recombinant adeno-associated virus (rAAV) vector, a recombinant adenoviral vector, a recombinant lentiviral vector or a recombinant herpes simplex virus (HSV) vector.

rAAV Particles

In some embodiments, the vector is a recombinant AAV (rAAV) vector. In some embodiments, the nucleic acid encoding one of more of the first guide RNA, the second guide RNA, or the Cas protein is flanked by one or more AAV inverted terminal repeat (ITR) sequences. In some embodiments, the viral particle is a recombinant AAV particle comprising a nucleic acid comprising a transgene flanked by one or two ITRs. In some embodiments, the nucleic acid encoding one of more of the first guide RNA, the second guide RNA, or the Cas protein is flanked by two AAV ITRs.

In some embodiments, the nucleic acid comprises one or two guide RNAs of the present disclosure and/or a nucleotide sequence encoding a Cas protein of the present disclosure operatively linked components in the direction of transcription, control sequences including transcription initiation and termination sequences, thereby forming an expression cassette. The expression cassette is flanked on the 5' and 3' end by at least one functional AAV ITR sequence. By "functional AAV ITR sequences" it is meant that the ITR sequences function as intended for the rescue, replication and packaging of the AAV virion. See Davidson et al., PNAS, 2000, 97(7)3428-32; Passini et al., J. Virol., 2003, 77(12):7034-40; and Pechan et al., Gene Ther., 2009, 16:10-16, all of which are incorporated herein in their entirety by reference. For practicing some aspects of the invention, the recombinant vectors comprise at least all of the sequences of AAV essential for encapsidation and the physical structures for infection by the rAAV. AAV ITRs for use in the vectors of the invention need not have a wild-type nucleotide sequence (e.g., as described in Kotin, Hum. Gene Ther., 1994, 5:793-801), and may be altered by the insertion, deletion or substitution of nucleotides or the AAV ITRs may be derived from any of several AAV serotypes. More than 40 serotypes of AAV are currently known, and new serotypes and variants of existing serotypes continue to be identified. See Gao et al., PNAS. 2002, 99(18): 11854-6; Gao et al., PNAS, 2003, 100(10):6081-6; and Bossis et al., J. Virol., 2003, 77(12):6799-810.

Use of any AAV serotype is considered within the scope of the present invention. In some embodiments, a rAAV vector is a vector derived from an AAV serotype, including without limitation, AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV ITRs or the like. In some embodiments, the nucleic acid in the AAV comprises an ITR of AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV or the like. In certain embodiments, the AAV ITRs are AAV2 ITRs.

In some embodiments, a vector may include a stuffer nucleic acid. In some embodiments, the stuffer nucleic acid may encode a green fluorescent protein. In some embodiments, the stuffer nucleic acid may be located between the promoter and the one or more of the one or two guide RNAs of the present disclosure and/or a nucleotide sequence encoding a Cas protein of the present disclosure.

In some aspects, the invention provides viral particles comprising a recombinant self-complementing genome. In some embodiments, the vector is a self-complementary vector, AAV viral particles with self-complementing genomes and methods of use of self-complementing AAV genomes are described in U.S. Pat. Nos. 6,596,535; 7,125, 717; 7,765,583; 7,785,888; 7,790,154; 7,846,729; 8,093, 054; and 8,361,457; and Wang Z., et al., (2003) Gene Ther 10:2105-2111, each of which are incorporated herein by reference in its entirety. A rAAV comprising a self-complementing genome will quickly form a double stranded DNA molecule by virtue of its partially complementing sequences (e.g., complementing coding and non-coding strands of a transgene). In some embodiments, the invention provides an AAV viral particle comprising an AAV genome, wherein the rAAV genome comprises a first heterologous polynucleotide sequence (e.g., one or two guide RNAs of the present disclosure and/or a nucleotide sequence encoding a Cas protein of the present disclosure) and a second heterologous polynucleotide sequence (e.g., the noncoding or antisense strand of the one or two guide RNAs of the present disclosure and/or a nucleotide sequence encoding a Cas protein of the present disclosure) wherein the first heterologous polynucleotide sequence can form intrastrand base pairs with the second polynucleotide sequence along most or all of its length.

In some embodiments, the first heterologous polynucleotide sequence and a second heterologous polynucleotide sequence are linked by a sequence that facilitates intrastrand basepairing; e.g., a hairpin DNA structure. Hairpin structures are known in the art, for example in siRNA molecules. In some embodiments, the first heterologous polynucleotide sequence and a second heterologous polynucleotide sequence are linked by a mutated ITR (e.g., the right ITR). The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid; an AAV ITR, the first heterologous polynucleotide sequence including regulatory sequences, the mutated AAV ITR, the second heterologous polynucleotide in reverse orientation to the first heterologous polynucleotide and a third AAV ITR.

In some embodiments, the first heterologous nucleic acid sequence and a second heterologous nucleic acid sequence are linked by a mutated ITR (e.g., the right ITR). In some embodiments, the ITR comprises the polynucleotide sequence 5'-CACTCCCTCTCTGCGCGCTCGCTCGCTC A CTGAGGCCGGGGCGACCAAAGGTCGCCCACGCC-CGGGCTTTGCCCGGGCG-3' (SEQ ID NO:24). The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid: an AAV ITR, the first heterologous polynucleotide sequence including regulatory sequences, the mutated AAV ITR, the second heterologous polynucleotide in reverse orientation to the first heterologous polynucleotide and a third AAV ITR.

In some embodiments, the vector is encapsidated in a viral particle. In some embodiments, the viral particle is a recombinant AAV viral particle comprising a recombinant AAV vector. Different AAV serotypes are used to optimize transduction of particular target cells or to target specific cell types within a particular target tissue (e.g., an ocular tissue). A rAAV particle can comprise viral proteins and viral nucleic acids of the same serotype or a mixed serotype. For example, in some embodiments a rAAV particle can comprise AAV2 capsid proteins of the invention and at least one AAV2 ITR or it can comprise AAV2 capsid proteins and at least one AAV1 ITR. Any combination of AAV serotypes for production of a rAAV particle is provided herein as if each combination had been expressly stated herein. In some embodiments, the invention provides rAAV particles comprising an AAV2 capsid of the invention. In some embodiments, the invention provides rAAV particles comprising an AAVrh8R capsid of the invention.

In some embodiments, the rAAV particles comprise an AAV1 capsid, an AAV2 capsid, an AAV3 capsid, an AAV4 capsid, an AAV5 capsid, an AAV6 capsid (e.g., a wild-type AAV6 capsid, or a variant AAV6 capsid such as ShH10, as described in U.S. PG Pub. 2012/0164106), an AAV7 capsid, an AAV8 capsid, an AAVrh8 capsid, an AAVrh8R capsid, an AAV9 capsid (e.g., a wild-type AAV9 capsid, or a modified AAV9 capsid as described in U.S. PG Pub. 2013/0323226), an AAV10 capsid, an AAVrh10 capsid, an AAV11 capsid, an AAV12 capsid, a tyrosine capsid mutant, a heparin binding capsid mutant, an AAV2R471A capsid, an AAVAAV2/2-7m8 capsid, an AAV DJ capsid (e.g., an AAV-DJ/8 capsid, an AAV-DJ/9 capsid, or any other of the capsids described in U.S. PG Pub. 2012/0066783), an AAV2 N587A capsid, an AAV2 E548A capsid, an AAV2 N708A capsid, an AAV V708K capsid, a goat AAV capsid, an AAV1/AAV2 chimeric capsid, a bovine AAV capsid, a mouse AAV capsid, a rAAV2/HBoV1 capsid, or an AAV capsid described in U.S. Pat. No. 8,283,151 or International Publication No. WO/2003/042397. In some embodiments, a mutant capsid protein maintains the ability to form an AAV capsid. In some embodiments, the rAAV particle comprises AAV5 tyrosine mutant capsid (Zhong L. et al., (2008) *Proc Natl Acad Sci USA* 105(22):7827-7832. In further embodiments, the rAAV particle comprises capsid proteins of an AAV serotype from Clades A-F (Gao, et al., *J. Virol.* 2004, 78(12):6381). In some embodiments, the rAAV particle comprises an AAV1 capsid protein or mutant thereof. In other embodiments, the rAAV particle comprises an AAV2 capsid protein or mutant thereof. In some embodiments, the AAV serotype is AAV1, AAV2, AAV5, AAV6, AAV7, AAV8, AAVrh8, AAVrh8R, AAV9, AAV10, or AAVrh10. In some embodiments, the rAAV particle comprises an AAV serotype 1 (AAV1) capsid. In some embodiments, the rAAV particle comprises an AAV serotype 2 (AAV2) capsid. In some embodiments, the recombinant AAV viral particle comprises an AAV1, AAV2, AAV8, AAVrh8R, AAV9, and/or AAVrh10 capsid. In some embodiments, the AAV1, AAV2, AAV8, AAVrh8R, AAV9, and/or AAVrh10 capsid comprises a tyrosine mutation or a heparan binding mutation. e.g., as described below.

The capsid of AAV (e.g., AAV2, AAVrh8R, etc.) is known to include three capsid proteins: VP1, VP2, and VP3. These proteins contain significant amounts of overlapping amino acid sequence and unique N-terminal sequences. An AAV2 capsid includes 60 subunits arranged by icosahedral symmetry (Xie. Q., et al. (2002) *Proc. Natl. Acad. Sci.* 99(16): 10405-10). VP1, VP2, and VP3 have been found to be present in a 1:1:10 ratio.

The binding between AAV2 capsid proteins and HSPG is known to occur via electrostatic interactions between basic AAV2 capsid protein residues and negatively charged glycosaminoglycan residues (Opie, S R et al., (2003) *J. Virol.* 77:6995-7006; Kern. A et al., (2003) *J. Virol.* 77:11072-11081). Specific capsid residues implicated in these interactions include R484, R487, K532, R585, and R588. Mutations in these residues have been shown to reduce AAV2 binding to Hela cells and heparan itself (Opie, S R et al., (2003) *J. Virol.* 77:6995-7006; Kern, A et al., (2003) *J. Virol.* 77:11072-11081; WO 2004/027019 A2, U.S. Pat. No. 7,629,322). Further, without wishing to be bound by theory, it is thought that amino acid substitution(s) at one or more of the residues corresponding to amino acids 484, 487, 532, 585 or 588, numbering based on VP1 numbering of AAV2 may modulate the transduction properties of AAV capsid types that do not bind to HSPG, or may modulate the transduction properties of AAV capsid types independent from their ability to bind HSPG.

In some embodiments, a rAAV particle bears a mutation in a capsid protein at a residue that interacts with HSPG or at one or more of the residues corresponding to amino acids 484, 487, 532, 585 or 588, numbering based on VP1 numbering of AAV2. Accordingly, in some embodiments, upon delivery the heterologous nucleic acid encoded by the rAAV vector is expressed at an increased level of expression, as compared to the level of expression of a heterologous nucleic acid of a rAAV particle comprising a rAAV capsid comprising a reference rAAV capsid protein (e.g., a wild-type rAAV capsid protein). In some embodiments, the expression of the nucleic acid is increased by at least about 10%, at least about 25%, at least about 50%, at least about 75%, or at least about 100%. In some embodiments, upon delivery the rAAV particle causes reduced neuroinflammation, as compared to a rAAV particle comprising a reference rAAV capsid protein (e.g., a wild-type rAAV capsid protein). In some embodiments, the neuroinflammation is reduced by at least about 10%, at least about 25%, at least about 50%, at least about 75%, or at least about 100%. A suitable reference rAAV capsid protein may include any capsid protein that lacks one or more amino acid substitutions at one or more positions that interact with a heparan sulfate proteoglycan (the reference capsid may thus contain one or more "background" substitutions that do not alter binding to HSPG).

In some embodiments, the rAAV particle comprises a) a rAAV capsid comprising rAAV capsid proteins comprising one or more amino acid substitutions at one or more positions that interacts with a heparan sulfate proteoglycan, and b) a rAAV vector comprising the heterologous nucleic acid and at least one AAV inverted terminal repeat.

In some embodiments, the one or more amino acid substitutions reduce binding of the rAAV particle to the heparan sulfate proteoglycan by about at least 10%, about at least 25%, about at least 50%, about at least 75%, or about at least 100%. In some embodiments, the one or more amino acid substitutions reduce binding of the rAAV particle to the heparan sulfate proteoglycan by about at least 10%, about at least 15%, about at least 20%, about at least 25%, about at least 30%, about at least 35%, about at least 40%, about at least 45%, about at least 50%, about at least 55%, about at least 60%, about at least 65%, about at least 70%, about at least 75%, about at least 80%, about at least 85%, about at least 90%, about at least 95%, or about at least 100% (as compared to binding of a rAAV particle comprising a wild-type capsid). In some embodiments, the one or more amino acid substitutions reduce binding of the rAAV particle to the heparan sulfate proteoglycan by any one of about 10% to about 100%, about 20% to about 100%, about 30% to about 100%, about 40% to about 100%, about 50% to about 100%, about 60% to about 100%, about 70% to about 100%, about 80% to about 100%, about 90% to about 100%, about 10% to about 90%, about 20% to about 90%, about 30% to about 90%, about 40% to about 90%, about 50% to about 90%, about 60% to about 90%, about 70% to about 90%, about 80% to about 90%, about 10% to about 80%, about 20% to about 80%, about 30% to about 80%, about 40% to about 80%, about 50% to about 80%, about 60% to about 80%, about 70% to about 80%, about 10% to about 70%, about 20% to about 70%, about 30% to about 70%, about 40% to about 70%, about 50% to about 70%, about 60% to about 70%, about 10% to about 60%, about 20% to about 60%, about 30% to about 60%, about 40% to about 60%, about 50% to about 60%, about 10% to about 50%, about 20% to about 50%, about 30% to about 50%, about 40% to about 50%, about 10% to about 40%, about 20% to about 40%, about 30% to about 40%, about 10% to about 30%, about 20% to about 30%, or about 10% to about 20%. (as compared to binding of a rAAV particle comprising a wild-type capsid). In some embodiments, the one or more amino acid substitutions results in no detectable binding of the rAAV particle to the heparan sulfate proteoglycan compared to binding of a wild-type rAAV particle. Means to measure binding of AAV particles to HSPG are known in the art; e.g., binding to a heparan sulfate chromatography media or binding to a cell known to express HSPG on its surface. For example, see Opie, S R et al., (2003) *J. Virol.* 77:6995-7006 and Kern, A et al., (2003) *J. Virol.* 77:11072-11081.

In some embodiments, the rAAV particles comprise one or more amino acid substitutions of capsid proteins that reduce or ablate binding of the rAAV particle to the heparan sulfate proteoglycan, and/or wherein the one or more amino acid substitutions is at position 484, 487, 532, 585 or 588, numbering based on VP1 numbering of AAV2. As used herein. "numbering based on VP1 of AAV2" refers to the amino acid of the recited capsid protein corresponding to the recited amino acid of VP1 of AAV2. For example, if one or more amino acid substitutions are at position 347, 350, 390, 395, 448, 451, 484, 487, 527, 532, 585 and/or 588, numbering based on VP1 of AAV2, then the one or more amino acid substitutions are at the amino acid(s) of the recited capsid protein corresponding to amino acids 347, 350, 390, 395, 448, 451, 484, 487, 527, 532, 585 and/or 588 of VP1 of AAV2. In some embodiments, the one or more amino acid substitutions is at position 484, 487, 532, 585 or 588 of VP1 of AAV2. In some embodiments, the one or more amino acid substitutions is at position 484, 487, 532, 585 or 588 of VP1 of AAV3, numbering based on VP1 of AAV2. In some embodiments, the one or more amino acid substitutions is at position 485, 488, 528, 533, 586 or 589, numbering based on VP1 numbering of AAVrh8R. In some embodiments, one or more amino acids at position(s) corresponding to amino acids 585 and/or 588 (numbering based on VP1 of AAV2) are replaced by arginine residues (e.g., S586 and/or T589 for AAV1 or AAV6; S586 and/or A589 for AAV9; A586 and/or T589 for AAVrh8R; Q588 and/or T591 for AAV8; and Q588 and/or A591 for AAVrh10). In other embodiments, one or more amino acids (e.g., arginine or lysine) at position(s) corresponding to amino acids 484, 487, 527 and/or 532 (numbering based on VP1 of AAV2) are replaced by non-positively charged amino acid(s) such as alanine (e.g., R485. R488. K528, and/or K533 for AAV1 or AAV6; R485, R488, K528, and/or R533 for AAV9 or AAVrh8R; and R487, R490. K530, and/or R535 for AAV8 or AAVrh10).

Other Viral Particles

In some embodiments, the vector is a recombinant adenoviral vector. In some embodiments, the viral particle is an adenoviral particle. In some embodiments, the adenoviral particle is a recombinant adenoviral particle. e.g., a polynucleotide vector comprising one or two guide RNAs of the present disclosure and/or a nucleotide sequence encoding a Cas protein of the present disclosure between two ITRs. In some embodiments, the adenoviral particle lacks or contains a defective copy of one or more E1 genes, which renders the adenovirus replication-defective. Adenoviruses include a linear, double-stranded DNA genome within a large (~950 Å), non-enveloped icosahedral capsid. Adenoviruses have a large genome that can incorporate more than 30 kb of heterologous sequence (e.g., in place of the E1 and/or E3 region), making them uniquely suited for use with larger heterologous genes. They are also known to infect dividing and non-dividing cells and do not naturally integrate into the host genome (although hybrid variants may possess this ability). In some embodiments, the adenoviral vector may be a first generation adenoviral vector with a heterologous sequence in place of E1. In some embodiments, the adenoviral vector may be a second generation adenoviral vector with additional mutations or deletions in E2A. E2B, and/or E4. In some embodiments, the adenoviral vector may be a third generation or gutted adenoviral vector that lacks all viral coding genes, retaining only the ITRs and packaging signal and requiring a helper adenovirus in trans for replication, and packaging. Adenoviral particles have been investigated for use as vectors for transient transfection of mammalian cells as well as gene therapy vectors. For further description, see. e.g., Danthinne. X, and Imperiale, M. J. (2000) *Gene Ther.* 7:1707-14 and Tatsis. N, and Ertl. H. C. (2004) *Mol. Ther.* 10:616-29.

In some embodiments, the viral particle is a recombinant adenoviral particle comprising a nucleic acid comprising one or two guide RNAs of the present disclosure and/or a nucleotide sequence encoding a Cas protein of the present disclosure. Use of any adenovirus serotype is considered within the scope of the present invention. In some embodiments, the recombinant adenoviral vector is a vector derived from an adenovirus serotype, including without limitation, Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the recombinant adenoviral vector is derived from adenovirus serotype 2 or a variant of adenoviral serotype 5.

In some embodiments, the vector is encapsidated in a viral particle. In some embodiments, the viral particle is a recombinant adenovirus particle encapsidating a recombinant adenoviral vector. In some embodiments, the recombinant viral particles comprise an adenoviral particle in combination with one or more foreign viral capsid proteins. Such combinations may be referred to as pseudotyped recombinant adenoviral particles. In some embodiments, foreign viral capsid proteins used in pseudotyped recombinant adenoviral particles are derived from a foreign virus or from another adenovirus serotype. In some embodiments, the foreign viral capsid proteins are derived from, including without limitation, reovirus type 3. Examples of vector and capsid protein combinations used in pseudotyped adenovirus particles can be found in the following references (Tatsis. N. et al. (2004) *Mol. Ther.* 10(4):616-629 and Ahi, Y. et al. (2011) *Curr. Gene Ther.* 11(4):307-320). Different adenovirus serotypes can be used to optimize transduction of particular target cells or to target specific cell types within a particular target tissue (e.g., a diseased tissue). Tissues or cells targeted by specific adenovirus serotypes, include without limitation, lung (e.g. HuAd3), spleen and liver (e.g. HuAd37), smooth muscle, synoviocytes, dendritic cells, cardiovascular cells, tumor cell lines (e.g. HuAd11), and dendritic cells (e.g. HuAd5 pseudotyped with reovirus type 3, HuAd30, or HuAd35). For further description, see Ahi. Y. et al. (2011) *Curr. Gene Ther.* 11(4):307-320. Kay. M. et al. (2001) *Nat. Med.* 7(1):33-40, and Tatsis, N. et al. (2004) *Mol. Ther.* 10(4):616-629. In some embodiments, the recombinant adenovirus particle may contain a capsid from an Adenovirus serotype including without limitation 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the recombinant adenovirus particle comprises an adenovirus serotype 2 capsid or a variant of an adenoviral serotype 5 capsid.

In some embodiments, the vector is a recombinant lentiviral vector. In some embodiments, the viral particle is a lentiviral particle. In some embodiments, the lentiviral particle is a recombinant lentiviral particle, e.g., a polynucleotide vector comprising one or two guide RNAs of the present disclosure and/or a nucleotide sequence encoding a Cas protein of the present disclosure between two LTRs. Lentiviruses are positive-sense, ssRNA retroviruses with a genome of approximately 10 kb. Lentiviruses are known to integrate into the genome of dividing and non-dividing cells. Lentiviral particles may be produced, for example, by transfecting multiple plasmids (typically the lentiviral genome and the genes required for replication and/or packaging are separated to prevent viral replication) into a packaging cell line, which packages the modified lentiviral genome into lentiviral particles. In some embodiments, a lentiviral particle may refer to a first generation vector that lacks the envelope protein. In some embodiments, a lentiviral particle may refer to a second generation vector that lacks all genes except the gag/pol and tat/rev regions. In some embodiments, a lentiviral particle may refer to a third generation vector that only contains the endogenous rev, gag, and pol genes and has a chimeric LTR for transduction without the tat gene (see Dull. T. et al. (1998) *J. Virol.* 72:8463-71). For further description, see Durand, S. and Cimarelli, A. (2011) *Viruses* 3:132-59.

In some embodiments, the viral particle is a recombinant lentiviral particle comprising a nucleic acid comprising one or two guide RNAs of the present disclosure and/or a nucleotide sequence encoding a Cas protein of the present disclosure. Use of any lentiviral vector is considered within the scope of the present invention. In some embodiments, the lentiviral vector is derived from a lentivirus including, without limitation, human immunodeficiency virus-1 (HIV-1), human immunodeficiency virus-2 (HIV-2), simian immunodeficiency virus (SIV), feline immunodeficiency virus (FIV), equine infectious anemia virus (EIAV), bovine immunodeficiency virus (BIV), Jembrana disease virus (JDV), visna virus (VV), and caprine arthritis encephalitis virus (CAEV).

In some embodiments, the vector is encapsidated in a viral particle. In some embodiments, the viral particle is a recombinant lentiviral particle encapsidating a recombinant lentiviral vector. In some embodiments, the recombinant viral particles comprise a lentivirus vector in combination with one or more foreign viral capsid proteins. Such combinations may be referred to as pseudotyped recombinant lentiviral particles. In some embodiments, foreign viral capsid proteins used in pseudotyped recombinant lentiviral particles are derived from a foreign virus. In some embodiments, the foreign viral capsid protein used in pseudotyped recombinant lentiviral particles is Vesicular stomatitis virus glycoprotein (VSV-GP). VSV-GP interacts with a ubiquitous cell receptor, providing broad tissue tropism to pseudotyped recombinant lentiviral particles. In addition, VSV-GP is thought to provide higher stability to pseudotyped recombinant lentiviral particles. In other embodiments, the foreign viral capsid proteins are derived from, including without limitation. Chandipura virus. Rabies virus. Mokola virus, Lymphocytic choriomeningitis virus (LCMV). Ross River virus (RRV), Sindbis virus, Semliki Forest virus (SFV), Venezuelan equine encephalitis virus. Ebola virus Reston, Ebola virus Zaire, Marburg virus, Lassa virus, Avian leukosis virus (ALV), Jaagsiekte sheep retrovirus (JSRV). Moloney Murine leukemia virus (MLV). Gibbon ape leukemia virus (GALV). Feline endogenous retrovirus (RD114). Human T-lymphotropic virus 1 (HTLV-1), Human foamy virus, Maedi-visna virus (MVV), SARS-CoV, Sendai virus, Respiratory syncytia virus (RSV), Human parainfluenza virus type 3, Hepatitis C virus (HCV), Influenza virus. Fowl plague virus (FPV), or *Autographa californica* multiple nucleopolyhedro virus (AcMNPV).

In some embodiments, the recombinant lentiviral vector is derived from a lentivirus pseudotyped with vesicular stomatitis virus (VSV), lymphocytic choriomeningitis virus (LCMV), Ross river virus (RRV), Ebola virus. Marburg virus, Mokala virus, Rabies virus, RD114, or variants therein. Examples of vector and capsid protein combinations used in pseudotyped Lentivirus particles can be found, for example, in Cronin. J. et al. (2005). *Curr. Gene Ther.* 5(4):387-398. Different pseudotyped recombinant lentiviral particles can be used to optimize transduction of particular target cells or to target specific cell types within a particular target tissue (e.g., a diseased tissue). For example, tissues targeted by specific pseudotyped recombinant lentiviral particles, include without limitation, liver (e.g. pseudotyped with a VSV-G, LCMV, RRV, or SeV F protein), lung (e.g, pseudotyped with an Ebola, Marburg, SeV F and HN, or JSRV protein), pancreatic islet cells (e.g, pseudotyped with an LCMV protein), central nervous system (e.g, pseudotyped with a VSV-G. LCMV. Rabies, or Mokola protein), retina (e.g, pseudotyped with a VSV-G or Mokola protein), monocytes or muscle (e.g, pseudotyped with a Mokola or Ebola protein), hematopoietic system (e.g, pseudotyped with an RD114 or GALV protein), or cancer cells (e.g, pseudotyped with a GALV or LCMV protein). For further description, see Cronin, J. et al. (2005). *Curr. Gene Ther.* 5(4):387-398 and Kay, M. et al. (2001) *Nat. Med.* 7(1):33-40. In some embodiments, the recombinant lentiviral particle comprises a capsid pseudotyped with vesicular stomatitis virus (VSV), lymphocytic choriomeningitis virus (LCMV). Ross river virus (RRV). Ebola virus, Marburg virus. Mokala virus, Rabies virus. RD114 or variants therein.

In some embodiments, the vector is an rHSV vector. In some embodiments, the viral particle is a herpes simplex virus (HSV) particle. In some embodiments, the HSV particle is a rHSV particle, e.g., a polynucleotide vector comprising one or two guide RNAs of the present disclosure and/or a nucleotide sequence encoding a Cas protein of the present disclosure between two TRs. HSV is an enveloped, double-stranded DNA virus with a genome of approximately 152 kb. Advantageously, approximately half of its genes are nonessential and may be deleted to accommodate heterologous sequence. HSV particles infect non-dividing cells. In addition, they naturally establish latency in neurons, travel by retrograde transport, and can be transferred across synapses, making them advantageous for transfection of neurons and/or gene therapy approaches involving the nervous system. In some embodiments, the HSV particle may be replication-defective or replication-competent (e.g., competent for a single replication cycle through inactivation of one or more late genes). For further description, see Manservigi, R. et al. (2010) *Open Virol. J.* 4:123-56.

In some embodiments, the viral particle is a rHSV particle comprising a nucleic acid comprising one or two guide RNAs of the present disclosure and/or a nucleotide sequence encoding a Cas protein of the present disclosure. Use of any HSV vector is considered within the scope of the present invention. In some embodiments, the HSV vector is derived from a HSV serotype, including without limitation. HSV-1 and HSV-2.

In some embodiments, the vector is encapsidated in a viral particle. In some embodiments, the viral particle is a recombinant HSV particle encapsidating a recombinant HSV vector. In some embodiments, the recombinant viral particles comprise a HSV vector in combination with one or more foreign viral capsid proteins. Such combinations may be referred to as pseudotyped rHSV particles. In some embodiments, foreign viral capsid proteins used in pseudotyped rHSV particles are derived from a foreign virus or from another HSV serotype. In some embodiments, the foreign viral capsid protein used in a pseudotyped rHSV particle is a Vesicular stomatitis virus glycoprotein (VSV-GP). VSV-GP interacts with a ubiquitous cell receptor, providing broad tissue tropism to pseudotyped rHSV particles. In addition, VSV-GP is thought to provide higher stability to pseudotyped rHSV particles. In other embodiments, the foreign viral capsid protein may be from a different HSV serotype. For example, an HSV-1 vector may contain one or more HSV-2 capsid proteins. Different HSV serotypes can be used to optimize transduction of particular target cells or to target specific cell types within a particular target tissue (e.g., a diseased tissue). Tissues or cells targeted by specific adenovirus serotypes include without limitation, central nervous system and neurons (e.g. HSV-1). For further description, see Manservigi, R. et al. (2010) *Open Virol J* 4:123-156. Kay, M. et al. (2001) *Nat. Med.* 7(1):33-40, and Meignier, B. et al. (1987) *J. Infect. Dis.* 155(5):921-930. In some embodiments, the recombinant HSV particle is an rHSV-1 particle or an rHSV-2 viral particle.

Production of Viral Particles

Numerous methods are known in the art for production of adenoviral vector particles. For example, for a gutted adenoviral vector, the adenoviral vector genome and a helper adenovirus genome may be transfected into a packaging cell line (e.g., a 293 cell line). In some embodiments, the helper adenovirus genome may contain recombination sites flanking its packaging signal, and both genomes may be transfected into a packaging cell line that expresses a recombinase (e.g., the Cre/loxP system may be used), such that the adenoviral vector of interest is packaged more efficiently than the helper adenovirus (see. e.g., Alba, R. et al. (2005) *Gene Ther.* 12 Suppl 1:S18-27). Adenoviral vectors may be harvested and purified using standard methods, such as those described herein.

Numerous methods are known in the art for production of lentiviral vector particles. For example, for a third-generation lentiviral vector, a vector containing the lentiviral genome of interest with gag and pol genes may be co-transfected into a packaging cell line (e.g., a 293 cell line) along with a vector containing a rev gene. The lentiviral genome of interest also contains a chimeric LTR that promotes transcription in the absence of Tat (see Dull. T. et al. (1998) *J. Virol.* 72:8463-71). Lentiviral vectors may be harvested and purified using methods (e.g., Segura M M, et al., (2013) *Expert Opin Biol Ther.* 13(7):987-1011) described herein.

Numerous methods are known in the art for production of HSV particles. HSV vectors may be harvested and purified using standard methods, such as those described herein. For example, for a replication-defective HSV vector, an HSV genome of interest that lacks all of the immediate early (IE) genes may be transfected into a complementing cell line that provides genes required for virus production, such as ICP4. ICP27, and ICP0 (see. e.g., Samaniego, L. A. et al. (1998) *J. Virol.* 72:3307-20). HSV vectors may be harvested and purified using methods described (e.g., Goins, W F et al., (2014) Herpes Simplex Virus Methods in Molecular Biology 1144:63-79).

Numerous methods are known in the art for production of rAAV vectors, including transfection, stable cell line production, and infectious hybrid virus production systems which include adenovirus-AAV hybrids, herpesvirus-AAV hybrids (Conway, J E et al., (1997) *J. Virology* 71(11):8780-8789) and baculovirus-AAV hybrids, rAAV production cultures for the production of rAAV virus particles all require; 1) suitable host cells, 2) suitable helper virus function, 3) AAV rep and cap genes and gene products; 4) a nucleic acid (such as a therapeutic nucleic acid) flanked by at least one AAV ITR sequences (e.g., an oversized rAAV vector genome); and 5) suitable media and media components to support rAAV production. In some embodiments, the suitable host cell is a primate host cell. In some embodiments, the suitable host cell is a human-derived cell lines such as HeLa. A549, 293, or Perc.6 cells. In some embodiments, the suitable helper virus function is provided by wild-type or mutant adenovirus (such as temperature sensitive adenovirus), herpes virus (HSV), baculovirus, or a plasmid construct providing helper functions. In some embodiments, the AAV rep and cap gene products may be from any AAV serotype. In general, but not obligatory, the AAV rep gene product is of the same serotype as the ITRs of the rAAV vector genome as long as the rep gene products may function to replicated and package the rAAV genome. Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), custom formulations such as those described in U.S. Pat. No. 6,566,118, and Sf-900 II SFM media as described in U.S. Pat. No. 6,723,551, each of which is incorporated herein by reference in its entirety, particularly with respect to custom media formulations for use in production of recombinant AAV vectors. In some embodiments, the AAV helper functions are provided by adenovirus or HSV. In some embodiments, the AAV helper functions are provide by baculovirus and the host cell is an insect cell (e.g., *Spodoptera frugiperda* (Sf9) cells). Examples of adenovirus helper functions for the replication of AAV include E1A functions, E1B functions. E2A functions, VA functions and E4orf6 functions. Baculoviruses available from depositories include *Autographa californica* nuclear polyhedrosis virus.

The rAAV particles can be produced using methods known in the art. See, e.g., U.S. Pat. Nos. 6,566,118; 6,989,264; and 6,995,006. In practicing the invention, host cells for producing rAAV particles include mammalian cells, insect cells, plant cells, microorganisms and yeast. Host cells can also be packaging cells in which the AAV rep and cap genes are stably maintained in the host cell or producer cells in which the AAV vector genome is stably maintained. Exemplary packaging and producer cells are derived from 293. A549 or HeLa cells, AAV vectors are purified and formulated using standard techniques known in the art.

In some embodiments, rAAV particles may be produced by a triple transfection method, such as the exemplary triple transfection method provided infra. Briefly, a plasmid containing a rep gene and a capsid gene, along with a helper adenoviral plasmid, may be transfected (e.g., using the calcium phosphate method) into a cell line (e.g., HEK-293 cells), and virus may be collected and optionally purified.

In some embodiments, rAAV particles may be produced by a producer cell line method (see, e.g., Martin et al., (2013) *Human Gene Therapy Methods* 24:253-269). Briefly, a cell line (e.g., a HeLa cell line) may be stably transfected with a plasmid containing a rep gene, a capsid gene, and a promoter-transgene sequence. Cell lines may be screened to select a lead clone for rAAV production, which may then be expanded to a production bioreactor and infected with an adenovirus (e.g., a wild-type adenovirus) as helper to initiate rAAV production. Virus may subsequently be harvested, adenovirus may be inactivated (e.g., by heat) and/or removed, and the rAAV particles may be purified. In some embodiments, the producer cell line is derived from HeLa, 293. A549, or Perc.6 cells. In some embodiments, the producer cell line is adapted for growth in suspension. In some embodiments, the AAV helper functions are provided by adenovirus. HSV or baculovirus.

In some embodiments, rAAV particles are collected from between about 48 hours and about 96 hours after the provision of helper functions. For example, in some embodiments, rAAV particles are collected about 48 hours, about 60 hours, about 72 hours, about 84 hours, or about 96 hours after the provision of helper functions. In some embodiments, rAAV particles are collected about 48 hours and about 96 hours, about 48 hours and about 84 hours, about 48 hours and about 72 hours, about 48 hours and about 60 hours, about 60 hours and about 96 hours, about 60 hours and about 84 hours, about 60 hours and about 72 hours, about 72 hours and about 96 hours, about 72 hours and about 84 hours, or about 84 hours and about 96 hours after the provision of helper functions.

Suitable rAAV production culture media of the present invention may be supplemented with serum or serum-derived recombinant proteins at a level of 0.5%-20% (v/v or w/v). Alternatively, as is known in the art, rAAV vectors may be produced in serum-free conditions which may also be referred to as media with no animal-derived products. One of ordinary skill in the art may appreciate that commercial or custom media designed to support production of rAAV vectors may also be supplemented with one or more cell culture components known in the art, including without limitation glucose, vitamins, amino acids, and or growth factors, in order to increase the titer of rAAV in production cultures.

rAAV production cultures can be grown under a variety of conditions (over a wide temperature range, for varying lengths of time, and the like) suitable to the particular host cell being utilized. As is known in the art, rAAV production cultures include attachment-dependent cultures which can be cultured in suitable attachment-dependent vessels such as, for example, roller bottles, hollow fiber filters, micro-carriers, and packed-bed or fluidized-bed bioreactors, rAAV vector production cultures may also include suspension-adapted host cells such as HeLa, 293, and SF-9 cells which can be cultured in a variety of ways including, for example, spinner flasks, stirred tank bioreactors, and disposable systems such as the Wave bag system.

rAAV vector particles of the invention may be harvested from rAAV production cultures by lysis of the host cells of the production culture or by harvest of the spent media from the production culture, provided the cells are cultured under conditions known in the art to cause release of rAAV particles into the media from intact cells, as described more fully in U.S. Pat. No. 6,566,118). Suitable methods of lysing cells are also known in the art and include for example multiple freeze/thaw cycles, sonication, microfluidization, and treatment with chemicals, such as detergents and/or proteases.

In a further embodiment, the viral particles are purified. The term "purified" as used herein includes a preparation of viral particles devoid of at least some of the other components that may also be present where the viral particles naturally occur or are initially prepared from. Thus, for example, isolated viral particles may be prepared using a purification technique to enrich it from a source mixture, such as a culture lysate or production culture supernatant. Enrichment can be measured in a variety of ways, such as, for example, by the proportion of DNase-resistant particles (DRPs) or genome copies (gc) present in a solution, or by infectivity, or it can be measured in relation to a second, potentially interfering substance present in the source mixture, such as contaminants, including production culture contaminants or in-process contaminants, including helper virus, media components, and the like.

In some embodiments, the viral production culture harvest is clarified to remove host cell debris. In some embodiments, the production culture harvest is clarified by filtration through a series of depth filters including, for example, a grade DOHC Millipore Millistak+HC Pod Filter, a grade A1HC Millipore Millistak+HC Pod Filter, and a 0.2 µm Filter Opticap XLIO Millipore Express SHC Hydrophilic Membrane filter. Clarification can also be achieved by a variety of other standard techniques known in the art, such as, centrifugation or filtration through any cellulose acetate filter of 0.2 µm or greater pore size known in the art.

In some embodiments, the viral production culture harvest is further treated with Benzonase® to digest any high molecular weight DNA present in the production culture. In some embodiments, the Benzonase® digestion is performed under standard conditions known in the art including, for example, a final concentration of 1-2.5 units/ml of Benzonase® at a temperature ranging from ambient to 37° C., for a period of 30 minutes to several hours.

rAAV particles may be isolated or purified using one or more of the following purification steps: equilibrium centrifugation; flow-through anionic exchange filtration; tangential flow filtration (TFF) for concentrating the rAAV particles; rAAV capture by apatite chromatography; heat inactivation of helper virus; rAAV capture by hydrophobic interaction chromatography; buffer exchange by size exclusion chromatography (SEC); nanofiltration; and rAAV capture by anionic exchange chromatography, cationic exchange chromatography, or affinity chromatography. These steps may be used alone, in various combinations, or in different orders. Methods to purify rAAV particles are found, for example, in Xiao et al., (1998) *Journal of Virology* 72:2224-2232; U.S. Pat. Nos. 6,989,264 and 8,137,948; and WO 2010/148143. Methods to purify adenovirus particles are found, for example, in Bo, H et al., (2014) *Eur. J. Pharm. Sci.* 67C: 119-125. Methods to purify lentivirus particles are found, for example, in Segura M M. et al., (2013) *Expert Opin Biol Ther.* 13(7):987-1011. Methods to purify HSV particles are found, for example, in Goins, W F et al., (2014) Herpes Simplex Virus Methods in Molecular Biology 1144: 63-79.

In some embodiments, the viral particle is in a pharmaceutical formulation. In some embodiments, the pharmaceutical formulation includes a pharmaceutically acceptable carrier. Such carriers are well known in the art (see. e.g., Remington's Pharmaceutical Sciences, 15th Edition, pp. 1035-1038 and 1570-1580). In some embodiments, the pharmaceutical compositions comprising a viral particle described herein and a pharmaceutically acceptable carrier is suitable for ocular injection. Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. The pharmaceutical composition may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidosage forms. The compositions are generally formulated as sterile and substantially isotonic solution.

VI. Methods of Treatment

Certain aspects of the present disclosure involve administering to an individual a therapeutically effective amount of a composition comprising a nucleic acid encoding an engineered, non-naturally occurring CRISPR-Cas system of the present disclosure, e.g., as described above.

In some embodiments, aspects of the present disclosure involve administering to an individual a therapeutically effective amount of a composition comprising a Cas protein of the present disclosure and one or more nucleic acid(s) comprising a first guide RNA and a second guide RNA wherein the first guide RNA and the second guide RNA hybridize to the opposite strands of the target DNA sequences flanking a mutation including a deep intronic mutation, e.g., as described above. That is to say, for any of the methods, compositions, and kits of the present disclosure, the Cas protein may be supplied as a nucleotide sequence encoding the Cas protein, or as a polypeptide. As a non-limiting example, a Cas protein may be administered with one or more guide RNAs (e.g., a sgRNA) using cationic lipid-mediated delivery (see, e.g., Zuris. J. A. et al. *Nat Biotechnol.* 33:73-80). In some embodiments, a Cas protein may be administered in a complex with one or more guide RNAs, e.g., as in a CRISPR-Cas effector complex. It will be appreciated that any of the delivery and/or administration methods described below may be used for delivery of a Cas protein administered with one or more guide RNAs. In some embodiments, the Cas protein is expressed from a self-limiting expression cassette as described above.

In some embodiments, the composition comprising a nucleic acid encoding an engineered, non-naturally occurring CRISPR-Cas system of the present disclosure (or a composition comprising a Cas protein of the present disclosure and one or more guide RNAs of the present disclosure) is administered intravenously, intramuscularly, subcutaneously, topically, orally, transdermally, intraperitoneally, intraorbitally, by implantation, by inhalation, intrathecally, intraventricularly, or intranasally.

In some embodiments, the composition comprising a nucleic acid encoding an engineered, non-naturally occurring CRISPR-Cas system of the present disclosure (or a composition comprising a Cas protein of the present disclosure and one or more guide RNAs of the present disclosure) is administered subretinally or intravitreally. Gene therapy protocols for retinal diseases, such as ocular diseases associated with a deep intronic mutation, require the localized delivery of the nucleic acid to the cells in the retina. The cells that will be the treatment target in these diseases are either the photoreceptor cells in the retina or the cells of the RPE underlying the neurosensory retina. Delivering nucleic acids to these cells requires injection into the subretinal space between the retina and the RPE.

In some aspects, the invention provides compositions comprising any of the nucleic acids described herein, optionally in a pharmaceutically acceptable excipient. As is well known in the art, pharmaceutically acceptable excipients are relatively inert substances that facilitate administration of a pharmacologically effective substance and can be supplied as liquid solutions or suspensions, as emulsions, or as solid forms suitable for dissolution or suspension in liquid prior to use. For example, an excipient can give form or consistency, or act as a diluent. Suitable excipients include but are not limited to stabilizing agents, wetting and emulsifying agents, salts for varying osmolarity, encapsulating agents, pH buffering substances, and buffers. Such excipients include any pharmaceutical agent suitable for direct delivery to the eye which may be administered without undue toxicity. Pharmaceutically acceptable excipients include, but are not limited to, sorbitol, any of the various TWEEN compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in REMINGTON'S PHARMACEUTICAL SCIENCES (Mack Pub. Co., N.J. 1991).

Generally, these compositions are formulated for administration by subretinal injection. Accordingly, these compositions can be combined with pharmaceutically acceptable vehicles such as saline, Ringer's balanced salt solution (pH 7.4), and the like. Although not required, the compositions may optionally be supplied in unit dosage form suitable for administration of a precise amount.

Methods of Subretinal Delivery

Methods of subretinal delivery are known in the art. For example, see WO 2009/105690, incorporated herein by reference. Briefly, the general method for delivering a composition (e.g., a nucleic acid encoding an engineered, non-naturally occurring CRISPR-Cas system of the present disclosure, which may be delivered through viral or non-viral delivery as described above) to the subretina of the macula and fovea may be illustrated by the following brief outline. This example is merely meant to illustrate certain features of the method, and is in no way meant to be limiting.

Generally, the vector can be delivered in the form of a composition injected intraocularly (subretinally) under direct observation using an operating microscope. This procedure may involve vitrectomy followed by injection of a vector suspension using a fine cannula through one or more small retinotomies into the subretinal space.

Briefly, an infusion cannula can be sutured in place to maintain a normal globe volume by infusion (of e.g., saline) throughout the operation. A vitrectomy is performed using a cannula of appropriate bore size (for example 20 to 27 gauge), wherein the volume of vitreous gel that is removed is replaced by infusion of saline or other isotonic solution from the infusion cannula. The vitrectomy is advantageously performed because (1) the removal of its cortex (the posterior hyaloid membrane) facilitates penetration of the retina by the cannula; (2) its removal and replacement with fluid (e.g., saline) creates space to accommodate the intraocular injection of vector, and (3) its controlled removal reduces the possibility of retinal tears and unplanned retinal detachment.

In some embodiments, the vector composition is directly injected into the subretinal space outside the central retina, by utilizing a cannula of the appropriate bore size (e.g., 27-45 gauge), thus creating a bleb in the subretinal space. In other embodiments, the subretinal injection of the vector composition is preceded by subretinal injection of a small volume (e.g., about 0.1 to about 0.5 ml) of an appropriate fluid (such as saline or Ringer's solution) into the subretinal space outside the central retina. This initial injection into the subretinal space establishes an initial fluid bleb within the subretinal space, causing localized retinal detachment at the location of the initial bleb. This initial fluid bleb can facilitate targeted delivery of the vector composition to the subretinal space (by defining the plane of injection prior to vector delivery), and minimize possible vector administration into the choroid and the possibility of injection or reflux into the vitreous cavity. In some embodiments, this initial fluid bleb can be further injected with fluids comprising one or more vector compositions and/or one or more additional therapeutic agents by administration of these fluids directly to the initial fluid bleb with either the same or additional fine bore cannulas.

Intraocular administration of the vector compositions and/or the initial small volume of fluid can be performed using a fine bore cannula (e.g., 27-45 gauge) attached to a syringe. In some embodiments, the plunger of this syringe may be driven by a mechanized device, such as by depression of a foot pedal. The fine bore cannula is advanced through the sclerotomy, across the vitreous cavity and into the retina at a site pre-determined in each subject according to the area of retina to be targeted (but outside the central retina). Under direct visualization the vector suspension is injected mechanically under the neurosensory retina causing a localized retinal detachment with a self-sealing non-expanding retinotomy. As noted above, the vector composition can be either directly injected into the subretinal space creating a bleb outside the central retina or the vector can be injected into an initial bleb outside the central retina, causing it to expand (and expanding the area of retinal detachment). In some embodiments, the injection of the vector composition is followed by injection of another fluid into the bleb.

Without wishing to be bound by theory, the rate and location of the subretinal injection(s) can result in localized shear forces that can damage the macula, fovea and/or underlying RPE cells. The subretinal injections may be performed at a rate that minimizes or avoids shear forces. In some embodiments, the vector composition is injected over about 15-17 minutes. In some embodiments, the vector is injected over about 17-20 minutes. In some embodiments, the vector composition is injected over about 20-22 minutes. In some embodiments, the vector composition is injected at a rate of about 35 to about 65 µl/min. In some embodiments, the vector composition is injected at a rate of about 35 µl/min. In some embodiments, the vector composition is injected at a rate of about 40 µl/min. In some embodiments, the vector composition is injected at a rate of about 45 µl/min. In some embodiments, the vector composition is injected at a rate of about 50 µl/min. In some embodiments, the vector composition is injected at a rate of about 55 µl/min. In some embodiments, the vector composition is injected at a rate of about 60 µl/min. In some embodiments, the vector composition is injected at a rate of about 65 µl/min. One of ordinary skill in the art would recognize that the rate and time of injection of the bleb may be directed by, for example, the volume of the vector composition or size of the bleb necessary to create sufficient retinal detachment to access the cells of central retina, the size of the cannula used to deliver the vector composition, and the ability to safely maintain the position of the cannula of the invention.

In some embodiments of the invention, the volume of the composition injected to the subretinal space of the retina is more than about any one of 1 µl, 2 µl, 3 µl, 4 µl, 5 µl, 6 µl, 7 µl, 8 µl, 9 µl, 10 µl, 15 µl, 20 µl, 25 µl, 50 µl, 75 µl, 100 µl, 200 µl, 300 µl, 400 µl, 500 µl, 600 µl, 700 µl, 800 µl, 900 µl, or 1 mL, or any amount therebetween.

In some embodiments, the methods comprise administration to the eye (e.g., by subretinal and/or intravitreal administration) an effective amount of recombinant viral particles comprising a vector of the present disclosure. In some embodiments, the viral titer of the composition is at least about any of $5 \times 10^{12}$, $6 \times 10^{12}$, $7 \times 10^{12}$, $8 \times 10^{12}$, $9 \times 10^{12}$, $10 \times 10^{12}$. $11 \times 10^{12}$. $15 \times 10^{12}$. $20 \times 10^{12}$, $25 \times 10^{12}$, $30 \times 10^{12}$, or $50 \times 10^{12}$ genome copies/mL. In some embodiments, the viral titer of the composition is about any of $5 \times 10^{12}$ to $6 \times 10^{12}$, $6 \times 10^{12}$ to $7 \times 10^{12}$, $7 \times 10^{12}$ to $8 \times 10^{12}$, $8 \times 10^{12}$ to $9 \times 10^{12}$, $9 \times 10^{12}$ to $10 \times 10^{12}$, $10 \times 10^{12}$ to $11 \times 10^{12}$, $11 \times 10^{12}$ to $15 \times 10^{12}$. $15 \times 10^{12}$ to $20 \times 10^{12}$, $20 \times 10^{12}$ to $25 \times 10^{12}$, $25 \times 10^{12}$ to $30 \times 10^{12}$, $30 \times 10^{12}$ to $50 \times 10^{12}$, or $50 \times 10^{12}$ to $100 \times 10^{12}$ genome copies/mL. In some embodiments, the viral titer of the composition is about any of $5 \times 10^{12}$ to $10 \times 10^{12}$, $10 \times 10^{12}$ to $25 \times 10^{12}$, or $25 \times 10^{12}$ to $50 \times 10^{12}$ genome copies/mL. In some embodiments, the viral titer of the composition is at least about any of $5 \times 10^9$, $6 \times 10^9$, $7 \times 10^9$, $8 \times 10^9$, $9 \times 10^9$, $10 \times 10^9$, $11 \times 10^9$, $15 \times 10^9$, $20 \times 10^9$, $25 \times 10^9$, $30 \times 10^9$, or $50 \times 10^9$ transducing units/mL. In some embodiments, the viral titer of the composition is about any of $5 \times 10^9$ to $6 \times 10$, $6 \times 10^9$ to $7 \times 10^9$. $7 \times 10^9$ to $8 \times 10^9$, $8 \times 10^9$ to $9 \times 10^9$. $9 \times 10^9$ to $10 \times 10^9$, $10 \times 10^9$ to $11 \times 10^9$, $11 \times 10^9$ to $15 \times 10^9$. $15 \times 10^9$ to $20 \times 10^9$, $20 \times 10^9$ to $25 \times 10^9$. $25 \times 10^9$ to $30 \times 10^9$, $30 \times 10^9$ to $50 \times 10^9$ or $50 \times 10^9$ to $100 \times 10^9$ transducing units/mL. In some embodiments, the viral titer of the composition is about any of $5 \times 10^9$ to $10 \times 10^9$, $10 \times 10^9$ to $15 \times 10^9$, $15 \times 10^9$ to $25 \times 10^9$, or $25 \times 10^9$ to $50 \times 10^9$ transducing units/mL. In some embodiments, the viral titer of the composition is at least any of about $5 \times 10^{10}$, $6 \times 10^{10}$, $7 \times 10^{10}$, $8 \times 10^{10}$, $9 \times 10^{10}$, $10 \times 10^{10}$. $11 \times 10^{10}$, $15 \times 10^{10}$, $20 \times 10^{10}$, $25 \times 10^{10}$, $30 \times 10^{10}$, $40 \times 10^{10}$, or $50 \times 10^{10}$ infectious units/mL. In some embodiments, the viral titer of the composition is at least any of about $5 \times 10^{10}$ to $6 \times 10^{10}$, $6 \times 10^{10}$ to $7 \times 10^{10}$, $7 \times 10^{10}$ to $8 \times 10^{10}$, $8 \times 10^{10}$ to $9 \times 10^{10}$, $9 \times 10^{10}$ to $10 \times 10^{10}$ to, $10 \times 10^{10}$ to $11 \times 10^{10}$. $11 \times 10^{10}$ to $15 \times 10^{10}$. $15 \times 10^{10}$ to $20 \times 10^{10}$, $20 \times 10^{10}$ to $25 \times 10^{10}$, $25 \times 10^{10}$ to $30 \times 10^{10}$, $30 \times 10^{10}$ to $40 \times 10^{10}$, $40 \times 10^{10}$ to $50 \times 10^{10}$, or $50 \times 10^{10}$ to $100 \times 10^{10}$ infectious units/mL. In some embodiments, the viral titer of the composition is at least any of about $5 \times 10^{10}$ to $10 \times 10^{10}$, $10 \times 10^{10}$ to $15 \times 10^{10}$. $15 \times 10^{10}$ to $25 \times 10^{10}$, or $25 \times 10^{10}$ to $50 \times 10^{10}$ infectious units/mL.

In some embodiments, the methods comprise administration to the eye (e.g., by subretinal and/or intravitreal administration) of an individual (e.g., a human) an effective amount of recombinant viral particles comprising a vector of the present disclosure. In some embodiments, the dose of viral particles administered to the individual is at least about any of $1 \times 10^8$ to about $1 \times 10^{13}$ genome copies/kg of body weight. In some embodiments, the dose of viral particles administered to the individual is about any of $1 \times 10^8$ to about $1 \times 10^{13}$ genome copies/kg of body weight.

One or multiple (e.g., 2, 3, or more) blebs can be created. Generally, the total volume of bleb or blebs created by the methods and systems of the invention cannot exceed the fluid volume of the eye, for example about 4 ml in a typical human subject. The total volume of each individual bleb can be at least about 0.3 ml, or at least about 0.5 ml in order to facilitate a retinal detachment of sufficient size to expose the cell types of the central retina and create a bleb of sufficient dependency for optimal manipulation. One of ordinary skill in the art will appreciate that in creating the bleb according to the methods and systems of the invention that the appropriate intraocular pressure must be maintained in order to avoid damage to the ocular structures. The size of each individual bleb may be, for example, about 0.5 to about 1.2 ml, about 0.8 to about 1.2 ml, about 0.9 to about 1.2 ml, about 0.9 to about 1.0 ml, about 1.0 to about 2.0 ml, about 1.0 to about 3.0 ml. Thus, in one example, to inject a total of 3 ml of vector composition suspension, 3 blebs of about 1 ml each can be established. The total volume of all blebs in combination may be, for example, about 0.5 to about 3.0 ml, about 0.8 to about 3.0 ml, about 0.9 to about 3.0 ml, about 1.0 to about 3.0 ml, about 0.5 to about 1.5 ml, about 0.5 to about 1.2 ml, about 0.9 to about 3.0 ml, about 0.9 to about 2.0 ml, about 0.9 to about 1.0 ml.

In order to safely and efficiently transduce areas of target retina (e.g., the central retina) outside the edge of the original location of the bleb, the bleb may be manipulated to reposition the bleb to the target area for transduction. Manipulation of the bleb can occur by the dependency of the bleb that is created by the volume of the bleb, repositioning of the eye containing the bleb, repositioning of the head of the human with an eye or eyes containing one or more blebs, and/or by means of a fluid-air exchange. This is particularly relevant to the central retina since this area typically resists detachment by subretinal injection. In some embodiments fluid-air exchange is utilized to reposition the bleb; fluid from the infusion cannula is temporarily replaced by air, e.g., from blowing air onto the surface of the retina. As the volume of the air displaces vitreous cavity fluid from the surface of the retina, the fluid in the vitreous cavity may flow out of a cannula. The temporary lack of pressure from the vitreous cavity fluid causes the bleb to move and gravitate to a dependent part of the eye. By positioning the eye globe appropriately, the bleb of subretinal vector composition is manipulated to involve adjacent areas (e.g., the macula and/or fovea). In some cases, the mass of the bleb is sufficient to cause it to gravitate, even without use of the fluid-air exchange. Movement of the bleb to the desired location may further be facilitated by altering the position of the subject's head, so as to allow the bleb to gravitate to the desired location in the eye. Once the desired configuration of the bleb is achieved, fluid is returned to the vitreous cavity. The fluid is an appropriate fluid, e.g., fresh saline. Generally, the subretinal vector composition may be left in situ without retinopexy to the retinotomy and without intraocular tamponade, and the retina will spontaneously reattach within about 48 hours.

By safely and effectively transducing ocular cells (e.g., RPE and/or photoreceptor cells of e.g., the macula and/or fovea) with a vector of the present disclosure, the methods of the invention may be used to treat an individual; e.g., a human, having an ocular disorder associated with a deep intronic mutation, wherein the transduced cells produce the CRISPR-Cas system in an amount sufficient to treat the ocular disorder.

An effective amount of vector (in some embodiments in the form of viral particles) is administered, depending on the objectives of treatment. For example, where a low percentage of transduction can achieve the desired therapeutic effect, then the objective of treatment is generally to meet or exceed this level of transduction. In some instances, this level of transduction can be achieved by transduction of only about 1 to 5% of the target cells, in some embodiments at least about 20% of the cells of the desired tissue type, in some embodiments at least about 50%, in some embodiments at least about 80%, in some embodiments at least about 95%, in some embodiments at least about 99% of the cells of the desired tissue type. As a guide, the number of viral particles administered per injection is generally between about $1 \times 10^6$ and about $1 \times 10^{14}$ particles, between about $1 \times 10^7$ and $1 \times 10^{13}$ particles, between about $1 \times 10^9$ and $1 \times 10^{12}$ particles or about $1 \times 10^{11}$ particles. The vector composition may be administered by one or more subretinal injections, either during the same procedure or spaced apart by days, weeks, months, or years. In some embodiments, multiple vectors may be used to treat the human.

In some embodiments, the administration to the retina of an effective amount of a vector or nucleic acid of the present disclosure transduces photoreceptor cells at or near the site of administration. In some embodiments, more than about any of 5%, 10%, 15%, 20%, 25%, 30%, 35%, 40%, 45%, 50%, 55%, 60%, 65%, 70%, 75% or 100% of photoreceptor cells are transduced. In some embodiments, about 5% to about 100%, about 10% to about 50%, about 10% to about 30%, about 25% to about 75%, about 25% to about 50%, or about 30% to about 50% of the photoreceptor cells are transduced. Methods to identify transduced photoreceptor cells are known in the art; for example, immunohistochemistry or the use of a marker such as enhanced green fluorescent protein can be used to detect transduction.

In some embodiments of the invention, the methods comprise administration to the subretina (e.g., the subretinal space) of a mammal an effective amount of a vector or nucleic acid of the present disclosure for treating an individual with an ocular disorder; e.g., a human with an ocular disorder associated with a deep intronic mutation. In some embodiments, the composition is injected to one or more locations in the subretina to allow expression of the nucleic acid in photoreceptor cells. In some embodiments, the composition is injected into any one of one, two, three, four, five, six, seven, eight, nine, ten or more than ten locations in the subretina.

In some embodiments the composition is administered to more than one location simultaneously or sequentially. In some embodiment, multiple injections are no more than one hour, two hours, three hours, four hours, five hours, six hours, nine hours, twelve hours or 24 hours apart. In some embodiment, multiple injections are one day, two days, three days, four days, five days, six days, seven days, ten days, 15 days, 20 days, 25 days, or 30 days apart. In some embodiment, multiple injections are one month, two months, three months, four months, five months, six months, eight months, ten months, or eleven month apart. In some embodiment, multiple injections are one year, two years, three years, four years, five years, six years, eight years, ten years, 15 years, 20 years, 25 years, 30 years, 35 years, 40 years, 45 years, 50 years, 55 years, or 60 years apart.

Methods of Intravitreal Injection

The general method for intravitreal injection may be illustrated by the following brief outline. This example is merely meant to illustrate certain features of the method, and is in no way meant to be limiting. Procedures for intravitreal injection are known in the art (see, e.g., Peyman. G. A., et al. (2009) *Retina* 29(7):875-912 and Fagan. X. J, and Al-Qureshi, S. (2013) *Clin. Experiment. Ophthalmol.* 41(5): 500-7).

Briefly, a subject for intravitreal injection may be prepared for the procedure by pupillary dilation, sterilization of the eye, and administration of anesthetic. Any suitable mydriatic agent known in the art may be used for pupillary dilation. Adequate pupillary dilation may be confirmed before treatment. Sterilization may be achieved by applying a sterilizing eye treatment, e.g., an iodide-containing solution such as Povidone-Iodine (BETADINE®). A similar solution may also be used to clean the eyelid, eyelashes, and any other nearby tissues (e.g., skin). Any suitable anesthetic may be used, such as lidocaine or proparacaine, at any suitable concentration. Anesthetic may be administered by any method known in the art, including without limitation topical drops, gels or jellies, and subconjuctival application of anesthetic.

Prior to injection, a sterilized eyelid speculum may be used to clear the eyelashes from the area. The site of the injection may be marked with a syringe. The site of the injection may be chosen based on the lens of the patient. For example, the injection site may be 3-3.5 mm from the limus in pseudophakic or aphakic patients, and 3.5-4 mm from the limbus in phakic patients. The patient may look in a direction opposite the injection site.

In some embodiments, the methods comprise administration to the eye (e.g., by subretinal and/or intravitreal administration) an effective amount of recombinant viral particles comprising a vector of the present disclosure. In some embodiments, the viral titer of the composition is at least about any of $5\times10^{12}$, $6\times10^{12}$, $7\times10^{12}$, $8\times10^{12}$, $9\times10^{12}$, $10\times10^{12}$, $11\times10^{12}$, $15\times10^{12}$, $20\times10^{12}$, $25\times10^{12}$, $30\times10^{12}$, or $50\times10^{12}$ genome copies/mL. In some embodiments, the viral titer of the composition is about any of $5\times10^{12}$ to $6\times10^{12}$, $6\times10^{12}$ to $7\times10^{12}$, $7\times10^{12}$ to $8\times10^{12}$, $8\times10^{12}$ to $9\times10^{12}$, $9\times10^{12}$ to $10\times10^{12}$, $10\times10^{12}$ to $11\times10^{12}$, $11\times10^{12}$ to $15\times10^{12}$, $15\times10^{12}$ to $20\times10^{12}$, $20\times10^{12}$ to $25\times10^{12}$, $25\times10^{12}$ to $30\times10^{12}$, $30\times10^{12}$ to $50\times10^{12}$, or $50\times10^{12}$ to $100\times10^{12}$ genome copies/mL. In some embodiments, the viral titer of the composition is about any of $5\times10^{12}$ to $10\times10^{12}$, $10\times10^{12}$ to $25\times10^{12}$, or $25\times10^{12}$ to $50\times10^{12}$ genome copies/mL. In some embodiments, the viral titer of the composition is at least about any of $5\times10^9$, $6\times10^9$, $7\times10^9$, $8\times10^9$, $9\times10^9$. $10\times10^9$, $11\times10^9$, $15\times10^9$, $20\times10^9$, $25\times10^9$, $30\times10^9$, or $50\times10^9$ transducing units/mL. In some embodiments, the viral titer of the composition is about any of $5\times10^9$ to $6\times10^9$, $6\times10^9$ to $7\times10^9$, $7\times10^9$ to $8\times10^9$, $8\times10^9$ to $9\times10^9$. $9\times10^9$ to $10\times10^9$. $10\times10^9$ to $11\times10^9$, $11\times10^9$ to $15\times10^9$. $15\times10^9$ to $20\times10^9$, $20\times10^9$ to $25\times10^9$, $25\times10^9$ to $30\times10^9$, $30\times10^9$ to $50\times10^9$ or $50\times10^9$ to $100\times10^9$ transducing units/mL. In some embodiments, the viral titer of the composition is about any of $5\times10^9$ to $10\times10^9$, $10\times10^9$ to $15\times10^9$. $15\times10^9$ to $25\times10^9$, or $25\times10^9$ to $50\times10^9$ transducing units/mL. In some embodiments, the viral titer of the composition is at least any of about $5\times10^{10}$, $6\times10^{10}$, $7\times10^{10}$. $8\times10^{10}$. $9\times10^{10}$, $10\times10^{10}$. $11\times10^{10}$, $15\times10^{10}$, $20\times10^{10}$, $25\times10^{10}$, $30\times10^{10}$, $40\times10^{10}$, or $50\times10^{10}$ infectious units/mL. In some embodiments, the viral titer of the composition is at least any of about $5\times10^{10}$ to $6\times10^{10}$, $6\times10^{10}$ to $7\times10^{10}$, $7\times10^{10}$ to $8\times10^{10}$, $8\times10^{10}$ to $9\times10^{10}$. $9\times10^{10}$ to $10\times10^{10}$. $10\times10^{10}$ to $11\times10^{10}$, $11\times10^{10}$ to $15\times10^{10}$. $15\times10^{10}$ to $20\times10^{10}$. $20\times10^{10}$ to $25\times10^{10}$. $25\times10^{10}$ to $30\times10^{10}$. $30\times10^{10}$ to $40\times10^{10}$ $40\times10^{10}$ to $50\times10^{10}$, or $50\times10^{10}$ to $100\times10^{10}$ infectious units/mL. In some embodiments, the viral titer of the composition is at least any of about $5\times10^{10}$ to $10\times10^{10}$. $10\times10^{10}$ to $15\times10^{10}$. $15\times10^{10}$ to $25\times10^{10}$, or $25\times10^{10}$ to $50\times10^{10}$ infectious units/mL.

In some embodiments, the methods comprise administration to the eye (e.g., by subretinal and/or intravitreal administration) of an individual (e.g., a human) an effective amount of recombinant viral particles comprising a vector of the present disclosure. In some embodiments, the dose of viral particles administered to the individual is at least about any of $1\times10^8$ to about $1\times10^{13}$ genome copies/kg of body weight. In some embodiments, the dose of viral particles administered to the individual is about any of $1\times10^8$ to about $1\times10^{13}$ genome copies/kg of body weight.

During injection, the needle may be inserted perpendicular to the sclera and pointed to the center of the eye. The needle may be inserted such that the tip ends in the vitreous, rather than the subretinal space. Any suitable volume known in the art for injection may be used. After injection, the eye may be treated with a sterilizing agent such as an antibiotic. The eye may also be rinsed to remove excess sterilizing agent.

Structure of Retina and Means to Determine Effectiveness of Nucleic Acid Delivery The retina is known to contain multiple layers. Cell layers in the retina may include the inner limiting membrane, nerve fiber, ganglion cell, inner plexiform, inner nuclear, outer plexiform, outer nuclear, external limiting membrane, photoreceptor, and retinal pigment epithelium layers. The layer most proximal to the vitreous is the inner limiting membrane. This layer may contain Müller cells, a class of glia. The nerve fiber layer may contain axons from ganglion cells that form the optic nerve. The ganglion cell layer may include ganglion cells and amacrine cells. The inner plexiform layer may contain synapses between dendrites of the ganglion and amacrine cells and axons of the bipolar cells. The inner nuclear layer may contain cell nuclei of amacrine, bipolar, and horizontal cells. The outer plexiform layer may contain synapses between horizontal cell dendrites and photoreceptor cell projections. The outer nuclear layer may contain photoreceptor cell bodies. The external or outer limiting membrane may include cell connections, such as adherens junctions and desmosomes, among Miller cell apical processes and between these processes and photoreceptor cell inner segments. The photoreceptor layer, also known as the layer of rod and cones and Jacob's membrane, may contain photoreceptor cells include rods and cones. The retinal layer most distal to the vitreous is the retinal pigment epithelium (RPE), which may include a layer of hexagonal epithelial cells containing pigment granules.

The retina is also known to contain many different cell types. Retinal neurons may include photoreceptor cells, bipolar cells, ganglion cells, amacrine cells, and horizontal cells. Photoreceptor cells are sensitive to light. They may sense light and respond by transmitting signals to the optic nerve through the bipolar cells and the ganglion cells. Photoreceptor cells may include rod cells, which generally sense light in low-light conditions, and cone cells, which generally sense color and brighter light perception. Bipolar cells may receive inputs from photoreceptor cells and synapse onto amacrine or ganglion cells. Ganglion cells may receive information from amacrine cells or horizontal cells, and their axons form the optic nerve. Horizontal cells may integrate inputs from multiple photoreceptors and aid in adjustment to light levels. Amacrine cells are interneurons that help regulate bipolar cells and provide inputs to ganglion cells. Glial cells of the retina may include Müller cells, astroglia, and microglia.

The effectiveness of nucleic acid delivery by subretinal or intravitreal injection can be monitored by several criteria as described herein. In some embodiments, the effectiveness is assayed by detecting the deletion of the deep intronic mutation and/or flanking sequence in a sample including one or more cells to which the nucleic acid(s) were delivered. Deletions may be detected by any means known in the art, including without limiting Southern blotting. PCR, qPCR, DNA sequencing (e.g., Sanger sequencing and next-generation sequencing), in situ hybridization, DNA microarray, and a Surveyor nuclease assay (see, e.g., Ran, F. A. et al. (2013)

Nat. Protoc. 8:2281-2308). Exemplary methods are illustrated in the Examples below.

In some embodiments, the effectiveness is assayed functionally. For example, after treatment in a subject using methods of the present invention, the subject may be assessed for e.g., an improvement and/or stabilization and/or delay in the progression of one or more signs or symptoms of the disease state by one or more clinical parameters. Examples of such tests are known in the art, and include objective as well as subjective (e.g., subject reported) measures. For example, to measure the effectiveness of a treatment on a subject's visual function, one or more of the following may be evaluated: the subject's subjective quality of vision or improved central vision function (e.g., an improvement in the subject's ability to read fluently and recognize faces), the subject's visual mobility (e.g., a decrease in time needed to navigate a maze), visual acuity (e.g., an improvement in the subject's LogMAR score), microperimetry (e.g., an improvement in the subject's dB score), dark-adapted perimetry (e.g., an improvement in the subject's dB score), fine matrix mapping (e.g., an improvement in the subject's dB score), Goldmann perimetry (e.g., a reduced size of scotomatous area (i.e, areas of blindness) and improvement of the ability to resolve smaller targets), flicker sensitivities (e.g., an improvement in Hertz), autofluorescence, and electrophysiology measurements (e.g., improvement in ERG). In some embodiments, the visual function is measured by the subject's visual mobility. In some embodiments, the visual function is measured by the subject's visual acuity. In some embodiments, the visual function is measured by microperimetry. In some embodiments, the visual function is measured by dark-adapted perimetry. In some embodiments, the visual function is measured by ERG. In some embodiments, the visual function is measured by the subject's subjective quality of vision.

In the case of diseases resulting in progressive degenerative visual function, treating the subject at an early age may not only result in a slowing or halting of the progression of the disease, it may also ameliorate or prevent visual function loss due to acquired amblyopia. Amblyopia may be of two types. In studies in nonhuman primates and kittens that are kept in total darkness from birth until even a few months of age, the animals even when subsequently exposed to light are functionally irreversibly blind despite having functional signals sent by the retina. This blindness occurs because the neural connections and "education" of the cortex is developmentally is arrested from birth due to stimulus arrest. It is unknown if this function could ever be restored. In the case of diseases of retinal degeneration, normal visual cortex circuitry was initially "learned" or developmentally appropriate until the point at which the degeneration created significant dysfunction. The loss of visual stimulus in terms of signaling in the dysfunctional eye creates "acquired" or "learned" dysfunction ("acquired amblyopia"), resulting in the brain's inability to interpret signals, or to "use" that eye. It is unknown in these cases of "acquired amblyopia" whether with improved signaling from the retina as a result of gene therapy of the amblyopic eye could ever result in a gain of more normal function in addition to a slowing of the progression or a stabilization of the disease state. In some embodiments, the human treated is less than 30 years of age. In some embodiments, the human treated is less than 20 years of age. In some embodiments, the human treated is less than 18 years of age. In some embodiments, the human treated is less than 15 years of age. In some embodiments, the human treated is less than 14 years of age. In some embodiments, the human treated is less than 13 years of age. In some embodiments, the human treated is less than 12 years of age. In some embodiments, the human treated is less than 10 years of age. In some embodiments, the human treated is less than 8 years of age. In some embodiments, the human treated is less than 6 years of age.

In some ocular disorders, there is a "nurse cell" phenomena, in which improving the function of one type of cell improves the function of another. For example, transduction of the RPE of the central retina by a nucleic acid of the invention may then improve the function of the rods, and in turn, improved rod function results in improved cone function. Accordingly, treatment of one type of cell may result in improved function in another.

The selection of a particular vector and composition depend on a number of different factors, including, but not limited to, the individual human's medical history and features of the condition and the individual being treated. The assessment of such features and the design of an appropriate therapeutic regimen is ultimately the responsibility of the prescribing physician.

In some embodiments, the human to be treated has a genetic ocular disorder (e.g., associated with a deep intronic mutation), but has not yet manifested clinical signs or symptoms. In some embodiments, the human to be treated has an ocular disorder (e.g., associated with a deep intronic mutation). In some embodiments, the human to be treated has manifested one or more signs or symptoms of an ocular disorder (e.g., associated with a deep intronic mutation). In some embodiments, a deep intronic mutation has been identified in the human to be treated.

Compositions of the invention can be used either alone or in combination with one or more additional therapeutic agents for treating ocular disorders. The interval between sequential administration can be in terms of at least (or, alternatively, less than) minutes, hours, or days.

In some embodiments, one or more additional therapeutic agents may be administered to the subretina or vitreous (e.g., through intravitreal administration). Non-limiting examples of the additional therapeutic agent include polypeptide neurotrophic factors (e.g., GDNF, CNTF, BDNF, FGF2. PEDF. EPO), polypeptide anti-angiogenic factors (e.g., sFlt, angiostatin, endostatin), anti-angiogenic nucleic acids (e.g., siRNA, miRNA, ribozyme), for example anti-angiogenic nucleic acids against VEGF, anti-angiogenic morpholinos, for example anti-angiogenic morpholinos against VEGF, anti-angiogenic antibodies and/or antibody fragments (e.g., Fab fragments), for example anti-angiogenic antibodies and/or antibody fragments against VEGF.

VII. Kits

The compositions, nucleic acids, and viral particles as described herein may be contained within a kit designed for use in one of the methods of the invention as described herein.

The compositions, nucleic acids, and viral particles of the invention may further be packaged into kits, wherein the kits may further comprise instructions for use. In some embodiments, the instructions for use include instructions according to one of the methods described herein.

In some embodiments, the kits further contain buffers and/or pharmaceutically acceptable excipients. As is well known in the art, pharmaceutically acceptable excipients are relatively inert substances that facilitate administration of a pharmacologically effective substance and can be supplied as liquid solutions or suspensions, as emulsions, or as solid forms suitable for dissolution or suspension in liquid prior to use. For example, an excipient can give form or consistency, or act as a diluent. Suitable excipients include but are not limited to stabilizing agents, wetting and emulsifying agents, salts for varying osmolarity, encapsulating agents, pH buffering substances, and buffers. Such excipients include any pharmaceutical agent suitable for direct delivery to the eye which may be administered without undue toxicity. Pharmaceutically acceptable excipients include, but are not limited to, sorbitol, any of the various TWEEN compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in REMINGTON'S PHARMACEUTICAL SCIENCES (Mack Pub. Co., N.J. 1991).

In some embodiments, pharmaceutically acceptable excipients may include pharmaceutically acceptable carriers. Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. Additional ingredients may also be used, for example preservatives, buffers, tonicity agents, antioxidants and stabilizers, nonionic wetting or clarifying agents, viscosity-increasing agents, and the like. The kits described herein can be packaged in single unit dosages or in multidosage forms. The contents of the kits are generally formulated as sterile and substantially isotonic solution.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Generating an In Vitro Model of Leber Congenital Amaurosis Using Crispr-Cas9 Technology Methods
Plasmids The pSpCas9 plasmid that expresses SpCas9 was ordered from Sigma (Catalog number: CAS9P-1EA). The BbsI restriction site in the BGH polyA was removed using the QuikChange Lightning Site-Directed Mutagenesis Kit (Stratagene) and a pair of mutagenesis primers (SEQ ID NOS: 28-29) following the manufacturer's protocol. A U6 promoter-BbsI:BbsI-sgRNA scaffold-U6 terminator cassette (SEQ ID NO: 30) was synthesized by GeneArt (Life Technologies) and inserted into the PciI and NruI restriction sites of the pSpCas9-BbsI null plasmid to generate a pSpCas9 (BB) plasmid. The sgRNA oligos (SEQ ID NOS: 1-2) were then subcloned into the two BbsI restriction sites of the pSpCas9(BB) plasmid following the protocol described previously (Ran, F. A. et al. (2013) *Nat. Protoc.* 8:2281-2308). Electroporation-Based Transfection Methods Sold Under the Trademark Nucleofection®

2.5 micrograms of the pSpCas9(BB)-U6-sgRNA plasmid DNA and 5 microliters of the ssODN (10 micromolar) (SEQ ID NO: 3) were co-transfected into $1\times10^6$ HEK 293FT cells using the electroporation kit (proprietary electroporation buffer and electroporation cuvettes) sold under the trademark AMAXA® SF CELL LINE 4D-NUCLEOFECTOR™ X KIT L (Lonza) and the program CM-130 in a 4D-NUCLEOFECTOR® System (Lonza), following the manufacturer's protocol.
Screening To identify clones bearing the c.2991+1655A>G mutation of CEP290, cells were dissociated into single cells at 48 hr post-co-transfection and serially diluted to a final concentration of 0.5 cells per 100 microliters to reduce the likelihood of having multiple cells per well. 100 microliters of diluted cells were plated into each well of nine 96-well plates. The cells were expanded in a 5% CO2, 37° C. incubator for 2 weeks.

235 single cell clones were identified and subjected to screening for the c.2991+1655A>G mutation of CEP290. Genomic DNA was extracted using the proprietary DNA extraction solution sold under the trademark QUICKEXTRACT® (Epicentre) and amplified with a DNA polymerase and reaction buffer sold under the trademark GOTAQ® Hot Start Green Master Mix (Promega) and PCR primers flanking the intronic mutation (SEQ ID NOS: 4-5). Amplification of the PCR products was achieved with the following cycling parameters: 1 cycle at 95° C. for 2 min; 35 cycles of 95° C. for 30 sec, 60° C. for 30 sec, and 72° C. for 3 min; 1 cycle at 72° C. for 15 min. The PCR products were subjected to SnaBI digestion and Sanger sequencing with a sequencing primer (SEQ ID NO: 6).
RT-qPCR mRNAs were extracted from WT, Het, and MT cells using the spin-column based RNA purification kit sold under the trademark RNEASY® Plus Mini Kit (Qiagen) according to manufacturer's protocol. 1 microgram of total RNA was used to synthesize cDNA using the RNase H+ reverse transcriptase cDNA synthesis kit sold under the trademark ISCRIPT™ (Bio-Rad) following manufacturer's protocol. cDNAs were subjected to real-time PCR amplification in a buffer containing Fast Plus EvaGreen qPCR Master Mix with low ROX (Biotium) and primers that specifically detect wild-type CEP290 mRNA (SEQ ID NOS: 7-8) and mutant CEP290 mRNA (SEQ ID NOS: 9-10), respectively, on an ABI Prism 7500 Real Time PCR System (Applied Biosystems). The following conditions were used: 1 cycle at 50° C. for 2 min; 1 cycle at 95° C. for 10 min; 40 cycles of 95° C. for 15 sec and 60° C. for 60 sec. The specificity of amplification products was determined from melting curve analysis performed at the end of each run using a cycle at 95° C. for 15 sec, 60° C. for 60 sec, 95° C. for 15 sec, and 60° C. for 15 sec. Data were analyzed using the SDS 2.3 software (Applied Biosystems). CEP290 expression levels were normalized to the expression levels of PPIA mRNA (for primer sequences please see SEQ ID NOS: 31-32).
Western Blot Analysis Cells were lysed in RIPA lysis buffer (Cell Signaling Technology) supplemented with 1 millimole/liter of phenylmethylsulfonyl fluoride (PMSF; Cell Signaling Technology) and 1× protease inhibitor cocktail (Cell Signaling Technology) on ice. The cells were then scraped, collected in eppendorf tubes and the lysates were clarified by centrifugation at 13,000 rpm for 6 min at 4° C. The samples were prepared by adding the 4× lithium dodecyl sulfate (LDS)

sample buffer sold under the trademark NUPAGE® and the 10× reducing agent sold under the trademark NUPAGE® (both from Life Technologies), heating at 70° C. for 10 min and centrifuging at 13,000 rpm for 1 min. Protein samples were loaded on the 3-8% Tris-Acetate gel sold under the trademark NUPAGE® along with the pre-stained protein standard sold under the trademark HIMARK™ (both from Life Technologies). The samples were resolved via gel electrophoresis at 180 volts for 1 hour. Running buffer used was Tris-Acetate SDS runner buffer (Life Technologies). For the transfer, polyvinylidine fluoride (PVDF) membranes were briefly treated in methanol and rinsed with water in order to make it hydrophilic. The transfer sandwich was prepared by sandwiching the PVDF membrane and the gel between filter papers and sponges in XCell II Blot Module (Life Technologies). Transfer buffer used was NUPAGE® 20× transfer buffer (Life Technologies) with 20% methanol. The transfer was carried out at 30 volts for 2 hours in XCell SureLock Mini-Cell (Life Technologies). After the transfer, the PVDF membranes were blocked in Pierce TBST buffer (Tris-buffered saline with Tween 20 detergent; Thermo Fisher Scientific) containing 1% nonfat dry milk, shaking at room temperature for 1 hour. The blots were then incubated in the primary antibody solution made in the block solution, rocking for overnight at 4° C. The primary antibodies used are a rabbit polyclonal anti-CEP290 antibody (a kind gift from Professor Hemant Khanna at University of Massachusetts at Worcester), a mouse monoclonal anti-Cas9 antibody (clone 7A9; Millipore), a HRP conjugated-rabbit monoclonal anti-β-Actin antibody (clone 13E5; Cell Signaling Technology). Unbound primary antibodies were washed 3 times for 10 min each with TBST. Secondary antibodies (Alexa Fluor 647 conjugated anti-rabbit or anti-mouse IgG; Cell Signaling Technology) in block solution were then added to the membranes and kept on a shaker for 1 hour at room temperature. The membranes were washed 3 times for 10 min each with TBST to reduce the non-specific background. The membranes were developed for 4 min using Pierce enhanced chemiluminescence (ECL) western blotting substrate (Thermo Fisher Scientific). The protein bands in the blots were finally visualized by exposing the film for various time intervals in a Kodak X-OMAT 2000 processor. To reprobe a blot for anti-β-Actin antibody, the membranes were first stripped by incubating at 37° C. for 30 min in Restore western blot stripping buffer (Thermo Fisher Scientific) and then reprobed with the anti-β-Actin antibody. The blotting data shown in this work are representative of at least three independent experiments.

Results

First, the CRISPR-Cas9 genome editing technology was used to generate a cellular model carrying the intronic splice mutation c.2991+1655 A>G in CEP290. This cellular model is a valuable tool for evaluating therapeutics for treating LCA patients that harbor the c.2991+1655 A>G mutation in CEP290.

Genome editing with the bacterial type II CRISPR-Cas9 system is initiated with the introduction of a double-stranded break (DSB) at a targeted genomic locus defined by sgRNA target sequence and protospacer adjacent motif (PAM), and followed by the repair of the DSB through either homology-directed repair (HDR) or non-homologous end-joining (NHEJ) (Jinek. M. et al. (2012) *Science* 337:816-821; Ran, F. A. et al. (2013) *Nat. Protoc.* 8:2281-2308). In the presence of a HDR template, the CRISPR-Cas9 system can be used to generate precise and defined modifications at a targeted locus through the HDR process.

To obtain targeted genomic DNA replacement, a plasmid that expresses both sgRNA and *S. pyogenes* Cas9 (SpCas9) along with a linear HDR template was introduced into 293FT cells via the electroporation method sold under the trademark NUCLEOFECTION®. The HDR template is a single-stranded DNA oligonucleotide (ssODN; SEQ ID NO: 3) that contains homology arms of 75 bp flanking the c.2991+1655A>G mutation along with mutated PAM (c.2991+1666C>G). The mutated PAM would avoid the donor ssODN being degraded by Cas9 in cells, and in the meantime introduce a unique SnaBI restriction site to the intron 26 of CEP290.

To obtain cells that carry the c.2991+1655A>G mutation of CEP290, 235 single cell clones were isolated and screened from sgRNA/SpCas9 and ssODN co-transfected cells. Genomic DNA was extracted and amplified with PCR primers flanking the intronic mutation (SEQ ID NOS: 4-5). The PCR products were subjected to SnaBI digestion and Sanger sequencing with a sequencing primer (SEQ ID NO: 6).

Among the 235 single cell clones, one clone contained the c.2991+1655A>G and c.2991+1666C>G mutations on both CEP290 alleles (hereafter referred to as the "mutant cells" or the "MT cells"). Another clone contained the two mutations on one CEP290 allele and the endogenous wild-type CEP290 DNA on the other allele (hereafter referred to as the "heterozygous cells" or the "Het cells"). Cells that contained two alleles of endogenous wild-type CEP290 are hereafter referred to as the "wild-type cells" or the "WT cells."

Expression levels of wild-type and mutant CEP290 mRNAs in wild-type, heterozygous, and mutant cells were measured by reverse transcription quantitative PCR (RT-qPCR) using primers that specifically detect wild-type CEP290 mRNA (SEQ ID NOS: 7-8) and mutant CEP290 mRNA (SEQ ID NOS: 9-10), respectively. Results were normalized to the expression levels of PPIA mRNA (SEQ ID NOS: 31-32).

Figure 3A:
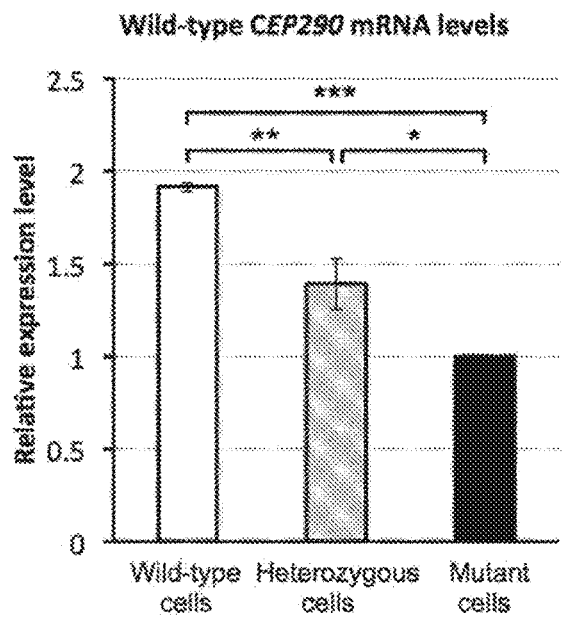
FIGS. 3A-3C show the mRNA (FIGS. 3A&3B) and protein (FIG. 3C) expression levels in different cell lines.
Figure 3B:
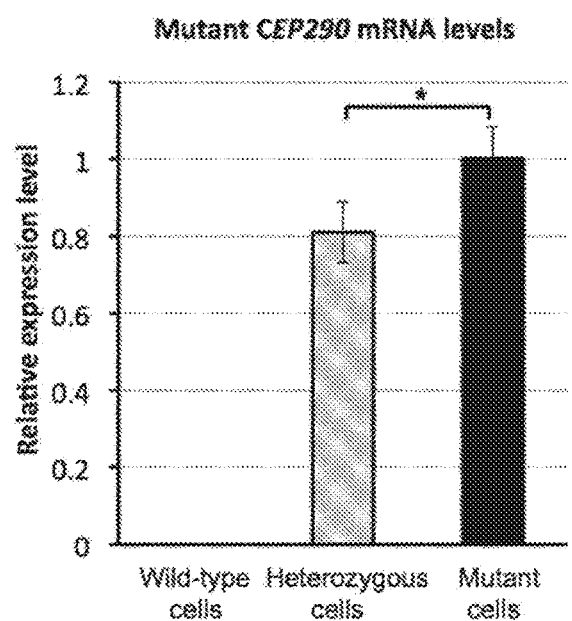

Compared to wild-type cells, the mRNA levels of wild-type CEP290 were reduced by 27% and 48% in heterozygous and mutant cells, respectively (FIG. 3A). As expected, wild-type cells did not express mutant CEP290 mRNA, whereas its levels were 24% higher in mutant cells than in heterozygous cells (FIG. 3B). Compared to heterozygous cells, mutant cells expressed significantly lower levels of wild-type CEP290 mRNA and significantly higher levels of mutant CEP290 mRNA. Therefore, this cellular model recapitulates the phenotype in LCA patients carrying the c.2991+1655 A>G mutation, as these patients express a ~50% reduced level of wild-type CEP290 mRNA (den Hollander, A. I. et al. (2006) *Am. J. Hum. Genet.* 79:556-561).

Figure 3C:

Protein levels of CEP290 in wild-type, heterozygous, and mutant cells were examined by Western blot analysis. Compared to wild-type cells, the CEP290 protein levels in heterozygous and mutant cells were greatly reduced (FIG. 3C). Mutant cells expressed lower levels of CEP290 protein compared to heterozygous cells (FIG. 3C). Therefore, the immunoblot data are consistent with the RT-qPCR data.

Example 2: Targeted Deletion of the c.2991+1655 A>G Mutation

Methods
Plasmids

An all-in-one expression vector was constructed with the Golden Gate cloning method as previously described (Sakuma, T. et al. (2014) *Sci. Rep.* 4:5400). Briefly, a DNA fragment that contains U6 promoter-BbsI:BbsI-sgRNA scaffold-U6 terminator-CMV promoter (SEQ ID NO: 33) was synthesized using the oligonucleotide synthesis platform marketed under the trademark by GENEART® (Life Technologies) and inserted into the PciI and NheI restriction sites of the pSpCas9-BbsI null plasmid described above to generate a pSpCas9(BBU) plasmid that is used to subclone the upstream sgRNA guide sequences. To construct a pSpCas9 (BBD) plasmid that is used to subclone the downstream sgRNA guide sequences, a PCR reaction was performed using the High-Fidelity DNA Polymerase sold under the trademark PHUSION® (New England BloLabs Inc) with the pSpCas9(BB) plasmid DNA as the DNA template and a pair of PCR primers (SEQ ID NOS: 34-35). The cycling parameters were: 1 cycle at 98° C. for 1 min; 35 cycles of 98° C. for 20 sec and 72° C. for 30 sec; 1 cycle at 72° C. for 5 min. The PCR product was inserted into the PciI and KpnI sites of the pSpCas9(BBU) plasmid. In this pSpCas9(BBD) plasmid, two BsaI sites flank the U6 promoter-driven sgRNA. The U1 sgRNA oligos (SEQ ID NOS: 11-12) were annealed and then subcloned into the two BbsI restriction sites of the pSpCas9(BBU) plasmid, and the D1, D2, and D3 sgRNA oligos (SEQ ID NOS: 13-18) were annealed and then subcloned into the two BbsI restriction sites of the pSpCas9(BBD) plasmid following the protocol described previously (Ran, F. A. et al. (2013) Nat. Protoc. 8:2281-2308). The resultant D1-D3 sgRNAs along with the U6 promoter were further cut out from the pSpCas9(BBD) plasmids using the restriction enzyme BsaI and then subcloned into the two BsaI sites in the pSpCas9(BBU)-U1 sgRNA plasmid. The resultant pSpCas9(BBUD) plasmids express two U6 promoter-driven sgRNAs and one CMV promoter-driven SpCas9. The oligos for two control sgRNAs (SEQ ID NOS: 36-39) were subcloned into the BbsI restriction sites of the same all-in-one expression vector using the method described above as the control plasmid.

Transfection and PCR Analysis

The paired sgRNAs-SpCas9 plasmids were transfected into wild-type, heterozygous, and mutant cells using the cationic-lipid transfection reagent sold under the trademark LIPOFECTAMINE® 3000 Transfection Reagent (Life Technologies) following manufacturer's protocol.

48 hr post-transfection, genomic DNA was extracted from cells using the proprietary DNA extraction solution sold under the trademark QUICKEXTRACT™ (Epicentre) and amplified with the proprietary formulation of Taq polymerase sold under the trademark GOTAQ® Hot Start Green Master Mix (Promega) and PCR primers flanking the intronic mutation (SEQ ID NOS: 4-5). Amplification of the PCR products was achieved with the following cycling parameters: 1 cycle at 95° C. for 2 min; 35 cycles of 95° C. for 30 sec, 60° C. for 30 sec, and 72° C. for 3 min; 1 cycle at 72° C. for 15 min. PCR products were then subjected to agarose gel electrophoresis.

Next-Generation Sequencing (NGS)

PCR products acquired above were sent to ACGT (Wheeling, IL) for NGS sequencing. The sample DNA were fragmented to an average 350 bp target fragment size by ultrasonication, and used for constructing a sequencing library using the PCR-free fragmented genomic DNA-adapter library preparation method sold under the trademark TRUSEQ® DNA PCR-free sample preparation kit. The library was quantified via Qubit and 2100 Bioanalyzer, and loaded onto an Illumina platform to generate PE150 reads. Approximately 150K reads (±20%) per sample were generated. Raw Illumina were de-multiplexed and converted into .fastq format, and low quality (Q<20) and short reads (N<50) were filtered out. The filtered reads were aligned to the reference sequences (wild-type DNA and truncated DNA) using Bowtie2. For quantification, the number of reads aligned to a 40 bp sequence flanking the U1 sgRNA cleavage site (20 bp before and 20 bp after the cleavage site) that are unique to either the wild-type DNA or the truncated DNA were used to calculate the percentage of wild-type and truncated DNA in each sample.

Results

Next, the model described above was used to test the approach for generating a targeted deletion of the c.2991+1655 A>G mutation.

One upstream sgRNA (U1, SEQ ID NO: 19) that targets a locus within the cryptic exon was expressed together with each of three downstream sgRNAs (D1, D2, D3; SEQ ID NOS: 20-22) in the same vector as SpCas9. The pairs of upstream and downstream sgRNAs all flank the c.2991+1655A>G mutation and are predicted to generate genomic deletions of 283 bp, 187 bp, and 231 bp, respectively, as previous studies have demonstrated that repair of paired sgRNAs-induced genomic deletion is largely accomplished by precise end joining (Brandl, C. et al. (2014) *FEBS Open Bio.* 5:26-35; Zheng. Q. et al. (2014) *Biotechniques* 57:115-124). Two control sgRNAs were subcloned into the same plasmid as control.

Figure 4A:
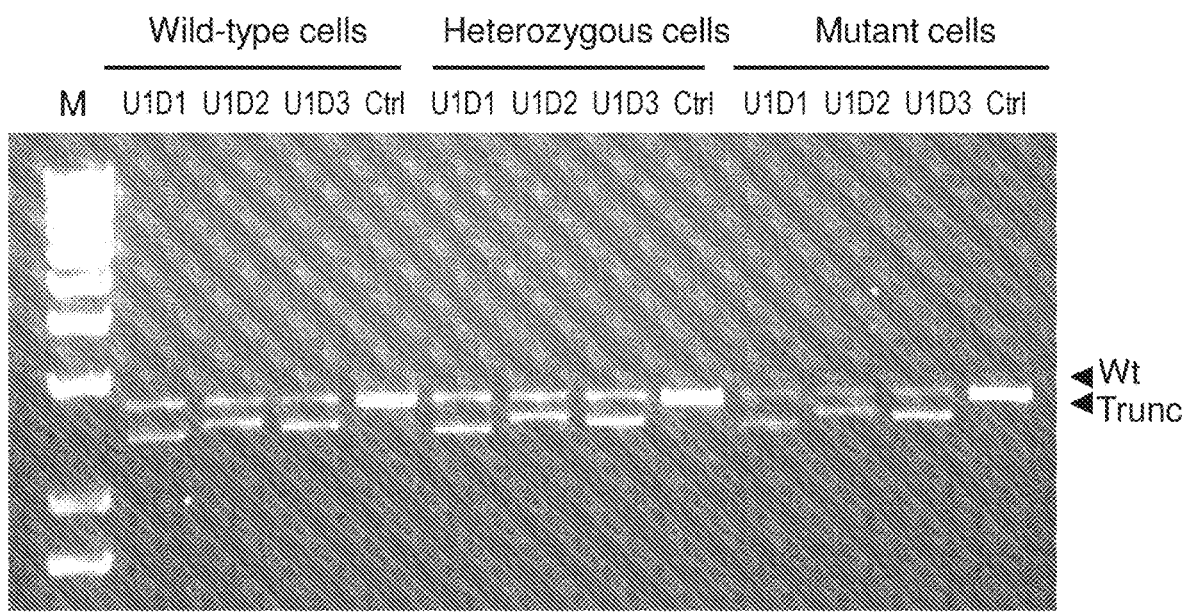
FIGS. 4A&4B show the efficiency of targeted deletion with paired sgRNAs and SpCas9, as determined by PCR (FIG. 4A) and next-generation sequencing (FIG. 4B).
Figure 4B:
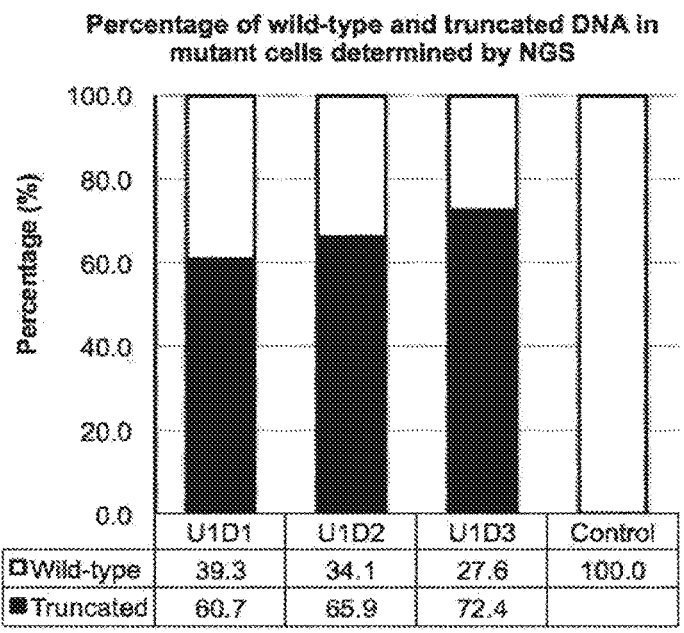

The paired sgRNAs-SpCas9 plasmids were transfected into wild-type, heterozygous, and mutant cells as described above, followed by PCR analysis using primers flanking the deletion regions (SEQ ID NOS: 4-5). Wild-type and truncated genomic fragments were resolved by gel electrophoresis. For all the three tested upstream/downstream sgRNA pairs. PCR products were detected that indicate the presence of expected genomic deletions, which were absent in the control sgRNAs-transfected cells (FIG. 4A). These results demonstrate that the paired sgRNAs and SpCas9 are capable of removing the c.2991+1655A>G mutation. Next-generation sequencing (NGS) analysis of the 4 PCR samples prepared from the mutant cells further revealed that 60.7%, 65.9%, and 72.4% NGS reads were aligned to the truncated DNA in U1D1-, U1D2-, and U1D3-transfected cells, respectively. Therefore, all the three sgRNA pairs and SpCas9 are highly efficient in removing the c.2991+1655A>G mutation.

To confirm that the paired sgRNAs were able to rescue wild-type CEP290 expression levels in heterozygous and mutant cells, wild-type, heterozygous and mutant cells were transfected with the plasmids that express paired sgRNAs and SpCas9, followed by RT-qPCR analysis for CEP290 mRNA as described above. Results were normalized to the expression levels of PPIA mRNA.

Figure 5A:
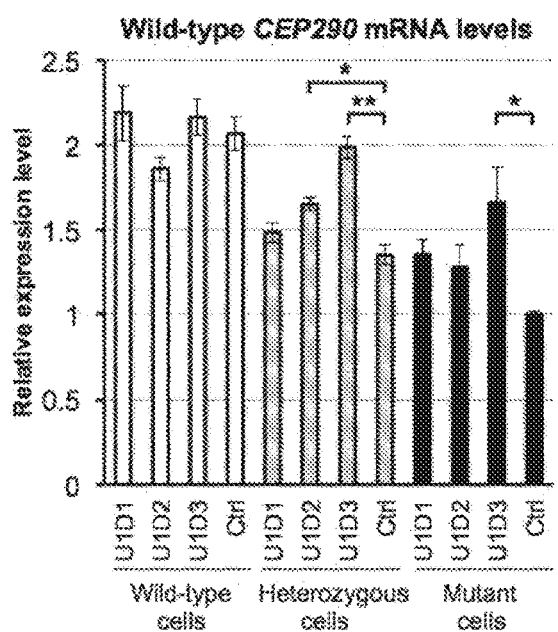
FIGS. 5A-5C show rescue of CEP290 expression with paired sgRNAs and SpCas9.
Figure 5B:
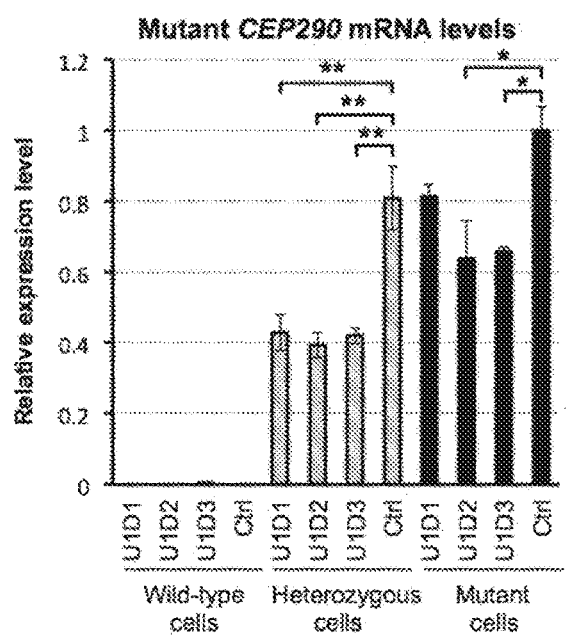

Compared to control sgRNAs, sgRNA pairs, especially the U1D3 pair, markedly rescued wild-type CEP290 mRNA levels (FIG. 5A) and reduced mutant CEP290 mRNA levels (FIG. 5B) in heterozygous and mutant cells. Importantly, none of the three sgRNA pairs significantly changed wild-type CEP290 mRNA levels (FIG. 5A), suggesting that the targeted genomic deletions did not interfere with normal splicing of CEP290 transcripts. The U1D3 sgRNA pair markedly rescued wild-type CEP290 mRNA levels in heterozygous and mutant cells to levels comparable to that in wild-type cells (FIG. 5A). The U1D2 sgRNA pair also significantly increased wild-type CEP290 mRNA levels in heterozygous cells (FIG. 5A). All three sgRNA pairs significantly reduced mutant CEP290 mRNA levels in heterozygous cells (FIG. 5B). The pairs of U1D2 and U D3 sgRNAs significantly reduced mutant CEP290 mRNA levels in MT cells (FIG. 5B).

Figure 5C:
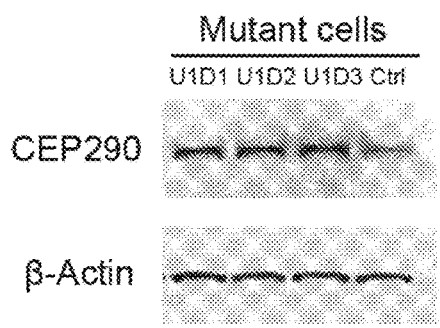

To confirm that the paired sgRNAs were able to rescue wild-type CEP290 protein expression in mutant cells, mutant cells were transfected with paired sgRNAs and SpCas9 and then subjected to Western blot analysis as described above. Compared to control sgRNAs, all three sgRNA pairs rescued CEP290 protein expression (FIG. 5C).

Taken together, these data demonstrate that the upstream/downstream sgRNA pairs, especially the U1D3 pair, are highly efficient in preventing the splicing of the mutant cryptic exon and restoring wild-type CEP290 expression. These results demonstrate that a pair of guide RNAs coupled with Cas9 can permanently delete the intron region flanking the c.2991+1655 A>G mutation of CEP290 for preventing the splicing of the cryptic exon inserted into the CEP290 mRNA.

Example 3: Developing a Self-Limiting Crispr-Cas9 System to Limit the SpCas9 Persistence Time Methods
Plasmids An AAV packaging plasmid pAAV-minCMV-SpCas9-NLS-SV40 pA was constructed for the self-limiting Crispr-Cas9 system. Briefly, a DNA fragment that contains a minimal promoter fragment derived from the CMV promoter (minCMV promoter) (SEQ ID NO: 56) was synthesized by GeneArt (Life Technologies) and inserted into the MluI and ApoI restriction sites of the Sigma pSpCas9 plasmid described above to generate a pminCMV-SpCas9-NLS-BGH pA plasmid. Next, a DNA fragment that contains SV40 early poly(A) signal (SV40 pA) (SEQ ID NO: 57) was synthesized by GeneArt (Life Technologies) and inserted into the XhoI and BbsI restriction sites of the above plasmid to generate a pminCMV-SpCas9-NLS-SV40 pA plasmid. Finally, the minCMV-SpCas9-NLS-SV40 pA fragment was subcloned into an AAV packaging plasmid to generate a pAAV-minCMV-SpCas9-NLS-SV40 pA.

To construct self-limiting pSpCas9 plasmid, the recognition sequences for the SpCas9 nuclease (U1 and D3 sgRNA target sequences plus corresponding PAM motifs; SEQ ID NOS: 58-59) were subcloned into the insertion site 1 (between minCMV promoter and SpCas9) and/or the insertion site 2 (between SpCas9-nuclear localization signal (NLS) and SV40 poly(A) signal).

The second AAV packaging plasmid for the self-limiting Crispr-Cas9 system is pAAV-U6-U1 sgRNA-U6-D3 sgRNA-BGH pA. To construct this plasmid, the U6-U1 sgRNA-U6-D3 sgRNA fragment was cut out from the pSpCas9(BBUD)-U1D3 plasmid using the restriction enzymes PciI and KpnI and then subcloned into the EcoRV and KpnI sites of the AAV packaging plasmid to generate a pAAV-U6-U1 sgRNA-U6-D3 sgRNA plasmid. For AAV titering purpose, a BGH pA fragment (SEQ ID NO: 60) was cloned into the SpeI and HindIII sites of this plasmid.

Results

CRISPR-Cas9 is a powerful tool for genome editing, but it is unclear how expression of the bacterial protein Cas9 will be tolerated in patients. CRISPR-Cas9 works quickly (hours to days) and its prolonged presence in cells is not necessary. Unwanted immune responses and potential safety problems can be caused by prolonged expression of exogenous protein. For example, expression of exogenous marker protein green fluorescent protein (GFP) can elicit substantial unwanted immunological responses (Stripecke R et al. (1999) *Gene Ther.* 6:1305-1312). In addition, a recent report suggested that there is induction of humoral immunity against Cas9 and the potential presence of a Cas9-specific cellular immune response after in vivo delivery of CRISPR-Cas9 (Wang, D. et al. (2015) *Hum. Gene Ther.* 26:432-442). Therefore, a "hit and go" approach in which exposure to Cas9 protein is restricted may be beneficial to in vivo delivery of CRISPR-Cas9. Such "hit and go" approach may also reduce the off-target effects since this will reduce the interaction time between Cas9 and unintended targets.

Figure 6A:
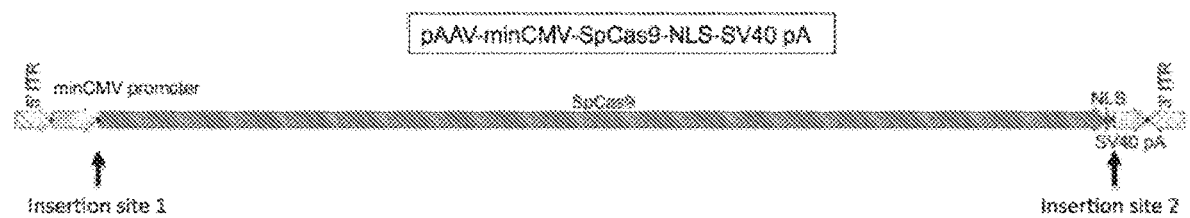
FIGS. 6A-6E show a self-limiting CRISPR-SpCas9 system.

To this end, we developed a self-limiting Crispr-Cas9 system to limit the SpCas9 persistence time by incorporating recognition site(s) for the sgRNA(s) into the SpCas9 vector itself such that the vector will be cut and destroyed shortly after SpCas9 expression begins. The self-limiting Crispr-Cas9 system comprises two vectors: a pAAV-U6-U1 sgRNA-U6-D3 ssRNA vector that expresses the sgRNA pair U1 and D3, and a pAAV-minCMV-SpCas9-NLS-SV40 pA vector that expresses a minCMV promoter-driven SpCas9. The recognition sequences for the U1 and/or D3 sgRNA (target sequences plus corresponding PAM motifs) are incorporated into either one or two of the two insertion sites in the second vector. The insertion site 1 is located between the minCMV promoter and the SpCas9 coding sequence, and the insertion site 2 is located between the nuclear localization signal (NLS) and the SV40 poly(A) signal (FIG. 6A). Therefore, in this self-limiting Crispr-Cas9 system, U1 and D3 sgRNAs will guide SpCas9 protein for both targeted genomic deletion and cleavage of the self-limiting SpCas9 vector itself, which will prevent the vector from making excessive SpCas9 protein.

To test the self-limiting Crispr-Cas9 system in vitro, mutant cells were transfected with the two vectors described above, followed by Western blot analysis (FIG. 6B), genomic DNA PCR (FIG. 6C), and RT-qPCR analysis for CEP290 mRNA (FIGS. 6D&6E) as described above.

Figure 6B:
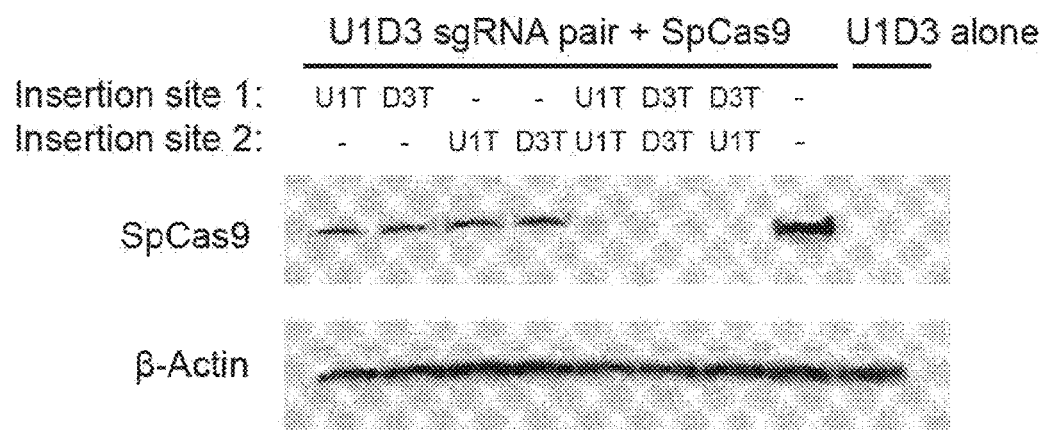

When single sgRNA recognition sequence (U1T or D3T; SEQ ID NOS: 58-59) was inserted into the self-limiting SpCas9 vector, the SpCas9 protein levels were greatly reduced compared to the control SpCas9 vector that does not contain the sgRNA recognition sequence (FIG. 6B). When two U1T, two D3T, or combined D3T and U1T were inserted into the self-limiting SpCas9 vector, the SpCas9 protein level was almost abolished (FIG. 6B). Therefore, the self-limiting Crispr-Cas9 system can effectively restrict SpCas9 expression.

Figure 6C:
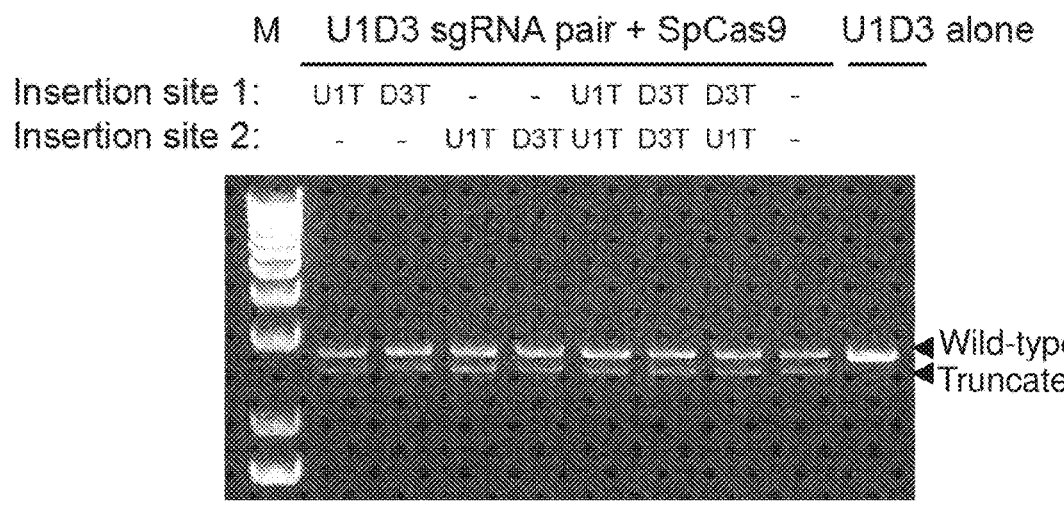

To confirm that the self-limiting Crispr-Cas9 system is still able to induce targeted gemomic deletion and remove the LCA10 c.2991+1655A>G mutation, we performed genomic DNA PCR analysis in the dual vectors-transfected mutant cells (FIG. 6C). The PCR band corresponding to the truncated DNA was present in both the control SpCas9 vector-transfected cells and the self-limiting SpCas9 vectors-transfected cells, suggesting that the self-limiting Crispr-Cas9 system is still able to remove the LCA10 intronic mutation despite the short persistence time of SpCas9. It is noteworthy that the genomic deletion observed in FIG. 6C was not as robust as the deletion seen in FIG. 4A. This could be due to different experimental conditions in these two studies. First, we used an all-in-one vector in FIG. 4A, and used dual vectors in FIG. 6C. Secondly, the SpCas9 expression was driven by a CMV promoter in FIG. 4A and driven by a minCMV promoter in FIG. 6C.

Figure 6D:
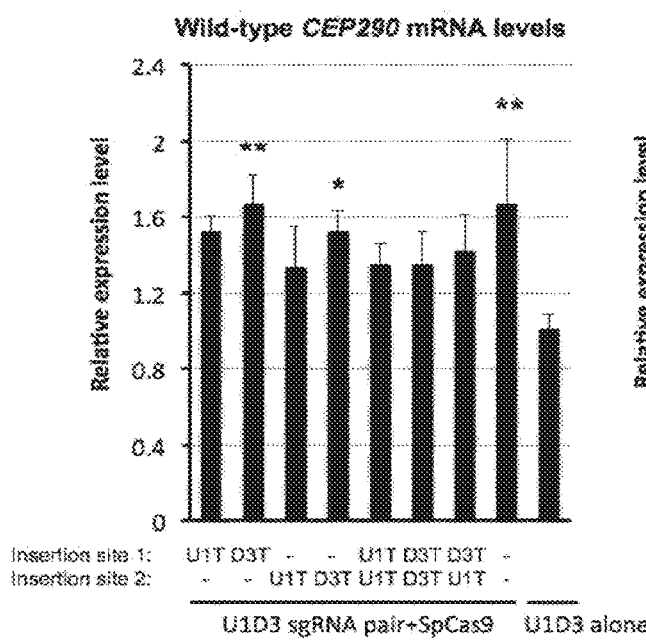
Figure 6E:
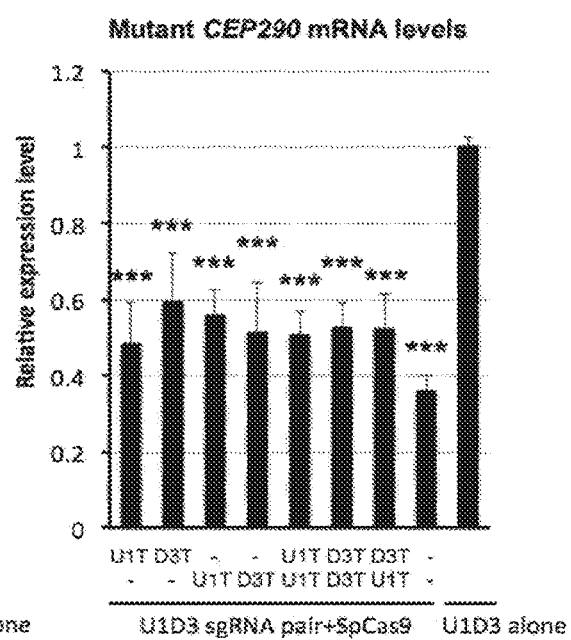

Next, we examined wild-type and mutant CEP290 mRNA levels in mutant cells transfected with the dual vectors. Compared to U1D3 sgRNAs alone (control), the control SpCas9 vector significantly rescued wild-type CEP290 mRNA levels in the mutant cells (FIG. 6D). Similarly, the SpCas9 vector that contains the D3 sgRNA recognition sequence at either insertion site significantly increased wild-type CEP290 mRNA levels (FIG. 6D). Other self-limiting SpCas9 vectors also increased wild-type CEP290 mRNA levels, although the differences were not statistically significant when compared to the control (FIG. 6D). In addition, all the self-limiting SpCas9 vectors and the control SpCas9 vector significantly reduced mutant CEP290 mRNA levels (FIG. 6E).

Taken together, these data demonstrate that the self-limiting Crispr-Cas9 system is able to restrict SpCas9 persistence time, remove the LCA10 c.2991+1655A>G mutation, rescue wild-type CEP290 expression, and reduce mutant CEP290 expression.

Example 4: Targeted Deletion of an Intronic Region of Mouse Cep290 Gene in the Mouse Reina Methods
Plasmids We used a dual AAV system for targeted genomic deletion in the mouse retina. The first AAV is produced with the AAV packaging plasmid pAAV-minCMV-SpCas9-NLS-SV40 pA as described above. The second AAV is produced with an AAV packaging plasmid pAAV-U6-U11 sgRNA-U6-D11 sgRNA-RK-EGFP-BGH pA. To construct this plasmid, the U11 sgRNA guide sequence (SEQ ID NO: 61) and D11 sgRNA guide sequence (SEQ ID NO: 62) were subcloned into pSpCas9(BBUD) plasmid as described above to generate a pSpCas9(BBUD)-U11D11 plasmid. A RK promoter-EGFP-BGH pA fragment (SEQ ID NO: 63) was inserted into the KpnI and XhoI sites of this plasmid, and then the entire U6-U11 sgRNA-U6-D11 sgRNA-RK-EGFP-BGH pA cassette was cut out from this plasmid using the restriction enzymes PciI and PmeI and then subcloned into the BamHI and SphI sites of the AAV packaging plasmid described above to generate the final plasmid. A control plasmid pAAV-RK-EGFP-BGH pA was also generated.

AAV Production

Recombinant AAV vectors were produced by triple transfection of human embryonic kidney carcinoma 293 cells (HEK-293) as previously described (Xiao, X. et al. (1998) *J. Virol* 72:2224-2232). Briefly, an AAV packaging plasmid, a plasmid containing the rep gene from serotype 2 and a capsid gene from serotype 5, and a helper adenoviral plasmid (Stratagene) were used. Virus was collected 72 hours post-transfection, purified by AVB Sepharose affinity chromatography (GE Healthcare). Genome copy (GC) titers of AAV vectors were determined by quantitative PCR analysis using the sequence-specific probes sold under the trademark TAQMAN® (Applied Biosystems) as described previously (Gerits, A. et al. (2015) *Neurophotonics*. 2:031209).

Animals 8-10 weeks old female C57BL/6J mice from the Jackson Laboratories (Bar Harbor, ME) were purchased and maintained at Sanofi's vivarium. The animals were given free access to food and water for the duration of the study. All animal procedures were conducted in compliance with the Animal Welfare Act, the Guide for the Care and Use of Laboratory Animals, the Office of Laboratory Animal Welfare, and in accordance to the ARVO Statement for the Use of Animals in Ophthalmic and Vision Research.

Subretinal AAV Injection

Mice were sedated using 3.5% isoflurane carried in 800 milliliter/min of oxygen delivered to the animal via a nose cone. Mydriasis and cycloplegia was induced in mice with a topical application of Tropicamide (Alcon. Fort Worth, TX). A pilot incision was made in the cornea and a 33 gauge blunt tipped needle was directed through the incision and advanced posteriorly between the iris and the lens capsule until the tip penetrated the posterior neurosensory retina, 1x 10 viral genome particles of AAV5-minCMV-SpCas9-NLS-SV40 pA (AAV5-SpCas9 in FIG. 7A) together with 1×10$^9$ viral genome particles of AAV5-U6-U11 sgRNA-U6-D11 sgRNA-RK-EGFP-BGH pA (AAV5-U11D11-RK-EGFP in FIG. 7A) or the control AAV5-U6-RK-EGFP-BGH pA (AAV5-RK-EGFP in FIG. 7B) were delivered to the OS eye of each mouse in the volume of one microliter over the time of one second. The needle was held in position for approximately five seconds before withdrawal. The animal was allowed to recover from anesthesia prior to returning to its cage.

EGFP expression in the retina was evaluated in live animals using a Micron IV Retinal Microscope (Phoenix Research Labs) at two and four weeks post-injection, and mice lacking EGFP expression were excluded from the study. All the animals were euthanized at four weeks post-injection.

Retina Dissection

Mouse eyes were enucleated and placed in Phosphate-buffered saline (PBS). Retinas were isolated with micro dissecting scissors under a dissecting microscope. The retinal pigment epithelium (RPE) layer was carefully removed.

Genomic DNA Expression and PCR Analysis

Retinas were homogenized in the proprietary DNA extraction solution sold under the trademark QUICKEXTRACT™ (Epicentre) with pestles powered by a cordless motor (VWR). Genomic DNA was extracted following manufacturer's instruction (Epicentre), diluted to 10 nanogram/microliter, and then amplified with the proprietary formulation of Taq polymerase sold under the trademark GOTAQ® Hot Start Green Master Mix (Promega) and PCR primers flanking the deleted region (SEQ ID NOS: 64-65). Amplification of the PCR products was achieved with the following cycling parameters: 1 cycle at 95° C. for 2 min; 35 cycles of 95° C. for 30 sec, 62° C. for 30 sec, and 72° C. for 2 min; 1 cycle at 72° C. for 12 min. PCR products were then subjected to agarose gel electrophoresis.

Results

Our study in the cellular model of LCA10 supported the efficiency of our paired sgRNAs and SpCas9 approach to remove the LCA10 c.2991+1655A>G mutation in vitro. Next, we assessed our CRISPR-Cas9 approach in an in vivo setting. Since currently there is no animal model that expresses the cryptic exon caused by the LCA10 intronic splice mutation, we thus tested if a pair of sgRNAs along with SpCas9 could induce targeted genomic deletion in the intron 25 of mouse Cep290 gene, which is homologous to the intron 26 of human CEP290 gene where the c.2991+1655A>G mutation is located.

We decided to use AAV vectors for in vivo gene delivery because of their low immunogenicity and range of serotypes allowing preferential infection of certain cell types. The retinal cells most affected by CEP290 mutations are photoreceptors, and previous studies have shown that AAV serotype 5 (AAV5) could efficiently transduce photoreceptors with subretinal injection (Boye, S. E. et al. (2012) *Hum. Gene Ther.* 23:1101-1115). Therefore, we decided to use AAV5 to deliver SpCas9 and paired sgRNAs to photoreceptors.

Figure 7A:
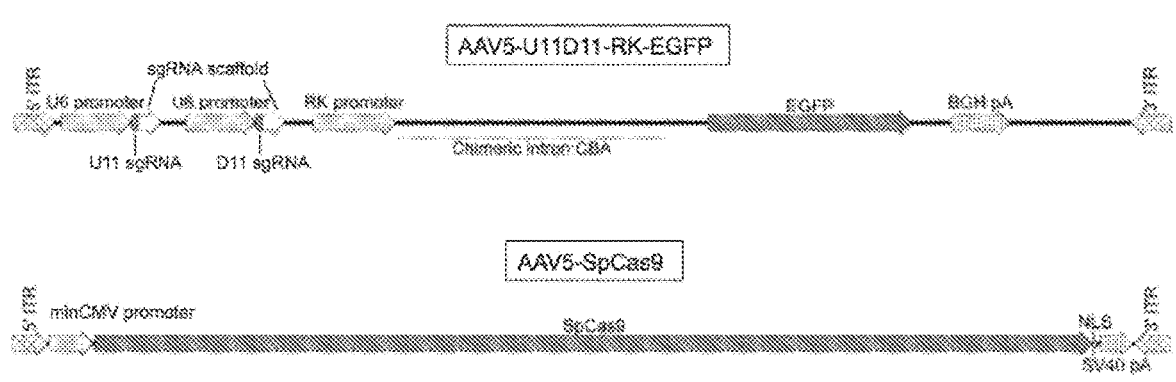
FIGS. 7A&7B show deletion of a region in the Intron 25 of Cep290 gene in the mouse retina by a dual AAV system.

Due to the low packaging capacity of an AAV vector (~4.8 kb) and the length of SpCas9 coding sequence, measuring in at 4.1 kb (see SEQ ID NO: 40 for amino acid sequence), it is challenging to package one SpCas9 component and two U6-sgRNA components in a single AAV vector. Therefore, we used a dual AAV system for our in vivo validation study (FIG. 7A). The first AAV vector is AAV5-U11D11-RK-EGFP, which expresses an upstream sgRNA U11 (SEQ ID NO: 61) and a downstream sgRNA D11 (SEQ ID NO: 62), as well as a rhodopsin kinase (RK) promoter-driven EGFP reporter gene. The U11 and D11 sgRNA pair are predicted to generate genomic deletion of 557 bp in the intron 25 of mouse Cep290 gene. A control AAV AAV5-RK-EGFP was also produced. The second AAV vector is AAV5-SpCas9, which expresses a minCMV promoter-driven SpCas9.

Figure 7B:
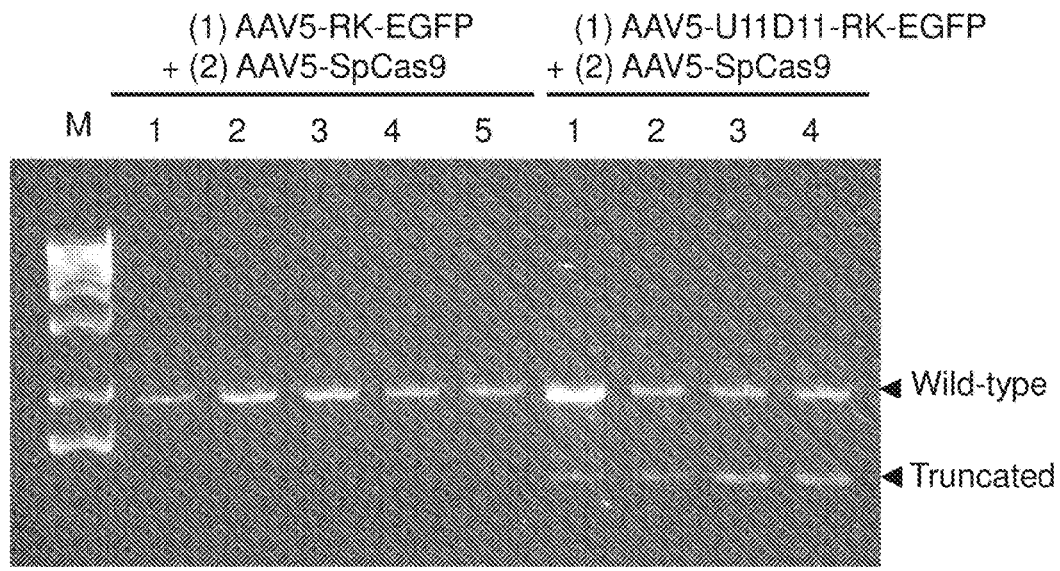

AAV5-U11D11-RK-EGFP (or AAV5-RK-EGFP) and AAV5-SpCas9 ($1\times10^9$ viral genome particles each) were co-injected into the subretinal space of adult C57BL/6J mice. EGFP expression in the retina was evaluated in live animals, and mice lacking EGFP expression were excluded from the study. At four weeks post-injection, the animals were euthanized, and genomic DNA was extracted from the retinas, followed by PCR analysis using primers flanking the deletion regions (SEQ ID NOS: 64-65). Wild-type and truncated genomic fragments were resolved by gel electrophoresis. For the animals injected with AAV5-U11D11-RK-EGFP and AAV5-SpCas9, PCR product was detected that indicates the presence of expected genomic deletion with the U11 and D11 sgRNA pair, which was absent in the animals injected with AAV5-RK-EGFP and AAV5-SpCas9 (FIG. 7B). These results demonstrate that our dual AAV system is capable of inducing targeted genomic deletion in vivo.

Example 5: Employing a Pair of Upstream/Downstream sgRNAs and SaCas9 to Remove the LCA10 c.2991+1655A>G Mutation Methods Plasmids To construct the SaCas9 plasmid, a minCMV-SaCas9-NLS-FLAG-BGH pA-U6-BsaI:BsaI-sgRNA scaffold fragment (SEQ ID NO: 66) was synthesized at GenScript and subcloned into the PciI and BbsI restriction sites of the Sigma pSpCas9 plasmid to replace the CMV-SpCas9-BGH pA cassette and generate a pminCMV-SaCas9-BGH pA-U6 plasmid. Five sgRNA guide sequences (aU1, aU2, aU3, aD1 aD2; SEQ ID NOS: 45-49) were identified using Benchling's online genome-editing design tool and then subcloned into the two BsaI restriction sites of the above plasmid. To pair up the upstream sgRNAs (aU1, aU2, aU3) and downstream sgRNAs (aD1, aD2), the U6-aD1 sgRNA cassette and U6-aD2 sgRNA cassette were cut out from their plasmids using the restriction enzymes KpnI and NotI, and then subcloned into the NotI site of the plasmid that expresses aU1, aU2, or aU3 sgRNA. As a result, we generated six plasmids that express six different sgRNA pairs (aU1aD1, aU1aD2, aU2aD1, aU2aD2, aU4aD1, aU4aD2). Finally, the minCMV-SaCas9-BGH pA-U6-paired sgRNAs fragments in these six plasmids were subcloned into an AAV packaging plasmid to generate pAAV-minCMV-SaCas9-BGH pA-U6-paired sgRNAs plasmids. A control plasmid pAAV-minCMV-SaCas9-BGH pA that does not express sgRNA was also generated.

Results

From the above studies we have demonstrated that a pair of upatream/downstream sgRNAs could efficiently guide SpCas9 to remove the LCA10 c.2991+1655A>G mutation and restore wild-type CEP290 expression. The length of SpCas9 coding sequence (~4.1 kb) makes it difficult to package one minCMV-SpCas9 component and two U6-sgRNA components in a single AAV vector. Ran et al. (Ran. F. A. et al. (2015) Nature 520:186-191) recently discovered a shorter Cas9 enzyme S, aureus Cas9 (SaCas9; 1053 amino acids; SEQ ID NO: 55) that also displays cleavage activity in mammalian cells. The smaller size of SaCas9 makes it possible to package one minCMV-SaCas9 component and two U6-sgRNA components in a single AAV vector. To test if paired sgRNAs and SaCas9 are also able to remove the LCA10 intronic mutation, we designed three upstream sgRNA guide sequences (aU1, aU2, aU3; SEQ ID NOS: 45-47) and two downstream sgRNA guide sequences (aD1, aD2; SEQ ID NOS: 48-49) specifically for SaCas9 using Benchling's online genome-editing design tool. The upstream/downstream sgRNAs were paired up and subcloned into the AAV packaging plasmid. The same plasmids also expressed a minCMV promoter-driven and human codon-optimized SaCas9 (SEQ ID NO: 66).

Figure 8A:
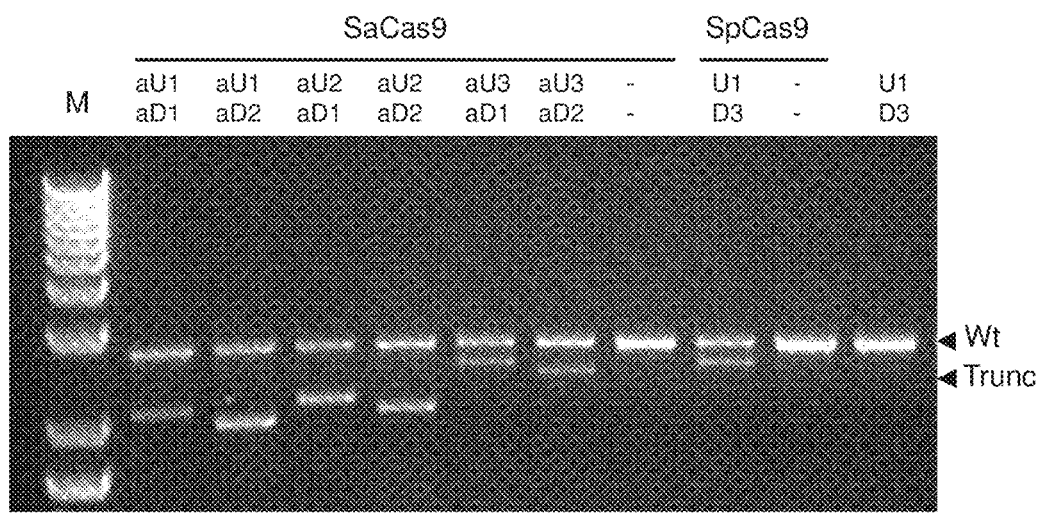
FIGS. 8A-8C show targeted deletion with S. aureus Cas9 (SaCas9) and SpCas9, as determined by PCR (FIG. 8A) and by RT-qPCR (FIGS. 8B&8C). Mutant cells were transfected with paired sgRNA pairs together with either SaCas9 or SpCas9. Note that paired sgRNAs and SaCas9 are in one AAV packaging plasmid, whereas paired sgRNAs and SpCas9 are in two separate AAV packaging plasmids.

The paired sgRNAs-SaCas9 plasmids were transfected into mutant cells as described above. To compare SaCas9 with SpCas9, mutant cells were also transfected with the dual SpCas9 AAV plasmids (pAAV-minCMV-SpCas9+pAAV-U1D3 sgRNA pair) or individual plasmids alone. PCR analysis was performed using primers flanking the deletion regions (SEQ ID NOS: 4-5). Wild-type and truncated genomic fragments were resolved by gel electrophoresis. For all the tested upstream/downstream sgRNA pairs, PCR products were detected that indicate the presence of expected genomic deletions, which were absent in the control plasmids-transfected cells (FIG. 8A). These results demonstrate that both SaCas9 and SpCas9 are able to work with paired sgRNAs to remove the LCA10 intronic splice mutation.

Figure 8B:
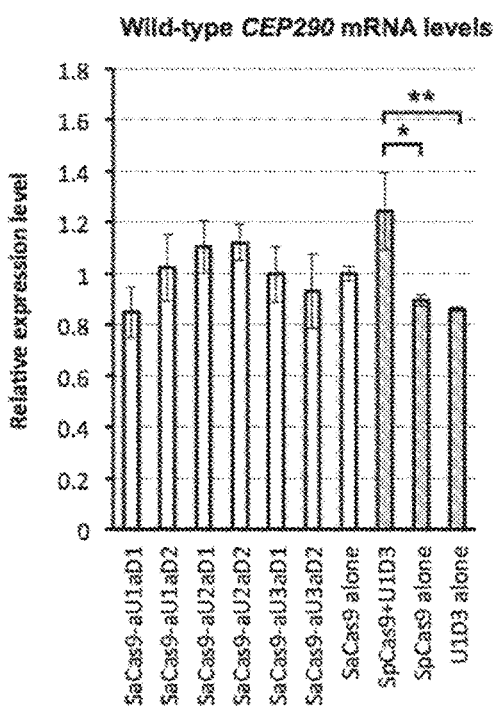
Figure 8C:
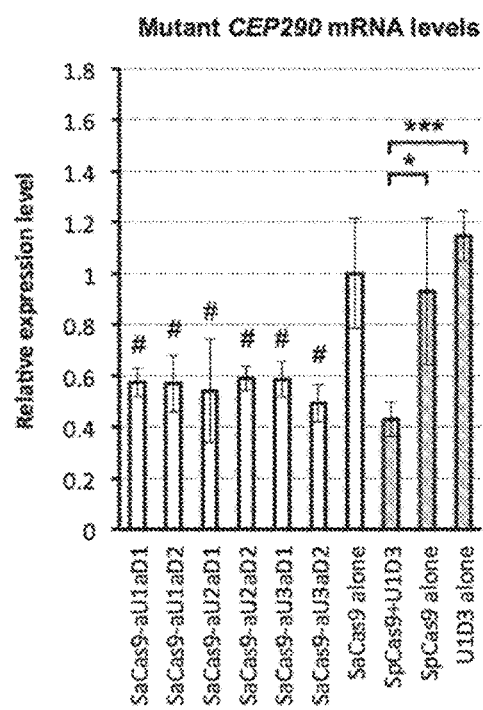

Next, we examined wild-type and mutant CEP290 mRNA levels in mutant cells transfected with above AAV packaging plasmids. Surprisingly, none of the upstream/downstream sgRNA pairs significantly increased wild-type CEP290 mRNA levels compared to the SaCas9 alone plasmid, although the aU2aD1 pair and the aU2aD2 pair showed a trend of increase (FIG. 8B). In contrast, the dual AAV plasmids for SpCas9 significantly rescued wild-type CEP290 mRNA levels compared to individual plasmids (FIG. 8B). All the paired sgRNAs-SaCas9 plasmids significantly reduced mutant CEP290 mRNA levels compared to the SaCas9 alone plasmid (FIG. 8C). Similarly, the dual AAV plasmids for SpCas9 significantly reduced mutant CEP290 mRNA levels compared to individual plasmids (FIG. 8C). Although in the current study SaCas9 is not as efficient as SpCas9 in rescuing wild-type CEP290 mRNA levels in mutant cells, we cannot exclude the possibility that a potent sgRNA pairs may guide SaCas9 to efficiently remove the LCA10 intronic splice mutation and significantly rescue wild-type CEP290 mRNA levels in mutant cells.

| SEQUENCES |
| --- |
| All nucleic sequences are presented 5' to 3' unless otherwise noted.<br>All amino acid sequences are presented N-terminus to C-terminus unless otherwise noted. |

Top strand oligonucleotide for the sgRNA used in homology-directed repair (HDR) (SEQ ID NO: 1)
caccgAAGACACTGCCAATAGGGAT Bottom strand oligonucleotide for the sgRNA used in homology-directed repair (HDR) (SEQ ID NO: 2)
aaacATCCCTATTGGCAGTGTCTTc HDR template (SEQ ID NO: 3)
CCACCCGCCTCGCCCTCCTAAAGTGCTGGGATTACAGATGTGAGCCACCGCACCTGGCCCCAGTTGTAATTGT
GAGTATCTCATACGTATCCCTATTGGCAGTGTCTTAGTTTTATTTTTTATTATCTTTATTGTGGCAGCCATTA
TTCCTGTCTCTA CEP290 Intron 26 F nucleic acid primer (SEQ ID NO: 4)
GGTCCCTGGCTTTTGTTCCT CEP290 Intron 26 R nucleic acid primer (SEQ ID NO: 5)
CAGGAGGCTGAGGGTGTTTT CEP290 Intron 26 sequencing primer (SEQ ID NO: 6)
ACTAGAGATGGGGTTTCACC Wild-type CEP290 F nucleic acid primer (SEQ ID NO: 7)
TGACTGCTAAGTACAGGGACATCTTG Wild-type CEP290 R nucleic acid primer (SEQ ID NO: 8)
AGGAGATGTTTTCACACTCCAGGT Mutant CEP290 F nucleic acid primer (SEQ ID NO: 9)
CTGGCCCCAGTTGTAATTTGTGA Mutant CEP290 R nucleic acid primer (SEQ ID NO: 10)
CTGTTCCCAGGCTTGTTCAATAGT Top strand oligonucleotide for the U1 sgRNA (SEQ ID NO: 11)
caccGGCGGGTGGACACGAGTTC Bottom strand oligonucleotide for the U1 sgRNA (SEQ ID NO: 12)
aaacCAACTCGTGATCCACCCGCC Top strand oligonucleotide for the D1 sgRNA (SEQ ID NO: 13)
caccgAAAGCTACCGGTTACCTGAA Bottom strand oligonucleotide for the D1 sgRNA (SEQ ID NO: 14)
aaacTTCAGGTAACCGGTAGCTTTc Top strand oligonucleotide for the D2 sgRNA (SEQ ID NO: 15)
caccgTCATTCTTGTGGCAGTAAGG Bottom strand oligonucleotide for the D2 sgRN (SEQ ID NO: 16)
aaacCCTTACTGCCACAAGAATGAc Top strand oligonucleotide for the D3 sgRNA (SEQ ID NO: 17)
caccGGAGTCACATGGGAGTCACA Bottom strand oligonucleotide for the D3 sgRNA (SEQ ID NO: 18)
aaacTGTGACTCCCATGTGACTCC U1 sgRNA sequence (SEQ ID NO: 19)
GGCGGGTGGATCACGAGTTCGTTTTAGAGCTAGAAATAGCAAGTTAAAATAAGGCTAGTCCGTTATCAACTTGAAAAAGTG
GCACCGAGTCGGTGCTTTTTT D1 sgRNA sequence (SEQ ID NO: 20)
GAAAGCTACCGGTTACCTGAAGTTTTAGAGCTAGAAATAGCAAGTTAAAATAAGGTAGTCCGTTATCAACTTGAAAAAGT
GGCACCGAGTCGGTGCTTTTTT D2 sgRNA sequence (SEQ ID NO: 21)
GTCATTCTTGTGGCAGTAAGGGTTTTAGAGCTAGAAATAGCAAGTTAAAATAAGGCTAGTCCGTTATCAACTTGAAAAAGT
GGCACCGAGTCGGTGCTTTTTT D3 sgRNA sequence (SEQ ID NO: 22)
GGAGTCACATGGGAGTTTTAGAGCTAGAAATACCAAGTTAAAATAAGGCTAGTCCGTTATCAACTTG
AAAAAGTGGCACCGAGTCGGTGCTTTTTT

| SEQUENCES |
|---|
| All nucleic sequences are presented 5' to 3' unless otherwise noted.<br>All amino acid sequences are presented N-terminus to C-terminus unless otherwise noted. |
| CEP290 intron 26 sequence (Note: c.2991 + 1655A > G mutation is the 1655<sup>th</sup> nucleotide in this sequence and is bolded and underlined) (SEQ ID NO: 23)<br>GTAAGTTTGTGTGATTCTTGAACCTTGTGAAATTAGCCATTTTTCTTCAATATTTTTGTGTTTGGGGGGATTT<br>GGCAGATTTTAATTAAAGTTTGCCTGCATTTATATAAATTTAACAGAGATATAATTATCCATATTATTCATTC<br>AGTTTAGTTATAAATATTTTGTTCCCACATAACACACACACACACACACAATATATTATCTATTTATAGTGGC<br>TGAATGACTTCTGAATGATTATCTAGATCATTCTCCTTAGGTCACTTGCATGATTTAGCTGAATCAAACCTCT<br>TTTAACCAGACATCTAAGAGAAAAAGGAGCATGAAACAGGTAGAATATTGTAATCAAAGGAGGGAAGCACTCA<br>TTAAGTGCCCATCCCTTTCTCTTACCCCTGTACCCAGAACAAACTATTCTCCCATGGTCCCTGGCTTTTGTTC<br>CTTGGAATGGATGTAGCCAACAGTAGCTGAAATATTAAGGGCTCTTCCTGGACCATGGATGCACTCTGTAAAT<br>TCTCATCATTTTTTATTGTAGAATAAATGTAGAATTTTAATGTAGAATAAATTTATTTAATGTAGAATAAAA<br>ATAAAAAAACTAGAGTAGAATATCATAAGTTACAATCTGTGAATATGGACCAGACCCTTTGTAGTTATCTTAC<br>AGCCACTTGAACTCTATACCTTTTACTGAGGACAGAACAAGCTCCTGATTTGTTCATCTTCCTCATCAGAAAT<br>AGAGGCTTATGGATTTTGGATTATTCTTATCTAAGATCCTTTCACAGGAGTAGAATAAGATCTAATTCTATTA<br>GCTCAAAAGCTTTTGCTGGCTCATAGAGACACATTCAGTAAATGAAAACGTTGTTCTGAGTAGCTTTCAGGAT<br>TCCTACTAAATTATGAGTCATGTTTATCAATATTATTTAGAAGTAATCATAATCAGTTTGCTTTCTGCTGCTT<br>TTGCCAAAGAGAGGTGATTATGTTACTTTTTATAGAAAATTATGCCTATTTAGTGTGGTGATAATTTATTTTT<br>TTCCATTCTCCATGTCCTCTGTCCTATCCTCTCCAGCATTAGAAAGTCCTAGGCAAGAGACATCTTGTGGATA<br>ATGTATCAATGAGTGATGTTTAACGTTATCATTTTCCCAAAGAGTATTTTTCATCTTTCCTAAAGATTTTTTT<br>TTTTTTTTTTTGAGATGGAGTTTCATTCTGTCACCCAGGCTGAGTGCAGTGGCACGATCTCGGCTTAACGCTT<br>ACTGCATCCTCTGCCTCCCAGATTCAAGCAGTTCTCCTGCCTCAGCCTCTGAGTAGCTGGGATTACAGGTGTG<br>CACCACCACACCAGCTAATTTTTTTTTTTTTTTTTTTTTGAGGCAGAGTCTCGCTCTGTCACCCAGGCT<br>GGAGTGCAGTGGCGCCATCTTGGCTCACTGCAAGCTCCACCTCCCGGGTTCAGGCCGTTCTCCTGCCTCAGCC<br>TCCTGAGTAGCTGGTACCACAGGCACCCACCATCATGCCCGGCTAATTTTTTGTATTTTTAGTAGAGATGGGG<br>TTTCACCTTGTTAGCCAGGATGGTGTCGATCTCCTGAACTCGTGATCCACCCGCCTCGGCCTCCTAAAGTGCT<br>GGGATTACAGATGTGAGCCACCGCACCTGGCCCCAGTTGTAATTGTGAGTATCTCATACCTATCCCTATTGGC<br>AGTGTCTTAGTTTTATTTTTTATTATCTTTATTGTGGCAGCCATTATTCCTGTCTCTATCTCCAGTCTTACAT<br>CCTCCTTACTGCCACAAGAATGATCATTCTAAACATGAATCCTACCCTGTGACTCCCATGTGACTCCCCGCCT<br>TAAAAACTGTCAAAAGCTACCGGTTACCTGAAGGGTAAAAGTCAAGTCCCCTACTTACCTCATGTCATCTAGA<br>GCAAGAGATGAACTAGCTGAGTTTTCTGACCACAGTGTTCTTTCTTATGTATGTTCTTTTGTACGTGCTCTTT<br>TCTATATATAGGGAACCATTTCTCTCTTCCAGTTGTTTTGCTCAGTGAATTTCTATTCCTGTTTCAAAACTTG<br>TTCAGGCATTACCTTTTTTTCTTAAGCATACTTTTTTTAATGGAACAAAGTCACTCCTGTCTACACTAGTTC<br>TGCATCTTATACATAGGTTTTGTACATAGTACATATTTATATCACATCAAATTATATGTGTTTACATATCTGT<br>CTTCCTTAATGGAATATAAGTCTTTTGATATAAGGAACTATTTAATTTGTTTCTGTGTGTTGAGTATCTCCTG<br>TTTGGCACAGAGTTCAAGCTAATACATGAGAGTGATTAGTGGTGGAGAGCCACAGTGCATGGTGTCAAATA<br>TGGTGCTTAGGAAATTATTGTTGCTTTTTGAGAGGTAAAGGTTCATGAGACTAGAGGTCACGAAAATCAGATT<br>TCATGTGTGAAGAATGGAATAGATAATAAGGAAATACAAAAACTGGATGGGTAATAAAGCAAAAGAAAAACTT<br>GAAATTTGATAGTAGAAGAAAAAAGAAATAGATGTAGATTGAGGTAGAATCAAGAAGAGGATTCTTTTTTTGT<br>TGTTTTTTTTTTTGAAACAGAGTCTCACTGTGTTGCCCAGGCTGGAGTGCAGTGGAGTGATCTTGGCTTACTG<br>CAACCTCTGCCTCCCAGGTTCAAGCGATTCTTCTGCTTCAGTCTCCCGAGTAGCTGGAATTACAGGTGCCCAC<br>CAGCACGGCCGGCTAATTTAGTAGAGACAGGGTTTTGCCATGTTGGCCGGGCTGGTCTCAAACTTTGGATCTC<br>AGGTAATCCGCCAGCCTCAACTTCCCAAAGTGCTGGGATTACAGGCATGAGCCACTGTGCCCAGCCTGTTTTT<br>TTTTTTTTAAAGGAGACCAGTGAAGTTTCAGGAGGAGGGAAAGAAAATTTAGAGTTACTAGGGAGAGAGTGAT<br>GAAGATAAGAGATGAAAGTGGTAATAAGGGAAATAGCAAAATATCAGGGTAGGTGGGAGAAAAAGAGATTTGT<br>AACAAACAATAGGATTATCCTGTGAAAAAGGATGAAAGGAAGAAAAAAATGGATAGAAAGATATTTAAAACAC<br>CCTCAGCCTCCTGTTTTCCCTCCTGTGTATTCATAGTATATAAAACTATAATTATGTACTTTACTTAAAAAT<br>ATATTATTAATACCTTATCGTGCTTATTTAATCATAGCATGTCCTCTTTTTAGTCTCATTACCCTGTTTGTAT<br>TATTCTTCATAACACTTAATACCTGACATTGTATTATATATTGGCTTATTTTCCAGGTACTCCACTCAAATAT<br>AAGTTCTAGGATATAATTTATTTATCACTGAAATCCATTGCTTAGAGTACCTGGCATGTAGTAAATAGGCATT<br>CTGTTTTTTCAAATAAAAAATAAAGGAACTTAAGATATATATTTATGTTATATCGCCAGCCTTTTTCCTCACA<br>GCTCTATTCTGTTGTACAGAATTACCTACTTTACAATTCCTGTGTTTCAAGGGGATCTCAAATTTAACGTGTC<br>CACAATGAACTCCTGATTTCTGTTTCTCTCCTAGTCATTCTTATTTCAATATATGTTCAGTTACCTAACCAGC<br>TAGTCAAGGCAGATACTTTAGAGTTATTCTGTAGTCATTCTTTTTCCCTACCATTTTTGTTTTCCAAATGTAA<br>TTTATGTGTGCTTCTTCATCCTCGCAGCTCTAACCCTTGTCCAAACCAGCATCATCACTCATCTGGAGTTCC<br>ACAATGTCTTTCTGGCTAGTTTCCCTGATTTCTCTATTGACCCCTTTATTCTCCACAGTGCAGCCAGAATGAT<br>TGTTTAAAACTTCCTCCTTAAAATCTTTAAATTGTTTTCTTTTATACGTTAAGTTAAATTCCAGTTCCTTGTC<br>TTGGCATGCCATGCCCTGCCTGGTGTGGCCCCTGATGGTCTCTCCAACTTCATGTTTTACTACTATTGACTCT<br>TATTTTTGCTTACTCTGCTTGGGTGCTCCAGTCCTCCAAATCATTTCCTGCTCCAATCATTTCAATCATTTTT<br>TCCTCTCAGATCTTATAGTATTCCAAATGCTTTCTTCCTTTGGAGCATCTGGGTTTACTAATAAATACTTCGT<br>ACCTCACAGTTCAGCTTAAATATCAATTATTTGGTGGTTAAGACATCCTTCAACCGCTCTATCTAAATGTTCC<br>TTTCTATTATTCACTGGCTCAGTACTCTGTTTTTATTTTCTTTCTAAATGTCAACTTTTTTTTTTTGAGTCA<br>GGGTCTCACTGTTGCCCAGGCTCGAGTGCAGTTGCACAATCATAGCTCATTGCAGCCTTGCCCTCCTGGGATC<br>AAGTAATTCTCCCACCTCAGCCTCCAAAATAGCTGGGATTACAGGTATGCATCACATGCTCAGCTAATTTTT<br>TGTGTTTTTTTGTAGAGATGAGGTCTCACTTTGTTGCCCAGGCTGGTCTCAAACTCCTGGACTCAAGTGATTC<br>TCCCACCTCAGCCTCCCAAAGTGCTGGGGTTACAGGTGTGAGCCACTGCACCTGGTCGATACTGACTTITTTT<br>TTTTTTTGAGATGGAGTTTTGCTCTGTTGCCCAGGCTAGAGCGCAGTGGTGTGATCTCAGCTCACTGCAACCT<br>CCACCTCCCAGGTTAAAGGGATTCTTCTGCCTCAGTCTCCTGAGTAGCTGGGATTACAGGCAAGTGCCATCAT<br>GACTGGCTAATTTTTGTATTTTTAGCACTATGTTTAGTACTGTGTTGGCCAGGCTTGTCTCGAACTCCTGACC<br>TCAAGTGATCCACCCACCTCAGCCTCCCAAAGTGCTGGGATTACAGGTGTGAGCCACCGTAATCGGCCAACAT<br>TGACATTTTTAGTAGACTTTTTGTTTGTTTACTTGCTTATTATCTGCTGCCTTCCACACTCTGGCGAAATCCT<br>GCCACCCACCCACACACACATAGGCACTGAATGGGCAGAACTCTGAAGGCCAGAATTTTATATTTCTTTTCAC<br>TGTAAACATCATCATCTGTCACTGATGGCACACTAGGATGCTCAGCAACTGTGTGCATGAAGGAAGTAAGCAC<br>TAGTTTGTGAAGGCTGCAAAACTCTTGAGTATTCTAAGAGTTTTGGCCAAATGAATGTACAGCTTTAGTGGC<br>AGAAGCTAATACTCAGAAATTGAGGCCGTATATTGGATAACACAGGATTTGGATGATTATTTTAAAATAATAT |

| SEQUENCES |
|---|
| All nucleic sequences are presented 5' to 3' unless otherwise noted. All amino acid sequences are presented N-terminus to C-terminus unless otherwise noted. |

TTTACATTGTATATATGTGTGTGTGTGTGTGTGTGTGTGTATGTGTGTGTGTGTATATATATGTA
TGTATGTGTATTAGTCCGTTCTCATGCTGCTATGAAGAAATACCTGAGACTGGGTAATTTATAAAGGAAAGAG
GTTTAATTGACTCACAGTTCCACAGAGCTGGGGAGGCCTCAGAAAACTTAACAGTTATGGCAGAAGGGGAAGC
AAACACATTTTTCTTCACATGGTGGCCGGAATTAGAAGAATGTGAGCCGAGCAAAGGGGAAAGCCCCTTATAA
AACCATCAGACATCGTGAGAACTTACTATTATGAGAATAGCGTGGGGGAAACCACCCCCACGATTCAATTACC
TCCCACCAAATCCCTCCCATGACATATGAGGATTATGGGAACTATGATTCAAGATGAGATTTGGGTAGGGACA
CAGCCAAACCATATCAGTATGTATATGTATACAAGTATTATATATATATGTATGTGTTTGTATGCATACATGT
ATTATATATGGAGGAAATTCTAATTTTGTAAAAAACTGGATTGTGAGTTTTAAGGAGATGTTATATAAAGTTA
AGACAATGTCATTTTGTGGTATTGGTCTGAATTACAATGTAGTTTCTTAGTGATATTTTTCCTTTATTcAG

Mutated ITR sequence (SEQ ID NO: 24)
CACTCCCTCTCTGCGCGCTCGCTCGCTCACTGAGGCCGGGCGACCAAAGGTCGCCCACGCCCGGGCTTTGCCC
GGGCG tracr sequence (SEQ ID NO: 25)
TAGCAAGTTAAAATAAGGCTAGTCCGTTATGAACTGGAAAAAGTGGCACGGAGTCGGTGC NLS sequences
PKKKRKV (SEQ ID NO: 26)
PKENENVEDPKKKRKVD (SEQ ID NO: 27)

Forward nucleic acid primer for BbsI restriction site mutation (SEQ ID NO: 28)
GGGAGGATTGGGAAGAGAATAGCAGGCATGCTG Reverse nucleic acid primer for BbsI restriction site mutation (SEQ ID NO: 29)
CAGCATGCCTGCTATTCTCTTCCCAATCCTCCC U6 promoter-BbsI:BbsI-sgRNA scaffold-U6 terminator cassette for constructing
pSpCas9(BB) with U6 promoter sequence underlined (SEQ ID NO: 30)
CACATGTGAGGGCCTATTTCCCATGATTCCTTCATATTTGCATATACGATACAAGGCTGTTAGAGAGATAAT
TGGAATTAATTTGACTGTAAACACAAAGATATTAGTACAAAATACGTGACGTAGAAAGTAATAATTTCTTGG
GTAGTTTGCAGTTTTAAAATTATGTTTTAAAATGGACTATCATATGCTTACCGTAACTTGAAAGTATTTCGA
TTTCTTGGCTTTATATATCTTGTGGAAAGGACGAAACACCGGGTCTTCGAGAAGACCTGTTTTAGAGCTAGA
AATAGCAAGTTAAAATAAGGCTAGTCCGTTATCAACTTGAAAAAGTGGCACCGAGTCGGTGCTTTTTTGTTT
TAGAGCTAGAAATAGCAAGTTAAAATAAGGCTAGTCCGTTTTTAGCGCGTGCGCCAATTCTGCAGACAAATG
GCTCTAGAGGTACCC PPIA F nucleic acid primer (SEQ ID NO: 31)
TTCATCTGCACTGCCAAGAC PPIA R nucleic acid primer (SEQ ID NO: 32)
TCGAGTTGTCCACAGTCAGC U6 promoter-BbsI:BbsI-sgRNA scaffold-U6 terminator-CMV promoter for constructing
pSpCas9(BBU) with U6 promoter and CMV promoter sequence underlined (SEQ ID NO:
33)
CTCACATGTGAGGGCCTATTTCCCATGATTCCTTCATATTTGCATATACGATACAAGGCTGTTAGAGAGATAA
TTGGAATTAATTTGACTGTAAACACAAAGATATTAGTACAAAATACGTGACGTAGAAAGTAATAATTTCTTGG
GTAGTTTGCAGTTTTAAAATTATGTTTTAAAATGGACTATCATATGCTTACCGTAACTTGAAAGTATTTCGAT
TTCTTGGCTTTATATATCTTGTGGAAAGGACGAAACACCGGGTCTTCGAGAAGACCTGTTTTAGAGCTAGAAA
TAGCAAGTTAAAATAAGGCTAGTCCGTTATCAACTTGAAAAAGTGGCACCGAGTCGSTGCTTTTTTGTTTTAG
AGCTAGAAATAGCAAGTTAAAATAAGGCTAGTCCGTTTTTAGCGCGTGCGCCAATTCTGCAGACAAATGGCTC
TAGAGACCGGCGCCGCTACAGGCTTTCCACCGGTGGTCTCTTCTAGAGGTACCCGTTACATCTAGTTATTAAT
AGTAATCAATTACGGGGTCATTAGTTCATAGCCCATATATGGAGTTCCGCGTTACATAACTTACGGTAAATGG
CCCGCCTGGCTGACCGCCCAACGACCCCCGCCCATTGACGTCAATAATGACGTATGTTCCCATAGTAACGCCA
ATAGGGACTTTCCATTGACGTCAATGGGTGGATATTTACGGTAAACTGCCCACTTGGCAGTACATCAAGTGT
ATCATATGCCAAGTACGCCCCCTATTGACGTCAATGACGGTAAATGGCCCGCCTGGCATTATGCCCAGTACAT
GACCTTATGGGACTTTCCTACTTGGCAGTACATCTACGTATTAGTCATCGCTATTACCATGGTGATGCGGTTT
TGGCAGTACATCAATGGGCGTGGATAGCGGTTTGACTCACGGGGATTTCCAAGTCTCCACCCCATTGACGTCA
ATGGGAGTTTGTTTTGGCACCAAAATCAACGGGACTTTCCAAAATGTCGTAACAACTCCGCCCCATTGACGCA
AATGGGCGGTAGGCGTGTACGGTGGGAGGTCTATATAAGCAGAGCTCTCTGGCTAACTAGAGAACCCACTGCT
TACTGGCTTATCGAAATTAATACGACTCACTATAGGGAGAACCAAGCTGGCTAGCCGC Forward nucleic acid primer for constructing pSpCas9(BBD) (SEQ ID NO: 34)
ATAACATGTGGTCTCACTCTAGAGGCATGTGAGGGCCTATTTCCC Reverse nucleic acid primer for constructing pSpCas9(BBD) (SEQ ID NO: 35)
TATGGTACCGGTCTCATAGAGCCATTTGTCTGCAGA Top strand oligonucleotide for the control 1 sgRNA (SEQ ID NO: 36)
caccGCACTACCCAGAGCTAACTCA

SEQUENCES

All nucleic sequences are presented 5' to 3' unless otherwise noted.
All amino acid sequences are presented N-terminus to C-terminus unless otherwise noted.

Bottom strand oligonucleotide for the control 1 sgRNA (SEQ ID NO: 37)
aaacTGAGTTAGCTCTGGTAGTGC Top strand oligonucleotide for the control 2 sgRNA (SEQ ID NO: 38)
caccgTGCGAATACGCCACGCGAT Bottom strand oligonucleotide for the control 2 sgRNA (SEQ ID NO: 39)
aaacATCGCGTGGCGTATTCGCAc

*S. pyogenes* Cas9 amino acid sequence (SEQ ID NO: 40)
MDKKYSIGLDIGTNSVGWAVITDEYKVPSKKFKVLGNTDRHSIKKNLIGALLFDSGETAEATRLKRTARRRYT
RRKNRICYLQEIFSNEMAKVDDSFFHRLEESFLVEEDKKHERHPIFGNIVDEVAYHEKYPTIYHLRKKLVDST
DKADLRLIYLALAHHIKFRGHFLIEGDLNPDNSDVDKLFIQLVQTYNQLFEENPINASGVDAKAILSARLSKS
RRLENLIAQLPGEKKNGLFGNLIALSLGLTPNFKSNFDLAEDAKLQLSKDTYDDDLDNLLAQIGDQYADLFLA
AKNLSDAILLSDILRVNTEITKAPLSASMIKRYDEHHQDLTLLKALVRQQLPEKYKEIFFDQSKNGYAGYIDG
GASQESFYKFIKPILEKMDGTEELLVKLNREDLLRKQRTFDNGSIPHQIHLGELKAILRRQEDFYPFLKDNRE
KIEKILTFRIPYYVGPLARGNSRFAWMTRKSEETITPWNFEEVVDKGASAQSFIERMTNFDKNLPNEKVLPKH
SLLYEYFTVYNELTKVKYVTEGMRKPAFLSGEQKKAIVDLLFKTNRKVTVKQLKEDYFKKIECFDSVEISGVE
DRFNASLGTYHDLLKIIKDKDFLDNEENEDIIEDIVLTLTLFEDREMIEERLKTYAHLFDDKVMKQLKRRRYT
GWGRLSRKLINGIRDKQSGKTILDFLKSDGFANRNFMQLIHDDSLTFKEDIQKAQVSGQGDSLHEHIANLAGS
PAIKKGILQTVKVVDELVKVMGRHKPENIVIEMARENQTTQKGQKNSRERMKRIEEGIKELGSQILKEHPVEN
TQLQNEKLYLYYLQNGRDMYVDQELDINRLSDYDVDHIVPQSFLKDDSIDNKVLTRSDKNRGKSDNVPSEEVV
KKMKNYWRQLLNAKLITQRKFDNLTKAERGGLSELDKAGFIKRQLVETRQRTKHVAQILDSRMNTKYDENDKL
IREVKVITLKSKLVSDFRKDFQFYKVREINNYHHAKDAYLNAVVGTALIKKYPKLESEFVYGDYKVYDVRKMI
AKSEQEIGKATAKYFFYSNIMNFFKTEITLANGEIRKRPLIETNGETGSIVWDKGRDFATVRKVLSMPQVKIV
KKTEVQTGGFSKESILPKRNSDKLIARKKDWDPKKYGGFDSPTVAYSVLVVAKVEKGKSKKLKSVKELLGITI
MERSSFEKNPIDFLEAKGYKEVKKDLIIKLPKYSLFELENGRKRMLASAGELQKGNELALPSKYVNFLYLASH
YEKLKGSPEDNEQKQLFVEQHKHYLDEIIEQISEFSKRVILADANLDKVLSAYNKHRDKPIREQAENIIHLFT
LTNLGAPAAFKYFDTTIDRKRYTSTKEVLDATLIHQSITGLYETRIDLSQLGGD U1 sgRNA guide/protospacer sequence (SEQ ID NO: 41)
GGCGGGTGGATCACGAGTTC D1 sgRNA guide/protospacer sequence (SEQ ID NO: 42)
AAAGCTACCGGTTACCTGAA D2 sgRNA guide/protospacer sequence (SEQ ID NO: 43)
TCATTCCTGTGGCAGTAAGG D3 sgRNA guide/protospacer sequence (SEQ ID NO: 44)
GGAGTCACATGGGAGTCACA aU1 sgRNA guide/protospacer sequence (SEQ ID NO: 45)
TTTAACGTTATCATTTTCCCA aU2 sgRNA guide/protospacer sequence (SEQ ID NO: 46)
AGTTTCATTCTGTCACCCAGG aU3 sgRNA guide/protospacer sequence (SEQ ID NO: 47)
AAAAATTAGCCGGGCATGATG aD1 sgRNA guide/protospacer sequence (SEQ ID NO: 48)
TGTAAGACTGGAGATAGAGAC aD2 sgRNA guide/protospacer sequence (SEQ ID NO: 49)
CTTTTGACAGTTTTTAAGGCG aU1 sgRNA sequence (SEQ ID NO: 50)
GTTTAACGTTATCATTTTCCCAGTTTTAGTACTCTGGAAACAGAATCTACTAAAACAAGGCAAAATGCCGTGTTTATCTCG
TCAACTTGTTGGCGAGATTTTT aU2 sgRNA sequence (SEQ ID NO: 51)
GAGTTTCATTCTGTCACCCAGGCTTTTAGTACTCTGCAAACAGAATCTACTAAAACAAGGCAAAATGCCGTGTTTATCTCC
TCAACTTGTTGGCGAGATTTTT aU3 sgRNA sequence (SEQ ID NO: 52)
GAAAAATTAGCCGGGCATGATGGTTTTAGTACTCTGGAAACAGAATCTACTAAAACAAGGCAAAATGCCGTGTTTATCTCG
TCAACTTGTTGGCGAGATTTTT aD1 sgRNA sequence SEQ ID NO: 53)
GTGTAAGACTGGAGATAGAGACGTTTTAGTACTCTGGAAACAGAATCTACTAAAACAAGGCAAAATGCCGTGTTTATCTCG
TCAACTTGTTGGCGAGATTTTT -continued

---
SEQUENCES

All nucleic sequences are presented 5' to 3' unless otherwise noted.
All amino acid sequences are presented N-terminus to C-terminus unless otherwise noted.

--- aD2 sgRNA sequence (SEQ ID NO: 54)
GCTTTTGACAGTTTTTAAGGCGGTTTTAGTACTCTGGAAACAGAATCTACTAAAACAAGGCAAAATGCCGTGTTTATCTCG
TCAACTTGTTGGCGAGATTTTT

*S. aureus* Cas9 amino acid sequence (SEQ ID NO: 55)
MKRNYILGLDIGITSVGYGIIDYETRDVIDAGVRLFKEANVENNEGRRSKRGARRLKRRRRHRIQRVKKLLFD
YNLLTDHSELSGINPYEARVKGLSQKLSEEEFSAALLHLAKRRGVHNVNEVEEDTGNBLSTKEQISRNSKALE
EKYVAELQLERLKKDGEVRGSINRFKTSDYVKEAKQLLKVQKAYHQLDQSFIDTYIDLLETRRTYYEGPGEGS
PFGWKDIKEWYEMLMGHCTYFPEELRSVKYAYNADLYNALNDLNNLVITRDENEKLEYYEKFQIIENVFKQKK
KPTLKQIAKEILVNEEDIKGYRVTSTGKPEFTNLKVYHDIKDITARKEIIENAELLDQIAKILTIYQSSEDIQ
EELTNLNSELTQEEIEQISNLKGYTGTHNLSLKAINLILDELWHTNDNQIAIFNRLKLVPKKVDLSQQKEIFT
TLVDDFILSPVVKRSFIQSIKVINAIIKKYGLPNDIIIELAREKNSKDAQKMINEMQKRNRQTNERIEEIIRT
TGKENAKYLIEKRKLHDMQEGKCLYSLEAIPLEDLLNNPFNYEVDHIIPRSVSFDNSFNNKVLVKOEENSKKG
NRTPFQYLSSSDSKISYETFKKHILNLAKGKGRISKTKKEYLLEERDIMRFSVQKDFINRKLVDTRYATRGLM
NLLRSYFRVNNLDVKVKSINGGFTSFLRRKWKFKKERNKGYKHHAEDALIIANADFIFKEWKKLDKAKKVMEN
QMFEEKQAESMPEIETEQBYKEIFITPHQIKHIKDFKDYKYSHRVDKKPNRELINDTLYSTRKDDKGNTLIVN
NLNGLYDKDNDKLKKLINKSPEKLLMYHHDPQTYQKLKLIMEQYGDEKNPLYKYYEEIGNYLTKYSKKDNGPV
IKKIKYYGNKLNAHLDITDDYPNSRNKVVKLSLKPYRFDVYLDNGVYKFVTVKNLDVIKKENYYEVNSKCYEE
AKKLKKISNQAEFIASFYNNDLIKINGELYRVIGVNNDLLNRIEVNMIDITYREYLENMNDKRPPRIIKTIAS
KTQSIKKYSTDILGNLYEVKSKKHPQIIKKG minCMV promoter-SpCas9 sequence for constructing pAAV-minCMV-SpCas9-NLS-
SV40 pA with minCMV promoter underlined (SEQ ID NO: 56)
TATACGCGTGTTGACACTAGTTCGCGAAATATTGACTCACGGGGATTTCCAAGTCTCCACCCCATTGACGTCA
ATGGGAGTTTGTTTTGGCACCAAAATCAACGGGACTTTCCAAAATGTCGTAACAACTCCGCCCCATTGACGCA
AATGGGCGGTAGGCGTGTACGGTGGGAGGTCTATATAAGCAGAGCTCGTTTAGTGAACCGTCAGATCGCCGCC
ACCATGGACAAGAAGTACAGCATCGGCCTGGACATCGGCACCAACTCTGTGGGCTGGGCCGTGATCACCGACG
AGTACAAGGTGCCCAGCAAGAAATTCAAG SV40 pA sequence for constructing pAAV-minCMV-SpCas9-NLS-SV40 pA with SV40
early poly (A) signal underlined (SEQ ID NO: 57)
TGACTCGAGAACTTGTTTATTGCAGCTTATAATGGTTACAAATAAAGCAATAGCATCACAAATTTCACAAATA
AAGCATTTTTTTCACTGCATTCTAGTTGTGGTTTGTCCAAACTCATCAATGTATCTTATCATGTCTGCAATAT
TTCGCGAGAAGACAATAGCAGG U1 sgRNA recognition sequence (U1T; U1 sgRNA guide sequence + PAM) (SEQ ID NO: 58)
GGCGGGTGGATCACGAGTTCAGG D3 sgRNA recognition sequence (D3T; D3 sgRNA guide sequence + PAM) (SEQ ID NO: 59)
GGAGTCACATGGGAGTCACAGGG BGH pA-containing fragment with BGH pA underlined (SEQ ID NO: 60)
CTAGTGGCGGCCGCTCGAGCATGCATCTAGAGGGCCCTATTCTATAGTGTCACCTAAATGCTAGAGCTCGCTG
ATCAGCCTCGACTGTGCCTTCTAGTTGCCAGCCATCTGTTGTTTGCCCCTCCCCCGTGCCTTCCTTGACCCTG
GAAGGTGCCACTCCCACTGTCCTTTCCTAATAAAATGAGGAAATTGCATCGCATTGTCTGAGTAGGTGTCATT
CTATTCTGGGGGGTGGGGTGGGGCAGGACAGCAAGGGGGAGGATTGGGAAGACAATAGCAGGCATGCTGGGGA
GCTAGAGTCGACCGGACCGCTGCAGGCATGCA U11 sgRNA guide/protospacer sequence (SEQ ID NO: 61)
GCATAAGGACTAAAGACCTA D11 sgRNA guide/protospacer sequence (SEQ ID NO: 62)
GGTAGTGGTTGAACTCACAA RK promoter-Chimeric intron-EGFP-BGH pA fragment (SEQ ID NO: 63)
GGGCCCCAGAAGCCTGGTGGTTGTTTGTCCTTCTCAGGGGAAAAGTGAGGCGGCCCCTTGGAGGAAGGGGCCG
GGCAGAATGATCTAATCGGATTCCAAGCAGCTCAGGGGATTGTCTTTTTCTAGCACCTTCTTGCCACTCCTAA
GCGTCCTCCGTGACCCCGGCTGGGATTTAGCCTGGTGCTGTGTCAGCCCCGGTCTCCCAGGGGCTTCCCAGTG
GTCCCCAGGAACCCTCGACAGGGCCCGGTCTCTCTCGTCCAGCAAGGGCAGGGACGGGCCACAGGCCAAGGGC
GGAGTCGCTGCGACGCTGCCTTCGCCCCGTGCCCCGCTCCCGCCTCGCGCCTCCCGCCCCGGCTCTGA
CTGACCGCGTTACTCCCACAGGTGAGCGGGCGGGACGGCCCTTCTCCTCCGGGCTGTAATTAGCGCTTGGTTT
AATGACGGCTTGTTTCTTTTCTGTGGCTGCGTGAAAGCCTTGAGGGGCTCCGGGAGGGCCCTTTGTGCGGGGG
GAGCGGCTCGGGGGGTGCGTGCGTGTGTGTGCGTGGGGAGCGCCGCGTGCGGCTCCGCGCTGCCCGGCGGC
TGTGAGCGCTGCGGGCGCGGCGCGGGGCTTTGTGCGCTCCGCAGTGTGCGCGAGGGGAGCGCGGCCGGGGGCG
GTGCCCCGCGGTGCGGGGGGGGCTGCGAGGGGAACAAAGGCTGCGTGCGGGGTGTGCGTGGGGGGGTGAGC
AGGGGGTGTGGGCGCGTCGGTCGGGCTGCAACCCCCCCTGCACCCCCTCCCCGAGTTGCTGAGCACGGCCCG
GCTTCGGGTGCGGGGCTCCGTACGGGGCGTGGCGCGGGCTCGCCGTGCCCGGCSGGGGTGGCGGCAGGTGG
GGGTGCCGGGCGGGCGGGGCCGCCTCGGGCCGGGAGGGCTCGGGGAGGGGCGCGGCGGCCCCGGAGCGC
CGGCGGCTGTCGAGGCGCGGCGAGCCGCAGCCATTGCCTTTTATGGTAATCGTGCGAGAGGGCGCAGGGACTT
CCTTTGTCCCAAATCTGTGCGGAGCCGAAATCTGGGAGGCGCCGCCGCACCCCCTCTAGCGGGCGCGGGGCGA
AGCGGTGCGGCGCCGGCAGGAAGGAAATGGGCGGGAGGGCCTTCGTGCGTCGCCGCGCCGCCGTCCCCTTCT CCCTCTCCAGCCTCGGGGCTGTCCGCGGGGGGACGGCTGCCTTCGGGGGGGACGGGGCAGGGCGGGGTTCGGC
TTCTGGCGTGTGACCGGCGGCTCTAGAGCCTCTGCTAACCATGTTCATGCCTTCTTCTTTTTCCTACAGCTCC
TGGGCAACGTGCTGGTTATTGTGCTGTCTCATCATTTTGGCAAAGAATTCTTCGAAAGATCTGCTAGCTTAAT
TAACCCGGTCGCCACCATGGTGAGCAAGGGCGAGGAGCTGTTCACCGGGGTGGTGCCCATCCTGGTCGAGCTG
GACGGCGACGTAAACGGCCACAAGTTCAGCGTGTCCGGCGAGGGCGAGGGCGATGCCACCTACGGCAAGCTGA
CCCTGAAGTTCATCTGCACCACCGGCAAGCTGCCCGTGCCCTGGCCCACCCTCGTGACCACCCTGACCTACGG
CGTGCAGTGCTTCAGCCGCTACCCCGACCACATGAAGCAGCACGACTTCTTCAAGTCCGCCATGCCCGAAGGC
TACGTCCAGGAGCGCACCATCTTCTTCAAGGACGACGGCAACTACAAGACCCGCGCCGAGGTGAAGTTCGAGG
GCGACACCCTGGTGAACCGCATCGAGCTGAAGGGCATCGACTTCAAGGAGGACGGCAACATCCTGGGGCACAA
GCTGGAGTACAACTACAACAGCCACAACGTCTATATCATGGCCGACAAGCAGAAGAACGGCATCAAGGTGAAC
TTCAAGATCCGCCACAACATCGAGGACGGCAGCGTGCAGCTCGCCGACCACTACCAGCAGAACACCCCCATCG
GCGACGGCCCCGTGCTGCTGCCCGACAACCACTACCTGAGCACCCAGTCCGCCCTGAGCAAAGACCCCAACGA
GAAGCGCGATCACATGGTCCTGCTGGAGTTCGTGACCGCCGCCGGGATCACTCTCGGCATGGACGAGCTGTAC
AAGTAAAGCGGCCAAATCGTACGCCTAGGTGATCAAGATCTGCTAGCTTAATTAACCCGGGACTAGTGGCGGC
CGCTCGAGCATGCATCTAGAGGGCCCTATTCTATAGTGTCACCTAAATGCTAGAGCTCGCTGATCAGCCTCGA
CTGTGCCTTCTAGTTGCCAGCCATCTGTTGTTTGCCCCTCCCCCGTGCCTTCCTTGACCCTGGAAGGTGCCAC
TCCCACTGTCCTTTCCTAATAAAATGAGGAAATTGCATCGCATTGTCTGAGTAGGTGTCATTCTATTCTGGGG
GGTGGGGTGGGGCAGGACAGCAAGGGGGAGGATTGGGAAGACAATAGCAGGCATGCTGGGGA Mouse Cep290 Intron 25 F nucleic acid primer (SEQ ID NO: 64)
CCCCTCGCCTGTACTGAAAG Mouse Cep290 Intron 25 R nucleic acid primer (SEQ ID NO: 65)
GCACATCATCTGAGGCAGGT minCMV-SaCas9-NLS-FLAG-BGH pA-U6-BsaI:BsaI-sgRNA scaffold fragment with
minCMV and SaCas9 sequence underlined (SEQ ID NO: 66)
ATGAATTCTCTAGACAATTGGACTCACGGCGATTTCCAAGTCTCCACCCATTGACGTCAATGGGAGTTTGTT
TTGGCACCAAAATCAACGGGACTTTCCAAAATGTCGTAACAACTCCGCCCCATTGACGCAAATGGGCGGTAGG
CGTGTACGGTGGGAGGTCTATATAAGCAGAGCTCGTTTAGTGAACCGTCAGATCACGCGTGCCACCATGAAGC
GGAACTACATCCTGGGCCTGGACATCGGCATCACCAGCGTGGGCTACGGCATCATCGACTACGAGACACGGGA
CGTGATCGATGCCGGCGTGCGGCTGTTCAAAGAGGCCAACGTGGAAAACAACGAGGGCAGGCGGACGGAGCAAGAGA
GGCGCCAGAAGGCTGAAGCGGCGGAGGCGGCATAGAATCCAGAGAGTGAAGAAGCTGCTGTTCGACTACAACC
TGCTGACCGACCACAGCGAGCTGAGCGGCATCAACCCCTACGAGGCCAGAGTGAAGGGCCTGAGCCAGAAGCT
GAGCGAGGAAGAGTTCTCTGCCGCCCTGCTGCACCTGGCCAAGAGAAGAGGCGTGCACAACGTGAACGAGGTG
GAAGAGGACACCGGCAACGAGCTGTCCACCAAAGAGCAGATCAGCCGGAACAGCAAGGCCCTGGAAGAGAAAT
ACGTGGCCGAACTGCAGCTGGAACGGCTGAAGAAAGACGGCGAAGTGCGGGGCAGCATCAACAGATTCAAGAC
CAGCGACTACGTGAAAGAAGCCAAACAGCTGCTGAAGGTGCAGAAGGCCTACCACCAGCTGGACCAGAGCTTC
ATCGACACCTACATCGACCTGCTGGAAACCCGGCGGACCTACTATGAGGGACCTGGCGAGSGCAGCCCCTTCG
GCTGGAAGGACATCAAAGAATGGTACGAGATGCTGATGGGCCACTGCACCTACTTCCCCGAGGAACTGCGGAG
CGTGAAGTACGCCTACAACGCCGACCTGTACAACGCCCTGAACGACCTGAACAATCTCGTGATCACCAGGGAC
GAGAACGAGAAGCTGGAATATTACGAGAAGTTCCAGATCATCGAAAACGTGTTCAAGCAGAAGAAGAAGCCCA
CCCTGAAGCAGATCGCCAAAGAAATCCTCGTGAACGAAGAGGATATTAAGGGCTACAGAGTGACCAGCACCGG
CAAGCCCGAGTTCACCAACCTGAAGGTGTACCACGACATCAAGGACATTACCGCCCGGAAAGAGATTATTGAG
AACGCCGAGCTGCTGGATCAGATTGCCAAGATCCTGACCATCTACCAGAGCAGCGAGGACATCCAGGAAGAAC
TGACCAATCTGAACTCCGAGCTGACCCAGGAAGAGATCGAGCAGATCTCTAATCTGAAGGGCTATACCGGCAC
CCACAACCTGAGCCTGAAGGCCATCAACCTGATCCTGGACGAGCTGTGGCACACCAACGACAACCAGATCGCT
ATCTTCAACCGGCTGAAGCTGGTGCCCAAGAAGGTGGACCTGTCCCAGCAGAAAGAGATCCCCACCACCCTGG
TGGACGACTTCATCCTGAGCCCCGTCGTGAAGAGAAGCTTCATCCAGAGCATCAAAGTGATCAACGCCATCAT
CAAGAAGTACGGCCTGCCCAACGACATCATTATCGAGCTCGCCCGCGAGAAGAACTCCAAGGACGCCCAGAAA
ATGATCAACGAGATGCAGAAGCGGAACCGGCAGACCAACGAGCGGATCGAGGAAATCATCCGGACCACCGGCA
AAGAGAACGCCAAGTACCTGATCGAGAAGATCAAGCTGCACGACATGCAGGAAGGCAAGTGCCTGTACAGCCT
GGAAGCCATCCCTCTGGAAGATCTGCTGAACAACCCCTTCAACTATGAGGTGGACCACATCATCCCCAGAAGC
GTGTCCTTCGACAACAGCTTCAACAACAAGGTGCTCGTGAAGCAGGAAGAAAACAGCAAGAAGGGCAACCGGA
CCCCATTCCAGTACCTGAGCAGCAGCGACAGCAAGATCAGCTACGAAACCTTCAAGAAGCACATCCTGAATCT
GGCCAAGGGCAAGGGCAGAATCAGCAAGACCAAGAAAGAGTATCTGCTGGAAGAACGGGACATCAACAGGTTC
TCCGTGCAGAAAGACTTTATCAACCGGAACCTGGTGGATACCAGATACGCCACCAGAGGCCTGATGAACCTGC
TGCGGAGCTACTTGAGAGTGAACAACCTGGACGTGAAAGTGAAGTCGATCAATGGCGGCTTCACCAGCTTTCT
GCGGCGGAAGTGGAAGTTTAAGAAAGAGCGGAACAAGGGGTACAAGCACCACGCCGAGGACGCCCTGATCATT
GCCAACGCCGATTTCATCTTCAAAGAGTGGAAGAAACTGGACAAGGCCAAAAAAGTGATGGAAAACCAGATGT
TCGAGGAAAAGCAGGCCGAGAGCATGCCCGAGATCGAAACCGAGCAGGAGTACAAAGAGATCTTCATCACCCC
CCACCAGATCAAGCACATTAAGGACTTCAAGGACTACAAGTACAGCCACCGGGTGGACAAGAAGCCTAATAGA
GAGCTGATTAACGACACCCTGTACTCCACCCGGAAGGACGACAAGGGCAACACCCTGATCGTGAACAATCTGA
ACGGCCTGTACGACAAGGACAATGACAAGCTGAAAAAGCTGATCAACAAGAGCCCCGAAAAGCTGCTGATGTA
CCACCACGACCCCCAGACCTACCAGAAACTGAAGCTGATTATGGAACAGTACGGCGACGAGAAGAATCCCCTG
TACAAGTACTACGAGGAAACCGGGAACTACCTGACCAAGTACTCCAAAAAGGACAACGGCCCCGTGATCAAGA
AGATTAAGTATTACGGCAACAAACTGAACGCCCATCTGGACATCACCGACGACTACCCCAACAGCAGGAACAA
GGTCGTGAAGCTGTCCCTGAAGCCCTACAGATTCGACGTGTACCTGGACAATGGCGTGTACAAGTTCGTGACA
GTGAAGAATCTGGATGTGATCAAAAAAGAAAACTACTACGAAGTGAATAGCAAGTGCTATGAGGAAGCTAAGA
AGCTGAAGAAGATCAGCAACCAGGCCGAGTTTATCGCCTCCTTCTACAACAACGATCTGATCAAGATCAACGG
CGAGCTGTATAGAGTGATCGGCGTGAACAACGACCTGCTGAACCGGATCGAAGTGAACATGATCGACATCACC
TACCGCGAGTACCTGGAAAACATGAACGACAAGAGGCCCCCCAGGATCATTAAGACAATCGCCTCCAAGACCC
AGAGCATTAAGAAGTACAGCACAGACATTCTGGGCAACCTGTATGAAGTGAAATCTAAGAAGCACCCTCAGAT -continued

| SEQUENCES |
|---|
| All nucleic sequences are presented 5' to 3' unless otherwise noted.<br>All amino acid sequences are presented N-terminus to C-terminus unless otherwise noted. |
| CATCAAAAAGGGCGGATCCCCCAAGAAAAAGCGCAAAGTGGACTACAAAGACGATGACGACAAGTGAGCTAGC<br>GACTGTGCCTTCTAGTTGCCAGCCATCTGTTGTTTGCCCCTCCCCCGTGCCTTCCTTGACCCTGGAAGGTGCC<br>ACTCCCACTGTCCTTTCCTAATAAAATGAGGAAATTGCATCGCATTGTCTGAGTAGGTGTCATTCTATTCTGG<br>GGGGTGGGGTGGGGCAGGACAGCAAGGGGGAGGATTGGGAAGAGAATAGCAGGCATGCTGGTACCTGAGGGCC<br>TATTTCCCATGATTCCTTCATATTTGCATATACGATACAAGGCTGTTAGAGAGATAATTGGAATTAATTTGAC<br>TGTAAACACAAAGATATTAGTACAAAATACGTGACGTAGAAAGTAATAATTTCTTGGGTAGTTTGCAGTTTTA<br>AAATTATGTTTTAAAATGGACTATCATATGCTTACCGTAACTTGAAAGTATTTCGATTTCTTGGCTTTATATA<br>TCTTGTGGAAAGGACGAAACACCGGAGACCACGGCAGGTCTCAGTTTTAGTACTCTGGAAACAGAATCTACTA<br>AAACAAGGCAAAATGCCGTGTTTATCTCGTCAACTTGTTGGCGAGATTTTTGCGGCCGCGTCGACAT |

What is claimed is:

1. A composition for cleaving a target DNA in a cell comprising:
   a) a nucleic acid encoding an engineered, non-naturally occurring Clustered Regularly Interspaced Short Palindromic Repeats (CRISPR)-CRISPR associated (Cas) (CRISPR-Cas) system comprising a first guide RNA and a second guide RNA, wherein the target DNA comprises a deep intronic mutation in a CEP290 gene and sequences flanking the mutation, wherein the first guide RNA and second guide RNA are capable of hybridizing to opposite strands of the flanking sequences; and
   b) a recombinant adeno-associated virus (rAAV) vector comprising a Cas expression cassette, wherein the Cas expression cassette comprises:
      i) a nucleotide sequence encoding a Cas9 protein operably linked to a promoter that is a single minimal CMV promoter consisting of nucleotides 34-216 of SEQ ID NO:56, and
      ii) a target site for a single guide RNA, wherein the first guide RNA or the second guide RNA is capable of hybridizing to the target site;
   wherein the Cas9 protein is capable of being expressed from the Cas expression cassette;
   wherein the Cas9 protein is capable of cleaving the target DNA sequences flanking the mutation to thereby excise a portion of target DNA comprising the mutation; and
   wherein the Cas9 protein is capable of cleaving the Cas expression cassette at the target site in the Cas expression cassette to thereby reduce expression of the Cas9 protein, as compared to expression of the Cas9 protein prior to cleavage of the Cas expression cassette.

2. The composition of claim 1, wherein the nucleic acid encoding the CRISPR-Cas system and the Cas expression cassette are located on the same or different vectors.

3. The composition of claim 2, wherein the vector encoding the CRISPR-Cas system is a recombinant adeno-associated virus (rAAV) vector, a recombinant adenoviral vector, a recombinant lentiviral vector or a recombinant herpes simplex virus (HSV) vector.

4. The composition of claim 1, wherein the deep intronic mutation is a c.2991+1655A>G mutation.

5. A composition for treating Leber congenital amaurosis associated with a deep intronic mutation in a target DNA acid of an individual comprising:

a) a nucleic acid encoding an engineered, non-naturally occurring Clustered Regularly Interspaced Short Palindromic Repeats (CRISPR)-CRISPR associated (Cas) (CRISPR-Cas) system comprising a first guide RNA and a second guide RNA, wherein the target DNA comprises a deep intronic mutation in a CEP290 gene and sequences flanking the mutation, wherein the first guide RNA and second guide RNA are capable of hybridizing to opposite strands of the flanking sequences; and b) a recombinant adeno-associated virus (rAAV) vector comprising a Cas expression cassette, wherein the Cas expression cassette comprises:

i) a nucleotide sequence encoding a Cas9 protein operably linked to a promoter that is a single minimal CMV promoter consisting of nucleotides 34-216 of SEQ ID NO:56, and ii) a target site for a single guide RNA, wherein the first guide RNA or the second guide RNA is capable of hybridizing to the target site;

wherein the Cas9 protein is capable of being expressed from the Cas expression cassette;

wherein the Cas9 protein is capable of cleaving the target DNA sequences flanking the mutation to thereby excise a portion of target DNA comprising the mutation; and wherein the Cas9 protein is capable of cleaving the Cas expression cassette at the single target site in the Cas expression cassette to thereby reduce expression of the Cas9 protein, as compared to expression of the Cas9 protein prior to cleavage of the Cas expression cassette.

6. The composition of claim 5, wherein the deep intronic mutation is a c.2991+1655A>G mutation.

* * * * *

SEQUENCE LISTING

<160> NUMBER OF SEQ ID NOS: 68

<210> SEQ ID NO 1
<211> LENGTH: 25
<212> TYPE: DNA
<213> ORGANISM: Artificial Sequence
<220> FEATURE:
<223> OTHER INFORMATION: Synthetic Construct

<400> SEQUENCE: 1
caccgaagac actgccaata gggat                                        25

<210> SEQ ID NO 2
<211> LENGTH: 25
<212> TYPE: DNA
<213> ORGANISM: Artificial Sequence
<220> FEATURE:
<223> OTHER INFORMATION: Synthetic Construct

<400> SEQUENCE: 2
aaacatccct attggcagtg tcttc                                        25

<210> SEQ ID NO 3
<211> LENGTH: 158
<212> TYPE: DNA
<213> ORGANISM: Artificial Sequence
<220> FEATURE:
<223> OTHER INFORMATION: Synthetic Construct

<400> SEQUENCE: 3
ccacccgcct cggcctccta aagtgctggg attacagatg tgagccaccg cacctggccc      60
cagttgtaat tgtgagtatc tcatacgtat ccctattggc agtgtcttag ttttatttt     120 tattatcttt attgtggcag ccattattcc tgtctcta                           158

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
ggtccctggc ttttgttcct                                              20

<210> SEQ ID NO 5
<211> LENGTH: 20
<212> TYPE: DNA

```
<213> ORGANISM: Artificial Sequence
<220> FEATURE:
<223> OTHER INFORMATION: Synthetic Construct

<400> SEQUENCE: 5
caggaggctg agggtgtttt                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
agtagagatg gggtttcacc                                               20

<210> SEQ ID NO 7
<211> LENGTH: 26
<212> TYPE: DNA
<213> ORGANISM: Artificial Sequence
<220> FEATURE:
<223> OTHER INFORMATION: Synthetic Construct

<400> SEQUENCE: 7
tgactgctaa gtacagggac atcttg                                        26

<210> SEQ ID NO 8
<211> LENGTH: 24
<212> TYPE: DNA
<213> ORGANISM: Artificial Sequence
<220> FEATURE:
<223> OTHER INFORMATION: Synthetic Construct

<400> SEQUENCE: 8
aggagatgtt ttcacactcc aggt                                          24

<210> SEQ ID NO 9
<211> LENGTH: 23
<212> TYPE: DNA
<213> ORGANISM: Artificial Sequence
<220> FEATURE:
<223> OTHER INFORMATION: Synthetic Construct

<400> SEQUENCE: 9
ctggccccag ttgtaatttg tga                                           23

<210> SEQ ID NO 10
<211> LENGTH: 24
<212> TYPE: DNA
<213> ORGANISM: Artificial Sequence
<220> FEATURE:
<223> OTHER INFORMATION: Synthetic Construct

<400> SEQUENCE: 10
ctgttcccag gcttgttcaa tagt                                          24

<210> SEQ ID NO 11
<211> LENGTH: 24
<212> TYPE: DNA
<213> ORGANISM: Artificial Sequence
<220> FEATURE:
<223> OTHER INFORMATION: Synthetic Construct

<400> SEQUENCE: 11
caccggcggg tggatcacga gttc                                          24
```

<210> SEQ ID NO 12
<211> LENGTH: 24
<212> TYPE: DNA
<213> ORGANISM: Artificial Sequence
<220> FEATURE:
<223> OTHER INFORMATION: Synthetic Construct

<400> SEQUENCE: 12
aaacgaactc gtgatccacc cgcc                                    24

<210> SEQ ID NO 13
<211> LENGTH: 25
<212> TYPE: DNA
<213> ORGANISM: Artificial Sequence
<220> FEATURE:
<223> OTHER INFORMATION: Synthetic Construct

<400> SEQUENCE: 13
caccgaaagc taccggttac ctgaa                                   25

<210> SEQ ID NO 14
<211> LENGTH: 25
<212> TYPE: DNA
<213> ORGANISM: Artificial Sequence
<220> FEATURE:
<223> OTHER INFORMATION: Synthetic Construct

<400> SEQUENCE: 14
aaacttcagg taaccggtag ctttc                                   25

<210> SEQ ID NO 15
<211> LENGTH: 25
<212> TYPE: DNA
<213> ORGANISM: Artificial Sequence
<220> FEATURE:
<223> OTHER INFORMATION: Synthetic Construct

<400> SEQUENCE: 15
caccgtcatt cttgtggcag taagg                                   25

<210> SEQ ID NO 16
<211> LENGTH: 25
<212> TYPE: DNA
<213> ORGANISM: Artificial Sequence
<220> FEATURE:
<223> OTHER INFORMATION: Synthetic Construct

<400> SEQUENCE: 16
aaacccttac tgccacaaga atgac                                   25

<210> SEQ ID NO 17
<211> LENGTH: 24
<212> TYPE: DNA
<213> ORGANISM: Artificial Sequence
<220> FEATURE:
<223> OTHER INFORMATION: Synthetic Construct

<400> SEQUENCE: 17
caccggagtc acatgggagt caca                                    24

<210> SEQ ID NO 18
<211> LENGTH: 24
<212> TYPE: DNA
<213> ORGANISM: Artificial Sequence
<220> FEATURE:

<223> OTHER INFORMATION: Synthetic Construct

<400> SEQUENCE: 18
aaactgtgac tcccatgtga ctcc    24

<210> SEQ ID NO 19
<211> LENGTH: 102
<212> TYPE: DNA
<213> ORGANISM: Artificial Sequence
<220> FEATURE:
<223> OTHER INFORMATION: Synthetic Construct

<400> SEQUENCE: 19
ggcgggtgga tcacgagttc gttttagagc tagaaatagc aagttaaaat aaggctagtc    60
cgttatcaac ttgaaaaagt ggcaccgagt cggtgctttt tt    102

<210> SEQ ID NO 20
<211> LENGTH: 103
<212> TYPE: DNA
<213> ORGANISM: Artificial Sequence
<220> FEATURE:
<223> OTHER INFORMATION: Synthetic Construct

<400> SEQUENCE: 20
gaaagctacc ggttacctga agttttagag ctagaaatag caagttaaaa taaggctagt    60
ccgttatcaa cttgaaaaag tggcaccgag tcggtgcttt ttt    103

<210> SEQ ID NO 21
<211> LENGTH: 103
<212> TYPE: DNA
<213> ORGANISM: Artificial Sequence
<220> FEATURE:
<223> OTHER INFORMATION: Synthetic Construct

<400> SEQUENCE: 21
gtcattcttg tggcagtaag ggttttagag ctagaaatag caagttaaaa taaggctagt    60
ccgttatcaa cttgaaaaag tggcaccgag tcggtgcttt ttt    103

<210> SEQ ID NO 22
<211> LENGTH: 102
<212> TYPE: DNA
<213> ORGANISM: Artificial Sequence
<220> FEATURE:
<223> OTHER INFORMATION: Synthetic Construct

<400> SEQUENCE: 22
ggagtcacat gggagtcaca gttttagagc tagaaatagc aagttaaaat aaggctagtc    60
cgttatcaac ttgaaaaagt ggcaccgagt cggtgctttt tt    102

<210> SEQ ID NO 23
<211> LENGTH: 5838
<212> TYPE: DNA
<213> ORGANISM: Homo Sapiens

<400> SEQUENCE: 23
gtaagtttgt gtgattcttg aaccttgtga aattagccat ttttcttcaa tattttgtg    60 tttgggggga tttggcagat tttaattaaa gtttgcctgc atttatataa atttaacaga    120
gatataatta tccatattat tcattcagtt tagttataaa tattttgttc ccacataaca    180
cacacacaca cacacaatat attatctatt tatagtggct gaatgacttc tgaatgatta    240
tctagatcat tctccttagg tcacttgcat gatttagctg aatcaaacct cttttaacca    300

-continued

```
gacatctaag agaaaaagga gcatgaaaca ggtagaatat tgtaatcaaa ggagggaagc      360
actcattaag tgcccatccc tttctcttac ccctgtaccc agaacaaact attctcccat      420
ggtccctggc ttttgttcct tggaatggat gtagccaaca gtagctgaaa tattaagggc      480
tcttcctgga ccatggatgc actctgtaaa ttctcatcat tttttattgt agaataaatg      540 tagaattta atgtagaata aatttattta atgtagaata aaaataaaa aaactagagt       600 agaatatcat aagttacaat ctgtgaatat ggaccagacc ctttgtagtt atcttacagc      660
cacttgaact ctatacctt tactgaggac agaacaagct cctgatttgt tcatcttcct      720
catcagaaat agaggcttat ggattttgga ttattcttat ctaagatcct ttcacaggag      780
tagaataaga tctaattcta ttagctcaaa gcttttgct ggctcataga gacacattca      840
gtaaatgaaa acgttgttct gagtagcttt caggattcct actaaattat gagtcatgtt      900
tatcaatatt atttagaagt aatcataatc agtttgcttt ctgctgcttt tgccaaagag      960
aggtgattat gttacttttt atagaaaatt atgcctattt agtgtggtga taatttattt     1020
ttttccattc tccatgtcct ctgtcctatc ctctccagca ttagaaagtc ctaggcaaga     1080
gacatcttgt ggataatgta tcaatgagtg atgtttaacg ttatcatttt cccaaagagt     1140 attttcatc tttcctaaag atttttttt ttttttttg agatggagtt tcattctgtc       1200
acccaggctg agtgcagtgg cacgatctcg gcttaacgct tactgcatcc tctgcctccc     1260
agattcaagc agttctcctg cctcagcctc tgagtagctg ggattacagg tgtgcaccac     1320
cacaccagct aatttttttt tttttttttt ttttttgag gcagagtctc gctctgtcac     1380
ccaggctgga gtgcagtggc gccatcttgg ctcactgcaa gctccacctc ccgggttcag     1440
gccgttctcc tgcctcagcc tcctgagtag ctggtaccac aggcacccac catcatgccc     1500
ggctaatttt ttgtattttt agtagagatg gggtttcacc ttgttagcca ggatggtgtc     1560
gatctcctga actcgtgatc cacccgcctc ggcctcctaa agtgctggga ttacagatgt     1620
gagccaccgc acctggcccc agttgtaatt gtgagtatct cataccctatc cctattggca     1680 gtgtcttagt tttattttt attatcttta ttgtggcagc cattattcct gtctctatct      1740
ccagtcttac atcctcctta ctgccacaag aatgatcatt ctaaacatga atcctaccct     1800
gtgactccca tgtgactccc cgccttaaaa actgtcaaaa gctaccggtt acctgaaggg     1860
taaaagtcaa gtcccctact tacctcatgt catctagagc aagagatgaa ctagctgagt     1920
tttctgacca cagtgttctt tcttatgtat gttcttttgt acgtgctctt ttctatatat     1980
agggaaccat ttctctcttc cagttgtttt gctcagtgaa tttctattcc tgtttcaaaa     2040
cttgttcagg cattaccttt ttttcttaa gcatactttt tttaatggaa caaagtcact     2100
cctgtctaca ctagttctgc atcttataca taggttttgt acatagtaca tatttatatc     2160
acatcaaatt atatgtgttt acatatctgt cttccttaat ggaatataag tcttttgata     2220
taaggaacta tttaatttgt ttctgtgtgt tgagtatctc ctgtttggca cagagttcaa     2280
gctaatacat gagagtgatt agtggtggag agccacagtg catgtggtgt caaatatggt     2340
gcttaggaaa ttattgttgc ttttgagag gtaaaggttc atgagactag aggtcacgaa     2400
aatcagattt catgtgtgaa gaatggaata gataataagg aaatacaaaa actggatggg     2460
taataaagca aaagaaaaac ttgaaatttg atagtagaag aaaaaagaaa tagatgtaga     2520
ttgaggtaga atcaagaaga ggattctttt tttgttgttt ttttttttga aacagagtct     2580
cactgtgttg cccaggctgg agtgcagtgg agtgatcttg gcttactgca acctctgcct     2640
```

```
cccaggttca agcgattctt ctgcttcagt ctcccgagta gctggaatta caggtgccca    2700
ccagcacggc cggctaattt agtagagaca gggttttgcc atgttggccg ggctggtctc    2760
aaactttgga tctcaggtaa tccgccagcc tcaacttccc aaagtgctgg gattacaggc    2820
atgagccact gtgcccagcc tgttttttttt ttttaaagg agaccagtga agtttcagga    2880
ggagggaaag aaaatttaga gttactaggg agagagtgat gaagataaga gatgaaagtg    2940
gtaataaggg aaatagcaaa atatcagggt aggtgggaga aaagagatt tgtaacaaac     3000
aataggatta tcctgtgaaa aaggatgaaa ggaagaaaaa aatggataga aagatattta    3060
aaacaccctc agcctcctgt tttccctcct gtgtattcat agtatataaa actataatta    3120
tgtactttac ttaaaaaata tattattatt accttatcgt gcttatttaa tcatagcatg    3180
tcctcttttt agtctcatta ccctgtttgt attattcttc ataacactta atacctgaca    3240
ttgtattata tattggctta ttttccaggt actccactca aatataagtt ctaggatata    3300
atttatttat cactgaaatc cattgctag agtacctggc atgtagtaaa taggcattct      3360
gttttttcaa ataaaaaata aaggaactta agatatatat ttatgttata tcgccagcct    3420
ttttcctcac agctctattc tgttgtacag aattacctac tttacaattc ctgtgtttca    3480
aggggatctc aaatttaacg tgtccacaat gaactcctga tttctgtttc tctcctagtc    3540
attcttattt caatatatgt tcagttacct aaccagctag tcaaggcaga tactttagag    3600
ttattctgta gtcattcttt ttccctacca ttttgttt ccaaatgtaa tttatgtgtg      3660
tcttcttcat cctcgcagct ctaacccttg tccaaccag catcatcact catctggagt     3720
tccacaatgt ctttctggct agtttccctg atttctctat tgaccccttt attctccaca    3780
gtgcagccag aatgattgtt taaaacttcc tccttaaaat ctttaaattg ttttctttta    3840
tacgttaagt taaattccag ttccttgtct tggcatgcca tgccctgcct ggtgtggccc    3900
ctgatggtct ctccaacttc atgttttact actattgact cttattttg cttactctgc     3960
ttgggtgctc cagtcctcca aatcatttcc tgctccaatc atttcaatca ttttttcctc    4020
tcagatctta tagtattcca aatgctttct tcctttggag catctgggtt tactaataaa    4080
tacttcgtac ctcacagttc agcttaaata tcaattattt ggtggttaag acatccttca    4140
accgctctat ctaaatgttc ctttctatta ttcactggct cagtactctg ttttttatttt   4200
ctttctaaat gtcaactttt ttttttttga gtcagggtct cactgttgcc caggctcgag    4260
tgcagttgca caatcatagc tcattgcagc cttgccctcc tgggatcaag taattctccc    4320
acctcagcct ccaaaatagc tgggattaca ggtatgcatc accatgctca gctaatttt     4380
tgtgttttt tgtagagatg aggtctcact tgttgccca ggctggtctc aaactcctgg      4440
actcaagtga ttctcccacc tcagcctccc aaagtgctgg ggttacaggt gtgagccact    4500
gcacctggtc gatactgact ttttttttt tttgagatgg agttttgctc tgttgcccag     4560
gctagagcgc agtggtgtga tctcagctca ctgcaacctc cacctcccag gttaaaggga    4620
ttcttctgcc tcagtctcct gagtagctgg gattacaggc aagtgccatc atgactggct    4680
aattttttgta ttttttagcac tatgtttagt actgtgttgg ccaggcttgt ctcgaactcc  4740
tgacctcaag tgatccaccc acctcagcct cccaaagtgc tgggattaca ggtgtgagcc    4800
accgtaatcg gccaacattg acattttttag tagactttt gtttgtttac ttgcttatta    4860
tctgctgcct tccacactct ggcgaaatcc tgccacccac ccacacacac ataggcactg    4920
aatgggcaga actctgaagg ccagaatttt atatttcttt tcactgtaaa catcatcatc    4980
tgtcactgat ggcacactag gatgctcagc aactgtgtgc atgaaggaag taagcactag    5040
```

```
tttgtgaagg ctgcaaaact cttgagtatt ctaagagttt tggccaaaat gaatgtacag    5100
ctttagtggc agaagctaat actcagaaat tgaggccgta tattggataa cacaggattt    5160
ggatgattat tttaaaataa tattttacat tgtatatatg tgtgtgtgtg tgtgtgtgtg    5220
tgtgtgtatg tgtgtgtgtg tgtatatata tatgtatgta tgtgtattag tccgttctca    5280
tgctgctatg aagaaatacc tgagactggg taatttataa aggaaagagg tttaattgac    5340
tcacagttcc acagagctgg ggaggcctca gaaaacttaa cagttatggc agaaggggaa    5400
gcaaacacat ttttcttcac atggtggccg gaattagaag aatgtgagcc gagcaaaggg    5460
gaaagcccct tataaaacca tcagacatcg tgagaactta ctattatgag aatagcgtgg    5520
gggaaaccac ccccacgatt caattacctc ccaccaaatc cctcccatga catatgagga    5580
ttatgggaac tatgattcaa gatgagattt gggtagggac acagccaaac catatcagta    5640
tgtatatgta tacaagtatt atatatatat gtatgtgttt gtatgcatac atgtattata    5700
tatggaggaa attctaattt tgtaaaaaac tggattgtga gttttaagga gatgttatat    5760
aaagttaaga caatgtcatt ttgtggtatt ggtctgaatt acaatgtagt ttcttagtga    5820
tatttttcct ttattcag                                                 5838

<210> SEQ ID NO 24
<211> LENGTH: 78
<212> TYPE: DNA
<213> ORGANISM: Artificial Sequence
<220> FEATURE:
<223> OTHER INFORMATION: Synthetic Construct

<400> SEQUENCE: 24
cactccctct ctgcgcgctc gctcgctcac tgaggccggg cgaccaaagg tcgcccacgc    60
ccgggctttg cccgggcg                                                 78

<210> SEQ ID NO 25
<211> LENGTH: 60
<212> TYPE: DNA
<213> ORGANISM: Artificial Sequence
<220> FEATURE:
<223> OTHER INFORMATION: Synthetic Construct

<400> SEQUENCE: 25
tagcaagtta aaataaggct agtccgttat caacttgaaa aagtggcacc gagtcggtgc    60

<210> SEQ ID NO 26
<211> LENGTH: 7
<212> TYPE: PRT
<213> ORGANISM: Simian vacuolating virus 40

<400> SEQUENCE: 26

Pro Lys Lys Lys Arg Lys Val
1               5

<210> SEQ ID NO 27
<211> LENGTH: 17
<212> TYPE: PRT
<213> ORGANISM: Simian vacuolating virus 40

<400> SEQUENCE: 27

Pro Lys Lys Lys Arg Lys Val Glu Asp Pro Lys Lys Arg Lys Val
1               5                   10                  15

Asp
```

<210> SEQ ID NO 28
<211> LENGTH: 33
<212> TYPE: DNA
<213> ORGANISM: Artificial Sequence
<220> FEATURE:
<223> OTHER INFORMATION: Synthetic Construct

<400> SEQUENCE: 28
gggaggattg ggaagagaat agcaggcatg ctg                          33

<210> SEQ ID NO 29
<211> LENGTH: 33
<212> TYPE: DNA
<213> ORGANISM: Artificial Sequence
<220> FEATURE:
<223> OTHER INFORMATION: Synthetic Construct

<400> SEQUENCE: 29
cagcatgcct gctattctct tcccaatcct ccc                          33

<210> SEQ ID NO 30
<211> LENGTH: 447
<212> TYPE: DNA
<213> ORGANISM: Artificial Sequence
<220> FEATURE:
<223> OTHER INFORMATION: Synthetic Construct

<400> SEQUENCE: 30
cacatgtgag ggcctatttc ccatgattcc ttcatatttg catatacgat acaaggctgt    60
tagagagata attggaatta atttgactgt aaacacaaag atattagtac aaaatacgtg   120
acgtagaaag taataatttc ttgggtagtt tgcagtttta aaattatgtt ttaaaatgga   180
ctatcatatg cttaccgtaa cttgaaagta tttcgatttc ttggctttat atatcttgtg   240
gaaaggacga acaccgggt cttcgagaag acctgtttta gagctagaaa tagcaagtta   300
aaataaggct agtccgttat caacttgaaa aagtggcacc gagtcggtgc ttttttgttt   360
tagagctaga aatagcaagt taaaataagg ctagtccgtt tttagcgcgt gcgccaattc   420
tgcagacaaa tggctctaga ggtaccc                                      447

<210> SEQ ID NO 31
<211> LENGTH: 20
<212> TYPE: DNA
<213> ORGANISM: Artificial Sequence
<220> FEATURE:
<223> OTHER INFORMATION: Synthetic Construct

<400> SEQUENCE: 31
ttcatctgca ctgccaagac                                         20

<210> SEQ ID NO 32
<211> LENGTH: 20
<212> TYPE: DNA
<213> ORGANISM: Artificial Sequence
<220> FEATURE:
<223> OTHER INFORMATION: Synthetic Construct

<400> SEQUENCE: 32
tcgagttgtc cacagtcagc                                         20

<210> SEQ ID NO 33
<211> LENGTH: 1153
<212> TYPE: DNA
<213> ORGANISM: Artificial Sequence
<220> FEATURE:
<223> OTHER INFORMATION: Synthetic Construct

<400> SEQUENCE: 33

```
ctcacatgtg agggcctatt tcccatgatt ccttcatatt tgcatatacg atacaaggct      60
gttagagaga taattggaat taatttgact gtaaacacaa agatattagt acaaaatacg     120
tgacgtagaa agtaataatt tcttgggtag tttgcagttt taaaattatg ttttaaaatg     180
gactatcata tgcttaccgt aacttgaaag tatttcgatt tcttggcttt atatatcttg     240
tggaaaggac gaaacaccgg gtcttcgaga agacctgttt tagagctaga aatagcaagt     300
taaaataagg ctagtccgtt atcaacttga aaaagtggca ccgagtcggt gcttttttgt     360
tttagagcta gaaatagcaa gttaaaataa ggctagtccg ttttttagcgc gtgcgccaat     420
tctgcagaca aatggctcta gagaccggcg ccgctacagg ctttccaccg gtggtctctt     480
ctagaggtac ccgttacatc tagttattaa tagtaatcaa ttacggggtc attagttcat     540
agcccatata tggagttccg cgttacataa cttacggtaa atggcccgcc tggctgaccg     600
cccaacgacc cccgcccatt gacgtcaata atgacgtatg ttcccatagt aacgccaata     660
gggactttcc attgacgtca atgggtggag tatttacggt aaactgccca cttggcagta     720
catcaagtgt atcatatgcc aagtacgccc cctattgacg tcaatgacgg taaatggccc     780
gcctggcatt atgcccagta catgacctta tgggactttc ctacttggca gtacatctac     840
gtattagtca tcgctattac catggtgatg cggttttggc agtacatcaa tgggcgtgga     900
tagcggtttg actcacgggg atttccaagt ctccacccca ttgacgtcaa tgggagtttg     960
ttttggcacc aaaatcaacg ggactttcca aatgtcgta acaactccgc cccattgacg    1020
caaatgggcg gtaggcgtgt acggtggag gtctatataa gcagagctct ctggctaact    1080
agagaaccca ctgcttactg gcttatcgaa attaatacga ctcactatag ggagaaccaa    1140
gctggctagc cgc                                                        1153
```

<210> SEQ ID NO 34
<211> LENGTH: 45
<212> TYPE: DNA
<213> ORGANISM: Artificial Sequence
<220> FEATURE:
<223> OTHER INFORMATION: Synthetic Construct

<400> SEQUENCE: 34

```
ataacatgtg gtctcactct agaggcatgt gagggcctat ttccc                      45
```

<210> SEQ ID NO 35
<211> LENGTH: 36
<212> TYPE: DNA
<213> ORGANISM: Artificial Sequence
<220> FEATURE:
<223> OTHER INFORMATION: Synthetic Construct

<400> SEQUENCE: 35

```
tatggtaccg gtctcataga gccatttgtc tgcaga                                36
```

<210> SEQ ID NO 36
<211> LENGTH: 24
<212> TYPE: DNA
<213> ORGANISM: Artificial Sequence
<220> FEATURE:
<223> OTHER INFORMATION: Synthetic Construct

<400> SEQUENCE: 36
caccgcacta ccagagctaa ctca                                              24

<210> SEQ ID NO 37
<211> LENGTH: 24
<212> TYPE: DNA
<213> ORGANISM: Artificial Sequence
<220> FEATURE:
<223> OTHER INFORMATION: Synthetic Construct

<400> SEQUENCE: 37
aaactgagtt agctctggta gtgc                                              24

<210> SEQ ID NO 38
<211> LENGTH: 24
<212> TYPE: DNA
<213> ORGANISM: Artificial Sequence
<220> FEATURE:
<223> OTHER INFORMATION: Synthetic Construct

<400> SEQUENCE: 38
caccgtgcga atacgccacg cgat                                              24

<210> SEQ ID NO 39
<211> LENGTH: 24
<212> TYPE: DNA
<213> ORGANISM: Artificial Sequence
<220> FEATURE:
<223> OTHER INFORMATION: Synthetic Construct

<400> SEQUENCE: 39
aaacatcgcg tggcgtattc gcac                                              24

<210> SEQ ID NO 40
<211> LENGTH: 1368
<212> TYPE: PRT
<213> ORGANISM: Streptococcus pyogenes

<400> SEQUENCE: 40

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175
```

```
Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
            245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
```

-continued

```
                595                 600                 605
Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala Lys
                1010                1015                1020
```

```
Ser Glu Gln Glu Ile Gly Lys Ala Thr Ala Lys Tyr Phe Phe Tyr Ser
1025                1030                1035                1040

Asn Ile Met Asn Phe Phe Lys Thr Glu Ile Thr Leu Ala Asn Gly Glu
            1045                1050                1055

Ile Arg Lys Arg Pro Leu Ile Glu Thr Asn Gly Glu Thr Gly Glu Ile
        1060                1065                1070

Val Trp Asp Lys Gly Arg Asp Phe Ala Thr Val Arg Lys Val Leu Ser
    1075                1080                1085

Met Pro Gln Val Asn Ile Val Lys Lys Thr Glu Val Gln Thr Gly Gly
1090                1095                1100

Phe Ser Lys Glu Ser Ile Leu Pro Lys Arg Asn Ser Asp Lys Leu Ile
1105                1110                1115                1120

Ala Arg Lys Lys Asp Trp Asp Pro Lys Lys Tyr Gly Gly Phe Asp Ser
            1125                1130                1135

Pro Thr Val Ala Tyr Ser Val Leu Val Val Ala Lys Val Glu Lys Gly
        1140                1145                1150

Lys Ser Lys Lys Leu Lys Ser Val Lys Glu Leu Leu Gly Ile Thr Ile
    1155                1160                1165

Met Glu Arg Ser Ser Phe Glu Lys Asn Pro Ile Asp Phe Leu Glu Ala
1170                1175                1180

Lys Gly Tyr Lys Glu Val Lys Lys Asp Leu Ile Ile Lys Leu Pro Lys
1185                1190                1195                1200

Tyr Ser Leu Phe Glu Leu Glu Asn Gly Arg Lys Arg Met Leu Ala Ser
        1205                1210                1215

Ala Gly Glu Leu Gln Lys Gly Asn Glu Leu Ala Leu Pro Ser Lys Tyr
    1220                1225                1230

Val Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys His
1250                1255                1260

Tyr Leu Asp Glu Ile Ile Glu Gln Ile Ser Glu Phe Ser Lys Arg Val
1265                1270                1275                1280

Ile Leu Ala Asp Ala Asn Leu Asp Lys Val Leu Ser Ala Tyr Asn Lys
            1285                1290                1295

His Arg Asp Lys Pro Ile Arg Glu Gln Ala Glu Asn Ile Ile His Leu
        1300                1305                1310

Phe Thr Leu Thr Asn Leu Gly Ala Pro Ala Ala Phe Lys Tyr Phe Asp
            1315                1320                1325

Thr Thr Ile Asp Arg Lys Arg Tyr Thr Ser Thr Lys Glu Val Leu Asp
    1330                1335                1340

Ala Thr Leu Ile His Gln Ser Ile Thr Gly Leu Tyr Glu Thr Arg Ile
1345                1350                1355                1360

Asp Leu Ser Gln Leu Gly Gly Asp
            1365

<210> SEQ ID NO 41
<211> LENGTH: 20
<212> TYPE: DNA
<213> ORGANISM: Artificial Sequence
<220> FEATURE:
<223> OTHER INFORMATION: Synthetic Construct

<400> SEQUENCE: 41
ggcgggtgga tcacgagttc                                                    20
```

<210> SEQ ID NO 42
<211> LENGTH: 20
<212> TYPE: DNA
<213> ORGANISM: Artificial Sequence
<220> FEATURE:
<223> OTHER INFORMATION: Synthetic Construct

<400> SEQUENCE: 42
aaagctaccg gttacctgaa            20

<210> SEQ ID NO 43
<211> LENGTH: 20
<212> TYPE: DNA
<213> ORGANISM: Artificial Sequence
<220> FEATURE:
<223> OTHER INFORMATION: Synthetic Construct

<400> SEQUENCE: 43
tcattcttgt ggcagtaagg            20

<210> SEQ ID NO 44
<211> LENGTH: 20
<212> TYPE: DNA
<213> ORGANISM: Artificial Sequence
<220> FEATURE:
<223> OTHER INFORMATION: Synthetic Construct

<400> SEQUENCE: 44
ggagtcacat gggagtcaca            20

<210> SEQ ID NO 45
<211> LENGTH: 21
<212> TYPE: DNA
<213> ORGANISM: Artificial Sequence
<220> FEATURE:
<223> OTHER INFORMATION: Synthetic Construct

<400> SEQUENCE: 45
tttaacgtta tcattttccc a            21

<210> SEQ ID NO 46
<211> LENGTH: 21
<212> TYPE: DNA
<213> ORGANISM: Artificial Sequence
<220> FEATURE:
<223> OTHER INFORMATION: Synthetic Construct

<400> SEQUENCE: 46
agtttcattc tgtcacccag g            21

<210> SEQ ID NO 47
<211> LENGTH: 21
<212> TYPE: DNA
<213> ORGANISM: Artificial Sequence
<220> FEATURE:
<223> OTHER INFORMATION: Synthetic Construct

<400> SEQUENCE: 47
aaaaattagc cgggcatgat g            21

<210> SEQ ID NO 48
<211> LENGTH: 21
<212> TYPE: DNA
<213> ORGANISM: Artificial Sequence
<220> FEATURE:
<223> OTHER INFORMATION: Synthetic Construct

<400> SEQUENCE: 48
tgtaagactg gagatagaga c                                             21

<210> SEQ ID NO 49
<211> LENGTH: 21
<212> TYPE: DNA
<213> ORGANISM: Artificial Sequence
<220> FEATURE:
<223> OTHER INFORMATION: Synthetic Construct

<400> SEQUENCE: 49
cttttgacag tttttaaggc g                                             21

<210> SEQ ID NO 50
<211> LENGTH: 103
<212> TYPE: DNA
<213> ORGANISM: Artificial Sequence
<220> FEATURE:
<223> OTHER INFORMATION: Synthetic Construct

<400> SEQUENCE: 50
gtttaacgtt atcatttcc cagttttagt actctggaaa cagaatctac taaaacaagg    60
caaaatgccg tgtttatctc gtcaacttgt tggcgagatt ttt                    103

<210> SEQ ID NO 51
<211> LENGTH: 103
<212> TYPE: DNA
<213> ORGANISM: Artificial Sequence
<220> FEATURE:
<223> OTHER INFORMATION: Synthetic Construct

<400> SEQUENCE: 51
gagtttcatt ctgtcaccca gggttttagt actctggaaa cagaatctac taaaacaagg    60
caaaatgccg tgtttatctc gtcaacttgt tggcgagatt ttt                    103

<210> SEQ ID NO 52
<211> LENGTH: 103
<212> TYPE: DNA
<213> ORGANISM: Artificial Sequence
<220> FEATURE:
<223> OTHER INFORMATION: Synthetic Construct

<400> SEQUENCE: 52
gaaaaattag ccgggcatga tggttttagt actctggaaa cagaatctac taaaacaagg    60
caaaatgccg tgtttatctc gtcaacttgt tggcgagatt ttt                    103

<210> SEQ ID NO 53
<211> LENGTH: 103
<212> TYPE: DNA
<213> ORGANISM: Artificial Sequence
<220> FEATURE:
<223> OTHER INFORMATION: Synthetic Construct

<400> SEQUENCE: 53
gtgtaagact ggagatagag acgttttagt actctggaaa cagaatctac taaaacaagg    60
caaaatgccg tgtttatctc gtcaacttgt tggcgagatt ttt                    103

<210> SEQ ID NO 54
<211> LENGTH: 103
<212> TYPE: DNA
<213> ORGANISM: Artificial Sequence
<220> FEATURE:

<223> OTHER INFORMATION: Synthetic Construct

<400> SEQUENCE: 54

```
gcttttgaca gttttttaagg cggttttagt actctggaaa cagaatctac taaaacaagg    60
caaaatgccg tgtttatctc gtcaacttgt tggcgagatt ttt                      103
```

<210> SEQ ID NO 55
<211> LENGTH: 1053
<212> TYPE: PRT
<213> ORGANISM: Staphylococcus aureus

<400> SEQUENCE: 55

```
Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335
```

```
Ala Arg Lys Glu Ile Ile Glu Asn Ala Glu Leu Leu Asp Gln Ile Ala
            340                 345                 350
Lys Ile Leu Thr Ile Tyr Gln Ser Ser Glu Asp Ile Gln Glu Glu Leu
            355                 360                 365
Thr Asn Leu Asn Ser Glu Leu Thr Gln Glu Glu Ile Glu Gln Ile Ser
            370                 375                 380
Asn Leu Lys Gly Tyr Thr Gly Thr His Asn Leu Ser Leu Lys Ala Ile
385                 390                 395                 400
Asn Leu Ile Leu Asp Glu Leu Trp His Thr Asn Asp Asn Gln Ile Ala
            405                 410                 415
Ile Phe Asn Arg Leu Lys Leu Val Pro Lys Lys Val Asp Leu Ser Gln
            420                 425                 430
Gln Lys Glu Ile Pro Thr Thr Leu Val Asp Asp Phe Ile Leu Ser Pro
            435                 440                 445
Val Val Lys Arg Ser Phe Ile Gln Ser Ile Lys Val Ile Asn Ala Ile
            450                 455                 460
Ile Lys Lys Tyr Gly Leu Pro Asn Asp Ile Ile Ile Glu Leu Ala Arg
465                 470                 475                 480
Glu Lys Asn Ser Lys Asp Ala Gln Lys Met Ile Asn Glu Met Gln Lys
            485                 490                 495
Arg Asn Arg Gln Thr Asn Glu Arg Ile Glu Glu Ile Ile Arg Thr Thr
            500                 505                 510
Gly Lys Glu Asn Ala Lys Tyr Leu Ile Glu Lys Ile Lys Leu His Asp
            515                 520                 525
Met Gln Glu Gly Lys Cys Leu Tyr Ser Leu Glu Ala Ile Pro Leu Glu
            530                 535                 540
Asp Leu Leu Asn Asn Pro Phe Asn Tyr Glu Val Asp His Ile Ile Pro
545                 550                 555                 560
Arg Ser Val Ser Phe Asp Asn Ser Phe Asn Asn Lys Val Leu Val Lys
            565                 570                 575
Gln Glu Glu Asn Ser Lys Lys Gly Asn Arg Thr Pro Phe Gln Tyr Leu
            580                 585                 590
Ser Ser Ser Asp Ser Lys Ile Ser Tyr Glu Thr Phe Lys Lys His Ile
            595                 600                 605
Leu Asn Leu Ala Lys Gly Lys Gly Arg Ile Ser Lys Thr Lys Lys Glu
            610                 615                 620
Tyr Leu Leu Glu Glu Arg Asp Ile Asn Arg Phe Ser Val Gln Lys Asp
625                 630                 635                 640
Phe Ile Asn Arg Asn Leu Val Asp Thr Arg Tyr Ala Thr Arg Gly Leu
            645                 650                 655
Met Asn Leu Leu Arg Ser Tyr Phe Arg Val Asn Asn Leu Asp Val Lys
            660                 665                 670
Val Lys Ser Ile Asn Gly Gly Phe Thr Ser Phe Leu Arg Arg Lys Trp
            675                 680                 685
Lys Phe Lys Lys Glu Arg Asn Lys Gly Tyr Lys His His Ala Glu Asp
            690                 695                 700
Ala Leu Ile Ile Ala Asn Ala Asp Phe Ile Phe Lys Glu Trp Lys Lys
705                 710                 715                 720
Leu Asp Lys Ala Lys Lys Val Met Glu Asn Gln Met Phe Glu Glu Lys
            725                 730                 735
Gln Ala Glu Ser Met Pro Glu Ile Glu Thr Glu Gln Glu Tyr Lys Glu
            740                 745                 750
Ile Phe Ile Thr Pro His Gln Ile Lys His Ile Lys Asp Phe Lys Asp
```

Tyr Lys Tyr Ser His Arg Val Asp Lys Lys Pro Asn Arg Glu Leu Ile
        770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Thr Gly Asn Tyr
850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
            885                 890                 895

Tyr Pro Asn Ser Arg Asn Lys Val Val Lys Leu Ser Leu Lys Pro Tyr
                900                 905                 910

Arg Phe Asp Val Tyr Leu Asp Asn Gly Val Tyr Lys Phe Val Thr Val
            915                 920                 925

Lys Asn Leu Asp Val Ile Lys Lys Glu Asn Tyr Tyr Glu Val Asn Ser
930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
                995                 1000                1005

Asn Asp Lys Arg Pro Pro Arg Ile Ile Lys Thr Ile Ala Ser Lys Thr
1010                1015                1020

Gln Ser Ile Lys Lys Tyr Ser Thr Asp Ile Leu Gly Asn Leu Tyr Glu
1025                1030                1035                1040

Val Lys Ser Lys Lys His Pro Gln Ile Ile Lys Lys Gly
                1045                1050

<210> SEQ ID NO 56
<211> LENGTH: 321
<212> TYPE: DNA
<213> ORGANISM: Artificial Sequence
<220> FEATURE:
<223> OTHER INFORMATION: Synthetic Construct

<400> SEQUENCE: 56
tatacgcgtg ttgacactag ttcgcgaaat attgactcac ggggatttcc aagtctccac    60
cccattgacg tcaatgggag tttgttttgg caccaaaatc aacgggactt tccaaaatgt   120
cgtaacaact ccgccccatt gacgcaaatg ggcggtaggc gtgtacggtg ggaggtctat   180
ataagcagag ctcgtttagt gaaccgtcag atcgccgcca ccatggacaa gaagtacagc   240
atcggcctgg acatcggcac caactctgtg gctgggccg tgatcaccga cgagtacaag   300
gtgcccagca agaaattcaa g                                              321

```
<210> SEQ ID NO 57
<211> LENGTH: 168
<212> TYPE: DNA
<213> ORGANISM: Artificial Sequence
<220> FEATURE:
<223> OTHER INFORMATION: Synthetic Construct

<400> SEQUENCE: 57
tgactcgaga acttgtttat tgcagcttat aatggttaca aataaagcaa tagcatcaca      60
aatttcacaa ataaagcatt tttttcactg cattctagtt gtggtttgtc caaactcatc     120
aatgtatctt atcatgtctg caatatttcg cgagaagaca atagcagg                  168

<210> SEQ ID NO 58
<211> LENGTH: 23
<212> TYPE: DNA
<213> ORGANISM: Artificial Sequence
<220> FEATURE:
<223> OTHER INFORMATION: Synthetic Construct

<400> SEQUENCE: 58
ggcgggtgga tcacgagttc agg                                              23

<210> SEQ ID NO 59
<211> LENGTH: 23
<212> TYPE: DNA
<213> ORGANISM: Artificial Sequence
<220> FEATURE:
<223> OTHER INFORMATION: Synthetic Construct

<400> SEQUENCE: 59
ggagtcacat gggagtcaca ggg                                              23

<210> SEQ ID NO 60
<211> LENGTH: 324
<212> TYPE: DNA
<213> ORGANISM: Artificial Sequence
<220> FEATURE:
<223> OTHER INFORMATION: Synthetic Construct

<400> SEQUENCE: 60
ctagtggcgg ccgctcgagc atgcatctag agggccctat tctatagtgt cacctaaatg      60
ctagagctcg ctgatcagcc tcgactgtgc cttctagttg ccagccatct gttgtttgcc     120
cctcccccgt gccttccttg accctggaag gtgccactcc cactgtcctt tcctaataaa     180
atgaggaaat tgcatcgcat tgtctgagta ggtgtcattc tattctgggg ggtggggtgg     240
ggcaggacag caaggggggag gattgggaag acaatagcag gcatgctggg gagctagagt     300
cgaccggacc gctgcaggca tgca                                            324

<210> SEQ ID NO 61
<211> LENGTH: 20
<212> TYPE: DNA
<213> ORGANISM: Artificial Sequence
<220> FEATURE:
<223> OTHER INFORMATION: Synthetic Construct

<400> SEQUENCE: 61
gcataaggac taaagaccta                                                  20

<210> SEQ ID NO 62
<211> LENGTH: 20
<212> TYPE: DNA
<213> ORGANISM: Artificial Sequence
<220> FEATURE:
```

<223> OTHER INFORMATION: Synthetic Construct

<400> SEQUENCE: 62
ggtagtggtt gaactcacaa                                            20

<210> SEQ ID NO 63
<211> LENGTH: 2471
<212> TYPE: DNA
<213> ORGANISM: Artificial Sequence
<220> FEATURE:
<223> OTHER INFORMATION: Synthetic Construct

<400> SEQUENCE: 63
gggccccaga agcctggtgg ttgtttgtcc ttctcagggg aaaagtgagg cggccccttg      60
gaggaagggg ccgggcagaa tgatctaatc ggattccaag cagctcaggg gattgtcttt     120
ttctagcacc ttcttgccac tcctaagcgt cctccgtgac cccggctggg atttagcctg     180
gtgctgtgtc agccccggtc tcccaggggc ttcccagtgg tccccaggaa ccctcgacag     240
ggcccggtct ctctcgtcca gcaagggcag ggacgggcca caggccaagg gcggagtcgc     300
tgcgacgctg ccttcgcccc gtgcccgct ccgccgccgc ctcgcgccgc ccgcccggc      360 tctgactgac cgcgttactc ccacaggtga gcgggcggga cggcccttct cctccgggct     420
gtaattagcg cttggtttaa tgacggcttg tttcttttct gtggctgcgt gaaagccttg     480
aggggctccg ggagggccct ttgtgcgggg ggagcggctc gggggtgcg tgcgtgtgtg     540 tgtgcgtggg gagcgccgcg tgcggctccg cgctgcccgg cggctgtgag cgctgcgggc     600
gcggcgcggg gctttgtgcg ctccgcagtg tgcgcgaggg gagcgcggcc ggggcggtg      660 ccccgcggtg cggggggggc tgcgagggga acaaaggctg cgtgcggggt gtgtgcgtgg     720
gggggtgagc aggggtgtg ggcgcgtcgg tcggctgca accccccctg caccccccctc     780 cccgagttgc tgagcacggc ccggcttcgg gtgcggggct ccgtacgggg cgtggcgcgg     840
ggctcgccgt gccgggcggg gggtggcggc aggtgggggt gccgggcggg gcggggccgc     900
ctcgggccgg ggagggctcg gggagggggc gcggcggccc ccggagcgcc ggcggctgtc     960
gaggcgcggc gagccgcagc cattgccttt tatggtaatc gtgcgagagg cgcagggac     1020 ttcctttgtc ccaaatctgt gcggagccga aatctgggag gcgccgccgc accccctcta    1080
gcgggcgcgg ggcgaagcgg tgcggcgccg gcaggaagga aatgggcggg gagggccttc    1140
gtgcgtcgcc gcgccgccgt cccttctcc ctctccagcc tcgggctgt ccgcgggggg     1200 acggctgcct tcgggggga cggggcaggg cggggttcgg cttctggcgt gtgaccggcg    1260
gctctagagc ctctgctaac catgttcatg ccttcttctt tttcctacag ctcctgggca    1320
acgtgctggt tattgtgctg tctcatcatt ttggcaaaga attcttcgaa agatctgcta    1380
gcttaattaa cccggtcgcc accatggtga gcaagggcga ggagctgttc accggggtgg    1440
tgcccatcct ggtcgagctg gacggcgacg taaacggcca caagttcagc gtgtccggcg    1500
agggcgaggg cgatgccacc tacggcaagc tgaccctgaa gttcatctgc accaccggca    1560
agctgcccgt gccctggccc accctcgtga ccaccctgac ctacggcgtg cagtgcttca    1620
gccgctaccc cgaccacatg aagcagcacg acttcttcaa gtccgccatg cccgaaggct    1680
acgtccagga gcgcaccatc ttcttcaagg acgacggcaa ctacaagacc cgcgccgagg    1740
tgaagttcga gggcgacacc ctggtgaacc gcatcgagct gaagggcatc gacttcaagg    1800
aggacggcaa catcctgggg cacaagctgg agtacaacta acagccac aacgtctata     1860 tcatggccga caagcagaag aacggcatca aggtgaactt caagatccgc cacaacatcg    1920

```
aggacggcag cgtgcagctc gccgaccact accagcagaa caccccatc ggcgacggcc      1980 ccgtgctgct gcccgacaac cactacctga gcacccagtc cgccctgagc aaagaccca      2040 acgagaagcg cgatcacatg gtcctgctgg agttcgtgac cgccgccggg atcactctcg      2100
gcatggacga gctgtacaag taaagcggcc aaatcgtacg cctaggtgat caagatctgc      2160
tagcttaatt aacccgggac tagtggcggc cgctcgagca tgcatctaga gggccctatt      2220
ctatagtgtc acctaaatgc tagagctcgc tgatcagcct cgactgtgcc ttctagttgc      2280
cagccatctg ttgtttgccc ctcccccgtg ccttccttga ccctggaagg tgccactccc      2340
actgtccttt cctaataaaa tgaggaaatt gcatcgcatt gtctgagtag gtgtcattct      2400
attctggggg gtggggtggg gcaggacagc aaggggagg attgggaaga caatagcagg      2460
catgctgggg a                                                           2471

<210> SEQ ID NO 64
<211> LENGTH: 20
<212> TYPE: DNA
<213> ORGANISM: Artificial Sequence
<220> FEATURE:
<223> OTHER INFORMATION: Synthetic Construct

<400> SEQUENCE: 64
cccctcgcct gtactgaaag                                                   20

<210> SEQ ID NO 65
<211> LENGTH: 20
<212> TYPE: DNA
<213> ORGANISM: Artificial Sequence
<220> FEATURE:
<223> OTHER INFORMATION: Synthetic Construct

<400> SEQUENCE: 65
gcacatcatc tgaggcaggt                                                   20

<210> SEQ ID NO 66
<211> LENGTH: 4009
<212> TYPE: DNA
<213> ORGANISM: Artificial Sequence
<220> FEATURE:
<223> OTHER INFORMATION: Synthetic Construct

<400> SEQUENCE: 66
atgaattctc tagacaattg gactcacggg gatttccaag tctccacccc attgacgtca      60
atgggagttt gttttggcac caaaatcaac gggactttcc aaaatgtcgt aacaactccg      120
ccccattgac gcaaatgggc ggtaggcgtg tacggtggga ggtctatata agcagagctc      180
gtttagtgaa ccgtcagatc acgcgtgcca ccatgaagcg gaactacatc ctgggcctgg      240
acatcggcat caccagcgtg ggctacggca tcatcgacta cgagacacgg gacgtgatcg      300
atgccggcgt gcggctgttc aaagaggcca acgtggaaaa caacgagggc aggcggagca      360
agaggagcgc cagaaggctg aagcggcgga ggcggcatag aatccagaga gtgaagaagc      420
tgctgttcga ctacaacctg ctgaccgacc acagcgagct gagcggcatc aaccctacg      480 aggccagagt gaagggcctg agccagaagc tgagcgagga agagttctct gccgccctgc      540
tgcacctggc caagagaaga ggcgtgcaca acgtgaacga ggtggaagag acaccggca      600 acgagctgtc caccaaagag cagatcagcc ggaacagcaa ggccctggaa gagaaatacg      660
tggccgaact gcagctggaa cggctgaaga aagacggcga agtgcggggc agcatcaaca      720
```

-continued

| | |
|---|---|
| gattcaagac cagcgactac gtgaaagaag ccaaacagct gctgaaggtg cagaaggcct | 780 |
| accaccagct ggaccagagc ttcatcgaca cctacatcga cctgctggaa acccggcgga | 840 |
| cctactatga gggacctggc gagggcagcc ccttcggctg aaggacatc aaagaatggt | 900 |
| acgagatgct gatgggccac tgcacctact tccccgagga actgcggagc gtgaagtacg | 960 |
| cctacaacgc cgacctgtac aacgccctga cgacctgaa caatctcgtg atcaccaggg | 1020 |
| acgagaacga gaagctggaa tattacgaga agttccagat catcgagaac gtgttcaagc | 1080 |
| agaagaagaa gcccaccctg aagcagatcg ccaaagaaat cctcgtgaac gaagaggata | 1140 |
| ttaagggcta cagagtgacc agcaccggca agcccgagtt caccaacctg aaggtgtacc | 1200 |
| acgacatcaa ggacattacc gcccggaaag agattattga gaacgccgag ctgctggatc | 1260 |
| agattgccaa gatcctgacc atctaccaga gcagcgagga catccaggaa gaactgacca | 1320 |
| atctgaactc cgagctgacc caggaagaga tcgagcagat ctctaatctg aagggctata | 1380 |
| ccggcaccca aacctgagc ctgaaggcca tcaacctgat cctggacgag ctgtggcaca | 1440 |
| ccaacgacaa ccagatcgct atcttcaacc ggctgaagct ggtgcccaag aaggtggacc | 1500 |
| tgtcccagca gaaagagatc ccaccaccc tggtggacga cttcatcctg agccccgtcg | 1560 |
| tgaagagaag cttcatccag agcatcaaag tgatcaacgc catcatcaag aagtacggcc | 1620 |
| tgcccaacga catcattatc gagctggccc gcgagaagaa ctccaaggac gcccagaaaa | 1680 |
| tgatcaacga gatgcagaag cggaaccggc agaccaacga gcggatcgag gaaatcatcc | 1740 |
| ggaccaccgg caaagagaac gccaagtacc tgatcgagaa gatcaagctg cacgacatgc | 1800 |
| aggaaggcaa gtgcctgtac agcctggaag ccatccctct ggaagatctg ctgaacaacc | 1860 |
| ccttcaacta tgaggtggac cacatcatcc ccagaagcgt gtccttcgac aacagcttca | 1920 |
| acaacaaggt gctcgtgaag caggaagaaa acagcaagaa gggcaaccgg accccattcc | 1980 |
| agtacctgag cagcagcgac agcaagatca gctacgaaac cttcaagaag cacatcctga | 2040 |
| atctggccaa gggcaagggc agaatcagca agaccaagaa agagtatctg ctggaagaac | 2100 |
| gggacatcaa caggttctcc gtgcagaaag acttcatcaa ccggaacctg gtggatacca | 2160 |
| gatacgccac cagaggcctg atgaacctgc tgcggagcta cttcagagtg aacaacctgg | 2220 |
| acgtgaaagt gaagtccatc aatggcggct tcaccagctt tctgcggcgg aagtggaagt | 2280 |
| ttaagaaaga gcgaacaag gggtacaagc accacgccga ggacgccctg atcattgcca | 2340 |
| acgccgattt catcttcaaa gagtggaaga aactggacaa ggccaaaaaa gtgatggaaa | 2400 |
| accagatgtt cgaggaaaag caggccgaga gcatgcccga gatcgaaacc gagcaggagt | 2460 |
| acaaagagat cttcatcacc ccccaccaga tcaagcacat taaggacttc aaggactaca | 2520 |
| agtacagcca ccgggtggac aagaagccta atagagagct gattaacgac accctgtact | 2580 |
| ccacccggaa ggacgacaag ggcaacaccc tgatcgtgaa caatctgaac ggcctgtacg | 2640 |
| acaaggacaa tgacaagctg aaaaagctga tcaacaagag ccccgaaaag ctgctgatgt | 2700 |
| accaccacga ccccagacc taccagaaac tgaagctgat tatggaacag tacggcgacg | 2760 |
| agaagaatcc cctgtacaag tactacgagg aaaccgggaa ctacctgacc aagtactcca | 2820 |
| aaaaggacaa cggccccgtg atcaagaaga ttaagtatta cggcaacaaa ctgaacgccc | 2880 |
| atctggacat caccgacgac taccccaaca gcagaaacaa ggtcgtgaag ctgtccctga | 2940 |
| agccctacag attcgacgtg tacctggaca atggcgtgta caagttcgtg accgtgaaga | 3000 |
| atctggatgt gatcaaaaaa gaaaactact acgaagtgaa tagcaagtgc tatgaggaag | 3060 |
| ctaagaagct gaagaagatc agcaaccagg ccgagtttat cgcctccttc tacaacaacg | 3120 |

```
atctgatcaa gatcaacggc gagctgtata gagtgatcgg cgtgaacaac gacctgctga    3180
accggatcga agtgaacatg atcgacatca cctaccgcga gtacctggaa aacatgaacg    3240
acaagaggcc ccccaggatc attaagacaa tcgcctccaa gacccagagc attaagaagt    3300
acagcacaga cattctgggc aacctgtatg aagtgaaatc taagaagcac cctcagatca    3360
tcaaaaaggg cggatccccc aagaaaaagc gcaaagtgga ctacaaagac gatgacgaca    3420
agtgagctag cgactgtgcc ttctagttgc cagccatctg ttgtttgccc ctcccccgtg    3480
ccttccttga ccctggaagg tgccactccc actgtccttt cctaataaaa tgaggaaatt    3540
gcatcgcatt gtctgagtag gtgtcattct attctggggg gtggggtggg gcaggacagc    3600 aaggggagg attgggaaga gaatagcagg catgctggta cctgagggcc tatttcccat     3660
gattccttca tatttgcata tacgatacaa ggctgttaga gagataattg gaattaattt    3720
gactgtaaac acaaagatat tagtacaaaa tacgtgacgt agaaagtaat aatttcttgg    3780
gtagtttgca gttttaaaat tatgttttaa aatggactat catatgctta ccgtaacttg    3840
aaagtatttc gatttcttgg ctttatatat cttgtggaaa ggacgaaaca ccggagacca    3900
cggcaggtct cagttttagt actctggaaa cagaatctac taaaacaagg caaaatgccg    3960
tgtttatctc gtcaacttgt tggcgagatt tttgcggccg cgtcgacat                4009

<210> SEQ ID NO 67
<211> LENGTH: 15
<212> TYPE: DNA
<213> ORGANISM: Homo sapiens

<400> SEQUENCE: 67
tgtaattgtg aatat                                                        15

<210> SEQ ID NO 68
<211> LENGTH: 15
<212> TYPE: DNA
<213> ORGANISM: Artificial Sequence
<220> FEATURE:
<223> OTHER INFORMATION: Synthetic Construct

<400> SEQUENCE: 68
tgtaattgtg agtat                                                        15
```